(12) United States Patent
Jones et al.

(10) Patent No.: US 9,951,088 B2
(45) Date of Patent: Apr. 24, 2018

(54) D2 RECEPTOR MODULATORS AND METHODS OF USE THEREOF IN THE TREATMENT OF DISEASES AND DISORDERS

(71) Applicant: SUNOVION PHARMACEUTICALS INC., Marlborough, MA (US)

(72) Inventors: Philip G. Jones, Danvers, MA (US); Robert Lew, Marlborough, MA (US); Kerry L. Spear, Concord, MA (US); Linghong Xie, Southborough, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

(21) Appl. No.: 14/399,334

(22) PCT Filed: May 9, 2013

(86) PCT No.: PCT/US2013/040238
§ 371 (c)(1),
(2) Date: Nov. 6, 2014

(87) PCT Pub. No.: WO2013/169964
PCT Pub. Date: Nov. 14, 2013

(65) Prior Publication Data
US 2015/0072974 A1    Mar. 12, 2015

Related U.S. Application Data

(60) Provisional application No. 61/644,947, filed on May 9, 2012.

(51) Int. Cl.
| | |
|---|---|
| *A61K 31/506* | (2006.01) |
| *C07D 513/04* | (2006.01) |
| *C07D 471/04* | (2006.01) |
| *C07D 401/14* | (2006.01) |
| *C07D 215/26* | (2006.01) |
| *C07D 231/56* | (2006.01) |
| *C07D 401/04* | (2006.01) |
| *C07D 401/12* | (2006.01) |
| *C07D 495/04* | (2006.01) |
| *C07D 519/00* | (2006.01) |
| *A61K 31/437* | (2006.01) |
| *A61K 31/4375* | (2006.01) |
| *A61K 31/4709* | (2006.01) |
| *A61K 31/496* | (2006.01) |
| *A61K 31/4985* | (2006.01) |
| *A61K 31/519* | (2006.01) |
| *A61K 31/551* | (2006.01) |
| *A61K 45/06* | (2006.01) |
| *A61K 31/444* | (2006.01) |

(52) U.S. Cl.
CPC .......... *C07D 513/04* (2013.01); *A61K 31/437* (2013.01); *A61K 31/4375* (2013.01); *A61K 31/444* (2013.01); *A61K 31/4709* (2013.01); *A61K 31/496* (2013.01); *A61K 31/4985* (2013.01); *A61K 31/519* (2013.01); *A61K 31/551* (2013.01); *A61K 45/06* (2013.01); *C07D 215/26* (2013.01); *C07D 231/56* (2013.01); *C07D 401/04* (2013.01); *C07D 401/12* (2013.01); *C07D 401/14* (2013.01); *C07D 471/04* (2013.01); *C07D 495/04* (2013.01); *C07D 519/00* (2013.01)

(58) Field of Classification Search
CPC .. C07D 513/04; C07D 215/26; C07D 231/56; C07D 401/04; C07D 401/12; C07D 401/14; C07D 471/04; C07D 495/04; C07D 519/00; A61K 31/437; A61K 31/4375; A61K 31/4709; A61K 31/496; A61K 31/4985; A61K 31/519; A61K 31/551; A61K 45/06
See application file for complete search history.

(56) References Cited

U.S. PATENT DOCUMENTS

| | | | | |
|---|---|---|---|---|
| 3,051,709 A | * | 8/1962 | Shapiro | C07C 35/32 250/396 R |
| 3,126,384 A | * | 3/1964 | Gaillot | C07D 215/42 424/456 |
| 3,787,411 A | * | 1/1974 | Ruschig | C07D 213/64 206/304 |
| 5,164,397 A | * | 11/1992 | George | C07D 239/42 514/275 |

(Continued)

FOREIGN PATENT DOCUMENTS

| | | | | |
|---|---|---|---|---|
| CN | 101712675 A | * | 5/2010 | |
| GB | 903346 A | * | 8/1962 | ............. A61K 38/24 |

(Continued)

OTHER PUBLICATIONS

CAS Abstract of CN 101712675 (Jun. 2, 2010).*
International Search Report for PCT/US13/40238, 6 pages (dated Aug. 27, 2013).
The English translation of the Japanese Office Action, dated Jan. 17, 2017, in the related Japanese Application No. 2015-511676.
D5. Allen et al., "Discovery of β-Arrestin-Biased Dopamine D2 Ligands for Probing Signal Transduction Pathways Essential for Antipsychotic Efficacy," PNAS, Nov. 8, 201, vol. 108, No. 45, pp. 18488-18493.

*Primary Examiner* — Alexander R Pagano

(57) ABSTRACT

Provided herein are heteroaryl compounds, methods of their synthesis, pharmaceutical compositions comprising the compounds, and methods of their use. In one embodiment, the compounds provided herein are useful for the treatment, prevention, and/or management of various disorders, such as CNS disorders and neurological disorders, including, but not limited to, e.g., psychosis, schizophrenia, depression, movement disorders, and Parkinson's disease.

16 Claims, No Drawings

(56) References Cited

U.S. PATENT DOCUMENTS

| | | | | |
|---|---|---|---|---|
| 5,192,799 | A * | 3/1993 | Tomino | C07C 217/18 514/469 |
| 6,534,522 | B2 * | 3/2003 | Bigge | C07D 211/14 514/307 |
| 7,160,888 | B2 * | 1/2007 | Johnson | C07D 471/04 514/230.5 |
| 9,156,822 | B2 * | 10/2015 | Jin | C07D 215/20 |
| 2005/0043309 | A1 | 2/2005 | Clark et al. | |
| 2006/0094719 | A1 * | 5/2006 | Howard, Jr. | C07D 209/44 514/235.2 |
| 2007/0060754 | A1 * | 3/2007 | Lindstrom | C07D 471/04 546/82 |
| 2008/0214553 | A1 * | 9/2008 | Letourneau | C07D 239/91 514/252.02 |
| 2008/0318998 | A1 * | 12/2008 | Prince | C07D 519/00 514/293 |
| 2009/0163545 | A1 * | 6/2009 | Goldfarb | A61K 31/122 514/312 |
| 2011/0160199 | A1 | 6/2011 | Li et al. | |
| 2013/0137679 | A1 * | 5/2013 | Jin | C07D 215/20 514/218 |

FOREIGN PATENT DOCUMENTS

| | | | | |
|---|---|---|---|---|
| WO | WO 2005019215 A1 * | 3/2005 | | C07D 471/04 |
| WO | WO 2006090272 A1 * | 8/2006 | | C07D 471/04 |
| WO | WO-2007/026959 A2 | 3/2007 | | |
| WO | WO-2012/003418 A2 | 1/2012 | | |
| WO | WO 2012003418 A2 * | 1/2012 | | C07D 215/20 |

* cited by examiner

D2 RECEPTOR MODULATORS AND METHODS OF USE THEREOF IN THE TREATMENT OF DISEASES AND DISORDERS

I. FIELD

Provided herein are heteroaryl compounds useful for treating various disorders or diseases, such as central nervous system (CNS) disorders or neurological disorders. Also provided herein are compositions comprising the compounds, and methods of use thereof.

II. BACKGROUND

The basal ganglia connects the cerebral cortex to brain systems that generate behavior. The striatum receives sensory input from the glutamatergic neurons of the neocortex. More than 95% of the neurons of the striatum are the GABAergic medium spiny neurons which are involved in a number of psychomotor functions. The activity of these neurons is modulated by dopamine. Dopamine exerts its functions on cellular activity through G-protein coupled receptors (e.g., D1, D2, D3, D4, and D5 receptors) and aberrant dopamine signaling has been implicated in a number of diseases such as schizophrenia, psychoses, Parkinson's disease, movement disorders, and other neuronal disorders such as attention deficit hyperactivity disorder, depression, and addiction.

Parkinson's disease is characterized by a loss of dopaminergic neurons in the substantia nigra pars compacta. Treatments for Parkinson's disease have focused on the replacement therapies to counteract this loss of dopamine input to the striatum either by L-dopa which is a dopamine precursor or by the administration of dopamine agonists such as pramipexole or ropinirole. Although these treatments are effective, the need for improved medications exists. The direct dopamine agonists are less effective than L-dopa, which despite being the most effective medication has a short half-life, and the resulting fluctuation in plasma concentrations is associated with the onset of dyskinesias. Dopamine agonists with improved efficacy and longer half-lives that produce a more constant plasma exposure are predicted to be improved medications for Parkinson's disease.

In contrast, schizophrenia is associated with an increase in striatal dopamine tone, particularly in the indirect pathway. Accordingly, the clinical efficacy of current antipsychotics correlates with their efficacy as D2 antagonists. However, these agents are known to produce extrapyramidal and other motoric adverse effects (Parkinsonism, dystonia, akathisia, tardive dyskinesia) following acute and chronic dosing. One pharmacological feature of many anti-psychotic drugs is that they typically block the D2/β-arrestin/Akt-GSK pathway which has long been implicated in schizophrenia while having different effects at the c-AMP pathway.

Dopamine partial agonists have been described as the "third generation" antipsychotics. These differentiate from the first and second generations in that their pharmacological effects are dependent on dopamine tone and the expression levels and receptor reserve. For instance, aripiprazole has been reported to be a partial agonist at the presynaptic D2 autoreceptors and in conditions of low dopamine tone. In fact, partial agonists will have a greater efficacy at these receptors due to their high receptor reserve. However, under conditions of high dopamine, as in schizophrenia, low efficacy partial agonists, such as aripiprazole, are effective antipsychotics with reduced motoric side effects due to an incomplete blockade of dopamine signaling in the striatum.

CNS disorders affect a wide range of the population with differing severity. For example, schizophrenia is a psychopathological disorder of unknown origin, which usually appears for the first time in early adulthood and is marked by characteristics, such as, psychotic symptoms, phasic progression and development, and deterioration in social behavior and professional capability. Characteristic psychotic symptoms include disorders of thought content (e.g., multiple, fragmentary, incoherent, implausible or simply delusional contents, or ideas of persecution) and of mentality (e.g., loss of association, flight of imagination, incoherence, or incomprehensibility), as well as disorders of perceptibility (e.g., hallucinations), emotions (e.g., superficial or inadequate emotions), self-perceptions, intentions, impulses, and inter-human relationships, and psychomotoric disorders (e.g., catatonia). Other symptoms are also associated with this disorder. See, e.g., *Diagnostic and Statistical Manual of Mental Disorders*, 4$^{th}$ Ed., American Psychiatric Association (1997) (DSM-IVT™).

Schizophrenia can be classified into various subgroups. For example, the paranoid type is characterized by delusions and hallucinations and absence of thought disorder, disorganized behavior, and affective flattening. The disorganized type, also named hebephrenic schizophrenia, is characterized by the presence of both thought disorder and affective flattening. The catatonic type is characterized by prominent psychomotor disturbances, including symptoms of catatonic stupor and waxy flexibility. In the undifferentiated type, psychotic symptoms are present but the criteria for paranoid, disorganized, or catatonic types have not been met.

The symptoms of schizophrenia normally manifest themselves in three broad categories, i.e., positive, negative and cognitive symptoms. Positive symptoms are those that represent an excess of normal experiences, such as hallucinations, disorganized speech, and delusions. Negative symptoms are those where the patient suffers from a lack of normal experiences, such as anhedonia, lack of motivation, inability to experience pleasure, and lack of social interaction. The cognitive symptoms relate to cognitive impairment in schizophrenics, such as lack of sustained attention, impairment of memory, and deficits in decision making. The current anti-psychotics are somewhat effective in treating the positive symptoms but are less effective in treating the negative or cognitive symptoms. For instance, the current typical or atypical anti-psychotics do not address cognitive or negative symptoms of schizophrenia, and only treat the positive symptoms in approximately 40% of patients.

Cognitive impairments include a decline in cognitive functions or cognitive domains, e.g., working memory, attention and vigilance, verbal learning and memory, visual learning and memory, reasoning and problem solving, e.g., executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts, difficulties in integrating thoughts, feelings and behavior, or difficulties in extinction of irrelevant thoughts.

These and other CNS or neurological disorders, such as, Parkinson's disease, movement disorders, affective disorders, addiction, among others, continue to affect the health and quality of life of many patients. Thus, there remains a great need for effective treatments of various CNS or neurological disorders, with reduced undesirable side effects.

Citation of any references in this Section of the application is not to be construed as an admission that such reference is prior art to the present application.

III. SUMMARY

Provided herein are compounds of formula (I), or pharmaceutically acceptable salts or stereoisomers thereof:

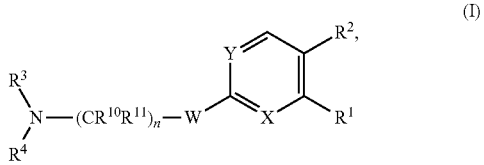

(I)

wherein $R^1$, $R^2$, $R^3$, $R^4$, $R^{10}$, $R^{11}$, X, Y, W, and n are defined herein elsewhere. The compounds are useful for treating various diseases or disorders, such as CNS disorders and neurological disorders.

Also provided herein are compositions or dosage forms comprising, a compound provided herein, or a pharmaceutically acceptable salt or stereoisomer thereof, and a pharmaceutically acceptable excipient, diluent, or carrier. In one embodiment, compositions or dosage forms provided herein may be co-administered with one or more additional active ingredients. In one embodiment, compositions or dosage forms provided herein may further comprise one or more additional active ingredients.

Also provided herein are methods for the treatment, prevention, and/or management of various disorders, such as a CNS disorder or a neurological disorder, e.g., the treatment, prevention, and/or amelioration of one or more symptoms of a disorder, using the compounds, or pharmaceutically acceptable salts or stereoisomers thereof, or the compositions provided herein. In one embodiment, a method provided herein further comprises administering to the subject a second active agent.

In one embodiment, provided herein is a method of treating, preventing, or managing a CNS disorder or a neurological disorder, comprising administering to a subject a therapeutically or prophylactically effective amount of a compound provided herein, or a pharmaceutically acceptable salt or stereoisomer thereof.

In one embodiment, the disorders provided herein include, but are not limited to, schizophrenia, psychosis, schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder, psychotic disorder due to a general medical condition, psychoaffective disorder, aggression, delirium, excitative psychosis, Tourette's syndrome, manic disorder, organic psychosis, or NOS psychosis.

In another embodiment, the disorders provided herein include, but are not limited to, Parkinson's disease, movement disorder, ataxia, dystonia, essential tremor, Huntington's disease, multiple system atrophy, myoclonus, progressive supranuclear palsy, rett syndrome, secondary parkinsonism, spasticity, tardive dyskinesia, Wilson's disease, dyskinesia, or restless leg syndrome.

In another embodiment, the disorders provided herein include, but are not limited to, affective disorder; depression; major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder (e.g., delusional disorder or schizophrenia); a bipolar disorder; bipolar I disorder; bipolar II disorder; cyclothymic disorder; attention deficit disorder (ADD); or attention deficit hyperactivity disorder (ADHD).

In another embodiment, the disorders provided herein include, but are not limited to, addiction or substance abuse.

In another embodiment, the disorders provided herein, include, but are not limited to, posttraumatic stress disorder, behavior disorder, neurodegenerative disease, Alzheimer's disease, dementia, mood disorder, anxiety, depression, major depressive disorder, unipolar depression, treatment resistant depression, dysthymia, affective disorder, seasonal affective disorder, obsessive-compulsive disorder, attention deficit disorder, attention deficit hyperactivity disorder, vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome, multiple sclerosis, sleep disorder, substance abuse or dependency, addiction, eating disorder, or autism.

In one embodiment, provided herein is a method of treating, preventing, and/or managing schizophrenia, psychosis, or Parkinson's disease, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing Parkinson's disease or a movement disorder, including but not limited to, Ataxia, dystonia, essential tremor, Huntington's disease, multiple system atrophy, myoclonus, Parkinson's disease, progressive supranuclear palsy, rett syndrome, secondary parkinsonism, spasticity, tardive dyskinesia, Wilson's disease, dyskinesia, and restless leg syndrome, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing schizophrenia, psychosis, or related disorders, including but not limited to, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, and organic psychosis, NOS psychosis, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing an affective disorder, including but not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder, attention deficit disorder (ADD), attention deficit hyperactivity disorder (ADHD), comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing addiction, substance abuse including alcohol, amphetamine, cocaine, and/or opiate addiction, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing posttraumatic stress disorder, behavior disorder, neurodegenerative disease, Alzheimer's disease, dementia, mood disorder, anxiety, depression, major depressive disorder, unipolar depression, treatment resistant depression, dysthymia, affective disorder, seasonal affective disorder, obsessive-compulsive disorder, attention deficit disorder, attention deficit hyperactivity disorder, vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome, multiple sclerosis, sleep disorder, substance abuse or dependency, addiction, eating disorder, or autism, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a disorder provided herein elsewhere (e.g., a CNS disorder or a neurological disorder), in a subject, such as a mammal, e.g., human, rodent (e.g., mice and rats), cat, dog, and non-human primate, among others. In one embodiment, provided herein is a method of treating, preventing, and/or ameliorating one or more symptoms associated with a disorder provided herein elsewhere (e.g., a CNS disorder or a neurological disorder), in a subject, such as a mammal, e.g., human, rodent (e.g., mice and rats), cat, dog, and non-human primate, among others. In one embodiment, the method provided herein comprises contacting a compound provided herein with a G-protein coupled receptor. In one embodiment, the method comprises contacting a compound provided herein with a D2 receptor.

In one embodiment, provided herein is a method of modulating D2 receptor activity. In one embodiment, the method comprises contacting a compound provided herein with a D2 receptor, which increases the D2 receptor activity. In one embodiment, the method comprises contacting a compound provided herein with a D2 receptor, which decreases the D2 receptor activity.

In another embodiment, provided herein is a method of modulating D2 receptor/β-arrestin interaction. In one embodiment, the method comprises contacting a compound provided herein with a D2 receptor, which modulates D2 receptor/β-arrestin interaction. In one embodiment, the method comprises contacting a compound provided herein with a D2 receptor, which antagonizes D2 receptor/β-arrestin activity. In one embodiment, the method comprises contacting a compound provided herein with a D2 receptor, which agonizes D2 receptor/β-arrestin activity. In one embodiment, the method comprises contacting a compound provided herein with a D2 receptor, which agonizes the D2 receptor and increases β-arrestin recruitment. In one embodiment, the method comprises contacting a compound provided herein with a D2 receptor, which antagonizes the D2 receptor and decreases β-arrestin recruitment.

In another embodiment, provided herein is a method of modulating other cellular functions. In one embodiment, the method comprises contacting a compound provided herein with a D2 receptor, which agonizes the D2 receptor and decreases cAMP production through a $G_i$-mediated mechanism. In one embodiment, the method comprises contacting a compound provided herein with a D2 receptor, which antagonizes the D2 receptor and prevents the D2-mediated decrease in cAMP production.

In one embodiment, the method comprises contacting a compound provided herein with a D2 receptor expressed in the central nervous system. In one embodiment, the method comprises contacting a cell with a compound provided herein. In an exemplary embodiment, the cell is a brain cell, such as, e.g., a MSN cell, a neuronal cell, or a glial cell.

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may be optionally substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-4}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere. In some embodiments, the alkenyl is optionally substituted with one or more halo.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere. In some embodiments, the alkynyl is optionally substituted with one or more halo.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere. In some embodiments, the cycloalkyl is optionally substituted with one or more halo.

As used herein, and unless otherwise specified, the term "heteroalkyl" refers to a stable straight or branched chain, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH═CH—O—$CH_3$, —Si($CH_3$)$_3$, —$CH_2$—CH═N—O$CH_3$, and —CH═CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere. In some embodiments, the heteroalkyl is optionally substituted with one or more halo.

As used herein, and unless otherwise specified, the term "alkoxyl" or "alkoxy" refers to a stable straight or branched chain, or cyclic hydrocarbon radical, or combinations thereof, consisting of the stated number of carbon atoms and from one or more, in one embodiment, one to three, O atoms, wherein at least one O atom is at the position where the alkoxyl or alkoxy group is attached to the remainder of the molecule. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere. In some embodiments, the alkoxyl is optionally substituted with one or more halo.

As used herein, and unless otherwise specified, the term "aminoalkyl" or "alkylamino" refers to a stable straight or branched chain, or cyclic hydrocarbon radical, or combinations thereof, consisting of the stated number of carbon atoms and from one or more, in one embodiment, one to three, N atoms, wherein at least one N atom is at the position where the aminoalkyl or alkylamino group is attached to the remainder of the molecule. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, and —NH—$CH_2$—$CH_2$—N($CH_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. An example of aralkyl includes, but is not limited to, benzyl. In certain embodiments, both alkyl and aryl may be optionally substituted with one or more substituents as described herein elsewhere.

As used herein, and unless otherwise specified, the term "heteroarylalkyl" or "heteroaralkyl" refers to a monovalent alkyl group substituted with heteroaryl. In certain embodiments, both alkyl and heteroaryl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N. In embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more 0, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (═O), —C(O)R$^a$, —C(O)R$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(═NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$VC(O)OR$^d$, —NR$^a$C(O)NR$^b$R$^c$, —NR$^a$C(═NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)R$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, muck, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice*

*of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, depression (e.g., major depressive disorder, dysthymia, and bipolar depressive disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder.

As used herein, and unless otherwise specified, the terms "psychosis," "schizophrenia," "obsessive-compulsive disorder," "substance abuse," "anxiety," "eating disorders," "migraine," and other CNS disorders described herein elsewhere are used herein in a manner consistent with their accepted meanings in the art. See, e.g., *Diagnostic and Statistical Manual of Mental Disorders,* 4$^{th}$ Ed., American Psychiatric Association (1997) (DSM-IV™).

As used herein, and unless otherwise specified, the term "affective disorder" includes depression, attention deficit disorder, attention deficit disorder with hyperactivity, bipolar and manic conditions, and the like. Additionally, in some embodiments, affective disorder can include an anxiety disorder (e.g., panic disorder, specific phobia, social phobia, obsessive-compulsive disorder, post-traumatic stress disorder, acute stress disorder, generalized anxiety disorder, anxiety disorder due to a general medical condition), and the like. The terms "attention deficit disorder" (ADD) and "attention deficit disorder with hyperactivity" (ADDH), or attention deficit hyperactivity disorder (ADHD), are used herein in accordance with the accepted meanings as found in the *Diagnostic and Statistical Manual of Mental Disorders*, 4th Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD), dysthymia, and treatment resistant depression. "Major depressive disorder" is used herein interchangeably with "unipolar depression" and "major depression." "Depression" may also include any condition commonly associated with depression, such as all forms of fatigue (e.g., chronic fatigue syndrome) and cognitive deficits.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

B. Compounds

In one embodiment, provided herein is a compound of formula (I):

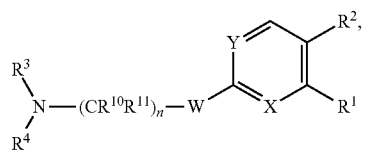

or a pharmaceutically acceptable salt or stereoisomer thereof, wherein n is 2, 3, or 4;
W is O, $NR^5$, or $CH_2$;
X is N or CH;
Y is N or CH;
each $R^{10}$ and each $R^{11}$ are independently H, F, OH, or $(C_1$-$C_4)$alkyl;

(i) $R^1$ is amido, sulfonamido, optionally substituted imidazolyl, or optionally substituted pyrazolyl; and $R^2$ is H, halogen, CN, $(C_1$-$C_4)$alkyl, or $(C_1$-$C_3)$alkoxyl; or (ii) $R^1$ and $R^2$ together with the carbon atoms to which they are attached form a 5-, 6-, or 7-membered aryl, heteroaryl, cycloalkyl, or heterocyclyl ring, each of which is optionally substituted with one to three $R^6$;

$R^3$ and $R^4$ together with the nitrogen atom to which they are attached form an optionally substituted heterocyclyl Q;

Q is

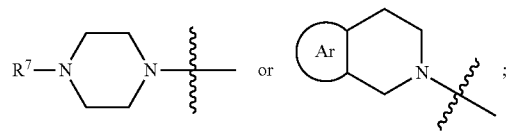

$R^5$ is H or $(C_1$-$C_3)$alkyl;
each $R^6$ is independently OH, keto, halogen, CN, $(C_1$-$C_3)$alkyl, or $(C_1$-$C_3)$alkoxyl;

$R^7$ is 5- to 10-membered aryl or heteroaryl, each optionally substituted with one to three substituents; and Ring Ar is a benzo, pyrazolo, pyrido, thieno, pyrimido, pyrazino, furano, pyridazino, thiazolo, or imidazolo ring, each optionally substituted with one to three substituents;

provided that:

(i) when Q is

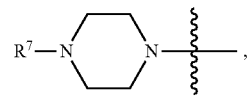

then

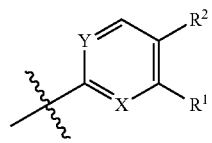

is not

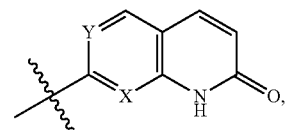

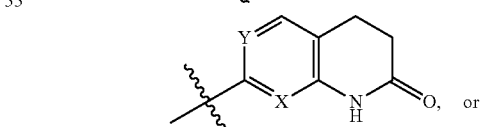

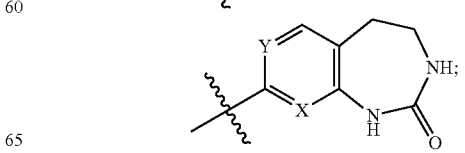

and (ii) when Ar is an optionally substituted benzo ring, then

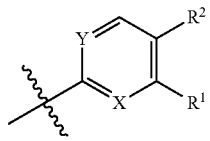

is not

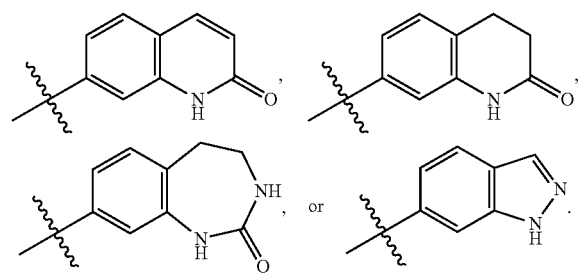

In one embodiment, n is 2. In one embodiment, n is 3. In one embodiment, n is 4.

In one embodiment, W is O. In one embodiment, W is $NR^5$. In one embodiment, W is NH. In one embodiment, W is $CH_2$.

In one embodiment, X is N. In one embodiment, X is CH.
In one embodiment, Y is N. In one embodiment, Y is CH.
In one embodiment, $R^{10}$ is H. In one embodiment, $R^{10}$ is F. In one embodiment, $R^{10}$ is OH. In one embodiment, $R^{10}$ is $(C_1-C_4)$alkyl.

In one embodiment, $R^{11}$ is H. In one embodiment, $R^{11}$ is F. In one embodiment, $R^{11}$ is OH. In one embodiment, $R^{11}$ is $(C_1-C_4)$alkyl.

In one embodiment, $R^1$ is amido, sulfonamido, optionally substituted imidazolyl, or optionally substituted pyrazolyl; and $R^2$ is H, halogen, CN, $(C_1-C_4)$alkyl, or $(C_1-C_3)$alkoxyl. In one embodiment, $R^1$ is amido. In one embodiment, $R^1$ is sulfonamido. In one embodiment, $R^1$ is optionally substituted imidazolyl. In one embodiment, $R^1$ is optionally substituted pyrazolyl. In one embodiment, $R^2$ is H. In one embodiment, $R^2$ is halogen. In one embodiment, $R^2$ is CN. In one embodiment, $R^2$ is $(C_1-C_4)$alkyl. In one embodiment, $R^2$ is $(C_1-C_3)$alkoxyl.

In one embodiment, $R^1$ and $R^2$ together with the carbon atoms to which they are attached form a 5-, 6-, or 7-membered aryl, heteroaryl, cycloalkyl, or heterocyclyl ring, each of which is optionally substituted with one to three $R^6$. In one embodiment, $R^1$ and $R^2$ together with the carbon atoms to which they are attached form a 5-membered heteroaryl ring, optionally substituted with one to three $R^6$. In one embodiment, $R^1$ and $R^2$ together with the carbon atoms to which they are attached form a 5-membered cycloalkyl ring, optionally substituted with one to three $R^6$. In one embodiment, $R^1$ and $R^2$ together with the carbon atoms to which they are attached form a 5-membered heterocyclyl ring, optionally substituted with one to three $R^6$. In one embodiment, $R^1$ and $R^2$ together with the carbon atoms to which they are attached form a 6-membered aryl ring, optionally substituted with one to three $R^6$. In one embodiment, $R^1$ and $R^2$ together with the carbon atoms to which they are attached form a 6-membered heteroaryl ring, optionally substituted with one to three $R^6$. In one embodiment, $R^1$ and $R^2$ together with the carbon atoms to which they are attached form a 6-membered cycloalkyl ring, optionally substituted with one to three $R^6$. In one embodiment, $R^1$ and $R^2$ together with the carbon atoms to which they are attached form a 6-membered heterocyclyl ring, optionally substituted with one to three $R^6$. In one embodiment, $R^1$ and $R^2$ together with the carbon atoms to which they are attached form a 7-membered heteroaryl ring, optionally substituted with one to three $R^6$. In one embodiment, $R^1$ and $R^2$ together with the carbon atoms to which they are attached form a 7-membered cycloalkyl ring, optionally substituted with one to three $R^6$. In one embodiment, $R^1$ and $R^2$ together with the carbon atoms to which they are attached form a 7-membered heterocyclyl ring, optionally substituted with one to three $R^6$.

In one embodiment, $R^3$ and $R^4$ together with the nitrogen atom to which they are attached form an optionally substituted heterocyclyl Q.

In one embodiment, Q is

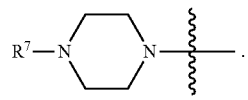

In one embodiment, Q is

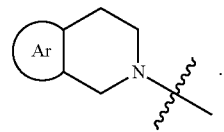

In one embodiment, $R^5$ is H. In one embodiment, $R^5$ is $(C_1-C_3)$alkyl.

In one embodiment, $R^6$ is OH. In one embodiment, $R^6$ is keto. In one embodiment, $R^6$ is halogen. In one embodiment, $R^6$ is CN. In one embodiment, $R^6$ is $(C_1-C_3)$alkyl. In one embodiment, $R^6$ is $(C_1-C_3)$alkoxyl.

In one embodiment, $R^7$ is 5- to 10-membered aryl, optionally substituted with one to three substituents. In one embodiment, $R^7$ is 5- to 10-membered heteroaryl, optionally substituted with one to three substituents. In one embodiment, $R^7$ is 5-membered aryl, optionally substituted with one to three substituents. In one embodiment, $R^7$ is 6-membered aryl, optionally substituted with one to three substituents. In one embodiment, $R^7$ is 7-membered aryl, optionally substituted with one to three substituents. In one embodiment, $R^7$ is 8-membered aryl, optionally substituted with one to three substituents. In one embodiment, $R^7$ is 9-membered aryl, optionally substituted with one to three substituents. In one embodiment, $R^7$ is 10-membered aryl, optionally substituted with one to three substituents. In one embodiment, $R^7$ is 5-membered heteroaryl, optionally substituted with one to three substituents. In one embodiment, $R^7$ is 6-membered heteroaryl, optionally substituted with one to three substituents. In one embodiment, $R^7$ is 7-membered heteroaryl, optionally substituted with one to three substituents. In one embodiment, $R^7$ is 8-membered heteroaryl, optionally substituted with one to three substituents. In one embodiment, $R^7$ is 9-membered heteroaryl, optionally substituted with one to three substituents. In one embodiment, $R^7$ is 10-membered heteroaryl, optionally substituted with one to three substituents.

In one embodiment, Ring Ar is a benzo, pyrazolo, pyrido, thieno, pyrimido, pyrazino, furano, pyridazino, thiazolo, or imidazolo ring, each optionally substituted with one to three substituents. In one embodiment, Ring Ar is a benzo ring, optionally substituted with one to three substituents. In one embodiment, Ring Ar is a pyrazolo ring, optionally substituted with one to three substituents. In one embodiment, Ring Ar is a pyrido ring, optionally substituted with one to three substituents. In one embodiment, Ring Ar is a thieno ring, optionally substituted with one to three substituents. In one embodiment, Ring Ar is a pyrimido ring, optionally substituted with one to three substituents. In one embodiment, Ring Ar is a pyrazino ring, optionally substituted with one to three substituents. In one embodiment, Ring Ar is a furano ring, optionally substituted with one to three substituents. In one embodiment, Ring Ar is a pyridazino ring, optionally substituted with one to three substituents. In one embodiment, Ring Ar is a thiazolo ring, optionally substituted with one to three substituents. In one embodiment, Ring Ar is a imidazolo ring, optionally substituted with one to three substituents.

In one embodiment, Q is

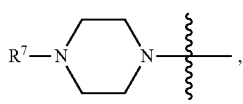

and

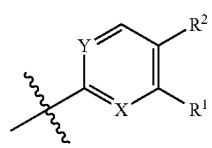

is not

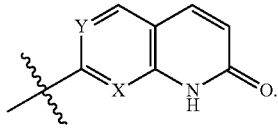

In one embodiment, Q is

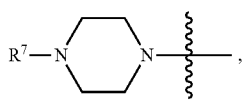

and

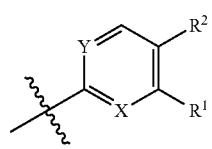

is not

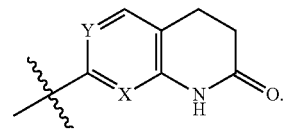

In one embodiment, Q is

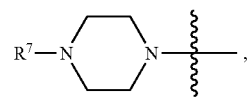

and

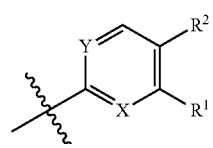

is not

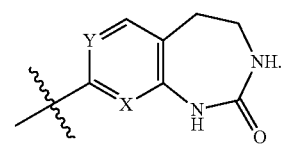

In one embodiment, Ar is an optionally substituted benzo ring, and

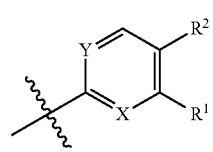

is not

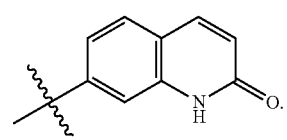 [SMILES: *c1ccc2ccc(=O)[nH]c2c1]

In one embodiment, Ar is an optionally substituted benzo ring, and

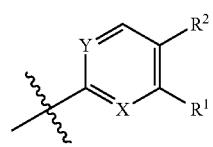

is not

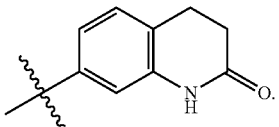 [SMILES: *c1ccc2c(c1)NC(=O)CC2]

In one embodiment, Ar is an optionally substituted benzo ring, and

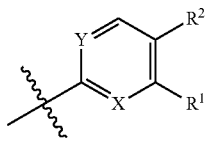

is not

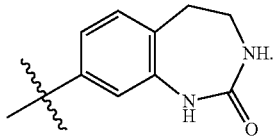 [SMILES: *c1ccc2c(c1)NC(=O)NCC2]

In one embodiment, Ar is an optionally substituted benzo ring, and

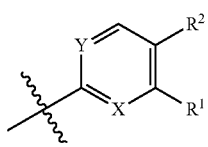

is not

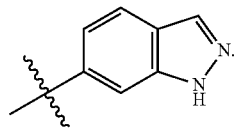 [SMILES: *c1ccc2cn[nH]c2c1]

In one embodiment, n is 4 and W is O. In one embodiment, W is O or $NR^5$. In one embodiment, n is 4, and W is O or $NR^5$.

In one embodiment, $R^{10}$ is H and $R^{11}$ is H.

In one embodiment, $R^1$ is

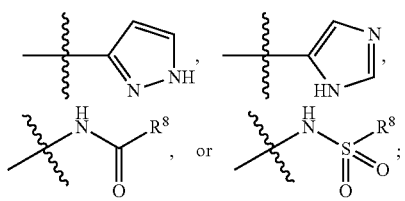

wherein $R^8$ is $(C_1-C_5)$alkyl or optionally substituted phenyl.
In one embodiment, $R^1$ is

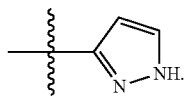

In one embodiment, $R^1$ is

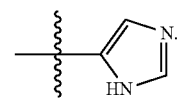

In one embodiment, $R^1$ is

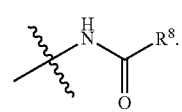

In one embodiment, $R^1$ is

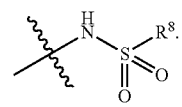

In one embodiment, $R^8$ is $(C_1-C_5)$alkyl or optionally substituted phenyl. In one embodiment, $R^8$ is $(C_1-C_5)$alkyl. In one embodiment, $R^8$ is optionally substituted phenyl.

In one embodiment,

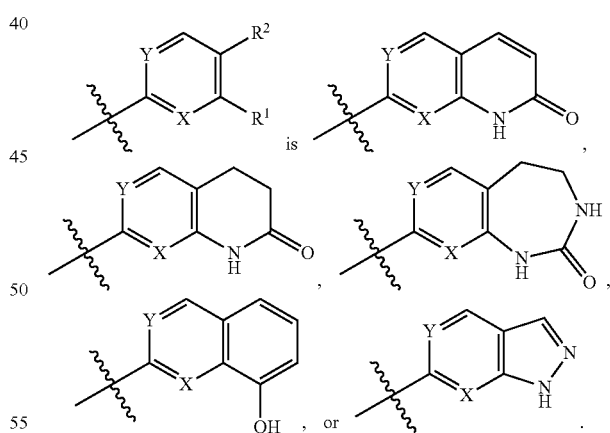

In one embodiment,

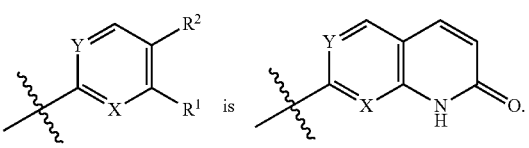

In one embodiment,

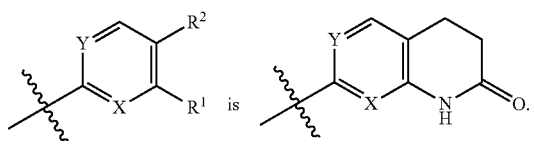 is 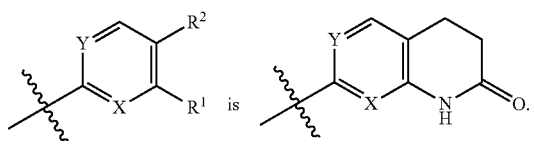

In one embodiment,

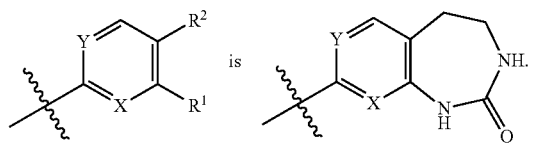 is 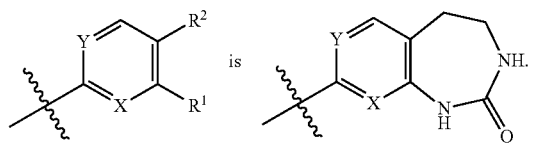

In one embodiment,

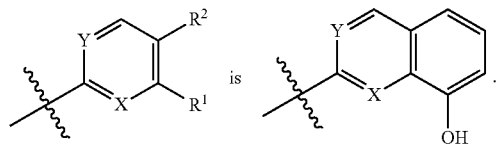 is 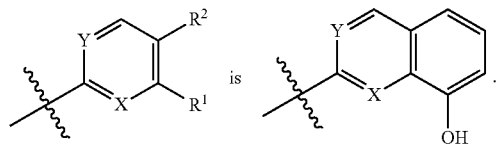

In one embodiment,

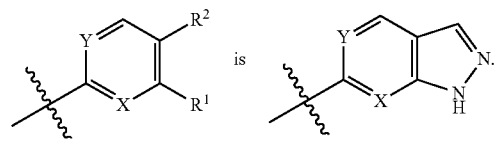 is 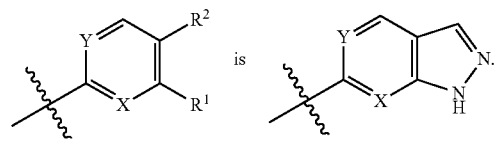

In one embodiment, provided herein is a compound of formula (II-a), or a pharmaceutically acceptable salt or stereoisomer thereof,

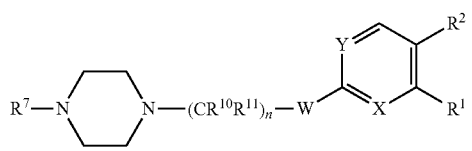

(II-a)

wherein $R^1$, $R^1$, $R^7$, $R^{10}$, $R^{11}$, X, Y, W, and n is defined herein elsewhere.

In one embodiment, provided herein is a compound of formula (II-b), or a pharmaceutically acceptable salt or stereoisomer thereof,

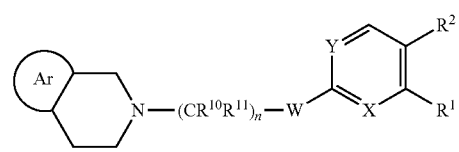

(II-b)

wherein $R^1$, $R^1$, $R^{10}$, $R^{11}$, X, Y, W, Ring Ar, and n is defined herein elsewhere.

In one embodiment, provided herein is a compound of formula (III-a), or a pharmaceutically acceptable salt or stereoisomer thereof,

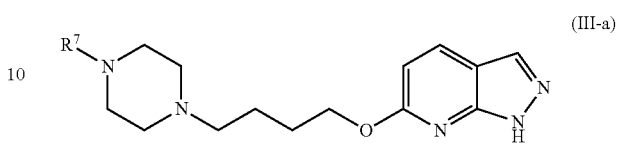

(III-a)

wherein $R^7$ is defined herein elsewhere. In one embodiment, $R^7$ is phenyl, pyridyl, pyridazinyl, pyrazinyl, pyrimidinyl, or naphthyl, each of which is optionally substituted with one to three substituents, independently selected from halo, cyano, alkylamino, dialkylamino, ($C_1$-$C_3$)alkyl optionally substituted with one or more fluoro, and ($C_1$-$C_3$)alkoxyl optionally substituted with one or more fluoro. In one embodiment, $R^7$ is optionally substituted phenyl. In one embodiment, $R^7$ is optionally substituted pyridyl. In one embodiment, $R^7$ is optionally substituted pyridazinyl. In one embodiment, $R^7$ is optionally substituted pyrazinyl. In one embodiment, $R^7$ is optionally substituted pyrimidinyl. In one embodiment, $R^7$ is optionally substituted naphthyl. In one embodiment, $R^7$ is phenyl, optionally substituted with one to three substituents, independently selected from halo and ($C_1$-$C_3$)alkyl optionally substituted with one or more fluoro (e.g., F, Cl, Me, or $CF_3$). In one embodiment, $R^7$ is pyridyl, optionally substituted with one to three substituents, independently selected from halo and ($C_1$-$C_3$)alkyl optionally substituted with one or more fluoro (e.g., F, Cl, Me, or $CF_3$). In one embodiment, $R^7$ is naphthyl.

Specific examples include, but are not limited to:

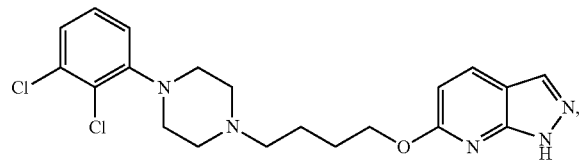

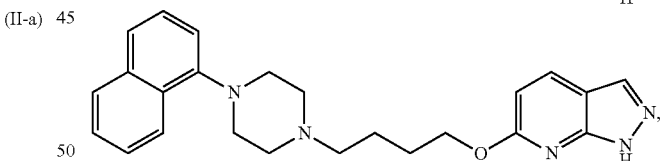

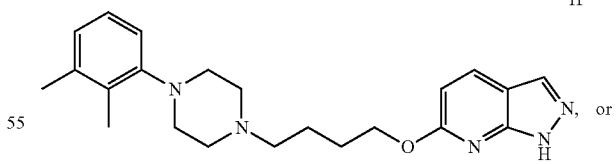, or

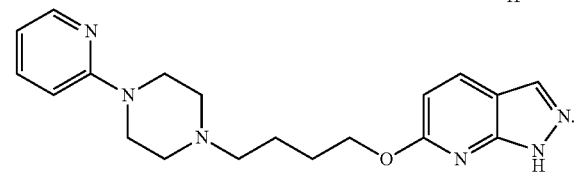

In one embodiment, provided herein is a compound of formula (III-b), or a pharmaceutically acceptable salt or stereoisomer thereof,

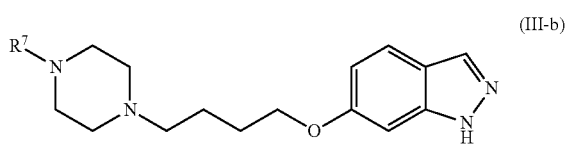

(III-b)

wherein R[7] is defined herein elsewhere. In one embodiment, R[7] is phenyl, pyridyl, pyrimidinyl, pyridazinyl, pyrazinyl, or naphthyl, each of which is optionally substituted with one to three substituents, independently selected from halo, cyano, alkylamino, dialkylamino, $(C_1-C_3)$alkyl optionally substituted with one or more fluoro, and $(C_1-C_3)$alkoxyl optionally substituted with one or more fluoro. In one embodiment, R[7] is optionally substituted phenyl. In one embodiment, R[7] is optionally substituted pyridyl. In one embodiment, R[7] is optionally substituted pyrimidinyl. In one embodiment, R[7] is optionally substituted pyridazinyl. In one embodiment, R[7] is optionally substituted pyrazinyl. In one embodiment, R[7] is optionally substituted naphthyl. In one embodiment, R[7] is phenyl, optionally substituted with one to three substituents, independently selected from halo, $(C_1-C_3)$alkyl optionally substituted with one or more fluoro, and $(C_1-C_3)$alkoxyl optionally substituted with one or more fluoro (e.g., F, Cl, Me, $CF_3$, OMe, $OCF_3$, or OEt). In one embodiment, R[7] is pyridyl, optionally substituted with one to three substituents, independently selected from halo, $(C_1-C_3)$alkyl optionally substituted with one or more fluoro, and $(C_1-C_3)$alkoxyl optionally substituted with one or more fluoro (e.g., F, Cl, Me, $CF_3$, OMe, or OEt). In one embodiment, R[7] is naphthyl.

Specific examples include, but are not limited to:

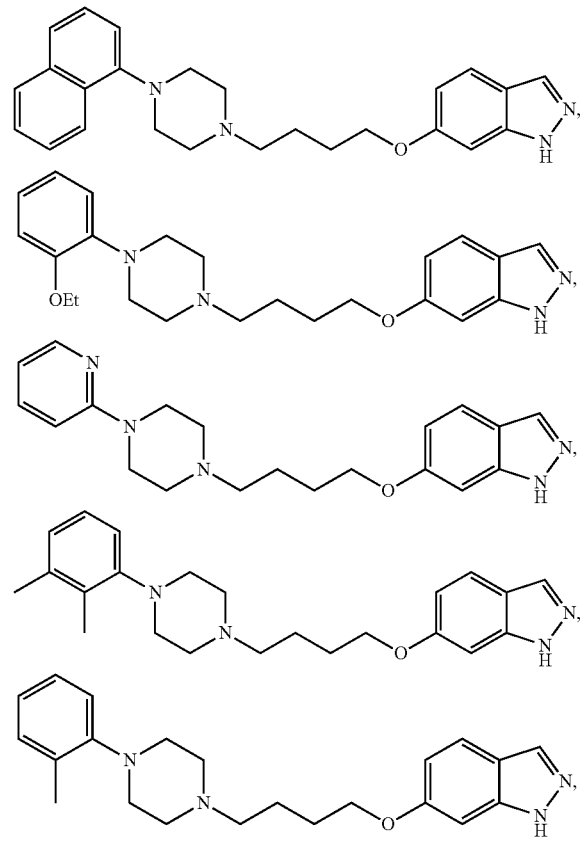

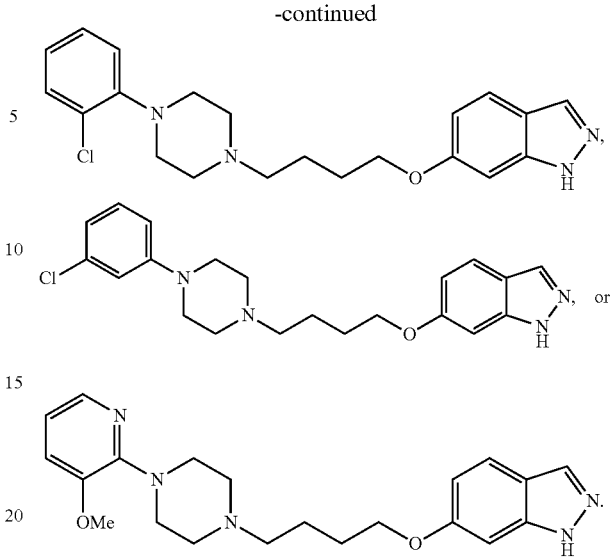

In one embodiment, provided herein is a compound of formula (III-c), or a pharmaceutically acceptable salt or stereoisomer thereof,

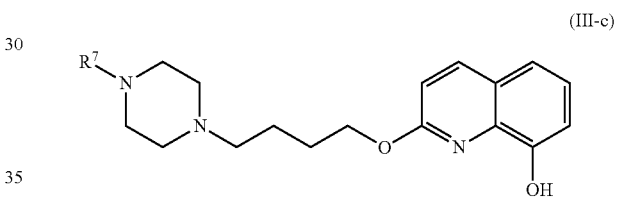

(III-c)

wherein R[7] is defined herein elsewhere. In one embodiment, R[7] is phenyl, pyridyl, pyrimidinyl, pyridazinyl, pyrazinyl, or naphthyl, each of which is optionally substituted with one to three substituents, independently selected from halo, cyano, alkylamino, dialkylamino, $(C_1-C_3)$alkyl optionally substituted with one or more fluoro, and $(C_1-C_3)$alkoxyl optionally substituted with one or more fluoro. In one embodiment, R[7] is optionally substituted phenyl. In one embodiment, R[7] is optionally substituted pyridyl. In one embodiment, R[7] is optionally substituted pyrimidinyl. In one embodiment, R[7] is optionally substituted pyridazinyl. In one embodiment, R[7] is optionally substituted pyrazinyl. In one embodiment, R[7] is optionally substituted naphthyl. In one embodiment, R[7] is phenyl, optionally substituted with one to three substituents, independently selected from halo, cyano, $(C_1-C_3)$alkyl optionally substituted with one or more fluoro, and $(C_1-C_3)$alkoxyl optionally substituted with one or more fluoro (e.g., F, Cl, CN, Me, Et, $CF_3$, OMe, OEt, OPr, or $OCF_3$). In one embodiment, R[7] is pyridyl, optionally substituted with one to three substituents, independently selected from halo, cyano, $(C_1-C_3)$alkyl optionally substituted with one or more fluoro, and $(C_1-C_3)$alkoxyl optionally substituted with one or more fluoro (e.g., F, Cl, CN, Me, Et, $CF_3$, OMe, OEt, OPr, or $OCF_3$). In one embodiment, R[7] is naphthyl.

Specific examples include, but are not limited to:

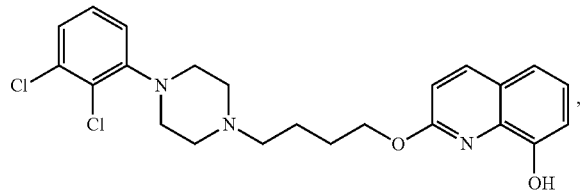
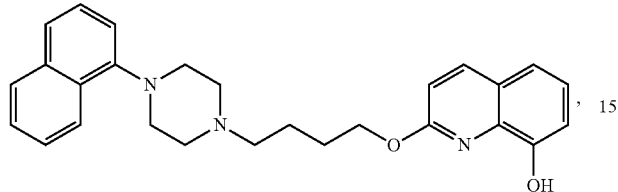
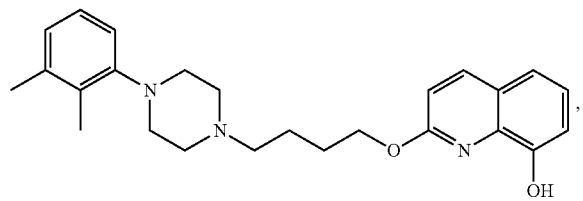
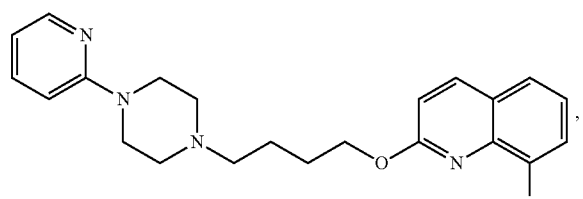
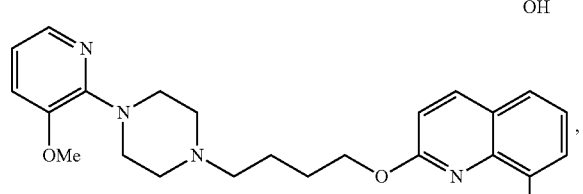
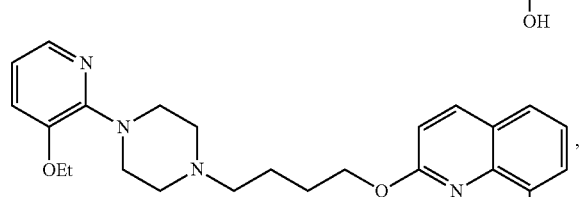
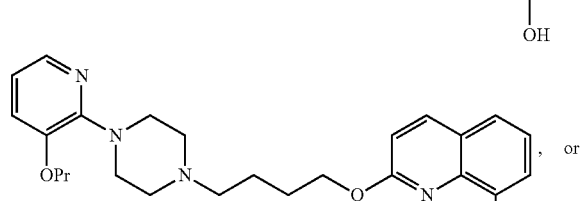
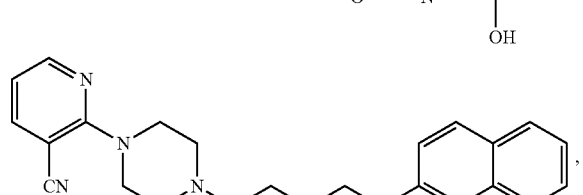

In one embodiment, provided herein is a compound of formula (III-d), or a pharmaceutically acceptable salt or stereoisomer thereof,

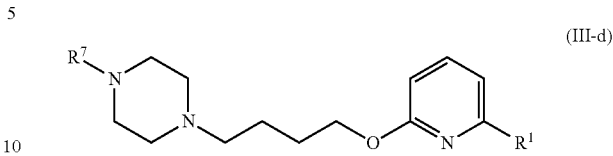

wherein $R^1$ and $R^7$ are defined herein elsewhere. In one embodiment, $R^1$ is

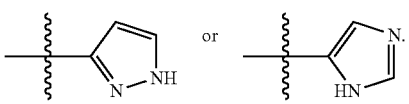 [SMILES: *c1cc[nH]n1 ; "or" ; *c1cnc[nH]1]

In one embodiment, $R^1$ is

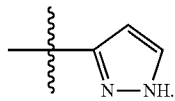 [SMILES: *c1cc[nH]n1]

In one embodiment, $R^1$ is

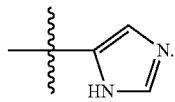 [SMILES: *c1cnc[nH]1]

In one embodiment, $R^7$ is phenyl, pyridyl, pyrimidinyl, pyridazinyl, pyrazinyl, or naphthyl, each of which is optionally substituted with one to three substituents, independently selected from halo, cyano, alkylamino, dialkylamino, ($C_1$-$C_3$)alkyl optionally substituted with one or more fluoro, and ($C_1$-$C_3$)alkoxyl optionally substituted with one or more fluoro. In one embodiment, $R^7$ is optionally substituted phenyl. In one embodiment, $R^7$ is optionally substituted pyridyl. In one embodiment, $R^7$ is optionally substituted pyrimidinyl. In one embodiment, $R^7$ is optionally substituted pyridazinyl. In one embodiment, $R^7$ is optionally substituted pyrazinyl. In one embodiment, $R^7$ is optionally substituted naphthyl. In one embodiment, $R^7$ is phenyl, optionally substituted with one to three substituents, independently selected from halo, cyano, ($C_1$-$C_3$)alkyl optionally substituted with one or more fluoro, and ($C_1$-$C_3$)alkoxyl optionally substituted with one or more fluoro (e.g., F, Cl, CN, Me, Et, $CF_3$, OMe, OEt, or $OCF_3$). In one embodiment, $R^7$ is pyridyl, optionally substituted with one to three substituents, independently selected from halo, cyano, ($C_1$-$C_3$)alkyl optionally substituted with one or more fluoro, and ($C_1$-$C_3$)alkoxyl optionally substituted with one or more fluoro (e.g., F, Cl, CN, Me, Et, $CF_3$, OMe, OEt, or $OCF_3$).

Specific examples include, but are not limited to:

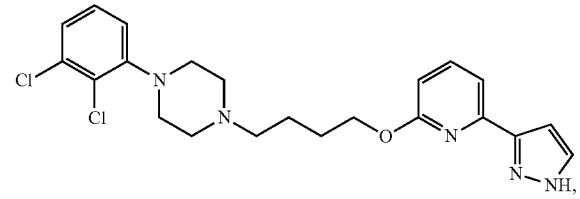

-continued

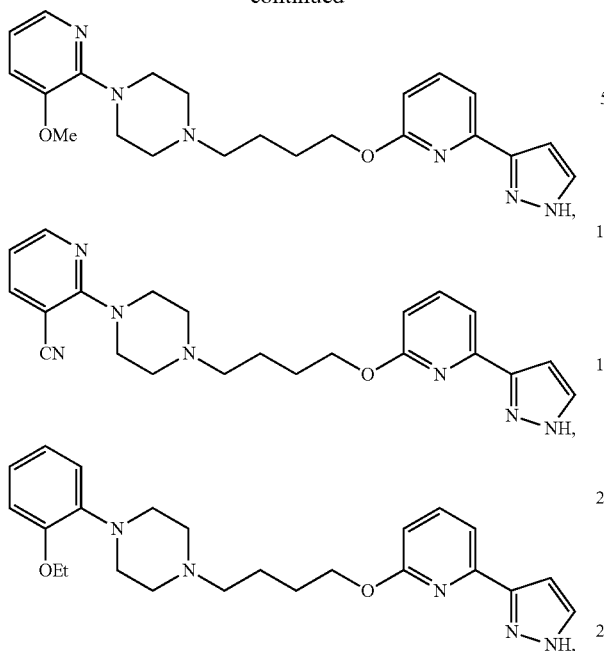

In one embodiment, provided herein is a compound of formula (IV-a), or a pharmaceutically acceptable salt or stereoisomer thereof,

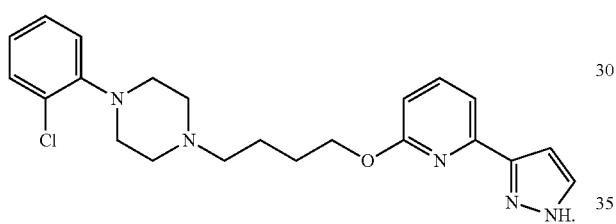

(IV-a)

wherein Ring Ar is defined herein elsewhere. In one embodiment, Ring Ar is a benzo or thieno ring, each of which is optionally substituted with one to three substituents, independently selected from halo, cyano, alkylamino, dialkylamino, $(C_1$-$C_3)$alkyl optionally substituted with one or more fluoro, and $(C_1$-$C_3)$alkoxyl optionally substituted with one or more fluoro. In one embodiment, Ring Ar is an optionally substituted benzo ring. In one embodiment, Ring Ar is an optionally substituted thieno ring. In one embodiment, Ring Ar is a benzo ring, optionally substituted with one to three substituents, independently selected from halo, cyano, $(C_1$-$C_3)$alkyl optionally substituted with one or more fluoro, and $(C_1$-$C_3)$alkoxyl optionally substituted with one or more fluoro (e.g., F, Cl, CN, Me, Et, $CF_3$, OMe, OEt, or $OCF_3$). In one embodiment, Ring Ar is a thieno ring.

Specific examples include, but are not limited to:

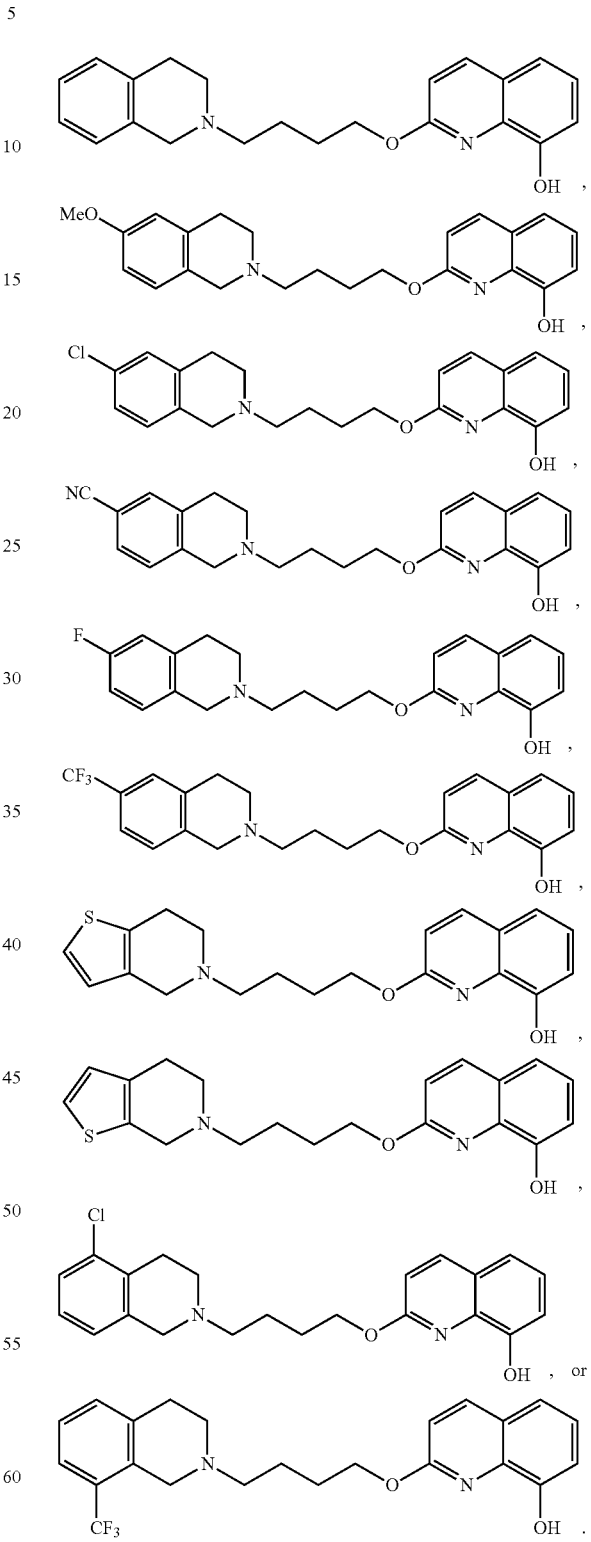

In one embodiment, provided herein is a compound of formula (IV-b), or a pharmaceutically acceptable salt or stereoisomer thereof, (IV-b)

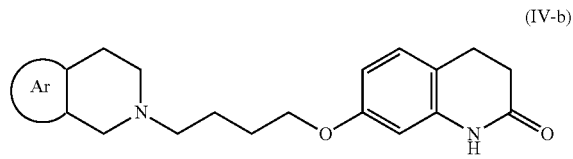

wherein Ring Ar is defined herein elsewhere. In one embodiment, Ring Ar is a pyrazolo, thieno, pyrimido, pyrazino, thiazolo, imidazolo, furano, or pyridazino ring, each of which is optionally substituted with one to three substituents, independently selected from halo, cyano, alkylamino, dialkylamino, $(C_1-C_3)$alkyl optionally substituted with one or more fluoro, $(C_1-C_3)$alkoxyl optionally substituted with one or more fluoro, optionally substituted phenyl, and optionally substituted pyridyl. In one embodiment, Ring Ar is an optionally substituted pyrazolo ring. In one embodiment, Ring Ar is a pyrazolo ring, optionally substituted with optionally substituted phenyl or optionally substituted pyridyl. In one embodiment, Ring Ar is an optionally substituted thieno ring. In one embodiment, Ring Ar is an optionally substituted pyrimido ring. In one embodiment, Ring Ar is an optionally substituted pyrazino ring. In one embodiment, Ring Ar is an optionally substituted thiazolo ring. In one embodiment, Ring Ar is an optionally substituted imidazolo ring. In one embodiment, Ring Ar is an optionally substituted furano ring. In one embodiment, Ring Ar is an optionally substituted pyridazino ring. In one embodiment, the optional substituents include, but are not limited to, halo, cyano, alkylamino, dialkylamino, $(C_1-C_3)$ alkyl optionally substituted with one or more fluoro, and $(C_1-C_3)$alkoxyl optionally substituted with one or more fluoro (e.g., Me, Et, NHMe, or NMe$_2$). In other embodiments, the optional substituents include, but are not limited to, optionally substituted phenyl, and optionally substituted pyridyl (e.g., phenyl, chlorophenyl, fluorophenyl, methoxyphenyl, or pyridyl).

Specific examples include, but are not limited to:

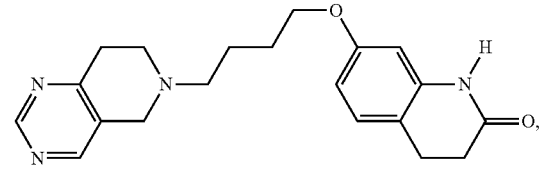

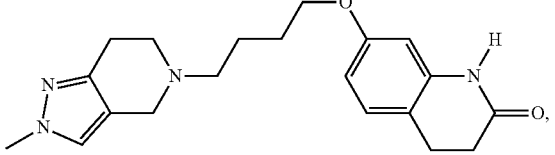

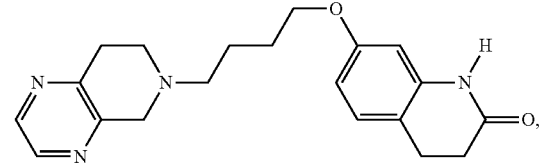

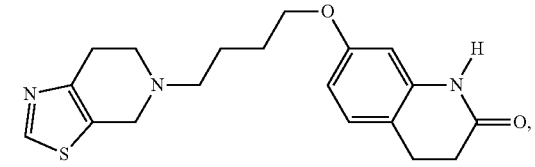

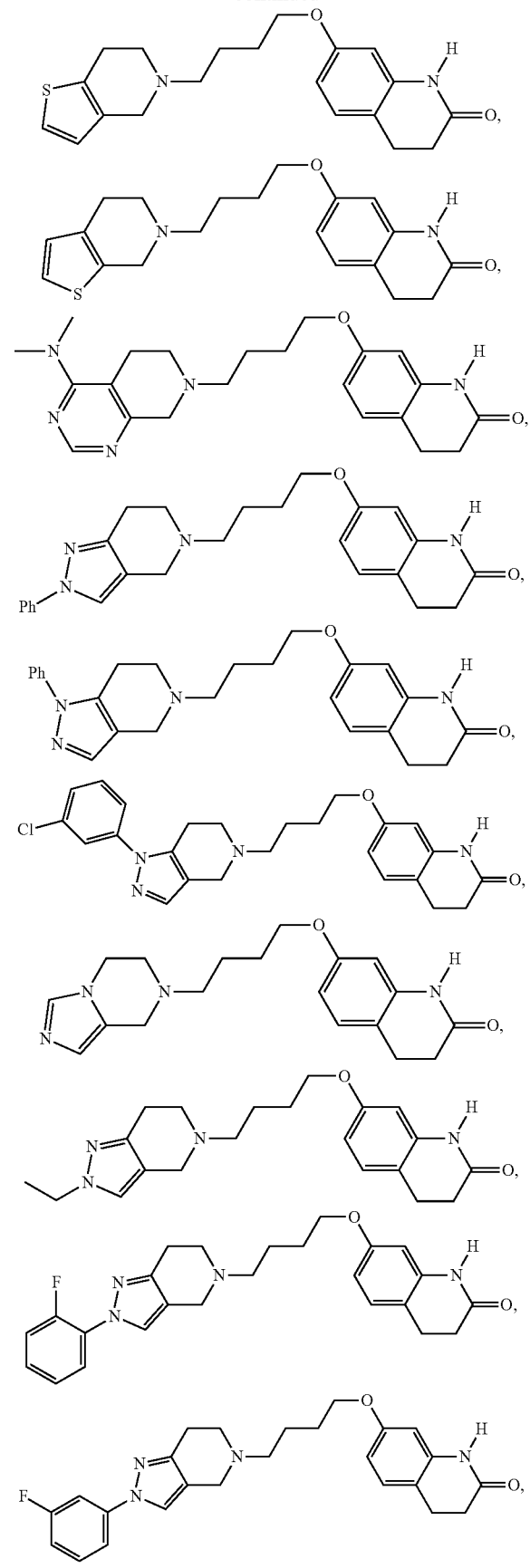

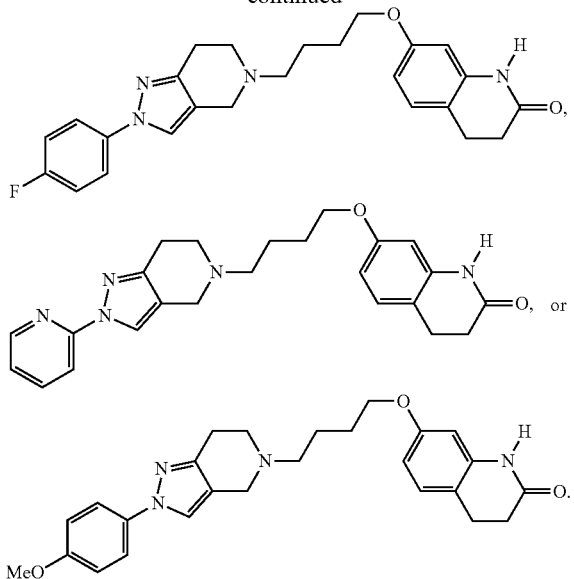

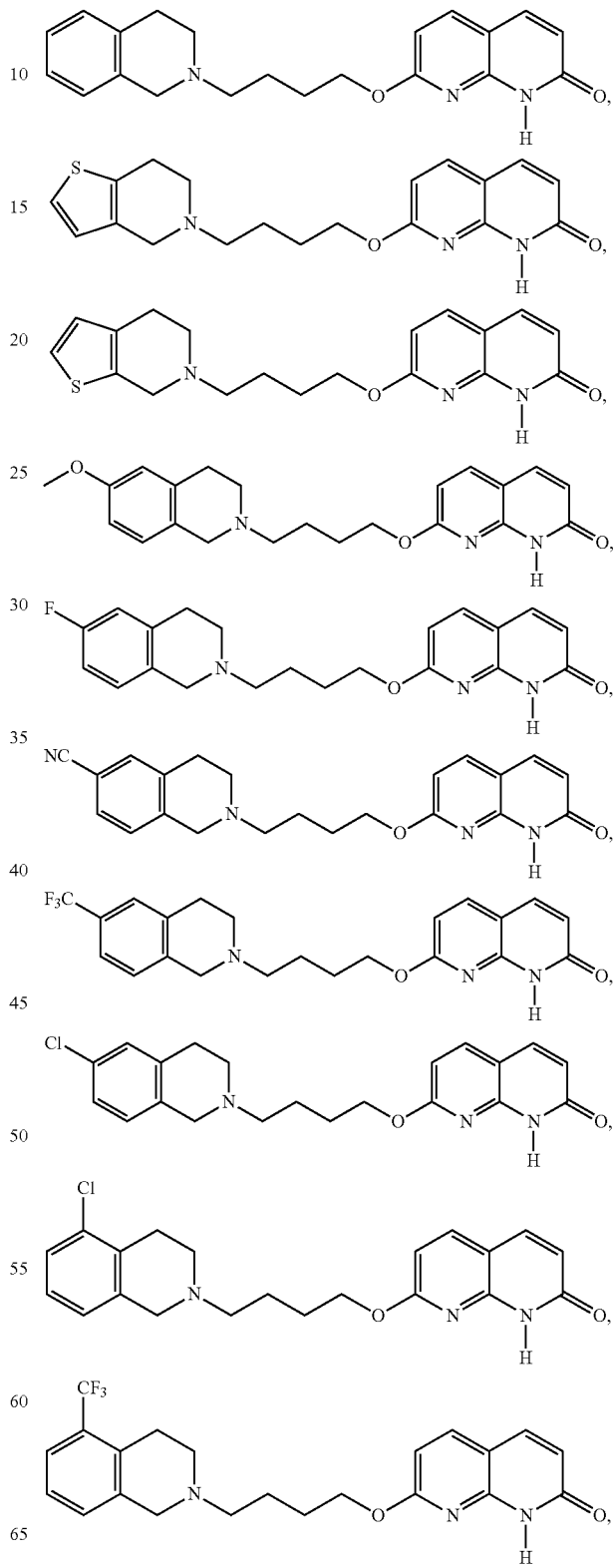

In one embodiment, provided herein is a compound of formula (IV-c), or a pharmaceutically acceptable salt or stereoisomer thereof, (IV-c)

wherein Ring Ar is defined herein elsewhere. In one embodiment, Ring Ar is a benzo, pyrazolo, thieno, pyrimido, pyrazino, thiazolo, imidazolo, furano, or pyridazino ring, each of which is optionally substituted with one to three substituents, independently selected from halo, cyano, alkylamino, dialkylamino, $(C_1$-$C_3)$alkyl optionally substituted with one or more fluoro, $(C_1$-$C_3)$alkoxyl optionally substituted with one or more fluoro, optionally substituted phenyl, and optionally substituted pyridyl. In one embodiment, Ring Ar is an optionally substituted benzo ring. In one embodiment, Ring Ar is an optionally substituted pyrazolo ring. In one embodiment, Ring Ar is a pyrazolo ring, optionally substituted with optionally substituted phenyl or optionally substituted pyridyl. In one embodiment, Ring Ar is an optionally substituted thieno ring. In one embodiment, Ring Ar is an optionally substituted pyrimido ring. In one embodiment, Ring Ar is an optionally substituted pyrazino ring. In one embodiment, Ring Ar is an optionally substituted thiazolo ring. In one embodiment, Ring Ar is an optionally substituted imidazolo ring. In one embodiment, Ring Ar is an optionally substituted furano ring. In one embodiment, Ring Ar is an optionally substituted pyridazino ring. In one embodiment, the optional substituents include, but are not limited to, halo, cyano, alkylamino, dialkylamino, $(C_1$-$C_3)$ alkyl optionally substituted with one or more fluoro, and $(C_1$-$C_3)$alkoxyl optionally substituted with one or more fluoro (e.g., F, Cl, CN, Me, $CF_3$, OMe, or $OCF_3$). In other embodiments, the optional substituents include, but are not limited to, optionally substituted phenyl, and optionally substituted pyridyl (e.g., phenyl or pyridyl).

Specific examples include, but are not limited to:

-continued

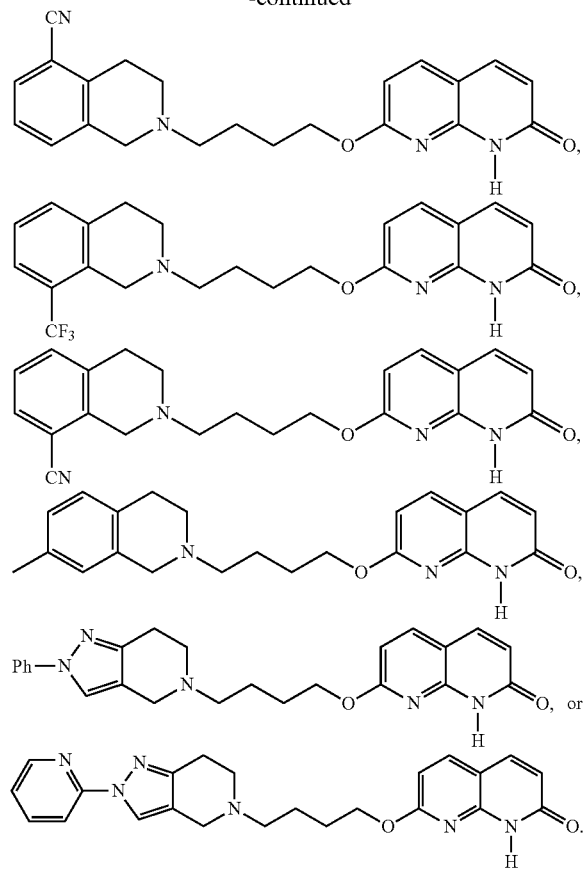

In one embodiment, provided herein is a compound of formula (IV-d), or a pharmaceutically acceptable salt or stereoisomer thereof, (IV-d)

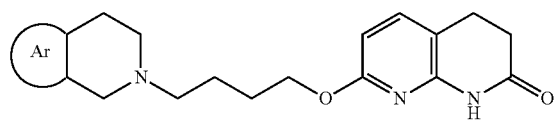

wherein Ring Ar is defined herein elsewhere. In one embodiment, Ring Ar is a benzo, pyrazolo, thieno, pyrimido, pyrazino, thiazolo, imidazolo, furano, or pyridazino ring, each of which is optionally substituted with one to three substituents, independently selected from halo, cyano, alkylamino, dialkylamino, ($C_1$-$C_3$)alkyl optionally substituted with one or more fluoro, ($C_1$-$C_3$)alkoxyl optionally substituted with one or more fluoro, optionally substituted phenyl, and optionally substituted pyridyl. In one embodiment, Ring Ar is an optionally substituted benzo ring. In one embodiment, Ring Ar is an optionally substituted pyrazolo ring. In one embodiment, Ring Ar is a pyrazolo ring, optionally substituted with optionally substituted phenyl or optionally substituted pyridyl. In one embodiment, Ring Ar is an optionally substituted thieno ring. In one embodiment, Ring Ar is an optionally substituted pyrimido ring. In one embodiment, Ring Ar is an optionally substituted pyrazino ring. In one embodiment, Ring Ar is an optionally substituted thiazolo ring. In one embodiment, Ring Ar is an optionally substituted imidazolo ring. In one embodiment, Ring Ar is an optionally substituted furano ring. In one embodiment, Ring Ar is an optionally substituted pyridazino ring. In one embodiment, the optional substituents include, but are not limited to, halo, cyano, alkylamino, dialkylamino, ($C_1$-$C_3$) alkyl optionally substituted with one or more fluoro, and ($C_1$-$C_3$)alkoxyl optionally substituted with one or more fluoro (e.g., F, Cl, CN, Me, $CF_3$, OMe, or $OCF_3$). In other embodiments, the optional substituents include, but are not limited to, optionally substituted phenyl, and optionally substituted pyridyl (e.g., phenyl or pyridyl).

Specific examples include, but are not limited to:

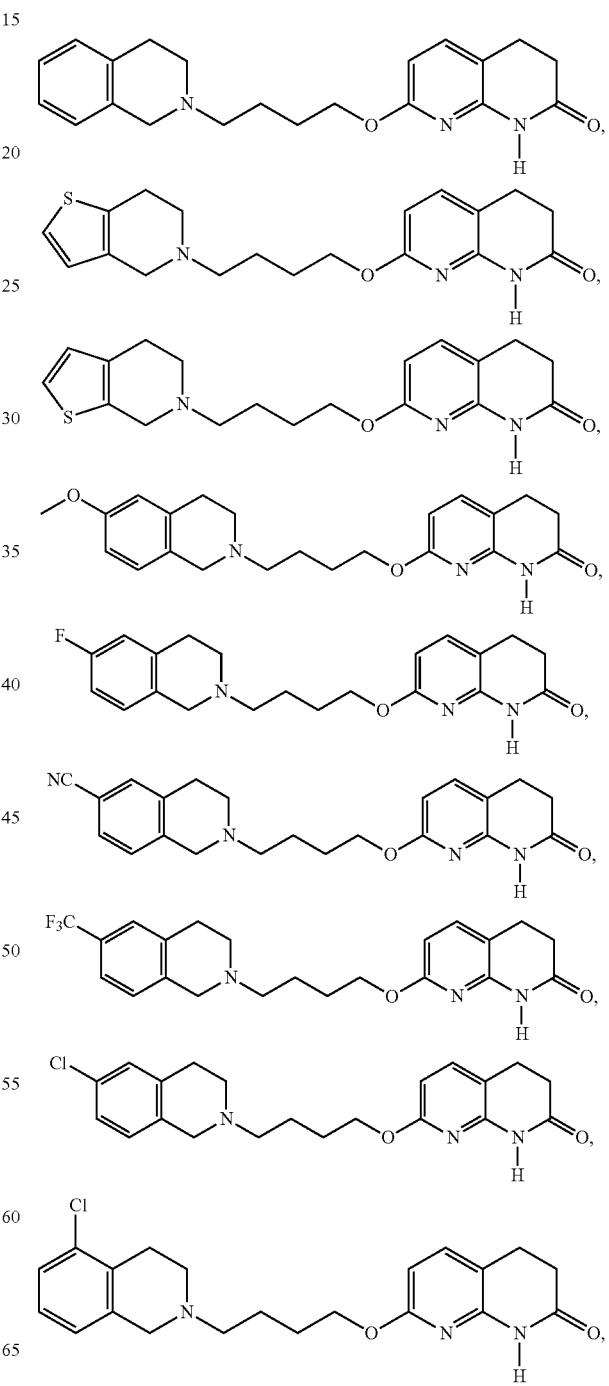

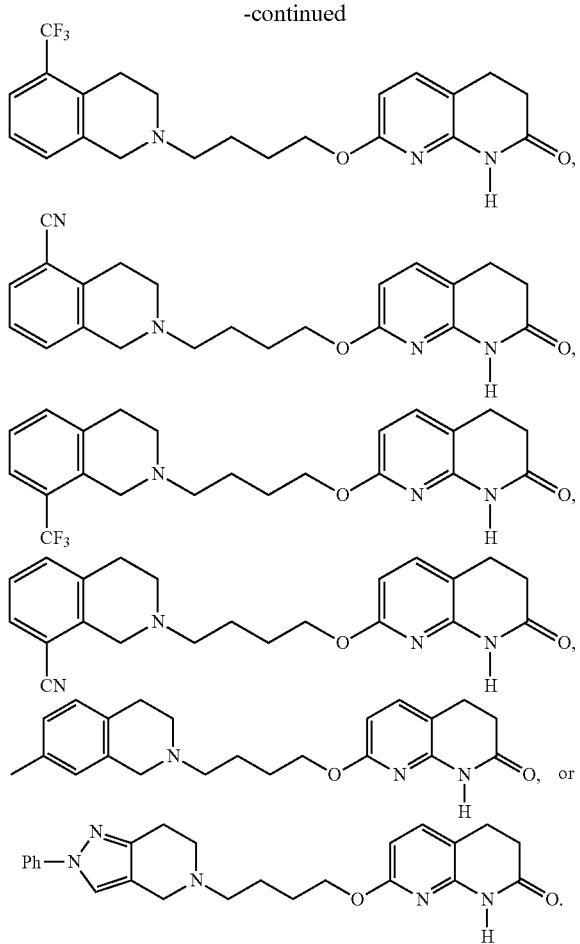

In one embodiment, provided herein is a compound of formula (IV-e), or a pharmaceutically acceptable salt or stereoisomer thereof,

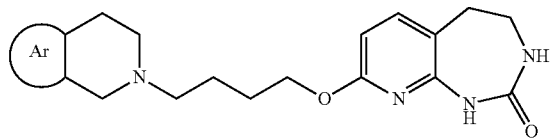

(IV-e)

wherein Ring Ar is defined herein elsewhere. In one embodiment, Ring Ar is a benzo, pyrazolo, thieno, pyrimido, pyrazino, thiazolo, imidazolo, furano, or pyridazino ring, each of which is optionally substituted with one to three substituents, independently selected from halo, cyano, alkylamino, dialkylamino, $(C_1-C_3)$alkyl optionally substituted with one or more fluoro, $(C_1-C_3)$alkoxyl optionally substituted with one or more fluoro, optionally substituted phenyl, and optionally substituted pyridyl. In one embodiment, Ring Ar is an optionally substituted benzo ring. In one embodiment, Ring Ar is an optionally substituted pyrazolo ring. In one embodiment, Ring Ar is a pyrazolo ring, optionally substituted with optionally substituted phenyl or optionally substituted pyridyl. In one embodiment, Ring Ar is an optionally substituted thieno ring. In one embodiment, Ring Ar is an optionally substituted pyrimido ring. In one embodiment, Ring Ar is an optionally substituted pyrazino ring. In one embodiment, Ring Ar is an optionally substituted thiazolo ring. In one embodiment, Ring Ar is an optionally substituted imidazolo ring. In one embodiment, Ring Ar is an optionally substituted furano ring. In one embodiment, Ring Ar is an optionally substituted pyridazino ring. In one embodiment, the optional substituents include, but are not limited to, halo, cyano, alkylamino, dialkylamino, $(C_1-C_3)$alkyl optionally substituted with one or more fluoro, and $(C_1-C_3)$alkoxyl optionally substituted with one or more fluoro (e.g., F or Cl). In other embodiments, the optional substituents include, but are not limited to, optionally substituted phenyl, and optionally substituted pyridyl (e.g., phenyl or pyridyl).

Specific examples include, but are not limited to:

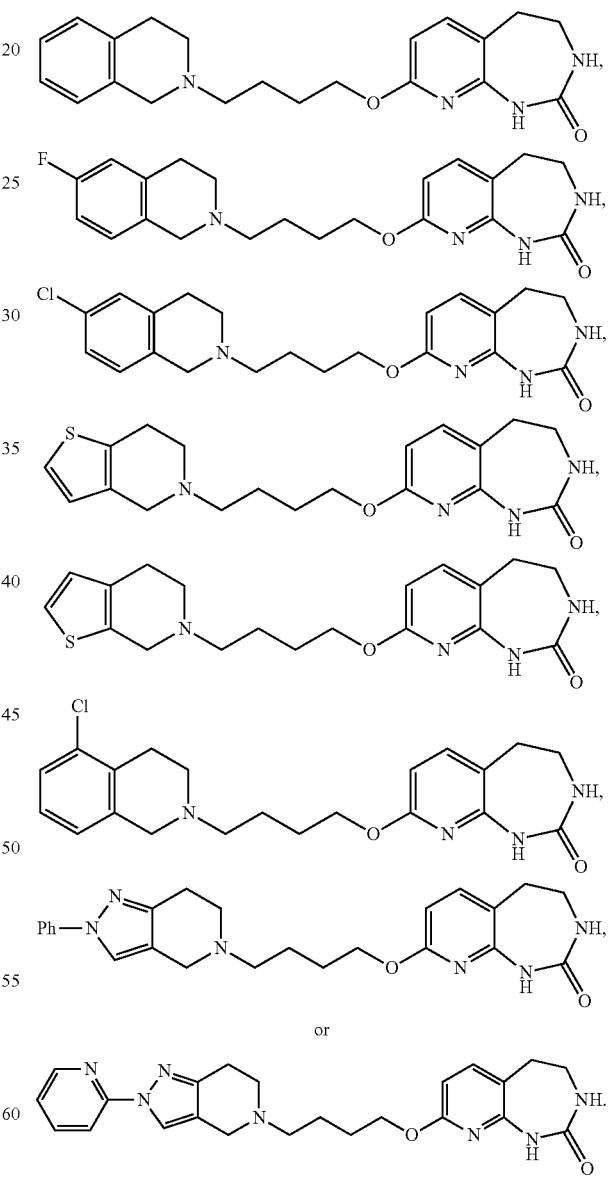

In one embodiment, provided herein is a compound of formula (N-f), or a pharmaceutically acceptable salt or stereoisomer thereof,

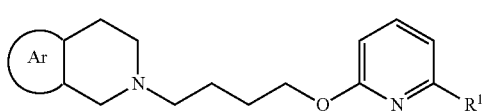

wherein Ring Ar and $R^1$ are defined herein elsewhere. In one embodiment, $R^1$ is —NHCO($C_1$-$C_3$)alkyl, —NHS(O)$_2$($C_1$-$C_3$)alkyl,

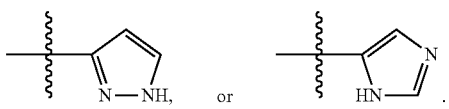 [SMILES: *c1cc[nH]n1 ; *c1cnc[nH]1 ; "or"]

In one embodiment, $R^1$ is —NHCO($C_1$-$C_3$)alkyl (e.g., —NHCOMe or —NHCOEt). In one embodiment, $R^1$ is —NHS(O)$_2$($C_1$-$C_3$)alkyl (e.g., —NHS(O)$_2$Me or —NHS(O)$_2$Et). In one embodiment, $R^1$ is

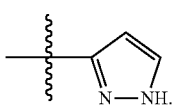

In one embodiment, $R^1$ is

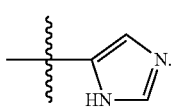

In one embodiment, Ring Ar is a benzo ring, optionally substituted with one to three substituents, independently selected from halo, cyano, alkylamino, dialkylamino, ($C_1$-$C_3$)alkyl optionally substituted with one or more fluoro, and ($C_1$-$C_3$)alkoxyl optionally substituted with one or more fluoro (e.g., F or Cl).

Specific examples include, but are not limited to:

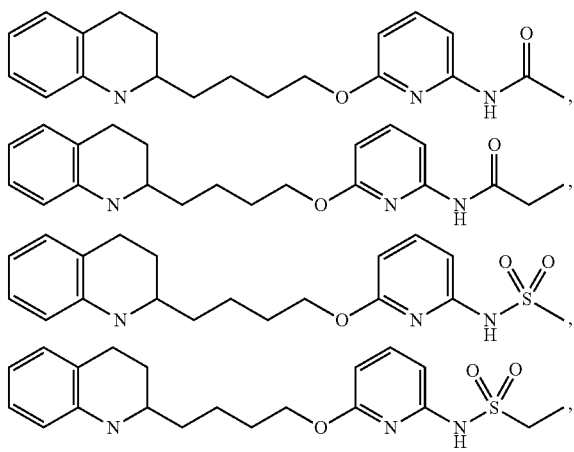

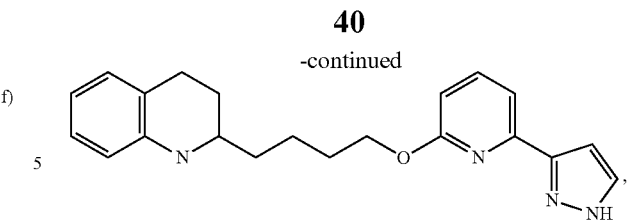

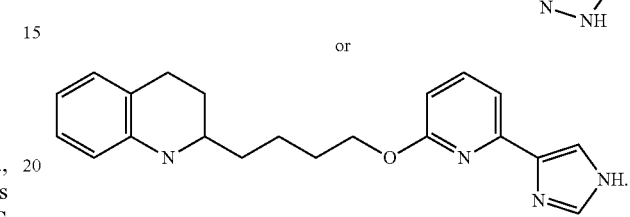

In one embodiment, provided herein is a compound, having the following structure:

Any of the combinations of $R^1$, $R^2$, $R^3$, $R^4$, $R^5$, $R^6$, $R^7$, $R^8$, $R^{10}$, $R^{11}$, X, Y, Q, W, Ring Ar, and n are encompassed by this disclosure and specifically provided herein.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one geometric (i.e., cis/trans) isomer or a mixture of geometric (i.e., cis/trans) isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism.

Unless otherwise specified, the term "compound" referred to herein, such as, e.g., a compound of formula (I), (II-A), (II-B), (III-a), (III-b), (III-c), (III-d), (IV-a), (IV-b), (IV-c), (IV-d), (IV-e), or (IV-f) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof. In one embodiment, the term "compound" referred to herein, such as, e.g., a compound of formula (I), (II-A), (II-B), (III-a), (III-b), (III-c), (III-d), (IV-a), (IV-b), (IV-c), (IV-d), (IV-e), or (IV-f) is intended to encompass a solvate (e.g., a hydrate) thereof.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. Synthetic Schemes

Schemes below provide exemplary synthetic methods for the preparation of the compounds provided herein. Similar methods may be employed to prepare the compounds provided herein. Suitable adjustments to reagents, protecting groups, reaction conditions, and reaction sequences may be employed to prepare a desired embodiment. The reactions may be scaled upwards or downwards to suit the amount of material to be prepared.

In one embodiment, the compounds provided herein may be prepared following Schemes I and II, using suitable starting materials known in the art and/or available from a commercial source. In one embodiment, the starting materials of Schemes I and II may be prepared from commercially available compounds using procedures and conditions known in the art. Exemplary procedures and conditions are provided herein elsewhere. Specific schemes for preparing compounds provided herein are shown below. Detailed reaction conditions are provided for various specific examples herein below. The following schemes may be modified with appropriate reagents, protecting groups, conditions, starting materials, or reaction sequences to suit the preparation of other embodiments provided herein.

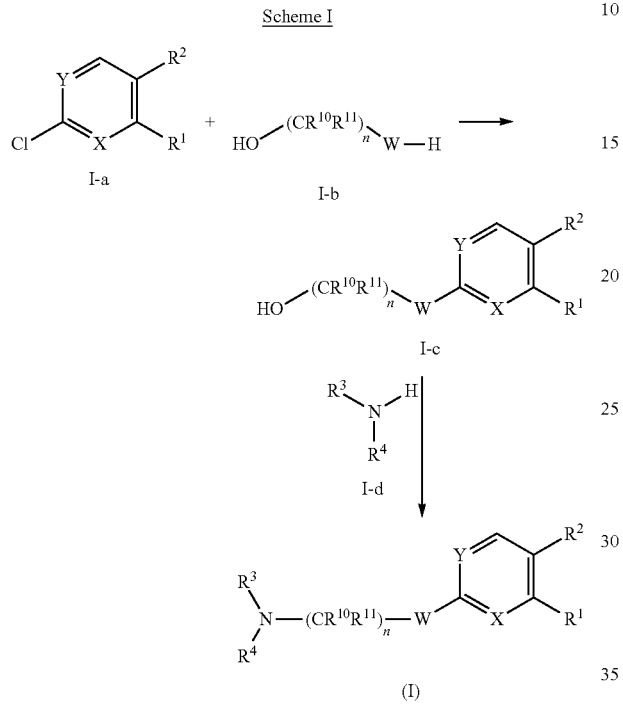

In one embodiment, a compound of formula (I) may be prepared following Scheme I. Compound (I-a) may be purchased from a commercial source, prepared following literature procedures, or prepared as described herein. Compound (I-a) is treated with (I-b), an amino-alcohol (when $W=NR^5$) or a diol (when $W=O$), in the presence or absence of a base, to yield (I-c). Compounds (I-c) is treated with tosyl chloride, followed by reaction with an amine (I-d) to render a compound of formula (I). Alternatively, compound (I-c) may be converted to, for example, an aldehyde, by oxidation (e.g., Swern oxidation), followed by reductive amination with (I-d) to afford a compound of formula (I). Compound (I-d) may be purchased from a commercial source or prepared following literature procedures. Optionally, further organic transformations may convert R, $R^1$, $R^2$, $R^3$, $R^4$ and/or $R^5$ to other suitable embodiments of R, $R^1$, $R^2$, $R^3$, $R^4$ and/or $R^5$ to provide additional embodiments of a compound of formula (I).

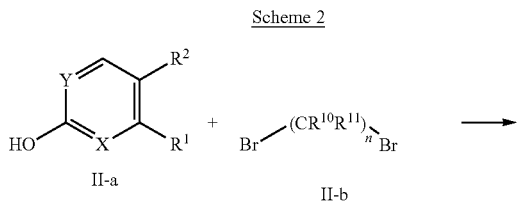

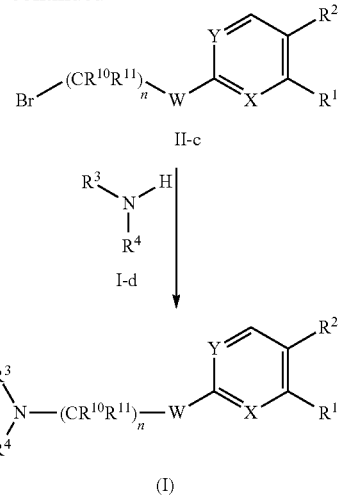

In one embodiment, a compound of formula (I) may also be prepared following Scheme II. Compound (II-a) may be purchased from a commercial source, prepared following literature procedures, or prepared as prescribed herein. Compound (II-a) is treated with an alkylating reagent (II-b) in the presence of a base, such as cesium carbonate, to generate (II-c), which is reacted with an amine (I-d) in the presence of a base, such as potassium carbonate, to render a compound of formula (I). Optionally, further organic transformations may convert R, $R^1$, $R^2$, $R^3$, $R^4$ and/or $R^5$ to other suitable embodiments of R, $R^1$, $R^2$, $R^3$, $R^4$ and/or $R^5$ to provide additional embodiments of a compound of formula (I).

In certain embodiments, the compounds provided herein are prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion. In certain embodiments, the compounds provided herein are prepared following one or more stereoselective reaction(s). In some embodiments, the compounds provided herein are prepared as a substantially pure stereoisomer.

D. Methods of Use

1. Modulation of Receptor Activity

In one embodiment, provided herein is a method of binding a compound provided herein to a dopamine receptor, such as, a D2 receptor. The method comprises contacting the dopamine receptor with a compound provided herein. In one embodiment, the binding to dopamine receptor is assessed using an in vitro binding assay, such as those known in the art.

In one embodiment, provided herein is a method of modulating (e.g., inhibiting or augmenting) the activity of a dopamine receptor, such as, a D2 receptor. In one embodiment, provided herein is a method of reducing the activity of a dopamine receptor, such as, a D2 receptor (e.g., partially or fully antagonizing). In one embodiment, provided herein is a method of increasing the activity of a dopamine receptor, such as, a D2 receptor (e.g., partially or fully agonizing). In one embodiment, the method comprises contacting a dopamine receptor, such as, a D2 receptor, with a compound provided herein, in vitro or in vivo. In one embodiment, the dopamine receptor, such as, a D2 receptor, is contacted by a compound provided herein by administering to a subject a therapeutically effective amount of the compound provided herein, or a pharmaceutically acceptable salt or stereoisomer thereof. The subject may be a human. In one embodiment, the dopamine receptor is D2 receptor.

In other embodiments, the compound provided herein reduces the activity of a dopamine receptor, such as, a D2 receptor. Reduction of receptor activity may be measured using assays known in the art. In some embodiments, the activity of the receptor is reduced by about 1%, about 5%, about 10%, about 20%, about 30%, about 40%, about 50%, about 60%, about 70%, about 80%, about 90%, about 95%, about 99% or more than about 99%, as compared with activity without contacting the receptor with a compound provided herein (e.g., vehicle condition). In one embodiment, the reduction of receptor activity is dose dependent. In other embodiments, the compound provided herein increases the activity of a dopamine receptor, such as, a D2 receptor. Increase of receptor activity may be measured using assays known in the art. In some embodiments, the activity of the receptor is increased by about 1%, about 5%, about 10%, about 20%, about 30%, about 40%, about 50%, about 60%, about 70%, about 80%, about 90%, about 95%, about 99% or more than about 99%, as compared with activity without contacting the receptor with a compound provided herein (e.g., vehicle condition). In one embodiment, the increase of receptor activity is dose dependent. Exemplary assay methods include, but are not limited to, in vitro binding assays and in vitro functional assays. In one embodiment, the functional assay utilizes an appropriate cell-line expressing a desired dopamine receptor, such as, a D2 receptor. In one embodiment, the functional assay utilizes a receptor purified following expression using an appropriate recombinant system. In one embodiment, inhibition of receptor activity may be assessed using a cAMP assay, for example, a fluorescent assay, utilizing a Fluorescein-labeled cAMP/cGMP substrate or a Homogeneous-Time-Resolved-Fluorescence (HTRF)-based assay. In one embodiment, the functional assay utilizes synaptosomes isolated from brain tissue of an appropriate organism. In one embodiment, the functional assay utilizes primary neuronal cultures prepared from brain tissue of an appropriate organism. In one embodiment, the assay is carried out in vivo and involves treatment of a test subject (e.g., a rodent) with a compound provided herein. In one embodiment, a test subject is treated with a reference compound or vehicle, as positive or negative controls. In one embodiment, the assay is followed by isolation of brain tissue and ex vivo analysis of substrate concentration (e.g., cAMP or cGMP) in the brain tissue. In one embodiment, the assay is followed by isolation of brain microdialysates and ex vivo analysis of substrate concentration (e.g., cAMP or cGMP) in the microdialysates.

In certain embodiments, provided herein are methods of reducing the activity of a dopamine receptor, such as, a D2 receptor, in a subject (e.g., human) comprising administering to the subject an effective amount of a compound provided herein. In some embodiments, the activity of the receptor is reduced by about 1%, about 5%, about 10%, about 20%, about 30%, about 40%, about 50%, about 60%, about 70%, about 80%, about 90%, about 95%, about 99%, or more than about 99%, when measured using an assay described herein elsewhere.

In certain embodiments, provided herein are methods of increasing the activity of a dopamine receptor, such as, a D2 receptor, in a subject (e.g., human) comprising administering to the subject an effective amount of a compound provided herein. In some embodiments, the activity of the receptor is increased by about 1%, about 5%, about 10%, about 20%, about 30%, about 40%, about 50%, about 60%, about 70%, about 80%, about 90%, about 95%, about 99%, or more than about 99%, when measured using an assay described herein elsewhere.

In one embodiment, without being limited to any particular theory, activation of a D2 receptor affects the activity of one or two or more pathways, for example, the cAMP pathway and/or the β-arrestin pathway. For instance, agonizing the D2 receptor results in a decrease in cAMP production and also an increase in the recruitment and activation of β-arrestin. Antagonizing the D2 receptor blocks the ability of an agonist, for example, dopamine, to decrease cAMP production and to increase β-arrestin recruitment. In one embodiment, certain compounds demonstrate only partial activity and are termed partial agonists. Partial agonists can block the effects of an agonist, with a net activity equivalent to the partial agonist's efficacy (for example, a partial agonist with a 60% maximal effect, will inhibit the response to a full agonist by 40%). Modulation of dopamine D2 signaling has therapeutic values. Without being limited to any particular theory, stimulating dopamine receptors often has therapeutic use in movement disorders, such as Parkinson's disease, whereas, anti-psychotic drugs typically are antagonists of the D2 receptor. Without being limited to any particular theory, antagonizing the D2 β-arrestin interaction is beneficial for anti-psychotic activity of drugs, such as olanzapine, risperidone, and the like. Without being limited to any particular theory, full agonists or high efficacy (e.g., greater than about 75%) agonists are more suitable as anti-Parkinson's medications. For example, pramipexole and ropinirole are used clinically and demonstrate an $E_{max}$ of at least about 90% in the assays provided herein. Aripiprazole (i.e., 7-{4-[4-(2,3-dichlorophenyl)piperazin-1-yl]butoxy}-3,4-dihydroquinolin-2(1H)-one), a partial D2 agonist, is clinically efficacious in schizophrenia. The efficacy of partial agonists is dependent on assay conditions, such as receptor expression levels and host cell-line, necessitating the use of caution when comparing data from different sources. In the assays provided herein, aripiprazole has $E_{max}$ and $I_{max}$ values of approximately about 40% and about 50% in the cAMP or β-arrestin agonist and antagonist assays, respectively, suggesting that a compound provided herein typically can have at least about 40% activity in the present agonist and antagonist assays to be effective treatments for schizophrenia and/or psychosis.

In one embodiment, a compound provided herein has an $E_{max}$ value of between about 50% and about 75% in a cAMP agonist assay. In one embodiment, a compound provided herein has an $E_{max}$ value of between about 40% and about 75% in a cAMP agonist assay. In one embodiment, a compound provided herein has an $E_{max}$ value of between about 25% and about 75% in a cAMP agonist assay. In one embodiment, a compound provided herein has an $E_{max}$ value of between about 10% and about 75% in a cAMP agonist assay. In one embodiment, a compound provided herein has an $E_{max}$ value of greater than about 75% in a cAMP agonist assay. In one embodiment, a compound provided herein has an $E_{max}$ value of greater than about 90% in a cAMP agonist assay. In one embodiment, a compound provided herein has an $E_{max}$ value of less than about 10% in a cAMP agonist assay.

In one embodiment, a compound provided herein has an $E_{max}$ value of between about 50% and about 75% in a β-arrestin agonist assay. In one embodiment, a compound provided herein has an $E_{max}$ value of between about 40% and about 75% in a β-arrestin agonist assay. In one embodiment, a compound provided herein has an $E_{max}$ value of between about 25% and about 75% in a β-arrestin agonist assay. In one embodiment, a compound provided herein has an $E_{max}$ value of between about 10% and about 75% in a β-arrestin agonist assay. In one embodiment, a compound provided herein has an $E_{max}$ value of greater than about 75% in a β-arrestin agonist assay. In one embodiment, a compound provided herein has an $E_{max}$ value of greater than about 90% in a β-arrestin agonist assay. In one embodiment, a compound provided herein has an $E_{max}$ value of less than about 10% in a β-arrestin agonist assay.

In one embodiment, a compound provided herein has an $I_{max}$ value of between about 50% and about 75% in a cAMP antagonist assay. In one embodiment, a compound provided herein has an $I_{max}$ value of between about 40% and about 75% in a cAMP antagonist assay. In one embodiment, a compound provided herein has an $I_{max}$ value of between about 25% and about 75% in a cAMP antagonist assay. In one embodiment, a compound provided herein has an $I_{max}$ value of between about 10% and about 75% in a cAMP antagonist assay. In one embodiment, a compound provided herein has an $I_{max}$ value of greater than about 75% in a cAMP antagonist assay. In one embodiment, a compound provided herein has an $I_{max}$ value of greater than about 90% in a cAMP antagonist assay. In one embodiment, a compound provided herein has an $I_{max}$ value of less than about 10% in a cAMP antagonist assay.

In one embodiment, a compound provided herein has an $I_{max}$ value of between about 50% and about 75% in a β-arrestin antagonist assay. In one embodiment, a compound provided herein has an $I_{max}$ value of between about 40% and about 75% in a β-arrestin antagonist assay. In one embodiment, a compound provided herein has an $I_{max}$ value of between about 25% and about 75% in a β-arrestin antagonist assay. In one embodiment, a compound provided herein has an $I_{max}$ value of between about 10% and about 75% in a β-arrestin antagonist assay. In one embodiment, a compound provided herein has an $I_{max}$ value of greater than about 75% in a β-arrestin antagonist assay. In one embodiment, a compound provided herein has an $I_{max}$ value of greater than about 90% in a β-arrestin antagonist assay. In one embodiment, a compound provided herein has an $I_{max}$ value of less than about 10% in a β-arrestin antagonist assay.

Modulation of receptor activity can be shown, for example, by performing various in vitro functional assays utilizing a cell type which expresses a certain type of receptor, such as a dopamine receptor, e.g., D2 receptor. In some embodiments, the compounds provided herein modulate the receptor activity in a dose-dependent manner, with an $EC_{50}$ or $IC_{50}$ of, for example, between about 0.1 nM and about 10 µM, between about 1 nM and about 1 µM, between about 1 nM and about 500 nM, and between about 1 nM and about 100 nM, in a functional assay, such as those described herein. In one embodiment, the $EC_{50}$ or $IC_{50}$ is less than about 0.01 nM, less than about 0.1 nM, less than about 1 nM, less than about 3 nM, less than about 10 nM, less than about 30 nM, less than about 100 nM, less than about 300 nM, less than about 1000 nM, less than about 3000 nM, or less than about 10000 nM. In one embodiment, the $EC_{50}$ or $IC_{50}$ is about 0.01 nM, about 0.1 nM, about 1 nM, about 3 nM, about 10 nM, about 30 nM, about 100 nM, about 300 nM, about 1000 nM, about 3000 nM, or about 10000 nM.

2. Treatment, Prevention, and/or Management of Disorders

In one embodiment, provided herein is a method for the treatment, prevention, and/or management of various disorders, including a CNS disorder or a neurological disorder, comprising administering a compound provided herein, or a pharmaceutically acceptable salt or stereoisomer thereof, or a composition provided herein. In one embodiment, provided herein is a method for the treatment, prevention, and/or amelioration of one or more symptoms of a disorder (e.g., a CNS disorder or a neurological disorder), comprising administering a compound provided herein, or a pharmaceutically acceptable salt or stereoisomer thereof, or a composition provided herein. In one embodiment, provided herein is a method of treating, preventing, and/or managing a CNS disorder or a neurological disorder, comprising administering to a subject a therapeutically or prophylactically effective amount of a compound provided herein, or a pharmaceutically acceptable salt or stereoisomer thereof. In one embodiment, a method provided herein further comprises administering to a subject a second active agent.

In one embodiment, the disorders being treated, prevented and/or managed using a method provided herein include, but are not limited to, Parkinson's disease, movement disorder, ataxia, dystonia, essential tremor, Huntington's disease, multiple system atrophy, myoclonus, progressive supranuclear palsy, rett syndrome, secondary parkinsonism, spasticity, tardive dyskinesia, Wilson's disease, dyskinesia, or restless leg syndrome. In one embodiment, without being limited by a particular theory, these disorders can typically be treated with a dopamine agonist, for example, a D2 agonist.

In one embodiment, the disorders being treated, prevented and/or managed using a method provided herein include, but are not limited to, schizophrenia, psychosis, schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, a disease having a psychosis component, psychotic disorder, brief psychotic disorder, Alzheimer's psychosis, Parkinson's psychosis, shared psychotic disorder, substance-induced psychotic disorder (e.g., cocaine, opiate, alcohol, nicotine, or amphetamine), psychotic disorder due to a general medical condition, psychoaffective disorder, aggression, delirium, excitative psychosis, Tourette's syndrome, manic disorder, organic psychosis, or NOS psychosis. In one embodiment, without being limited by a particular theory, these disorders can typically be treated with a dopamine antagonist, for example, a D2 antagonist.

In one embodiment, the disorders being treated, prevented and/or managed using a method provided herein include, but are not limited to, affective disorder; depression; a major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; unipolar depression; treatment resistant depression; dysthymic disorder; minor depressive disorder; premenstrual dysphoric disorder; post-psychotic depressive disorder of schizophrenia; a major depressive disorder superimposed on a psychotic disorder (e.g., delusional disorder or schizophrenia); a bipolar disorder; bipolar I disorder; bipolar II disorder; cyclothymic disorder; seasonal affective disorder; attention deficit disorder (ADD); or attention deficit hyperactivity disorder (ADHD). In one embodiment, without being limited by a particular theory, these disorders can typically be treated with a dopamine agonist or partial agonist, for example, a D2 agonist or partial agonist.

In one embodiment, the disorders being treated, prevented and/or managed using a method provided herein include, but are not limited to, addiction or substance abuse or dependency (e.g., alcohol, nicotine, amphetamine, cocaine, or opiate addiction). In one embodiment, without being limited by a particular theory, these disorders can typically be treated with a dopamine antagonist or partial agonist, for example, a D2 antagonist or partial agonist.

In one embodiment, the disorders being treated, prevented and/or managed using a method provided herein include, but are not limited to, posttraumatic stress disorder, behavior disorder, neurodegenerative disease, Alzheimer's disease, dementia, mood disorder, anxiety, obsessive-compulsive disorder, vertigo, pain, neuropathic pain, sensitization accompanying neuropathic pain, inflammatory pain, fibromyalgia, migraine, cognitive disorder, cognitive impairment, cognitive impairment associated with schizophrenia, cognitive deficit in Alzheimer's disease, cognitive deficit in Parkinson's disease, multiple sclerosis, sleep disorder, eating disorder, or autism.

In one embodiment, the disorder being treated, prevented and/or managed using a method provided herein is a disorder known in the art that affects the central nervous system (e.g., a CNS disorder). In one embodiment, the disorder being treated, prevented and/or managed using a method provided herein is a disorder known in the art that affects the neurological system (e.g., a neurological disorder).

In one embodiment, provided herein is a method of treating, preventing, and/or managing Parkinson's disease, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a movement disorder, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing Parkinson's disease or a movement disorder, including but not limited to, ataxia, dystonia, essential tremor, Huntington's disease, multiple system atrophy, myoclonus, progressive supranuclear palsy, rett syndrome, secondary parkinsonism, spasticity, tardive dyskinesia, Wilson's disease, dyskinesia, and restless leg syndrome, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a movement disorder, including but not limited to, Parkinson's disease and Huntington's disease, comprising administering to a subject an effective amount of a compound provided herein. In one embodiment, provided herein is a method of treating, preventing, and/or managing a movement disorder, including but not limited to, Parkinson's disease, L-dopa induced dyskinesia, peak dose dyskinesia, restless leg syndrome, and Huntington's disease, comprising administering to a subject an effective amount of a compound provided herein. In one embodiment, the movement disorders provided herein that can be treated, prevented, and/or managed using a compound or a pharmaceutical composition provided herein include, but are not limited to, Huntington's disease, Parkinson's disease, restless leg syndrome, and essential tremor.

In one embodiment, provided herein is a method of treating, preventing, and/or managing schizophrenia, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing psychosis, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing schizophrenia or psychosis, including but not limited to, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, a disease having a psychosis component, psychotic disorder, brief psychotic disorder, Alzheimer's psychosis, Parkinson's psychosis, shared psychotic disorder, substance-induced psychotic disorder (e.g., cocaine, opiate, alcohol, nicotine, or amphetamine), psychotic disorder due to a general medical condition, psychoaffective disorder, aggression, delirium, excitative psychosis, Tourette's syndrome, manic disorder, organic psychosis, and NOS psychosis, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing schizophrenia, including, but not limited to, a schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, or delusional disorder, comprising administering a compound provided herein, or a pharmaceutically acceptable salt or stereoisomer thereof, or a pharmaceutical composition provided herein, to a subject in need thereof. In one embodiment, the compounds provided herein treat, prevent, and/or ameliorate one or more positive symptoms of schizophrenia. In one embodiment, the compounds provided herein treat, prevent, and/or ameliorate one or more negative symptoms of schizophrenia. In one embodiment, the compounds provided herein treat, prevent, and/or ameliorate one or more cognitive symptoms of schizophrenia.

In one embodiment, provided herein is a method of treating, preventing, and/or managing psychosis, including, but not limited to, a disease having a psychosis component, psychotic disorder, brief psychotic disorder, Alzheimer's psychosis, Parkinson's psychosis, shared psychotic disorder, substance-induced psychotic disorder (e.g., cocaine, opiate, alcohol, or amphetamine), psychotic disorder due to a general medical condition, psychoaffective disorder, aggression, delirium, excitative psychosis, Tourette's syndrome, manic disorder, organic psychosis, or NOS psychosis, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a disease having a psychosis component, including but not limited to psychotic disorder, brief psychotic disorder, Alzheimer's psychosis, Parkinson's psychosis, shared psychotic disorder, substance-induced psychotic disorder (e.g., cocaine, opiate, alcohol, or amphetamine), psychotic disorder due to a general medical condition, psychoaffective disorder, aggression, delirium, excitative psychosis, Tourette's syndrome, manic disorder, organic psychosis, and NOS psychosis, comprising administering to a subject an effective amount of a compound provided herein.

In one embodiment, provided herein is a method of treating, preventing, and/or managing a psychotic disorder or a psychotic condition, including but not limited to, schizophrenia, delusional disorder, and drug induced psychosis, among others, comprising administering to a subject an effective amount of a compound provided herein.

In one embodiment, the psychotic disorders provided herein that can be treated, prevented, and/or managed using a compound or a pharmaceutical composition provided herein include, but are not limited to, schizophrenia, e.g., of the paranoid, disorganized, catatonic, undifferentiated, and/or residual type; schizophreniform disorder; schizoaffective disorder, e.g., of the delusional and/or depressive type; delusional disorder; substance-induced psychotic disorder, e.g., psychosis induced by alcohol, amphetamine, cannabis, cocaine, hallucinogens, inhalants, opioids, and/or phencyclidine; personality disorder of the paranoid type; and personality disorder of the schizoid type.

In one embodiment, provided herein is a method of treating, preventing, and/or managing a neurologic disorder, including but not limited to, schizophrenia of a paranoid, disorganized, catatonic, undifferentiated or residual type, schizophreniform disorder; schizoaffective disorder of the delusional type or the depressive type, delusional disorder, substance-induced psychotic disorder, psychosis induced by alcohol, amphetamine, cannabis, cocaine, hallucinogens, inhalants, opioids, or phencyclidine, personality disorder of the paranoid type, and personality disorder of the schizoid type, comprising administering to a subject an effective amount of a compound provided herein.

In one embodiment, provided herein is a method of treating, preventing, and/or managing an affective disorder, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing depression, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing an affective disorder or depression, including but not limited to, a major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; unipolar depression; treatment resistant depression; dysthymic disorder; minor depressive disorder; premenstrual dysphoric disorder; post-psychotic depressive disorder of schizophrenia; a major depressive disorder superimposed on a psychotic disorder (e.g., delusional disorder or schizophrenia); a bipolar disorder (e.g., bipolar I disorder, bipolar II disorder, or cyclothymic disorder); seasonal affective disorder; an anxiety disorder (e.g., panic disorder, specific phobia, social phobia, obsessive-compulsive disorder, posttraumatic stress disorder, acute stress disorder, generalized anxiety disorder, anxiety disorder due to a general medical condition); attention deficit disorder (ADD); and attention deficit hyperactivity disorder (ADHD); comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a neurologic disorder, including but not limited to, major depressive episode of the mild, moderate or severe type, manic or mixed mood episode, hypomanic mood episode, depressive episode with atypical features, depressive episode with melancholic features, depressive episode with catatonic features, mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder comprising a delusional disorder or schizophrenia, bipolar disorder, bipolar I disorder, bipolar II disorder, or cyclothymic disorder, comprising administering to a subject an effective amount of a compound provided herein.

In one embodiment, provided herein is a method of treating, preventing, and/or managing attention deficit disorder (ADD) or attention deficit hyperactivity disorder (ADHD), comprising administering to a subject an effective amount of a compound provided herein.

In one embodiment, provided herein is a method of treating, preventing, and/or managing addiction, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing substance abuse or dependency, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing addiction or substance abuse or dependency, including but not limited to, addiction to, dependency on, or abuse of alcohol, nicotine, amphetamine, cocaine, or opiate, comprising administering a compound provided herein, or a pharmaceutically acceptable salt or stereoisomer thereof, or a pharmaceutical composition provided herein, to a subject in need thereof.

In one embodiment, provided herein is a method of treating, preventing, and/or managing a drug addiction, including but not limited to, an alcohol, amphetamine, cocaine, and/or opiate addiction, comprising administering to a subject an effective amount of a compound provided herein. In one embodiment, the drug addiction provided herein represents an abnormal desire for a drug and is generally characterized by motivational disturbances such a compulsion to take the desired drug and episodes of intense drug craving.

In one embodiment, provided herein is a method of treating, preventing, and/or managing substance abuse, comprising administering to a subject an effective amount of a compound provided herein. In one embodiment, provided herein is a method of treating, preventing, and/or managing substance dependency, comprising administering to a subject an effective amount of a compound provided herein.

In other embodiments, provided herein is a method of treating, preventing, and/or managing a CNS disorder or a neurological disorder, including, but not limited to, post-traumatic stress disorder, behavior disorder, neurodegenerative disease, Alzheimer's disease, dementia, mood disorder, anxiety, obsessive-compulsive disorder, vertigo, pain, neuropathic pain, sensitization accompanying neuropathic pain, inflammatory pain, fibromyalgia, migraine, cognitive disorder, cognitive impairment, cognitive impairment associated with schizophrenia, cognitive deficit in Alzheimer's disease, cognitive deficit in Parkinson's disease, multiple sclerosis, sleep disorder, eating disorder, or autism, comprising administering a compound provided herein, or a pharmaceutically acceptable salt or stereoisomer thereof, or a pharmaceutical composition provided herein, to a subject in need thereof.

In one embodiment, the neurological disorder is excessive daytime sleepiness. In another embodiment, the neurological disorder is cognitive impairment. In another embodiment, the neurological disorder is mood disorders. In another embodiment, the neurological disorder is attention disorders. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, provided herein is a method of treating, preventing, and/or managing cognitive impairment, including but not limited to cognitive impairment associated with schizophrenia, cognitive deficit in Alzheimer's disease, cognitive deficit in Parkinson's disease, comprising administering to a subject an effective amount of a compound provided herein.

In one embodiment, provided herein is a method of treating, preventing, and/or managing a disorder comprising a symptom of deficiency in attention and/or cognition, comprising administering to a subject an effective amount of a compound provided herein. In one embodiment, deficiency in attention and/or cognition provided herein may represent a subnormal functioning in one or more cognitive aspects, such as, e.g., memory, intellect, learning ability, and/or logic ability, in a particular subject relative to other subjects within the same general population and/or age group. In one embodiment, deficiency in attention and/or cognition provided herein may represent a reduction in a particular sub-population's functioning in one or more cognitive aspects, such as, e.g., in age-related cognitive decline.

In one embodiment, the disorders comprising a symptom of deficiency in attention and/or cognition provided herein that can be treated, prevented, and/or managed with a compound or a pharmaceutical composition provided herein, include, but are not limited to, dementia, e.g., dementia in Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, or AIDS-related dementia; delirium; amnestic disorder; post-traumatic stress disorder; mental retardation; learning disorder, e.g., reading disorder, mathematics disorder, or a disorder of written expression; attention-deficit/hyperactivity disorder; and age-related cognitive decline.

In one embodiment, without being limited by a particular theory, the compounds provided herein may have pro-cognitive effects, such as passive avoidance, novel object recognition, social recognition, and attention-set shifting (e.g., in an in vivo animal model). Further, without being limited by a particular theory, the compounds provided herein may improve social memory, increase the acquisition of an environment, and reverse scopolamine-induced deficits (e.g., in an in vivo animal model). The compounds provided herein may also reverse scopolamine-induced deficits in a passive avoidance memory test (e.g., in an in vivo animal model).

In one embodiment, provided herein is a method of treating, preventing, and/or managing a neurodegenerative disease, comprising administering to a subject an effective amount of a compound provided herein. In one embodiment, the neurodegenerative disease is Parkinson's disease. In another embodiment, the neurodegenerative disorder is Alzheimer's disease.

In one embodiment, provided herein is a method of treating, preventing, and/or managing mood disorder, bipolar disorder, anxiety, depression, major depressive disorder, unipolar depression, treatment resistant depression, dysthymia, affective disorder, seasonal affective disorder, or obsessive-compulsive disorder, comprising administering to a subject an effective amount of a compound provided herein.

In one embodiment, provided herein is a method of treating, preventing, and/or managing a mood disorder or a mood episode, comprising administering to a subject an effective amount of a compound provided herein. In one embodiment, the mood disorders or mood episodes provided herein that can be treated, prevented, and/or managed with a compound or a pharmaceutical composition provided herein include, but are not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder.

In one embodiment, provided herein is a method of treating, preventing, and/or managing posttraumatic stress disorder or behavior disorder, comprising administering to a subject an effective amount of a compound provided herein.

In one embodiment, provided herein is a method of treating, preventing, and/or managing an anxiety disorder, including but not limited to, panic and obsessive-compulsive disorder, comprising administering to a subject an effective amount of a compound provided herein. In one embodiment, provided herein is a method of treating, preventing, and/or managing an anxiety disorder, including but not limited to, panic disorder, agoraphobia, specific phobia, social phobia, obsessive-compulsive disorder, post-traumatic stress disorder, acute stress disorder, and generalized anxiety disorder, comprising administering to a subject an effective amount of a compound provided herein.

In one embodiment, provided herein is a method of treating, preventing, and/or managing a neurodegenerative disease, including but not limited to Huntington's disease, Alzheimer's disease, and Parkinson's disease, comprising administering to a subject an effective amount of a compound provided herein.

In one embodiment, provided herein is a method of treating, preventing, and/or managing a neurodegenerative disorder or neurodegenerative condition, comprising administering to a subject an effective amount of a compound provided herein. In one embodiment, the neurodegenerative disorder or neurodegenerative condition provided herein that can be treated, prevented, and/or managed with a compound or a pharmaceutical composition provided herein represents a disorder or condition that is caused by the dysfunction and/or death of neurons in the central nervous system. The treatment of these disorders and conditions can be facilitated by administration of an agent which prevents the dysfunction or death of neurons at risk and/or enhances the function of damaged or healthy neurons to compensate for the loss of function caused by the dysfunction or death of at-risk neurons. In one embodiment, the neurodegenerative disorders or neurodegenerative conditions provided herein that can be treated, prevented, and/or managed with a compound or a pharmaceutical composition provided herein include, but are not limited to, Parkinson's disease; Huntington's disease; dementia, e.g., Alzheimer's disease, multi-infarct dementia, AIDS-related dementia, and Fronto temporal dementia; neurodegeneration associated with cerebral trauma; neurodegeneration associated with stroke; neurodegeneration associated with cerebral infarct; hypoglycemia-induced neurodegeneration; neurodegeneration associated with neurotoxin poisoning; and multi-system atrophy. In one embodiment, the neurodegenerative disorders or neurodegenerative conditions provided herein comprise neurodegeneration of striatal medium spiny neurons in a subject. In one embodiment, the neurodegenerative disorder or neurodegenerative condition is Huntington's disease.

In one embodiment, provided herein is a method of treating, preventing, and/or managing a neurologic disorder, including but not limited to, neurodegeneration associated with cerebral trauma, neurodegeneration associated with stroke, neurodegeneration associated with cerebral infarct, hypoglycemia-induced neurodegeneration, neurodegeneration associated with neurotoxin poisoning, or multi-system atrophy, comprising administering to a subject an effective amount of a compound provided herein.

Neurological disorders may also include cerebral function disorders, including without limitation, senile dementia, Alzheimer's type dementia, cognition, memory loss, amnesia/amnestic syndrome, lowering of attention, speech disorders, autism, and hyperkinetic syndrome.

In one embodiment, provided herein is a method of treating, preventing, and/or managing dementia, comprising administering to a subject an effective amount of a compound provided herein.

In one embodiment, provided herein is a method of treating, preventing, and/or managing a neurologic disorder, including but not limited to, dementia, Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, AIDS-related dementia, delirium, amnestic disorder, post-traumatic stress disorder, mental retardation, learning disorder, reading disorder, mathematics disorder, disorder of written expression, attention-deficit-hyperactivity disorder, age-related cognitive decline, and Fronto temporal dementia, comprising administering to a subject an effective amount of a compound provided herein.

In one embodiment, provided herein is a method of treating, preventing, and/or managing vertigo, comprising administering to a subject an effective amount of a compound provided herein.

In one embodiment, provided herein is a method of treating, preventing, and/or managing multiple sclerosis, sleep disorder, eating disorder, or autism, comprising administering to a subject an effective amount of a compound provided herein.

In one embodiment, provided herein is a method of treating, preventing, and/or managing pain, neuropathic pain, sensitization accompanying neuropathic pain, inflammatory pain, migraine or fibromyalgia, comprising administering to a subject an effective amount of a compound provided herein.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

In some embodiments, the neurological disorder provided herein is: depression (e.g., major depressive disorder, bipolar disorder, unipolar disorder, treatment resistant depression, dysthymia, and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; and substance abuse or dependency (e.g., cocaine addiction, nicotine addiction, or other drug addiction).

In one embodiment, provided herein is a method of treating, preventing, and/or managing schizophrenia, psychosis, or depression, comprising administering to a subject an effective amount of a compound provided herein. In one embodiment, provided herein is a method of treating, preventing, and/or managing a neurologic disorder, including but not limited to, Parkinson's disease or movement disorder, comprising administering to a subject an effective amount of a compound provided herein.

In one embodiment, provided herein is a method of treating, preventing, and/or managing a disorder provided herein (e.g., a CNS disorder or a neurological disorder), in a subject, such as a mammal, e.g., human, rodent (e.g., mice and rats), cat, dog, and non-human primate, among others. In one embodiment, provided herein is a method of treating, preventing, and/or ameliorating one or more symptoms associated with a disorder provided herein (e.g., a CNS disorder or a neurological disorder), in a subject, such as a mammal, e.g., human, rodent (e.g., mice and rats), cat, dog, and non-human primate, among others. In one embodiment, the method provided herein comprises contacting a compound provided herein with a G-protein coupled receptor. In one embodiment, the method comprises contacting a compound provided herein with a D2 receptor.

In one embodiment, provided herein is a method of administering a compound provided herein in a disease model that is known in the art. In one embodiment, the disease model is an animal model. In one embodiment, provided herein is a method of administering the compound provided herein in an animal model that is predictive of efficacy in the treatment of certain diseases in a human. The method comprises administering a compound provided herein in a subject. In one embodiment, the method comprises administering to a subject a therapeutically effective amount of a compound provided herein, or a pharmaceutically acceptable salt or stereoisomer thereof. In one embodiment, the method comprises treatment of a test subject (e.g., a mice or rat) with a compound provided herein. In one embodiment, the method comprises treatment of a test subject (e.g., a mice or rat) with a compound provided herein as well as a reference compound. In one embodiment, the in vivo activity of the compound provided herein is dose dependent. In one embodiment, without being limited to a particular theory, the method provided herein comprises administering an effective amount of a compound provided herein to modulate the activity of one or more signaling pathways utilized by a D2 receptor (e.g., cAMP and/or β-arrestin) in a subject.

In one embodiment, provided herein is a method of treating, preventing, and/or managing various disorders, including, but not limited to, a CNS disorder or a neurological disorder, wherein the method comprises administering to a subject a therapeutically or prophylactically effective amount of a composition or a compound provided herein. In one embodiment, the subject is a human. In one embodiment, the subject is an animal. In one embodiment, the compounds provided herein are highly brain penetrable in the subject. In certain embodiments, the efficacious concentration of the compounds provided herein is less than 10 nM, less than 100 nM, less than 1 µM, less than 10 µM, less than 100 µM, or less than 1 mM. In one embodiment, the compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of efficacy in humans.

In some embodiments, the compounds provided herein are active in at least one model, which can be used to measure the activity of the compounds and estimate their efficacy in treating a CNS disorder or a neurological disorder. For example, the compounds provided herein are active in at least one model for schizophrenia, psychosis, Parkinson's disease, movement disorder, affective disorder, depression, addiction, or substance abuse or dependency. The compounds are active when they induce a desired response in the animal (e.g., mice) by a statistically significant amount compared to vehicle-treated animals.

In other embodiments, provided herein is a method of effecting a therapeutic effect as described herein elsewhere. The method comprises administering to a subject (e.g., a mammal) a therapeutically effective amount of a compound or a composition provided herein. The particular therapeutic effects may be measured using any model system known in the art and described herein, such as those involving an animal model of a disease.

In one embodiment, the compounds provided herein are useful to treat, prevent, and/or manage two or more conditions/disorders, which are co-morbid, such as psychosis and depression.

In one embodiment, provided herein is a method of using the compounds provided herein as psycho-stimulants, which may have fewer abuse liabilities than those generally associated with other classes of psycho-stimulants.

In one embodiment, the compounds provided herein treat, prevent, and/or manage a CNS disorder or a neurological disorder, without causing addiction to said compounds. In one embodiment, the compounds described herein treat, prevent, and/or manage a central nervous disorder, while reducing undesirable side effects.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. The dosage may be formulated as a single or multiple unit dosage formulation. In one embodiment, the compound is given in single or divided doses per day.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients (e.g., a second active agent provided herein elsewhere). Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences*, 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising, active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In other embodiments, dosage forms comprise the second active ingredient. The specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. Examples

Certain embodiments are illustrated by the following non-limiting examples.

A. Compound Synthesis

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., J. Org. Chem., 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, elemental microanalysis, and melting point. Proton magnetic resonance ($^1$H NMR) spectra were determined using a NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

1. Synthesis of 6-(4-(4-(2,3-dichlorophenyl)piperazin-1-yl)butoxy)-1H-pyrazolo[3,4-b]pyridine (Compound 1)

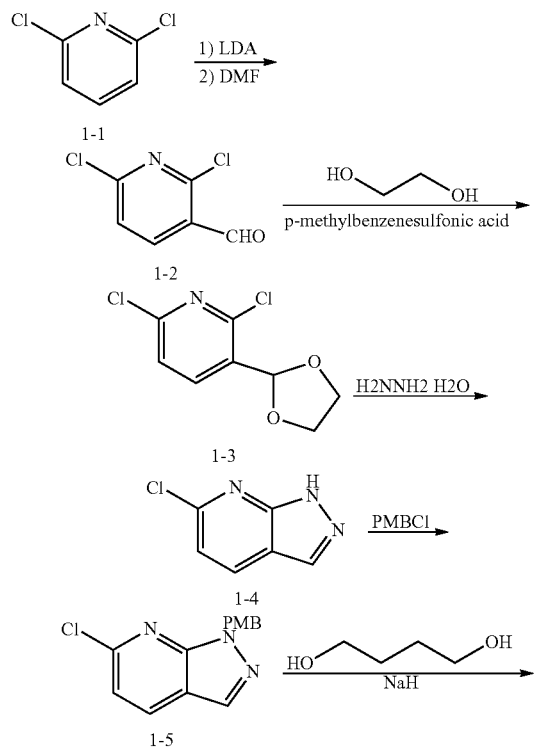

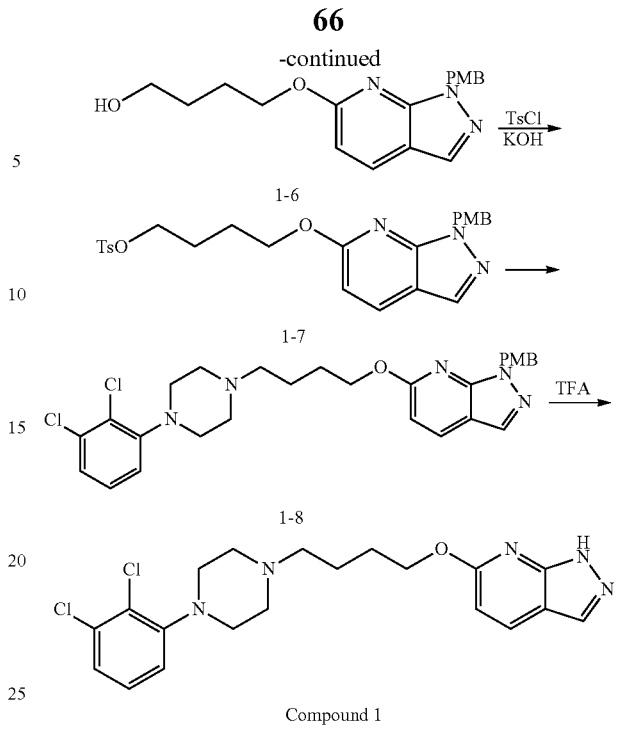

(a) Synthesis of 2,6-dichloronicotinaldehyde (1-2)

Lithium diisopropylamide (2 M, 20.5 mL, 40.53 mmol, 1.2 eq.) was added into anhydrous tetrahydrofuran (20 mL) at −78° C. Compound 1-1 (5.0 g, 33.78 mmol, 1.0 eq.) in tetrahydrofuran (20 mL) was added dropwise over 1 h at −78° C. N,N-Dimethylformamide (7.5 g, 101.35 mmol, 3.0 eq.) was added into the solution, and the mixture was stirred for another 2 h at −78° C. Saturated ammonium chloride (60 mL) was added to the mixture to quench the reaction. The solution was evaporated to remove tetrahydrofuran and extracted with ethyl acetate (3×50 mL). The organic layer was collected, dried over sodium sulfate, and evaporated to give the crude product, which was purified by silica gel column chromatography (100% petroleum ether to ethyl acetate:petroleum ether=1:10) to give compound 1-2 as a white solid (3.5 g, yield: 59%). MS (ESI) m/z 176.0 [M+H]$^+$.

(b) Synthesis of 2,6-dichloro-3-(1,3-dioxolan-2-yl) pyridine (1-3)

To a solution of compound 1-2 (3.5 g, 0.02 mol, 1.0 eq.) in toluene (80 mL) was added ethane-1,2-diol (2.5 g, 0.04 mol, 2.0 eq.) and p-methylbenzenesulfonic acid (0.76 g, 4 mmol, 0.2 eq.). The mixture was heated to reflux for 1 h. Then the mixture was evaporated and purified by silica gel column chromatography (petroleum ether:ethyl acetate=5:1) to give compound 1-3 as a white solid (3.9 g, yield: 89%). MS (ESI) m/z 220[M+H]$^+$.

(c) Synthesis of diethyl 6-chloro-1H-pyrazolo[3,4-b]pyridine (1-4)

To a solution of compound 1-3 (3.0 g, 13.70 mmol, 1.0 eq) in butan-1-ol (8 mL) was added hydrazine hydrate (1.48 g, 24.66 mmol, 1.8 eq). The mixture was heated to 150° C. and stirred for 1 h in a sealed tube. After cooling, the mixture was filtered and evaporated to give crude product, which was purified by silica gel column chromatography (dichloromethane:methanol=10:1) to provide compound 1-4 as a yellow solid (600 mg, yield: 28.6%). MS (ESI) m/z 154 [M+H]$^+$.

(d) Synthesis of 6-chloro-1-(4-methoxybenzyl)-1H-pyrazolo[3,4-b]pyridine (1-5)

A mixture of compound 1-4 (600 mg, 3.92 mmol, 1.0 eq.), 1-(chloromethyl)-4-methoxybenzene (1044 mg, 6.67 mmol, 1.7 eq.), and potassium carbonate (1624 mg, 11.76 mmol, 3.0 eq) in acetonitrile (15 mL) was stirred at 60° C. for 1 h. The mixture was diluted with aq. sodium bicarbonate (30 mL) and extracted with dichloromethane (3×30 mL). The combined organic phase was dried, concentrated and purified by flash column chromatography (petroleum ether:ethyl acetate=5:1) to provide compound 1-5 as a pale yellow oil (610 mg, yield: 57%). MS (ESI) m/z 274.0 [M+H]$^+$.

(e) Synthesis of 4-(1-(4-methoxybenzyl)-1H-pyrazolo[3,4-b]pyridin-6-yloxy)butan-1-ol (1-6)

A mixture of compound 1-5 (610 mg, 2.23 mmol, 1.0 eq.), butane-1,4-diol (604 mg, 6.70 mmol, 3.0 eq.), sodium hydride (60% w/w, 268 mg, 6.70 mmol, 3.0 eq.) in N,N-dimethylformamide (10 mL) was stirred at room temperature overnight. The mixture was diluted with aq. sodium bicarbonate (30 mL) and extracted with dichloromethane (3×30 mL). The combined organic phase was dried, concentrated and purified by flash column (petroleum ether:ethyl acetate=2:1) to give compound 1-6 as a clear oil (380 mg, yield: 52%). MS (ESI) m/z 328.2 [M+H]$^+$.

(f) Synthesis of 4-(1-(4-methoxybenzyl)-1H-pyrazolo[3,4-b]pyridin-6-yloxy)butyl 4-methylbenzenesulfonate (1-7)

To a solution of compound 1-6 (230 mg, 0.7 mmol, 1.0 eq.) and potassium hydroxide (118 mg, 2.1 mmol, 3.0 eq.) in acetonitrile (5 mL) was added tosyl chloride (266 mg, 1.4 mmol, 2.0 eq.) in portions at 0° C. The mixture was stirred at room temperature overnight. The resulting solution was concentrated in vacuum to give a residue which was dissolved in ethyl acetate (15 mL) and then washed with brine (3×5 mL). The organic layer was dried over anhydrous sodium sulfate, filtered and concentrated in vacuum to give the crude product which was purified by prep-TLC (petroleum ether:ethyl acetate=12:5) to afford compound 1-7 as a yellow oil (180 mg, yield: 53%). MS (ESI): m/z 482 [M+H]$^+$.

(g) Synthesis of 6-(4-(4-(2,3-dichlorophenyl)piperazin-1-yl)butoxy)-1-(4-methoxy-benzyl)-1H-pyrazolo[3,4-b]pyridine (1-8)

A mixture of compound 1-7 (25 mg, 0.052 mmol, 1.0 eq.), 1-(2,3-dichlorophenyl)piperazine (60.1 mg, 0.26 mmol, 5.0 eq.), and potassium carbonate (55 mg, 0.4 mmol, 7.7 eq.) in tert-butanol (10.0 mL) was heated at 60° C. for 48 h. The mixture was diluted with water (30 mL) and extracted with dichloromethane (3×30 mL). The combined organic phase was dried, concentrated and purified by flash column chromatography (petroleum ether:ethyl acetate=1:1) to give compound 1-8 (23 mg, yield: 82%). MS (ESI) m/z 540.2 [M+H]$^+$.

(h) Synthesis of 6-(4-(4-(2,3-dichlorophenyl)piperazin-1-yl)butoxy)-1H-pyrazolo[3,4-b]pyridine (Compound 1)

A mixture of compound 1-8 (23 mg, 0.042 mmol) in trifluoroacetic acid (5.0 mL) was heated at 60° C. overnight. The mixture was diluted with aq. potassium carbonate (30 mL) and extracted with dichloromethane (3×30 mL). The combined organic phase was dried, concentrated and purified by flash column chromatography (dichloromethane:methanol=20:1) to give compound 1 (17 mg, yield: 95%). MS (ESI) m/z 420.2 [M+H]$^+$. $^1$H NMR (400 MHz, CDCl$_3$): δ 7.95 (s, 1H), 7.91 (d, J=8.4 Hz, 1H), 7.11-7.17 (m, 2H), 6.95 (dd, J=2.8 Hz, 7.2 Hz, 1H), 6.61 (d, J=8.8 Hz, 1H), 4.46 (t, J=4.8 Hz, 2H), 3.10 (br, 4H), 2.70 (br, 4H), 2.56 (t, J=7.6 Hz, 2H), 1.87-1.92 (m, 2H), 1.77-1.82 (m, 2H).

2. Synthesis of 6-(4-(4-(naphthalen-1-yl)piperazin-1-yl)butoxy)-1H-pyrazolo[3,4-b]pyridine (Compound 2)

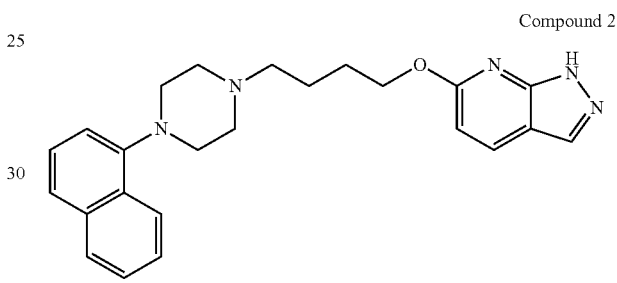

Compound 2

This compound was prepared in 53% yield (last step) (13 mg) as described for Compound 1 but using 1-(naphthalene-1-yl)piperazine as the starting material. MS (ESI): m/z 402 [M+H]$^+$. $^1$H NMR (400 MHz, CDCl$_3$): δ 8.17-8.21 (m, 1H), 7.94 (s, 1H), 7.90 (d, J=8.4 Hz, 1H), 7.80-7.84 (m, 1H), 7.54 (d, J=8 Hz, 1H), 7.43-7.49 (m, 2H), 7.39(t, J=8 Hz, 1H), 7.08 (d, J=8 Hz, 1H), 6.62 (d, J=8.4 Hz, 1H), 4.47 (t, J=6.4 Hz, 2H), 3.19 (br, 4H), 2.81 (br, 4H), 2.62 (t, J=7.6 Hz, 2H), 1.85-1.95 (m, 2H), 1.79-1.84 (m, 2H).

3. Synthesis of 6-(4-(4-(2,3-dimethylphenyl)piperazin-1-yl)butoxy)-1H-pyrazolo[3,4-b]pyridine (Compound 3)

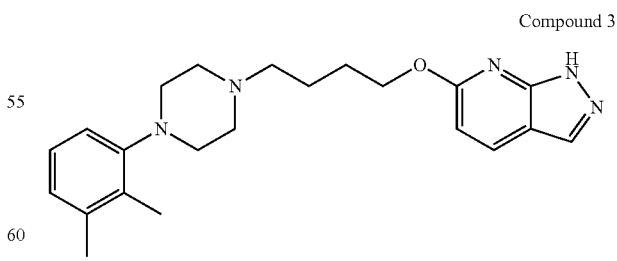

Compound 3

This compound was prepared in 81% yield (last step) (24 mg) as a pale-yellow oil as described for Compound 1 but using 1-(2,3-dimethylphenyl)piperazine as the starting material. MS (ESI): m/z 380 [M+H]$^+$. $^1$H NMR (400 MHz, CDCl$_3$): δ 11.8 (br, 1H), 7.93 (s, 1H), 7.90 (d, J=8.8 Hz, 1H), 7.06 (t, J=8 Hz, 1H), 6.90 (t, J=6.4 Hz, 2H), 6.60 (d, J=8.4 Hz, 1H), 4.46 (t, J=6.4 Hz, 2H), 2.93 (t, J=4.8 Hz, 4H), 2.66-2.76 (m, 4H), 2.53 (t, J=8 Hz, 2H), 2.26 (s, 3H), 2.21 (s, 3H), 1.86-1.93 (m, 2H), 1.74-1.80 (m, 2H).

4. Synthesis of 6-(4-(4-(pyridin-2-yl)piperazin-1-yl)butoxy)-1H-pyrazolo[3,4-b]pyridine (Compound 4)

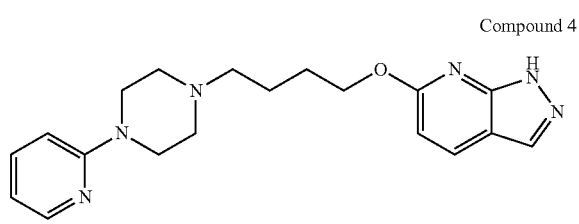 [SMILES: c1ccc(N2CCN(CCCCOc3ccc4cn[nH]c4n3)CC2)nc1]

Compound 4

This compound was prepared in 67% yield (last step) (25 mg) as a pale-yellow oil as described for Compound 1 but using 1-(pyridin-2-yl)piperazine as the starting material. MS (ESI): m/z 353 [M+H]$^+$. $^1$H NMR (400 MHz, CDCl$_3$): δ 8.19-8.21 (m, 1H), 7.93 (s, 1H), 7.89 (d, J=8.4 Hz, 1H), 7.44-7.48 (m, 1H), 6.58-6.64 (m, 3H), 4.45 (t, J=6 Hz, 2H), 3.58 (t, J=4.8 Hz, 4H), 2.61 (t, J=4.8 Hz, 4H), 2.51 (t, J=8 Hz, 2H), 1.84-1.91 (m, 2H), 1.74-1.80 (m, 2H).

5. Synthesis of 2-(4-(4-(2,3-dichlorophenyl)piperazin-1-yl)butoxy)quinolin-8-ol (Compound 5)

extracted with ethyl acetate (50 mL×3). The organic layers were combined, dried over sodium sulfate and concentrated to dryness to afford 5-2 (1.8 g, 40% yield) as a brown solid. MS (ESI): m/z 238 [M+H]$^+$.

(b) Synthesis of 2-hydroxyquinolin-8-yl acetate (5-3)

A solution of quinolin-8-ol-N-oxide (5-2) (322 mg, 2 mmol) in acetic anhydride (4 mL) was stirred at 140° C. for 5 hours and then cooled to room temperature. Acetic anhydride was removed under reduced pressure. The residue was neutralized to pH 7 with saturated sodium bicarbonate solution, then extracted with ethyl acetate (20 mL×3). The organic layers were combined, dried over sodium sulfate and concentrated to dryness to give a tan oil, which was treated with ethanol to provide compound 5-3 (138 mg, 34% yield) as a brown solid. MS (ESI): m/z 204 [M+H]$^+$.

(c) Synthesis of 2-(4-bromobutoxy)quinolin-8-yl acetate (5-4)

To a solution of 2-hydroxyquinolin-8-yl acetate (5-3) (406 mg, 2 mmol) and 1,4-dibromobutane (432 mg, 2 mmol) in N,N-dimethylformamide (10 mL) at 90° C., was added cesium carbonate (652 mg, 326 mg). The mixture was stirred for 10 minutes and was purified by reverse phase column chromatography (acetonitrile:water=50:1 with 0.01% NH$_4$OH) to give compound 5-4 (280 mg, 41% yield) as a light yellow oil. MS (ESI): m/z 338, 340 [M+H]$^+$.

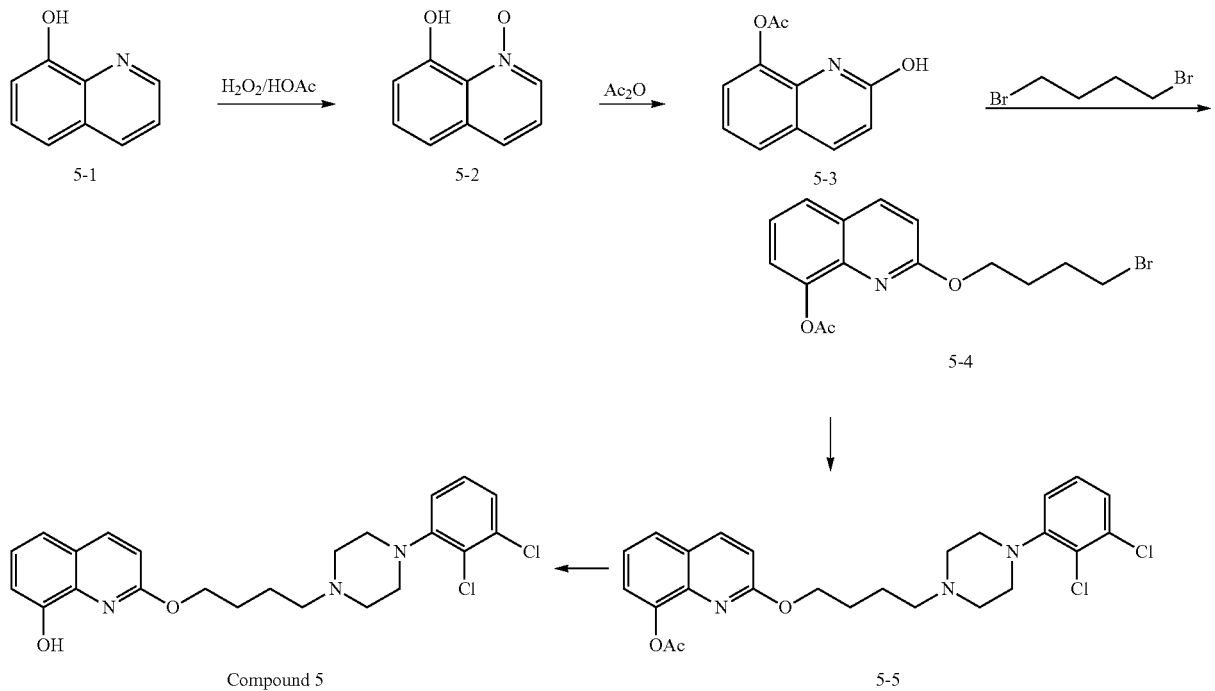

(a) Synthesis of quinolin-8-ol-N-oxide (5-2)

A solution of quinolin-8-ol (4 g, 27.6 mmol) in 35% hydrogen peroxide solution (10 ml) in acetic acid (25 mL) was stirred at 70° C. for 16 hours. After the reaction mixture was neutralized to pH 12 with ammonium hydroxide, it was (d) Synthesis of 2-(4-(4-(2,3-dichlorophenyl)piperazin-1-yl)butoxy) quinolin-8-yl acetate (5-5)

To a solution of 2-(4-bromobutoxy)quinolin-8-yl acetate (5-4) (50 mg, 0.15 mmol) and 1-(2,3-dichlorophenyl)piperazine (35 mg, 0.15 mmol) in N,N-dimethylformamide (2 mL), potassium carbonate (42 mg, 0.3 mmol) was added. The mixture was stirred at 40° C. for 2 h and was then purified by reverse phase column chromatography (acetonitrile:water=25:75 with 0.01% NH₄OH) to give a crude product. The crude product was directly used for the next step without further purification. MS (ESI): m/z 489 [M+H]⁺.

(e) Synthesis of 2-(4-(4-(2,3-dichlorophenyl)piperazin-1-yl)butoxy)quinolin-8-ol (Compound 5)

A mixture of 2-(4-(4-(2,3-dichlorophenyl)piperazin-1-yl)butoxy)quinolin-8-yl acetate (5-5) (72 mg, 0.15 mmol) and potassium carbonate (42 mg, 0.3 mmol) in methanol was stirred at 60° C. for 30 minutes. Methanol was removed in vacuo, and the residue was purified by prep-HPLC (basic eluent) to afford compound 5 (13 mg, 20% yield) as a light yellow solid. MS (ESI): m/z 446 [M+H]⁺. ¹H NMR (400 MHz, CDCl₃): δ 8.00 (d, J=8.4 Hz, 1H), 7.59 (bs, 1H), 7.26 (m, 2H), 7.13 (m, 3H), 6.95 (dd, J=2.8, 6.8 Hz, 1H), 6.91 (d, J=8.8 Hz, 1H), 4.49 (t, J=6.4 Hz, 2H), 3.08 (s, 4H), 2.67 (s, 4H), 2.52 (t, J=7.2 Hz, 2H), 1.92 (m, 2H), 1.76 (m, 2H).

6. Synthesis of 2-(4-(4-(naphthalen-1-yl)piperazin-1-yl)butoxy)quinolin-8-ol (Compound 6)

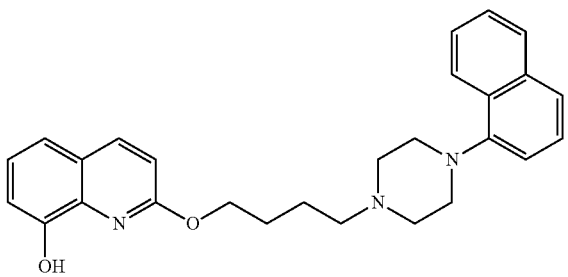

Compound 6

This compound was prepared in 21% yield (last step) (27 mg) as a yellow solid as described for Compound 5 but using 1-(naphthalen-1-yl)piperazine as the starting material. MS (ESI): m/z 428 [M+H]⁺. ¹H NMR (400 MHz, CDCl₃): δ 8.20 (m, 1H), 7.99 (d, J=8.4 Hz, 1H), 7.81 (m, 1H), 7.54 (d, J=8.4 Hz, 1H), 7.46 (m, 2H), 7.39 (t, J=7.6 Hz, 1H), 7.28 (m, 1H), 7.24 (m, 1H), 7.14 (dd, J=2.0 Hz, 7.2 Hz, 1H), 7.08 (m, 1H), 6.93 (d, J=8.4 Hz, 1H), 4.50 (t, J=6.8 Hz, 2H), 3.16 (s, 4H), 2.78 (s, 4H), 2.58 (t, J=7.6 Hz, 2H), 1.93 (m, 1H), 1.80 (m, 1H).

7. Synthesis of 2-(4-(4-(2,3-dimethylphenyl)piperazin-1-yl)butoxy)quinolin-8-ol (Compound 7)

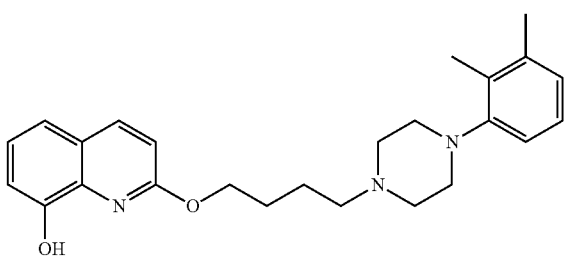

Compound 7

This compound was prepared in 18% yield (last step) (22 mg) as a yellow solid as described for Compound 5 but using 1-(2,3-dimethylphenyl)piperazine as the starting material. MS (ESI): m/z 406 [M+H]⁺. ¹H NMR (400 MHz, CDCl₃): δ 7.98 (d, J=8.8 Hz, 1H), 7.59 (bs, 1H), 7.28 (m, 2H), 7.23 (m, 3H), 7.14 (dd, J=1.6 Hz, 7.2 Hz, 1H), 7.07 (t, J=7.6 Hz, 1H), 6.91 (t, J=8.4 Hz, 2H), 4.49 (t, J=6.0 Hz, 2H), 2.93 (t, J=4.8 Hz, 4H), 2.66 (s, 4H), 2.53 (t, J=7.6 Hz, 2H), 2.25 (s, 3H), 2.20 (s, 3H), 1.91 (m, 1H), 1.79 (m, 1H).

8. Synthesis of 2-(4-(4-(pyridin-2-yl)piperazin-1-yl)butoxy)quinolin-8-ol (Compound 8)

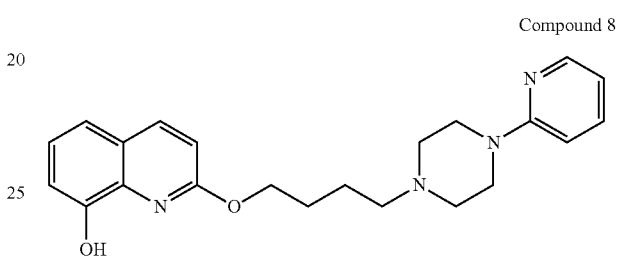

Compound 8

This compound was prepared in 22% yield (last step) (25 mg) as a yellow solid as described for Compound 5 but using 1-(pyridin-2-yl)piperazine as the starting material. MS (ESI): m/z 379 [M+H]⁺. ¹H NMR (400 MHz, CDCl₃): δ 8.19 (dd, J=1.6 Hz, 4.8 Hz, 1H), 7.99 (d, J=9.2 Hz, 1H), 7.47 (m, 1H), 7.28 (m, 1H), 7.24 (m, 1H), 7.13 (dd, J=1.6 Hz, 6.8 Hz, 1H), 6.91 (d, J=8.8 Hz, 1H), 6.63 (m, 2H), 4.49 (t, J=6.4 Hz, 2H), 3.56 (t, J=4.8 Hz, 4H), 2.58 (t, J=5.2 Hz, 4H), 2.49 (t, J=7.2 Hz, 2H), 1.90 (m, 1H), 1.78 (m, 1H).

9. Synthesis of 2-(4-(4-(3-methoxypyridin-2-yl)piperazin-1-yl)butoxy)quinolin-8-ol (Compound 9)

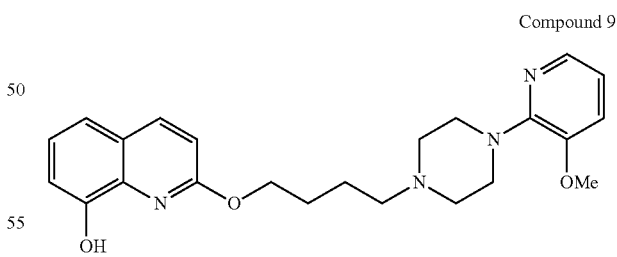

Compound 9

This compound was prepared in 7% yield (last step) (4 mg) as a yellow solid as described for Compound 5 but using 1-(3-methoxypyridin-2-yl)piperazine as the starting material. MS (ESI): m/z 409 [M+H]⁺. ¹H NMR (400 MHz, CD₃OD): δ 8.85 (d, J=8.4 Hz, 1H), 7.84 (d, J=7.6 Hz, 1H), 7.81 (d, J=6.0 Hz, 1H), 7.65 (d, J=8.8 Hz, 1H), 7.60-7.53 (m, 2H), 4.06 (s, 4H), 3.74 (brs, 4H), 3.42 (brs, 4H), 2.14 (brs, 4H).

10. Synthesis of 2-(4-(4-(3-ethoxypyridin-2-yl)piperazin-1-yl)butoxy)quinolin-8-ol (Compound 10)

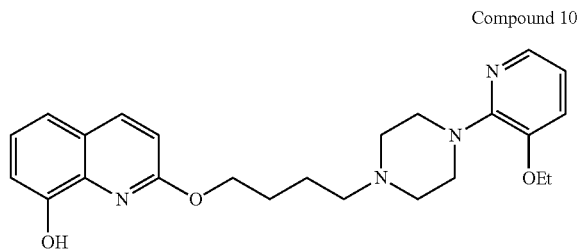

Compound 10

This compound was prepared in 17% yield (last step) (11 mg) as a yellow solid as described for Compound 5 but using 1-(3-ethoxypyridin-2-yl)piperazine as the starting material. MS (ESI): m/z 423 [M+H]$^+$. $^1$H NMR (400 MHz, CDCl$_3$): δ 8.00 (d, J=7.2 Hz, 1H), 7.87 (dd, J$_1$=4.0 Hz, J$_2$=0.8 Hz, 1H), 7.60 (brs, 1H), 7.29-7.25 (m, 2H), 7.15 (dd, J$_1$=6.0 Hz, J$_2$=1.2 Hz, 1H), 7.02 (d, J=5.6 Hz, 1H), 6.93 (d, J=7.2 Hz, 1H), 6.80 (m, 1H), 4.50 (t, J=5.6 Hz, 2H), 4.05 (q, J=5.6 Hz, 2H), 3.49 (brs, 4H), 2.67 (brs, 4H), 2.52 (t, J=6.0 Hz, 2H), 1.92 (m, 2H), 1.77 (m, 2H), 1.47 (t, J=5.2 Hz, 3H).

11. Synthesis of 2-(4-(4-(3-propoxypyridin-2-yl)piperazin-1-yl)butoxy)quinolin-8-ol (Compound 11)

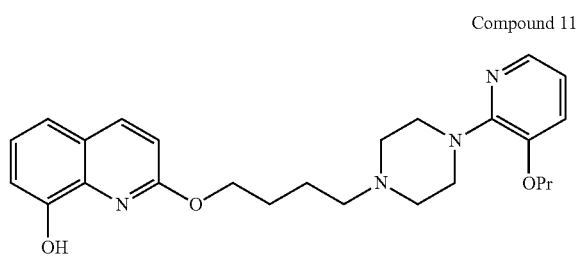

Compound 11

This compound was prepared in 20% yield (last step) (20 mg) as a yellow oil as described for Compound 5 but using 1-(3-propoxypyridin-2-yl)piperazine as the starting material. MS (ESI): m/z 437.2 [M+H]$^+$. $^1$H NMR (400 MHz, CDCl$_3$): δ 8.01-8.03 (d, J=8.8 Hz, 1H), 7.86-7.87 (d, J=4.4 Hz, 1H), 7.25-7.32 (m, 2H), 7.14-7.16 (m, 2H), 7.91-7.96 (m, 2H), 4.49-4.52 (t, J=6.0 Hz, 2H), 4.28 (s, 2H), 3.94-3.99 (m, 2H), 3.65 (s, 4H), 3.08-3.20 (m, 4H), 1.83-2.08 (m, 6H), 1.05-1.08 (t, J=7.6 Hz, 2H).

12. Synthesis of 2-(4-(3,4-dihydroisoquinolin-2(1H)-yl)butoxy)quinolin-8-ol (Compound 12)

Compound 12

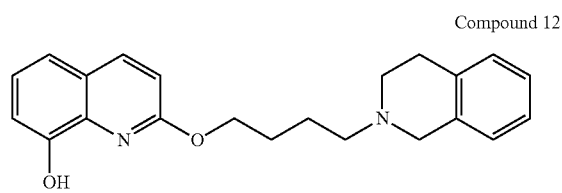 [SMILES: Oc1cccc2ccc(OCCCCN3CCc4ccccc4C3)nc12]

This compound was prepared in 18% yield (last step) (9.2 mg) as a yellow oil as described for Compound 5 but using 1,2,3,4-tetrahydroisoquinoline as the starting material. MS (ESI): m/z 349 [M+H]$^+$. $^1$H NMR (400 MHz, CDCl$_3$): δ 8.00 (d, J=8.8 Hz, 1H), 7.31-7.25 (m, 2H), 7.17-7.10 (m, 4H), 7.05-7.03 (m, 1H), 4.51 (t, J=6.4 Hz, 2H), 3.69 (s, 2H), 2.95 (t, J=6.0 Hz, 2H), 2.80 (t, J=6.0 Hz, 2H), 2.64 (t, J=7.2 Hz, 2H), 1.95 (m, 2H), 1.86 (m, 2H).

13. Synthesis of 2-(4-(6-methoxy-3,4-dihydroisoquinolin-2(1H)-yl)butoxy)quinolin-8-ol (Compound 13)

Compound 13

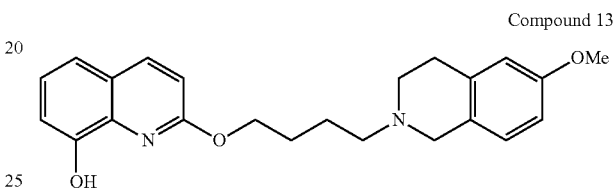

This compound was prepared in 25% yield (last step) (14 mg) as a yellow solid as described for Compound 5 but using 6-methoxy-1,2,3,4-tetrahydroisoquinoline as the starting material. MS (ESI): m/z 379 [M+H]$^+$. $^1$H NMR (400 MHz, CDCl$_3$): δ 8.00 (d, J=8.4 Hz, 1H), 7.31-7.26 (m, 2H), 7.15 (dd, J$_1$=6.8 Hz, J$_2$=1.6 Hz, 1H), 6.55 (d, J=8.4 Hz, 1H), 6.27 (d, J=9.2 Hz, 1H), 4.51 (t, J=6.4 Hz, 2H), 3.78 (s, 3H), 3.67 (s, 2H), 2.92 (m, 2H), 2.82 (t, J=5.6 Hz, 2H), 2.67 (t, J=7.6 Hz, 2H), 1.95-1.86 (m, 4H).

14. Synthesis of 2-(4-(6-chloro-3,4-dihydroisoquinolin-2(1H)-yl)butoxy)quinolin-8-ol (Compound 14)

Compound 14

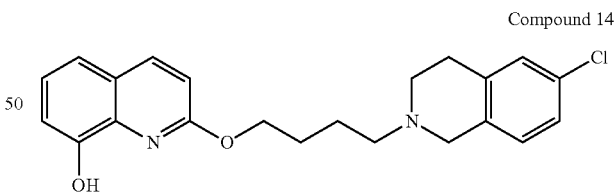

This compound was prepared in 17% yield (last step) (10 mg) as a yellow solid as described for Compound 5 but using 6-chloro-1,2,3,4-tetrahydroisoquinoline as the starting material. MS (ESI): m/z 383 [M+H]$^+$. $^1$H NMR (400 MHz, CDCl$_3$): δ 8.00 (d, J=8.4 Hz, 1H), 7.31-7.26 (m, 2H), 7.15 (dd, J$_1$=6.8 Hz, J$_2$=1.6 Hz, 1H), 6.55 (d, J=8.4 Hz, 1H), 6.27 (d, J=9.2 Hz, 1H), 4.51 (t, J=6.4 Hz, 2H), 3.78 (s, 3H), 3.67 (s, 2H), 2.92 (m, 2H), 2.82 (t, J=5.6 Hz, 2H), 2.67 (t, J=7.6 Hz, 2H), 1.95-1.86 (m, 4H).

15. Synthesis of 2-(4-((8-hydroxyquinolin-2-yl)oxy)butyl)-1,2,3,4-tetrahydroisoquinoline-6-carbonitrile (Compound 15)

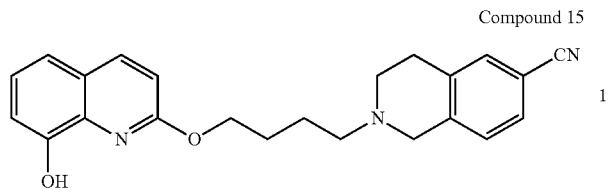

Compound 15

This compound was prepared in 11% yield (last step) (9.8 mg) as a yellow solid as described for Compound 5 but using 1,2,3,4-tetrahydroisoquinoline-6-carbonitrile as the starting material. MS (ESI): m/z 374 [M+H]$^+$. $^1$H NMR (400 MHz, CDCl$_3$): δ 8.11 (d, J=8.4 Hz, 1H), 7.67 (s, 1H), 7.63 (d, J=8.0 Hz, 1H), 7.40 (d, J=8.0 Hz, 1H), 7.31-7.25 (m, 2H), 7.11-7.07 (m, 1H), 6.96 (d, J=8.8 Hz, 1H), 4.82-4.52 (m, 4H), 3.85-3.33 (m, 4H), 3.25 (s, 2H), 2.13-1.95 (m, 4H).

16. Synthesis of 2-(4-(6-fluoro-3,4-dihydroisoquinolin-2(1H)-yl)butoxy)quinolin-8-ol (Compound 16)

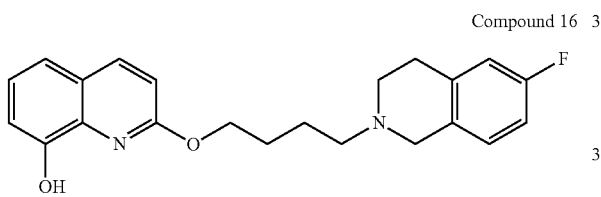 [SMILES: COc1ccc2c(c1)CCN(CCCCOc1ccc3cccc(O)c3n1)C2]

Compound 16

This compound was prepared in 14% yield (last step) (12 mg) as a yellow solid as described for Compound 5 but using 6-fluoro-1,2,3,4-tetrahydroisoquinoline as the starting material. MS (ESI): m/z 367 [M+H]$^+$. $^1$H NMR (400 MHz, CDCl$_3$): δ 8.13 (d, J=9.2 Hz, 1H), 7.32-7.21 (m, 3H), 7.11-7.05 (m, 1H), 6.98 (d, J=8.8 Hz, 1H), 4.65-4.60 (m, 3H), 4.35 (d, J=17.2 Hz, 1H), 3.82 (d, J=1.6 Hz, 1H), 3.50-3.41 (m, 3H), 3.23-3.14 (m, 2H), 2.12-1.97 (m, 4H).

17. Synthesis of 2-(4-(6-(trifluoromethyl)-3,4-dihydroisoquinolin-2(1H)-yl)butoxy)quinolin-8-ol (Compound 17)

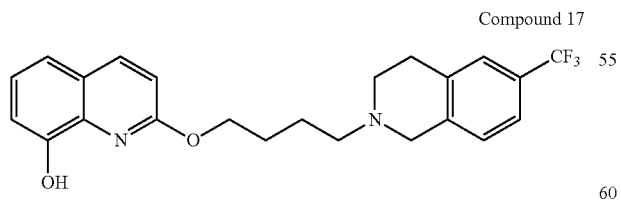

Compound 17

This compound was prepared in 17% yield (last step) (16.7 mg) as a yellow solid as described for Compound 5 but using 6-(trifluoromethyl)-1,2,3,4-tetrahydroisoquinoline as the starting material. MS (ESI): m/z 417 [M+H]$^+$. $^1$H NMR (400 MHz, CDCl$_3$): δ 8.03 (d, J=8.8 Hz, 1H), 7.51 (s, 1H), 7.48 (d, J=8.4 Hz, 1H), 7.30 (d, J=8.0 Hz, 1H), 7.21-7.15 (m, 2H), 7.01-6.97 (m, 2H), 6.87 (d, J=9.2 Hz, 1H), 4.78-4.45 (m, 3H), 4.36 (d, J=5.6 Hz, 1H), 3.73 (t, J=6.4 Hz, 1H), 3.56-3.30 (m, 3H), 3.21-3.17 (m, 2H), 2.04-1.87 (m, 4H).

18. Synthesis of 2-(4-(6,7-dihydrothieno[3,2-c]pyridin-5(4H)-yl)butoxy)quinolin-8-ol (Compound 18)

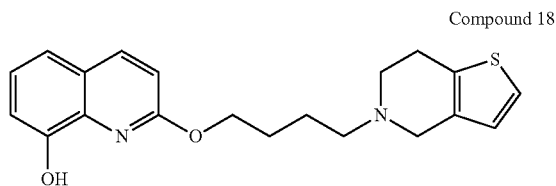 [SMILES: Oc1cccc2ccc(OCCCCN3CCc4sccc4C3)nc12]

Compound 18

This compound was prepared in 20% yield (last step) (16 mg) as a yellow solid as described for Compound 5 but using 4,5,6,7-tetrahydrothieno[3,2-c]pyridine as the starting material. MS (ESI): m/z 355 [M+H]$^+$. $^1$H NMR (400 MHz, CD$_3$OD): δ 8.11 (d, J=8.8 Hz, 1H), 7.39 (d, J=5.2 Hz, 1H), 7.29 (m, 2H), 7.08 (dd, J$_1$=6.4 Hz, J$_2$=2.4 Hz, 1H), 6.96 (d, J=8.4 Hz, 1H), 6.88 (d, J=5.2 Hz, 1H), 4.63 (t, J=6.0 Hz, 3H), 4.26 (s, 1H), 3.87 (s, 1H), 3.44 (d, J=8.4 Hz, 3H), 3.23 (t, s, 2H), 1.99 (m, 4H).

19. Synthesis of 2-(4-(4,5-dihydrothieno[2,3-c]pyridin-6(7H)-yl)butoxy)quinolin-8-ol (Compound 19)

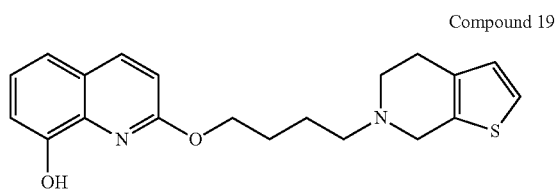 [SMILES: Oc1cccc2ccc(OCCCCN3CCc4ccsc4C3)nc12]

Compound 19

This compound was prepared in 20% yield (last step) (15 mg) as a yellow solid as described for Compound 5 but using 4,5,6,7-tetrahydrothieno[2,3-c]pyridine as the starting material. MS (ESI): m/z 355 [M+H]$^+$. $^1$H NMR (400 MHz, CDCl$_3$): δ 8.00 (d, J=7.2 Hz, 1H), 7.58 (brs, 1H), 7.29-7.20 (m, 2H), 7.15 (dd, J$_1$=5.6 Hz, J$_2$=1.2 Hz, 1H), 7.10 (d, J=4.0 Hz, 1H), 6.39 (d, J=7.2 Hz, 1H), 6.79 (d, J=4.0 Hz, 1H), 4.51 (t, J=5.2 Hz, 2H), 3.74 (s, 3H), 2.82 (m, 2H), 2.78 (m, 2H), 2.67 (t, J=5.6 Hz, 2H), 1.94 (m, 2H), 1.83 (m, 2H).

20. Synthesis of 2-(4-(5-chloro-3,4-dihydroisoquinolin-2(1H)-yl)butoxy)quinolin-8-ol (Compound 20)

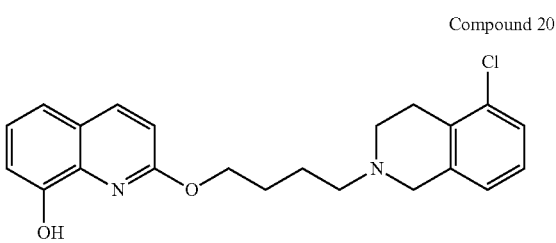 [SMILES: Oc1cccc2ccc(OCCCCN3CCc4c(Cl)cccc4C3)nc12]

Compound 20

This compound was prepared in 19% yield (last step) (15 mg) as described for Compound 5 but using 5-chloro-1,2,3,4-tetrahydroisoquinoline as the starting material. MS (ESI): m/z 383 [M+H]$^+$. $^1$H NMR (400 MHz, CDCl$_3$): δ 8.00 (d, J=8.8 Hz, 1H), 7.36 (d, J=8.0 Hz, 1H), 7.28 (d, J=7.2 Hz, 1H), 7.21 (m, 2H), 7.14 (dd, J$_1$=7.6 Hz, J$_2$=1.6 Hz, 1H), 7.02 (d, J=7.2 Hz, 1H), 6.88 (d, J=8.8 Hz, 1H), 4.73 (m, 1H), 4.97 (t, J=5.6 Hz, 2H), 4.09 (s, 1H), 3.81 (s, 1H), 3.26 (m, 5H), 2.08 (m, 2H), 1.95 (t, J=6.0 Hz, 2H).

21. Synthesis of 2-(4-(8-(trifluoromethyl)-3,4-dihydroisoquinolin-2(1H)-yl)butoxy)quinolin-8-ol (Compound 21)

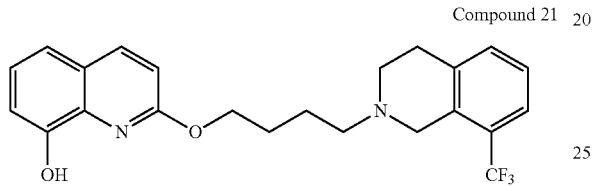

Compound 21

This compound was prepared in 32% yield (last step) (30 mg) as described for Compound 5 but using 8-(trifluoromethyl)-1,2,3,4-tetrahydroisoquinoline as the starting material. MS (ESI): m/z 417.4 [M+H]$^+$. $^1$H NMR (400 MHz, CDCl$_3$): δ 8.00-8.02 (d, J=8.8 Hz, 1H), 7.60-7.62 (m, 1H), 7.38-7.43 (m, 2H), 7.25-7.32 (m, 2H), 7.14-7.16 (m, 1H), 6.89-6.91 (d, J=9.2 Hz, 1H), 4.75 (s, 1H), 4.51 (m, 2H), 4.43 (s, 1H), 3.85 (s, 1H), 3.30 (m, 5H), 2.10 (m, 2H), 1.95 (m, 2H).

22. Synthesis of 2-(4-(4-((8-hydroxyquinolin-2-yl)oxy)butyl)piperazin-1-yl)nicotinonitrile (Compound 22)

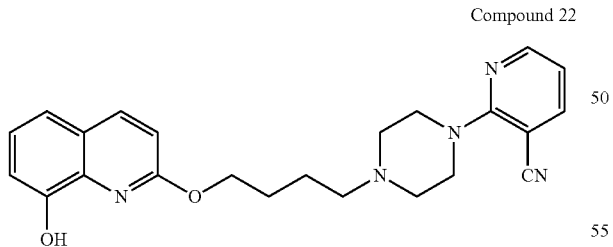

Compound 22

This compound was prepared in 15% yield (last step) (11 mg) as described for Compound 5 but using 2-(piperazin-1-yl)nicotinonitrile as the starting material. MS (ESI): m/z 404 [M+H]$^+$. $^1$H NMR (400 MHz, CDCl$_3$): δ 8.34 (dd, J=2.4 Hz, 4.8 Hz, 1H), 8.00 (d, J=8.8 Hz, 1H), 7.77 (dd, J=1.6 Hz, 7.2 Hz, 1H), 7.60 (br, 1H), 7.31-7.24 (m, 2H), 7.15 (dd, J=1.6 Hz, 7.2 Hz, 1H), 6.93 (d, J=8.8 Hz, 1H), 6.74 (dd, J=5.2 Hz, 8.0 Hz, 1H), 4.50 (t, J=6.4 Hz, 2H), 3.78 (t, J=4.8 Hz, 4H), 2.64 (t, J=4.8 Hz, 4H), 2.52 (t, J=7.2 Hz, 2H), 1.96-1.89 (m, 2H), 1.81-1.73 (m, 2H).

23. Synthesis of 7-(4-(7,8-dihydropyrido[4,3-d]pyrimidin-6(5H)-yl)butoxy)-3,4-dihydroquinolin-2(1H)-one (Compound 23)

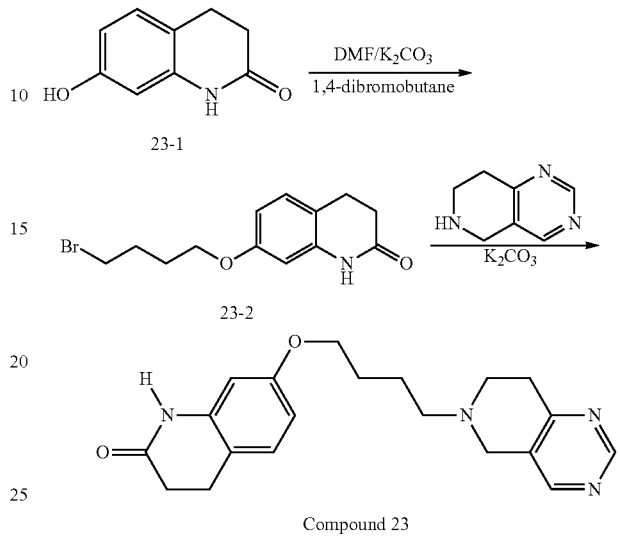

Compound 23

(a) Synthesis of 7-(4-bromobutoxy)-3,4-dihydroquinolin-2(1H)-one (23-2)

To a mixture of 7-hydroxy-3,4-dihydroquinolin-2(1H)-one (23-1) (14.0 g, 85.9 mmol, 1.0 eq) and potassium carbonate (17.8 g, 129 mmol, 1.5 eq) in N,N-dimethylformamide (200 mL) was added 1,4-dibromobutane (46.0 g, 215 mmol, 2.5 eq). The mixture was stirred at 50° C. overnight. The reaction mixture was poured into 500 mL of water, extracted with ethyl acetate (200 mL×2), dried over sodium sulfate and concentrated in vacuo to give the crude product, which was purified by silica gel column chromatography (petroleum ether:ethyl acetate=5:1) to give compound 23-2 as a white solid (8.2 g, yield: 32%). MS (ESI): m/z 298, 300 [M+H]$^+$.

(b) Synthesis of 7-(4-(7,8-dihydropyrido[4,3-d]pyrimidin-6(5H)-yl)butoxy)-3,4-dihydroquinolin-2(1H)-one (Compound 23)

To a mixture of compound 23-2 (60 mg, 0.2 mmol, 1.0 eq) and 5,6,7,8-tetrahydropyrido[4,3-d]pyrimidine hydrochloride (52 mg, 0.3 mmol, 1.5 eq) in acetonitrile (10 mL) was added potassium carbonate (83 mg, 0.6 mmol, 3.0 eq). The mixture was stirred and refluxed for 4 hours. The reaction mixture was then concentrated in vacuo to give the crude product, which was purified by reverse phase column (acetonitrile in water, 40% v/v, with 0.01% aqueous ammonia) to give compound 23 as a white solid. (26 mg, yield: 50%). MS (ESI): m/z 353 [M+H]$^+$. $^1$H NMR (400 MHz, CDCl$_3$): δ 8.97 (brs, 1H), 8.77 (s, 1H), 8.39 (s, 1H), 7.04-7.02 (d, J=8.4 Hz, 1H), 6.53-6.50 (dd, J$^1$=2.4 Hz, J$^2$=2.4 Hz, 1H), 6.37 (d, J=2.0 Hz, 1H), 3.99-3.96 (t, J=6.0 Hz, 2H), 3.63 (s, 2H), 3.03-3.00 (t, J=6.0 Hz, 2H), 2.91-2.83 (m, 4H), 2.65-2.60 (m, 4H), 1.88-1.75 (m, 4H).

24. Synthesis of 7-(4-(2-methyl-6,7-dihydro-2H-pyrazolo[4,3-c]pyridin-5(4H)-yl)butoxy)-3,4-dihydroquinolin-2(1H)-one (Compound 24)

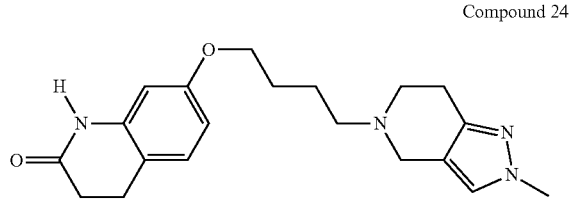 [SMILES: Cn1cc2c(n1)CCN(CCCCOc1ccc3c(c1)NC(=O)CC3)C2]

Compound 24

This compound was prepared in 48% yield as described for Compound 23 but using 2-methyl-4,5,6,7-tetrahydro-2H-pyrazolo[4,3-c]pyridine as the starting material. MS (ESI): m/z 355 [M+H]$^+$. $^1$H NMR (400 MHz, CDCl$_3$): δ 8.01 (brs, 1H), 7.07-7.03 (m, 2H), 6.54-6.51 (dd, J$^1$=2.8 Hz, J$^2$=2.8 Hz, 1H), 6.33 (d, J=2.4 Hz, 1H), 3.97 (t, J=6.0 Hz, 2H), 3.84 (s, 3H), 3.53 (s, 2H), 2.90 (t, J=7.2 Hz, 2H), 2.80 (s, 4H), 2.64-2.59 (m, 4H), 1.87-1.72 (m, 4H).

25. Synthesis of 7-(4-(7,8-dihydropyrido[3,4-b]pyrazin-6(5H)-yl)butoxy)-3,4-dihydroquinolin-2(1H)-one (Compound 25)

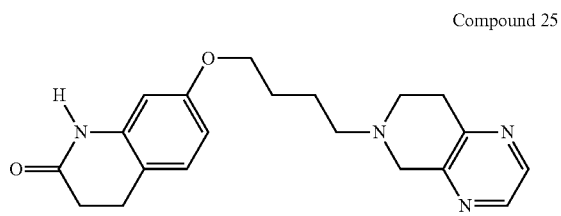 [SMILES: O=C1CCc2ccc(OCCCCN3CCc4nccnc4C3)cc2N1]

Compound 25

This compound was prepared in 57.6% yield as a light brown solid as described for Compound 23 but using 5,6,7,8-tetrahydropyrido[3,4-b]pyrazine as the starting material. MS (ESI): m/z 353 [M+H]$^+$. $^1$H NMR (400 MHz, CDCl$_3$): δ 8.92 (brs, 1H), 8.36-8.32 (dd, J$^1$=2.4 Hz, J$^2$=2.4 Hz, 2H), 7.03-7.01 (d, J=8.4 Hz, 1H), 6.52-6.50 (dd, J$^1$=2.4 Hz, J$^2$=2.4 Hz, 1H), 6.38 (d, J=2.4 Hz, 1H), 3.98-3.95 (t, J=5.6 Hz, 2H), 3.77 (s, 2H), 3.09-3.06 (t, J=5.6 Hz, 2H), 2.90-2.85 (m, 4H), 2.67-2.59 (m, 4H), 1.86-1.76 (m, 4H).

26. Synthesis of 7-(4-(6,7-dihydrothiazolo[5,4-c]pyridin-5(4H)-yl)butoxy)-3,4-dihydroquinolin-2(1H)-one (Compound 26)

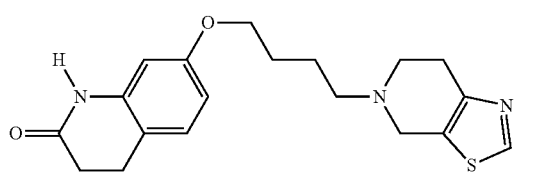

Compound 26

This compound was prepared in 43% yield as described for Compound 23 but using 4,5,6,7-tetrahydrothiazolo[5,4-c]pyridine as the starting material. MS (ESI): m/z 358 [M+H]$^+$. $^1$H NMR (400 MHz, CDCl$_3$): δ 8.64 (s, 1H), 8.44 (s, 1H), 7.04 (d, J=8.4 Hz, 1H), 6.53-6.51 (dd, J$^1$=2.4 Hz, J$^2$=2.0 Hz, 1H), 6.36 (d, J=2.0 Hz, 1H), 3.97 (t, J=6.0 Hz, 2H), 3.79 (s, 2H), 3.00-2.97 (m, 2H), 2.94-2.85 (m, 4H), 2.68 (t, J=7.2 Hz, 2H), 2.64-2.58 (m, 2H), 1.88-1.75 (m, 4H).

27. Synthesis of 7-(4-(6,7-dihydrothieno[3,2-c]pyridin-5(4H)-yl)butoxy)-3,4-dihydroquinolin-2(1H)-one (Compound 27)

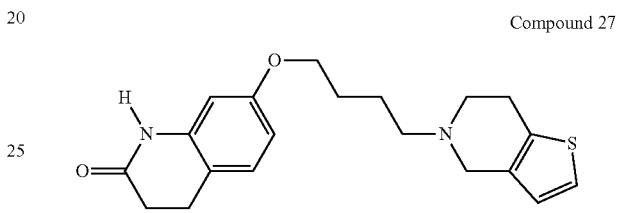

Compound 27

This compound was prepared in 48.9% yield as described for Compound 23 but using 4,5,6,7-tetrahydrothieno[3,2-c]pyridine as the starting material. MS (ESI): m/z 357 [M+H]$^+$. $^1$H NMR (400 MHz, CDCl$_3$): δ 7.69(s, 1H), 7.11 (d, J=5.2 Hz, 1H), 7.05 (d, J=8.4 Hz, 1H), 6.74 (d, J=4.8 Hz, 1H), 6.54-6.52 (dd, J$^1$=2.4 Hz, J$^2$=2.4 Hz, 1H), 6.30 (d, J=2.0 Hz, 1H), 3.98 (t, J=6.0 Hz, 2H), 3.66(s, 2H), 2.95-2.89 (m, 6H), 2.70-2.61 (m, 2H), 1.87-1.84 (m, 4H).

28. Synthesis of 7-(4-(4,5-dihydrothieno[2,3-c]pyridin-6(7H)-yl)butoxy)-3,4-dihydroquinolin-2(1H)-one (Compound 28)

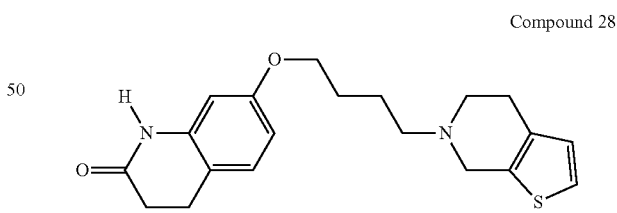

Compound 28

This compound was prepared in 39% yield as described for Compound 23 but using 4,5,6,7-tetrahydrothieno[2,3-c]pyridine as the starting material. MS (ESI): m/z 357 [M+H]$^+$. $^1$H NMR (400 MHz, CDCl$_3$): δ 8.20 (brs, 1H), 7.10-7.04 (dd, J$^1$=4.8 Hz, J$^2$=8.0 Hz, 1H), 6.79 (d, J=5.2 Hz, 1H), 6.55-6.52 (dd, J$^1$=2.4 Hz, J$^2$=2.4 Hz, 1H), 6.33 (d, J=2.0 Hz, 2H), 3.98 (t, J=6.0 Hz, 2H), 3.71 (s, 2H), 2.90 (t, J=6.8 Hz, 2H), 2.82-2.74 (m, 4H), 2.65-2.61 (m, 4H), 1.89-1.73 (m, 4H).

29. Synthesis of 7-(4-(4-(dimethylamino)-5,6-dihydropyrido[3,4-d]pyrimidin-7(8H)-yl)butoxy)-3,4-dihydroquinolin-2(1H)-one (Compound 29)

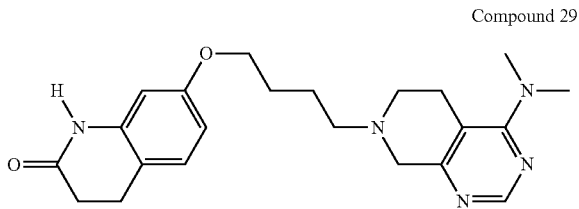 [SMILES: CN(C)c1ncnc2c1CCN(CCCCOc1ccc3c(c1)NC(=O)CC3)C2]

Compound 29

This compound was prepared in 27% yield as described for Compound 23 but using N,N-dimethyl-5,6,7,8-tetrahydropyrido[3,4-d]pyrimidin-4-amine as the starting material. MS (ESI): m/z 396.1 [M+H]$^+$. $^1$H NMR (400 MHz, CDCl$_3$): δ 8.46 (s, 1H), 7.91 (brs, 1H), 7.05 (d, J=8.0 Hz, 1H), 6.55-6.52 (dd, J$^1$=2.4 Hz, J$^2$=2.8 Hz, 1H), 6.32 (d, J=2.0 Hz, 1H), 3.98 (t, J=5.6 Hz, 2H), 3.62 (s, 2H), 3.07 (s, 6H), 2.90 (t, J=7.2 Hz, 2H), 2.80 (t, J=5.6 Hz, 2H), 2.67-2.57 (m, 6H), 1.80-1.74 (m, 4H).

30. Synthesis of 7-(4-(2-phenyl-6,7-dihydro-2H-pyrazolo[4,3-c]pyridin-5(4H)-yl)butoxy)-3,4-dihydroquinolin-2(1H)-one (Compound 30)

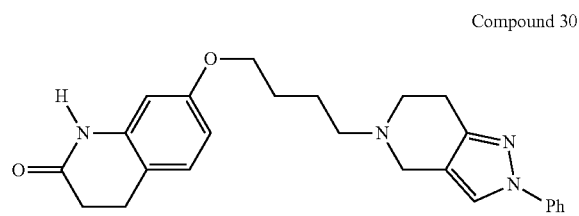 [SMILES: O=C1CCc2ccc(OCCCCN3CCc4nn(-c5ccccc5)cc4C3)cc2N1]

Compound 30

This compound was prepared in 42% yield as described for Compound 23 but using 2-phenyl-4,5,6,7-tetrahydro-2H-pyrazolo[4,3-c]pyridine as the starting material. MS (ESI): m/z 417.1 [M+H]$^+$. HPLC purity=99%. $^1$H NMR (400 MHz, CDCl$_3$): δ 7.64-7.62 (dd, J$^1$=1.2 Hz, J$^2$=1.2 Hz, 3H), 7.47-7.41 (m, 3H), 7.25-7.24 (m, 1H), 7.05 (d, J=8.4 Hz, 1H), 6.55-6.52 (dd, J$^1$=2.4 Hz, J$^2$=2.4 Hz, 1H), 6.30 (d, J=2.8 Hz, 1H), 3.99 (t, J=5.6 Hz, 2H), 3.65 (s, 2H), 2.94-2.88 (m, 6H), 2.69-2.60 (m, 4H), 1.88-1.80 (m, 4H).

31. Synthesis of 7-(4-(1-phenyl-6,7-dihydro-1H-pyrazolo[4,3-c]pyridin-5(4H)-yl)butoxy)-3,4-dihydroquinolin-2(1H)-one (Compound 31)

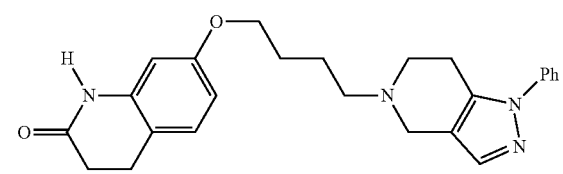

Compound 31

This compound was prepared in 39% yield as described for Compound 23 but using 1-phenyl-4,5,6,7-tetrahydro-1H-pyrazolo[4,3-c]pyridine as the starting material. MS (ESI): m/z 417.1 [M+H]$^+$. $^1$H NMR (400 MHz, CDCl$_3$): δ 7.57 (s, 1H), 7.53-7.44 (m, 5H), 7.34-7.31 (t, J=7.2 Hz, 1H), 7.06 (d, J=8.4 Hz, 1H), 6.56-6.53 (dd, J$^1$=2.4 Hz, J$^2$=2.4 Hz, 1H), 6.30 (d, J=2.4 Hz, 1H), 3.99 (t, J=5.6 Hz, 2H), 3.61 (s, 2H), 2.93-2.82 (m, 6H), 2.70-2.61 (m, 4H), 1.90-1.74 (m, 4H).

32. Synthesis of 7-(4-(1-(3-chlorophenyl)-6,7-dihydro-1H-pyrazolo[4,3-c]pyridin-5(4H)-yl)butoxy)-3,4-dihydroquinolin-2(1H)-one (Compound 32)

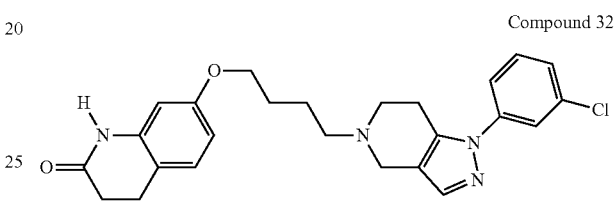

Compound 32

This compound was prepared in 45% yield as described for Compound 23 but using 1-(3-chlorophenyl)-4,5,6,7-tetrahydro-1H-pyrazolo[4,3-c]pyridine as the starting material. MS (ESI): m/z 451.1 [M+H]$^+$. $^1$H NMR (400 MHz, CDCl$_3$): δ 7.57 (t, J=1.6 Hz, 1H), 7.53-7.48 (m, 2H), 7.44-7.36 (m, 2H), 731-7.28 (m, 1H), 7.06 (d, J=4.0 Hz, 1H), 6.56-6.53 (dd, J$^1$=2.4 Hz, J$^2$=2.0 Hz, 1H), 6.30 (d, J=2.4 Hz, 1H), 3.99 (t, J=6.0 Hz, 2H), 3.59 (s, 2H), 2.93-2.81 (m, 6H), 2.69-2.61 (m, 4H), 1.89-1.76 (m, 4H).

33. Synthesis of 7-(4-(5,6-dihydroimidazo[1,5-a]pyrazin-7(8H)-yl)butoxy)-3,4-dihydroquinolin-2(1H)-one (Compound 33)

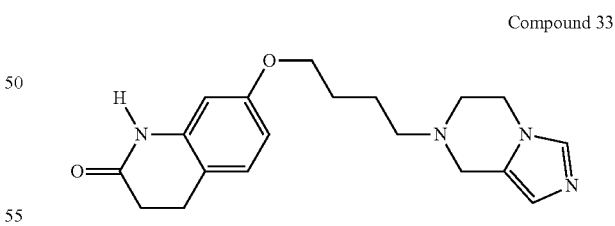

Compound 33

This compound was prepared in 10% yield as described for Compound 23 but using 5,6,7,8-tetrahydroimidazo[1,5-a]pyrazine as the starting material. MS (ESI): m/z 341.1 [M+H]$^+$. $^1$H NMR (400 MHz, CDCl$_3$): δ 8.15 (s, 1H), 7.41 (s, 1H), 7.05 (d, J=8.4 Hz, 1H), 6.78 (s, 1H), 6.54-6.51 (dd, J$^1$=2.4 Hz, J$^2$=2.4 Hz, 1H), 6.33 (d, J=2.0 Hz, 1H), 4.06 (t, J=5.6 Hz, 2H), 3.97 (t, J=5.6 Hz, 2H), 3.68 (s, 2H), 2.92-2.84 (m, 4H), 2.64-2.60 (m, 4H), 1.88-1.82 (m, 2H), 1.80-1.71 (m, 2H).

34. Synthesis of 7-(4-(2-ethyl-6,7-dihydro-2H-pyrazolo[4,3-c]pyridin-5(4H)-yl)butoxy)-3,4-dihydroquinolin-2(1H)-one (Compound 34)

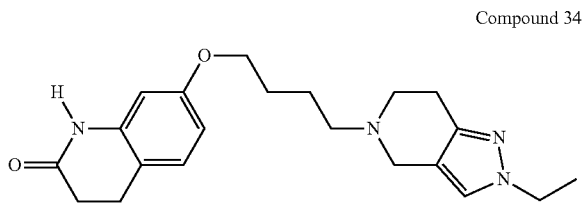 [SMILES: CCn1cc2c(n1)CCN(CCCCOc1ccc3c(c1)NC(=O)CC3)C2]

Compound 34

This compound was prepared in 19% yield as described for Compound 23 but using 2-ethyl-4,5,6,7-tetrahydro-2H-pyrazolo[4,3-c]pyridine as the starting material. MS (ESI): m/z 369.1 [M+H]$^+$. $^1$H NMR (400 MHz, CDCl$_3$): δ 8.22 (s, 1H), 7.10 (s, 1H), 7.04 (d, J=8.4 Hz, 1H), 6.54-6.51 (dd, J$^1$=2.4 Hz, J$^2$=2.4 Hz, 1H), 6.34 (d, J=2.8 Hz, 1H), 4.13-4.07 (q, J=3.2 Hz, 2H), 3.97 (t, J=6.4 Hz, 2H), 3.52 (s, 2H), 2.91-2.77 (m, 6H), 2.64-2.58 (m, 4H), 1.87-1.71 (m, 4H), 1.45 (t, J=7.2 Hz, 3H).

35. Synthesis of 7-(4-(2-(2-fluorophenyl)-6,7-dihydro-2H-pyrazolo[4,3-c]pyridin-5(4H)-yl)butoxy)-3,4-dihydroquinolin-2(1H)-one (Compound 35)

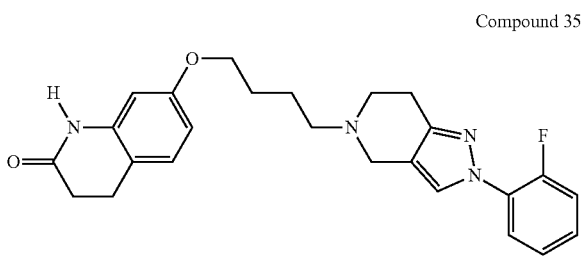 [SMILES: O=C1CCc2ccc(OCCCCN3CCc4nn(-c5ccccc5F)cc4C3)cc2N1]

Compound 35

This compound was prepared in 57% yield as described for Compound 23 but using 2-(2-fluorophenyl)-4,5,6,7-tetrahydro-2H-pyrazolo[4,3-c]pyridine as the starting material. MS (ESI): m/z 435.1 [M+H]$^+$. $^1$H NMR (400 MHz, CDCl$_3$): δ 7.94 (s, 1H), 7.88-7.83 (m, 1H), 7.72 (d, J=2.8 Hz, 1H), 7.25-7.18 (m, 3H), 7.05 (d, J=8.4 Hz, 1H), 6.55-6.52 (dd, J$^1$=2.4 Hz, J$^2$=2.0 Hz, 1H), 6.33 (d, J=2.4 Hz, 1H), 3.99 (t, J=6.0 Hz, 2H), 3.64 (s, 2H), 2.95-2.88 (m, 6H), 2.68-2.61 (m, 4H), 1.90-1.76 (m, 4H).

36. Synthesis of 7-(4-(2-(3-fluorophenyl)-6,7-dihydro-2H-pyrazolo[4,3-c]pyridin-5(4H)-yl)butoxy)-3,4-dihydroquinolin-2(1H)-one (Compound 36)

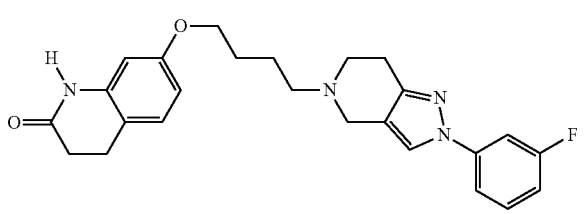

Compound 36

This compound was prepared in 61% yield as described for Compound 23 but using 2-(3-fluorophenyl)-4,5,6,7-tetrahydro-2H-pyrazolo[4,3-c]pyridine as the starting material. MS (ESI): m/z 435.1 [M+H]$^+$. $^1$H NMR (400 MHz, CDCl$_3$): δ 7.73 (s, 1H), 7.48 (s, 1H), 7.44-7.38 (m, 1H), 7.33-7.28 (m, 2H), 7.07-7.00 (m, 2H), 6.56-6.53 (dd, J$^1$=2.8 Hz, J$^2$=2.4 Hz, 1H), 6.31 (d, J=2.0 Hz, 1H), 3.99 (t, J=5.6 Hz, 2H), 3.59 (s, 2H), 2.94-2.89 (m, 6H), 2.69-2.61 (m, 4H), 1.90-1.76 (m, 4H).

37. Synthesis of 7-(4-(2-(4-fluorophenyl)-6,7-dihydro-2H-pyrazolo[4,3-c]pyridin-5(4H)-yl)butoxy)-3,4-dihydroquinolin-2(1H)-one (Compound 37)

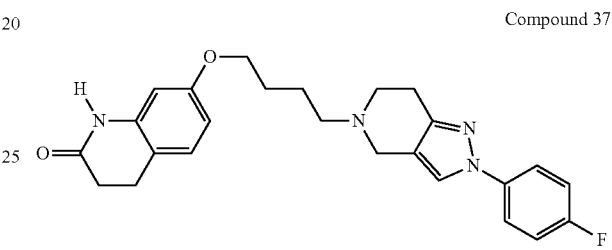

Compound 37

This compound was prepared in 66% yield as described for Compound 23 but using 2-(4-fluorophenyl)-4,5,6,7-tetrahydro-2H-pyrazolo[4,3-c]pyridine as the starting material. MS (ESI): m/z 435.1 [M+H]$^+$. $^1$H NMR (400 MHz, CDCl$_3$): δ 7.62-7.57 (m, 4H), 7.14-7.04 (m, 3H), 6.55-6.52 (dd, J$^1$=2.8 Hz, J$^2$=2.4 Hz, 1H), 6.30 (d, J=2.4 Hz, 1H), 3.99 (t, J=5.6 Hz, 2H), 3.63 (s, 2H), 2.92-2.87 (m, 6H), 2.67-2.60 (m, 4H), 1.88-1.77 (m, 4H).

38. Synthesis of 7-(4-(2-(pyridin-2-yl)-6,7-dihydro-2H-pyrazolo[4,3-c]pyridin-5(4H)-yl)butoxy)-3,4-dihydroquinolin-2(1H)-one (Compound 38)

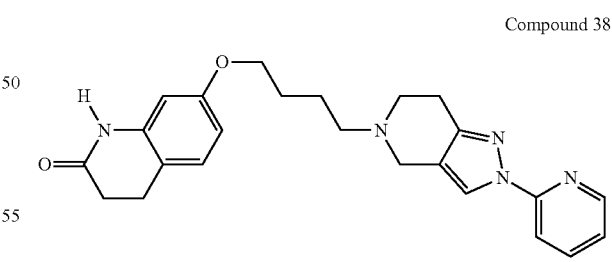

Compound 38

This compound was prepared in 32% yield as described for Compound 23 but using 2-(pyridin-2-yl)-4,5,6,7-tetrahydro-2H-pyrazolo[4,3-c]pyridine as the starting material. MS (ESI): m/z 418.1 [M+H]$^+$. $^1$H NMR (400 MHz, CDCl$_3$): δ 8.39 (d, J=4.0 Hz, 1H), 8.27 (s, 1H), 7.90 (d, J=8.4 Hz, 1H), 7.79-7.75 (t, J=7.2 Hz, 1H), 7.13 (t, J=6.4 Hz, 1H), 7.05 (d, J=8.0 Hz, 1H), 6.55-6.52 (dd, J$^1$=2.4 Hz, J$^2$=2.4 Hz, 1H), 6.33-6.30 (m, 1H), 3.99 (t, J=5.6 Hz, 2H), 3.63 (s, 2H), 2.92-2.86 (m, 6H), 2.66-2.60 (m, 4H), 1.89-1.78 (m, 4H).

39. Synthesis of 7-(4-(2-(4-methoxyphenyl)-6,7-dihydro-2H-pyrazolo[4,3-c]pyridin-5(4H)-yl)butoxy)-3,4-dihydroquinolin-2(1H)-one (Compound 39)

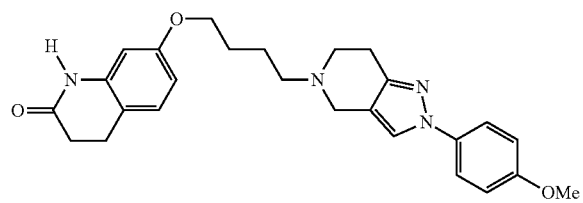

Compound 39

This compound was prepared in 39% yield as described for Compound 23 but using 2-(4-methoxyphenyl)-4,5,6,7-tetrahydro-2H-pyrazolo[4,3-c]pyridine as the starting material. MS (ESI): m/z 447.1 [M+H]$^+$. $^1$H NMR (400 MHz, CDCl$_3$): δ 7.55-7.50 (m, 4H), 7.05 (d, J=8.4 Hz, 1H), 6.97-6.93 (m, 2H), 6.55-6.52 (dd, J$^1$=2.0 Hz, J$^2$=2.4 Hz, 1H), 6.30 (d, J=2.8 Hz, 1H), 3.99 (t, J=5.6 Hz, 2H), 3.67 (brs, 2H), 2.94-2.88 (m, 6H), 2.69-2.60 (m, 4H), 1.86-1.85 (m, 4H).

40. Synthesis of N-(6-(4-(3,4-dihydroisoquinolin-2(1H)-yl)butoxy)pyridin-2-yl)acetamide (Compound 40)

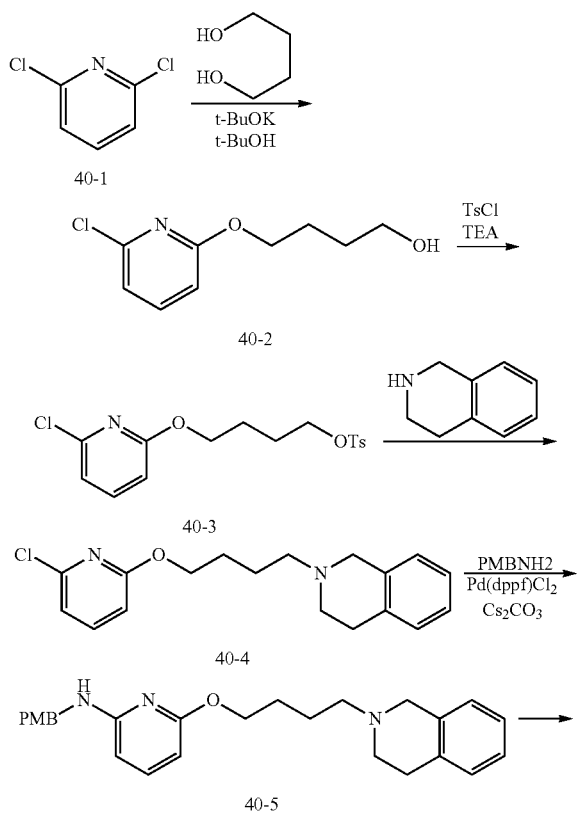

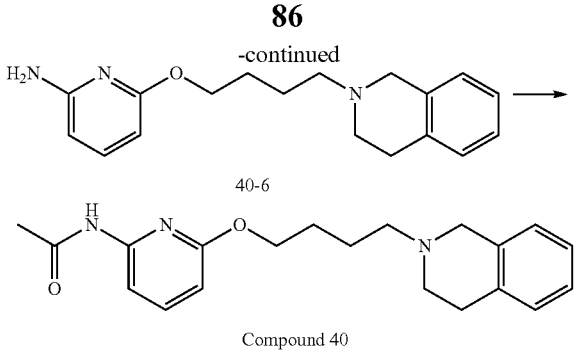

Compound 40

(a) Synthesis of 4-(6-chloropyridin-2-yloxy)butan-1-ol (40-2)

A mixture of compound 40-1 (3.0 g, 20.4 mmol, 1.0 eq.), butane-1,4-diol (2.39 g, 26.5 mmol, 1.3 eq.), and potassium tert-butanolate (4.57 g, 40.8 mmol, 2.0 eq.) in 100 mL of tert-butanol was heated to 90° C. for 2 h. The mixture was evaporated to remove tert-butanol and then quenched with 80 mL of water. The mixture was extracted with 30 mL of ethyl acetate twice. The organic phase was washed with brine, dried over anhydrous sodium sulfate and evaporated to give the crude product, which was purified by column chromatography (silica gel, petroleum ether to ethyl acetate/petroleum ether=1/3) to afford 4-(6-chloropyridin-2-yloxy)butan-1-ol as a colorless oil (2.7 g, yield: 65.9%). MS (ESI): m/z 202 [M+H]$^+$.

(b) Synthesis of 4-(6-chloropyridin-2-yloxy)butyl 4-methylbenzenesulfonate (40-3)

To a solution of compound 40-2 (2.6 g, 12.9 mmol, 1.0 eq.) and triethylamine (1.44 g, 14.2 mmol, 1.1 eq.) in 25 mL of dichloromethane, was added 4-methylbenzene-1-sulfonyl chloride (2.47 g, 13.0 mmol, 1.0 eq.) in 20 mL of chloromethane dropwise at 0° C. The mixture was stirred at room temperature overnight. The solvent was evaporated to afford the crude product, which was purified by column chromatography (silica gel, ethyl acetate/petroleum ether=1/8) to give 4-(6-chloropyridin-2-yloxy)butyl 4-methylbenzenesulfonate as a colorless oil (3.5 g, yield: 76.3%).

(c) Synthesis of 2-(4-(6-chloropyridin-2-yloxy)butyl)-1,2,3,4-tetrahydro-isoquinoline (40-4)

A mixture of compound 40-3 (3.5 g, 9.86 mmol, 1.0 eq.) and 1,2,3,4-tetrahydro-isoquinoline (6.56 g, 48.3 mmol, 5.0 eq.) in tert-butanol (50 mL) was heated at 120° C. for 4 h. The mixture was quenched with 100 mL of brine and extracted with 30 mL of ethyl acetate twice. The organic phase was washed with brine, dried over anhydrous sodium sulfate and evaporated to give the crude product, which was purified by column chromatography (silica gel, ethyl acetate/petroleum ether=1/5) to afford 2-(4-(6-chloropyridin-2-yloxy)butyl)-1,2,3,4-tetrahydro-isoquinoline as a yellow oil (3.0 g, yield: 96.5%). MS (ESI): m/z 319, 317 [M+H]$^+$.

(d) Synthesis of 6-(4-(3,4-dihydroisoquinolin-2(1H)-yl)butoxy)-N-(4-methoxy-benzyl)-pyridin-2-amine (40-5)

A mixture of compound 40-4 (1.0 g, 3.16 mmol, 1.0 eq.), (4-methoxyphenyl)methanamine (2.16 g, 15.8 mmol, 5.0 eq.), 1,1'-bis(diphenylphosphino)-ferrocene-palladium (II) dichloride dichloromethane (260 mg, 0.316 mmol, 0.1 eq.), and cesium carbonate (3.08 g, 9.48 mmol, 3.0 eq.) in 20 mL of dioxane was heated at 110° C. under nitrogen for 4 h. The mixture was quenched with 30 mL of water and extracted with 20 mL of ethyl acetate twice. The organic phase was washed with brine, dried over anhydrous sodium sulfate and evaporated to give the crude product, which was purified by column chromatography (silica gel, ethyl acetate/dichloromethane=1/4) to afford 6-(4-(3,4-dihydroisoquinolin-2 (1H)-yl)butoxy)-N-(4-methoxybenzyl)-pyridin-2-amine as a yellow oil (800 mg, yield: 60.7%). MS (ESI): m/z 418 [M+H]$^+$.

(e) Synthesis of 6-(4-(3,4-dihydroisoquinolin-2 (1H)-yl)butoxy)pyridin-2-amine (40-6)

A mixture of compound 40-5 (800 mg, 1.92 mmol, 1.0 eq) and 2,2,2-trifluoroacetic acid (20 mL) was heated to reflux overnight. The mixture was cooled and evaporated to remove 2,2,2-trifluoroacetic acid and quenched with aqueous sodium bicarbonate to pH 7-8. The mixture was extracted with 5 mL of chloromethane three times. The organic phase was washed with brine, dried over anhydrous sodium sulfate and evaporated to dryness in vacuum to afford 6-(4-(3,4-dihydroisoquinolin-2(1H)-yl)butoxy)pyridin-2-amine as a brown oil (566 mg, yield: 99.5%). The crude product was used in next steps without further purification. MS (ESI): m/z 298 [M+H]$^+$.

(f) Synthesis of N-(6-(4-(3,4-dihydroisoquinolin-2 (1H)-yl)-butoxy)pyridin-2-yl)-acetamide (Compound 40)

To a mixture of compound 40-6 (30 mg, 0.101 mmol, 1.0 eq.) and triethylamine (12 mg, 0.121 mmol, 1.2 eq.) in 1 mL of dichloromethane was added acetyl chloride (9 mg, 0.11 mmol, 1.1 eq.) at room temperature. The mixture was stirred at this temperature for 1 h. The mixture was evaporated to give the crude product, which was purified with prep-TLC (silica gel, ethyl acetate/petroleum ether=1/1) to afford N-(6-(4-(3,4-dihydroisoquinolin-2(1H)-yl)-butoxy)pyridin-2-yl)-acetamide (Compound 40) as a colorless oil (10 mg, yield: 29.4%). MS (ESI): m/z 340 [M+H]$^+$. $^1$H NMR (400 MHz, CDCl$_3$): δ 7.70 (d, J=7.6 Hz, 1H), 7.64 (bs, 1H), 7.57 (t, J=8.0 Hz, 1H), 7.13-7.08 (m, 3H), 7.02-7.00 (m, 1H), 6.45 (d, J=8.0 Hz, 1H), 4.22 (t, J=6.0 Hz, 2H), 3.65 (s, 2H), 2.91 (t, J=6.0 Hz, 2H), 2.75 (t, J=6.0 Hz, 2H), 2.58 (t, J=7.2 Hz, 2H), 2.19 (s, 3H), 1.85-1.80 (m, 2H), 1.78-1.74 (m, 2H).

41. Synthesis of N-(6-(4-(3,4-dihydroisoquinolin-2 (1H)-yl)butoxy)pyridin-2-yl)-propionamide (Compound 41)

Compound 41

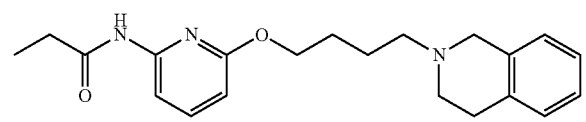

This compound was prepared in 34% yield by reacting Compound 40-6 with propionyl chloride. MS (ESI): m/z 354 [M+H]$^+$. NMR (400 MHz, CDCl$_3$): δ 7.73 (d, J=7.6 Hz, 1H), 7.59-7.55 (m, 2H), 7.13-7.08 (m, 3H), 7.02-7.00 (m, 1H), 6.45 (d, J=8.8 Hz, 1H), 4.22 (t, J=6.4 Hz, 2H), 3.64 (s, 2H), 2.91 (t, J=6.0 Hz, 2H), 2.74 (t, J=6.0 Hz, 2H), 2.58 (t, J=7.2 Hz, 2H), 2.41 (q, J=7.6 Hz, 2H), 1.85-1.74 (m, 4H), 1.25 (s, J=7.6 Hz, 3H).

42. Synthesis of N-(6-(4-(3,4-dihydroisoquinolin-2 (1H)-yl)butoxy)pyridin-2-yl)methanesulfonamide (Compound 42)

Compound 42

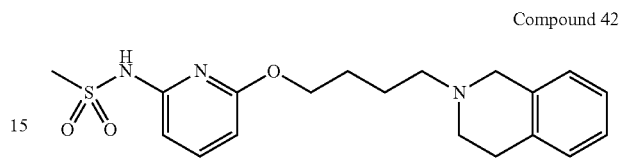

This compound was prepared in 60% yield by reacting Compound 40-6 with methanesulfonyl chloride. MS (ESI): m/z 376 [M+H]$^+$. $^1$H NMR (400 MHz, CD$_3$OD): δ 7.57 (t, J=8.0 Hz, 1H), 7.12-7.10 (m, 3H), 7.07-7.04 (m, 1H), 6.49 (d, J=8.0 Hz, 1H), 6.42 (d, J=8.0 Hz, 1H), 4.35 (t, J=6.4 Hz, 2H), 3.69 (s, 2H), 3.31 (s, 3H), 2.94 (t, J=6.0 Hz, 2H), 2.82 (t, J=6.0 Hz, 2H), 2.63 (t, J=8.0 Hz, 2H), 1.87-1.77 (m, 4H).

43. Synthesis of N-(6-(4-(3,4-dihydroisoquinolin-2 (1H)-yl)butoxy)pyridin-2-yl)-ethanesulfonamide (Compound 43)

Compound 43

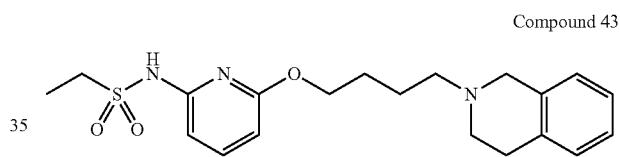

This compound was prepared in 43% yield by reacting Compound 40-6 with ethanesulfonyl chloride. MS (ESI): m/z 390 [M+H]$^+$. NMR (400 MHz, CD$_3$OD): δ 7.56 (t, J=8.0 Hz, 1H), 7.14-7.10 (m, 3H), 7.07-7.05 (m, 1H), 6.51 (d, J=8.0 Hz, 1H), 6.42 (d, J=8.0 Hz, 1H), 4.35 (t, J=6.0 Hz, 2H), 3.69 (s, 2H), 3.49 (q, J=7.2 Hz, 2H), 2.93 (t, J=6.0 Hz, 2H), 2.81 (t, J=6.0 Hz, 2H), 2.62 (d, J=8.0 Hz, 1H), 1.84-1.81 (m, 4H), 1.35 (t, J=7.2 Hz, 3H).

44. Synthesis of 2-(4-((6-(1H-pyrazol-3-yl)pyridin-2-yl)oxy)butyl)-1,2,3,4-tetrahydroisoquinoline (Compound 44)

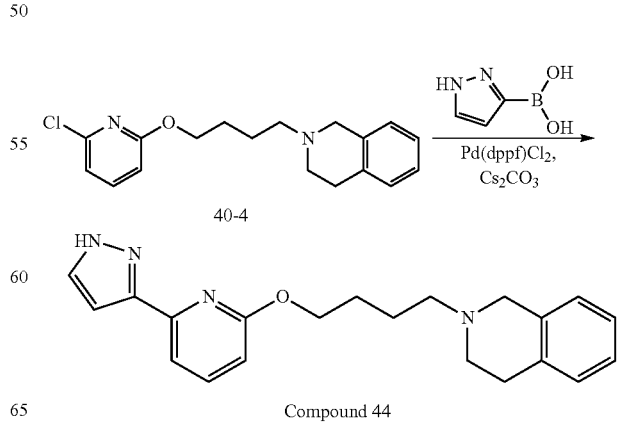

40-4

Compound 44

A microwave vial was charged with 2-(4-(6-chloropyridin-2-yloxy)butyl)-1,2,3,4-tetrahydroisoquinoline (compound 40-4) (145 mg, 0.46 mmol), 1H-pyrazol-3-ylboronic acid (154 mg, 1.38 mmol), 1,1'-bis(diphenylphosphino)ferrocene]dichloro-palladium (II) (20 mg), and cesium carbonate (450 mg, 1.38 mmol) in 1,4-dioxane (1 mL) and N,N-dimethylformamide (1 mL). The mixture was stirred at 110° C. for 1.5 h under microwave irradiation. The resulting mixture was concentrated to give a residue, which was purified by reverse-phase column chromatography (acetonitrile/water=24/76, with 0.1% trifluoroacetic acid) and then prep-HPLC to afford Compound 44 as a yellow oil (18 mg, yield: 11%). MS (ESI): m/z 349 [M+H]$^+$. $^1$H NMR (400 MHz, CDCl$_3$): δ 7.59-7.63 (m, 2H), 7.25-7.26 (m, 1H), 7.08-7.13 (m, 3H), 7.01-7.03 (m, 1H), 6.71 (d, J=2 Hz, 1H), 6.67 (d, J=8 Hz, 1H), 4.42 (t, J=6.4 Hz, 2H), 3.67 (s, 2H), 2.92 (t, J=6 Hz, 2H), 2.77 (t, J=6 Hz, 2H), 2.61 (t, J=7.2 Hz, 2H), 1.86-1.93 (m, 2H), 1.77-1.84 (m, 2H).

45. Synthesis of 2-(4-((6-(1H-pyrazol-3-yl)pyridin-2-yl)oxy)butyl)-5-chloro-1,2,3,4-tetrahydroisoquinoline (Compound 45)

Compound 45

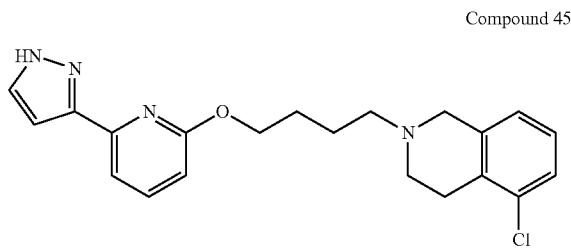 [SMILES: Clc1cccc2c1CCN(CCCCOc1cccc(-c3cc[nH]n3)n1)C2]

This compound was prepared in 52% yield using the procedures described for Compounds 40 and 44 but using 5-chloro-1,2,3,4-tetrahydroisoquinoline as the amine starting material. MS (ESI): m/z 383 [M+H]$^+$. $^1$H NMR (400 MHz, CDCl$_3$): δ 7.58-7.62 (m, 2H), 7.22-7.27 (m, 1H), 7.18 (d, J=8 Hz, 1H), 7.05 (t, J=8 Hz, 1H), 6.92 (d, J=8 Hz, 1H), 6.72 (br, 1H), 6.66 (d, J=8 Hz, 1H), 4.41 (t, J=6.4 Hz, 2H), 3.62 (s, 2H), 2.87 (t, J=6 Hz, 2H), 2.77 (t, J=6 Hz, 2H), 2.59 (t, J=7.2 Hz, 2H), 1.85-1.92 (m, 2H), 1.74-1.80 (m, 2H).

46. Synthesis of 1-(4-((6-(1H-pyrazol-3-yl)pyridin-2-yl)oxy)butyl)-4-(2,3-dichlorophenyl)piperazine (Compound 46)

Compound 46

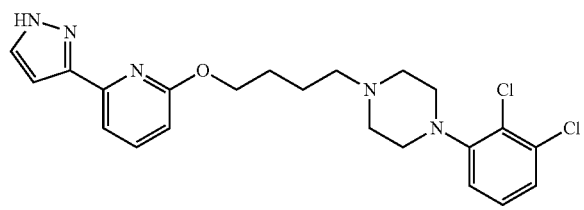

This compound was prepared in 29% yield using the procedures described for Compounds 40 and 44 but using 1-(2,3-dichlorophenyl)piperazine as the amine starting material. MS (ESI): m/z 446 [M+H]$^+$. $^1$H NMR (400 MHz, CDCl$_3$): δ 7.60-7.64 (m, 2H), 7.25-7.27 (m, 1H), 7.11-7.16 (m, 2H), 6.93-6.98 (m, 1H), 6.72 (d, J=2 Hz, 1H), 6.67 (d, J=8.4 Hz, 1H), 4.41 (t, J=6 Hz, 2H), 3.08 (br, 4H), 2.67 (br, 4H), 2.51 (t, J=7.6 Hz, 2H), 1.83-1.92 (m, 2H), 1.70-1.78 (m, 2H).

47. Synthesis of 1-(4-((6-(1H-pyrazol-3-yl)pyridin-2-yl)oxy)butyl)-4-(3-methoxypyridin-2-yl)piperazine (Compound 47)

Compound 47

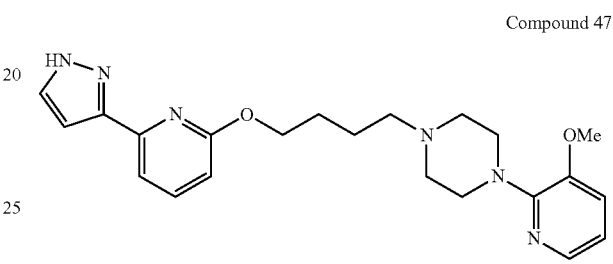

This compound was prepared in 76% yield using the procedures described for Compounds 40 and 44 but using 1-(3-methoxypyridin-2-yl)piperazine as the amine starting material. MS (ESI): m/z 409 [M+H]$^+$. $^1$H NMR (400 MHz, CDCl$_3$): δ 7.88 (dd, $^1$J=4.8 Hz, $^2$J=1.2 Hz, 1H), 7.59-7.63 (m, 2H), 7.26-7.27 (m, 1H), 7.02 (dd, $^1$J=8 Hz, $^2$J=1.2 Hz, 1H), 6.82 (dd, $^1$J=8.2 Hz, $^2$J=5.2 Hz, 1H), 6.73 (br, 1H), 6.66 (d, J=8.4 Hz, 1H), 4.39 (t, J=6 Hz, 2H), 3.84 (s, 3H), 3.44 (br, 4H), 2.64 (t, J=4.8 Hz, 4H), 2.49 (t, J=7.6 Hz, 2H), 1.82-1.89 (m, 2H), 1.71-1.77 (m, 2H).

48. Synthesis of 2-(4-(4-((6-(1H-pyrazol-3-yl)pyridin-2-yl)oxy)butyl)piperazin-1-yl)nicotinonitrile (Compound 48)

Compound 48

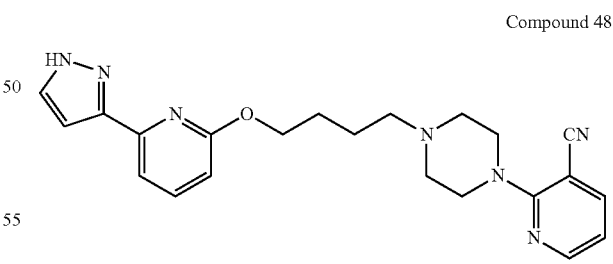

This compound was prepared in 50% yield using the procedures described for Compounds 40 and 44 but using 2-(piperazin-1-yl)nicotinonitrile as the amine starting material. MS (ESI): m/z 404.3 [M+H]$^+$. $^1$H NMR (400 MHz, CDCl$_3$): δ 8.34 (dd, J=2.4 Hz, 4.8 Hz, 1H), 7.77 (dd, J=1.6 Hz, 7.6 Hz, 1H), 7.65-7.61 (m, 2H), 7.27 (t, J=3.2 Hz, 1H), 6.76-6.73 (m, 2H), 6.68 (d, J=8.4 Hz, 1H), 4.41 (t, J=6.4 Hz, 2H), 3.77 (t, J=4.8 Hz, 4H), 2.64 (t, J=4.4 Hz, 4H), 2.51 (t, J=8.4 Hz, 2H), 1.91-1.84 (m, 2H), 1.79-1.73 (m, 2H).

49. Synthesis of 1-(4-((6-(1H-pyrazol-3-yl)pyridin-2-yl)oxy)butyl)-4-(2-ethoxyphenyl)piperazine (Compound 49)

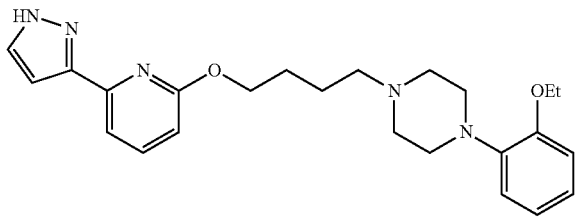

Compound 49

This compound was prepared in 50% yield using the procedures described for Compounds 40 and 44 but using 1-(2-ethoxyphenyl)piperazine as the amine starting material. MS (ESI): m/z 422.3 [M+H]$^+$. $^1$H NMR (400 MHz, CDCl$_3$): δ 7.64-7.60 (m, 2H), 7.29 (br, 1H), 6.99-6.89 (m, 3H), 6.85 (d, J=7.6 Hz, 1H), 6.74 (br, 1H), 6.68 (d, J=8.4 Hz, 1H), 4.41 (t, J=6.4 Hz, 2H), 4.07 (q, J=6.8 Hz, 2H), 3.15 (br, 4H), 2.69 (br, 4H), 2.51 (t, J=7.6 Hz, 2H), 1.91-1.84 (m, 2H), 1.79-1.72 (m, 2H), 1.46 (t, J=6.8 Hz, 3H).

50. Synthesis of 1-(4-((6-(1H-pyrazol-3-yl)pyridin-2-yl)oxy)butyl)-4-(2-chlorophenyl)piperazine (Compound 50)

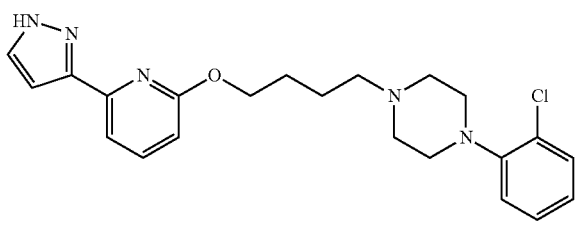

Compound 50

This compound was prepared in 80% yield using the procedures described for Compounds 40 and 44 but using 1-(2-chlorophenyl)piperazine as the amine starting material. MS (ESI): m/z 412.2 [M+H]$^+$. $^1$H NMR (400 MHz, CDCl$_3$): δ 7.65-7.61 (m, 2H), 7.36 (dd, J=1.2 Hz, 7.6 Hz, 1H), 7.27 (t, J=4.4 Hz, 1H), 7.22 (dt, J=1.2 Hz, 8.0 Hz, 1H), 7.06 (dd, J=1.2 Hz, 8.0 Hz, 1H), 6.97 (dt, J=1.2 Hz, 7.6 Hz, 1H), 6.74 (br, 1H), 6.68 (d, J=8.4 Hz, 1H), 4.42 (t, J=6.4 Hz, 2H), 3.12 (br, 4H), 2.70 (br, 4H), 2.54 (t, J=7.6 Hz, 2H), 1.92-1.85 (m, 2H), 1.80-1.72 (m, 2H).

51. Synthesis of 2-(4-((6-(1H-imidazol-4-yl)pyridin-2-yl)oxy)butyl)-1,2,3,4-tetrahydroisoquinoline (Compound 51)

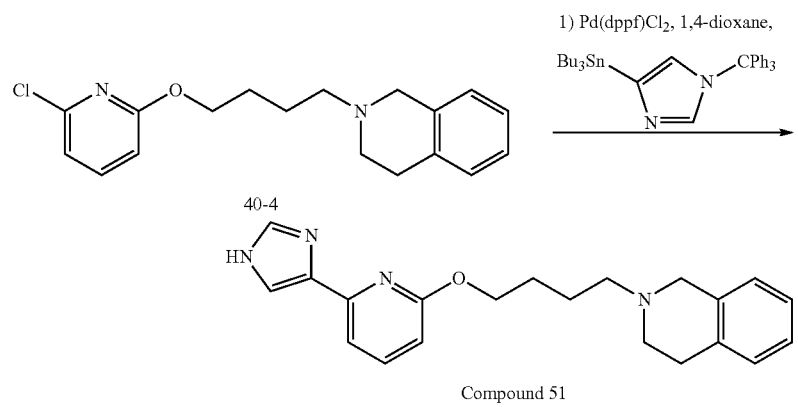

Compound 51

A microwave vial was charged with 4-(tributylstannyl)-1-trityl-1H-imidazole (50 mg, 0.08 mmol), 2-(4-(6-chloropyridin-2-yloxy)butyl)-1,2,3,4-tetrahydroiso-quinoline (40-4) (25 mg, 0.08 mmol) and 1,1'-bis(diphenylphosphino)-ferrocene]-dichloropalladium (II) (10 mg) in 1,4-dioxane (1 mL) and N,N-dimethylformamide (1 mL). The mixture was stirred at 100° C. overnight. The resulting mixture was concentrated to give a residue, which was purified by reverse phase column chromatography (acetonitrile/water=24/76, with 0.1% ammonium hydroxide) to afford 2-(4-(6-(1-trityl-1H-imidazol-4-yl)pyridin-2-yloxy)butyl)-1,2,3,4-tetrahydroisoquinoline.

To a mixture of 2-(4-(6-(1-trityl-1H-imidazol-4-yl)pyridin-2-yloxy)butyl)-1,2,3,4-tetrahydroisoquinoline (7 mg, 0.012 mmol) in methanol (1 mL) was added 4 M hydrochloric acid in methanol (1 mL). The mixture was stirred at room temperature for 2 h, and was then concentrated in vacuum to give the crude product, which was purified by prep-TLC (dichloromethane/methanol=10/1, with 1% triethylamine) to give Compound 51 as a yellow oil (3.2 mg, yield: 77%). MS (ESI): m/z 349 [M+H]$^+$. $^1$H NMR (400 MHz, CDCl$_3$): δ 7.55-7.59 (m, 3H), 7.28 (d, J=7.6 Hz, 1H), 7.10-7.17 (m, 3H), 7.02-7.04 (m, 1H), 6.57 (d, J=8.4 Hz, 1H), 4.39 (d, J=6.4 Hz, 2H), 3.76 (s, 2H), 2.96 (t, J=6 Hz, 2H), 2.86 (t, J=6 Hz, 2H), 2.70 (t, J=7.2 Hz, 2H), 1.82-1.92 (m, 4H).

52. Synthesis of 7-(4-(3,4-dihydroisoquinolin-2(1H)-yl)butoxy)-1,8-naphthyridin-2(1H)-one (Compound 52)

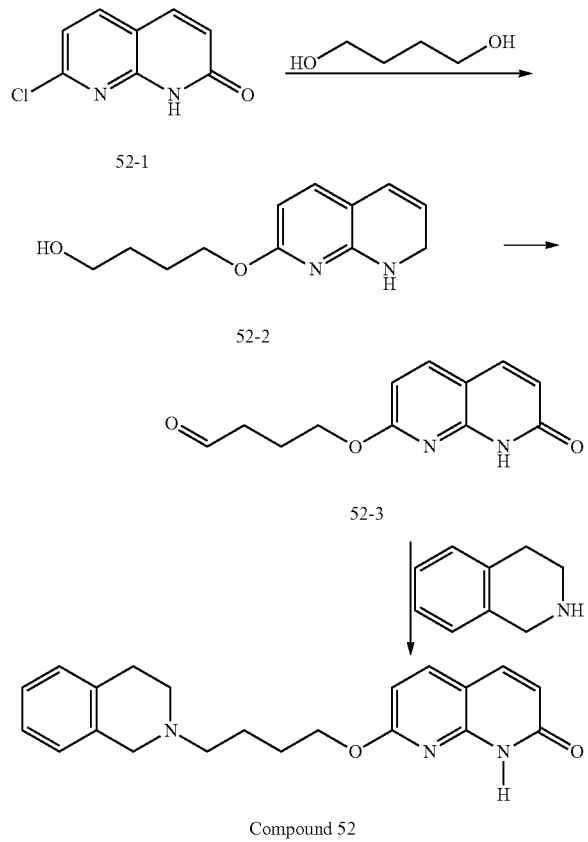

(a) Synthesis of 7-(4-hydroxybutoxy)-1,8-naphthyridin-2(1H)-one (52-2)

A mixture of 7-chloro-1,8-naphthyridin-2(1H)-one (52-1) (1.26 g, 7 mmol) and cesium carbonate (4.56 g, 14 mmol) was stirred at 115° C. overnight. The mixture was diluted with methanol (6 mL) and purified by reverse phase column chromatography (acetonitrile water=17:83, with 0.01% NH$_4$OH) to afford compound 52-2 (1.15 g, 70% yield) as a light yellow solid. MS (ESI): m/z 235 [M+H]$^+$.

(b) Synthesis of 4-(7-oxo-7,8-dihydro-1,8-naphthyridin-2-yloxy)butanal (52-3)

To a solution of 7-(4-hydroxybutoxy)-1,8-naphthyridin-2(1H)-one (52-2) (702 mg, 3 mmol) in dimethylsulfoxide (12 mL) and tetrahydrofuran (3 mL), was added 2-iodoxybenzoic acid (1.008 g, 3.6 mmol). After stirring at 40° C. overnight, the reaction mixture was treated with water (20 mL) and then extracted with ethyl acetate (100 mL×3). The combined organic layers were washed with brine, dried over sodium sulfate and concentrated in vacuo to give compound 52-3 (436 mg, 63% yield) as a yellow solid. MS (ESI): m/z 233 [M+H]$^+$.

(c) Synthesis of 7-(4-(3,4-dihydroisoquinolin-2(1H)-yl)butoxy)-1,8-naphthyridin-2(1H)-one (Compound 52)

To a solution of 4-(7-oxo-7,8-dihydro-1,8-naphthyridin-2-yloxy)butanal (52-3) (24 mg, 0.1 mmol) and 1,2,3,4-tetrahydroisoquinoline (16 mg, 0.12 mmol) in dichloromethane (6 mL), was added acetic acid (6 mg, 0.1 mmol). After stirring for 30 min, sodium triacetoxy-borohydride (42 mg, 0.2 mmol) was added. The mixture was stirred for another 2 h, then diluted with water (10 mL), and extracted with dichloromethane (20 mL). The organic layer was concentrated in vacuo, and the residue was purified by prep-HPLC to afford Compound 52 (15 mg, 43% yield) as a pale yellow solid. MS (ESI): m/z 350 [M+H]$^+$. $^1$H NMR (400 MHz, CDCl$_3$): δ 9.80 (bs, 1H), 7.70 (d, J=8.4 Hz, 1H), 7.62 (d, J=8.8 Hz, 1H), 7.11 (m, 3H), 7.00 (m, 1H), 6.58 (d, J=8.4 Hz, 1H), 6.53 (d, J=9.6 Hz, 1H), 4.41 (t, J=6.4 Hz, 2H), 3.68 (s, 2H), 2.92 (t, J=6.0 Hz, 2H), 2.78 (t, J=6.0 Hz, 2H), 2.62 (t, J=7.2 Hz, 2H), 1.81 (m, 4H).

53. Synthesis of 7-(4-(6,7-dihydrothieno[3,2-c]pyridin-5(4H)-yl)butoxy)-1,8-naphthyridin-2(1H)-one (Compound 53)

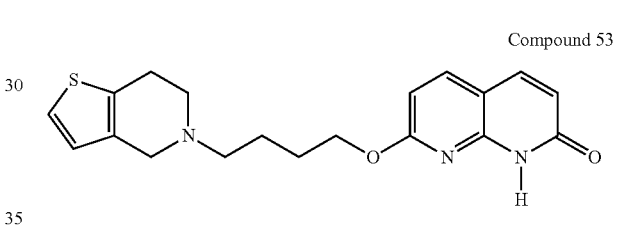

Compound 53

This compound was prepared in 34% yield using the procedures described for Compound 52 but using 4,5,6,7-tetrahydrothieno[3,2-c]pyridine as the amine starting material. MS (ESI): m/z 356 [M+H]$^+$. $^1$H NMR (400 MHz, CDCl$_3$): δ 9.46 (bs, 1H), 7.71 (d, J=8.4 Hz, 1H), 7.62 (d, J=9.6 Hz, 1H), 7.07 (d, J=4.8 Hz, 1H), 6.72 (d, J=5.2 Hz, 2H), 6.59 (d, J=8.4 Hz, 1H), 6.52 (d, J=9.2 Hz, 1H), 4.40 (t, J=6.4 Hz, 2H), 3.58 (s, 2H), 2.90 (t, J=5.6 Hz, 2H), 2.81 (t, J=5.2 Hz, 2H), 2.62 (t, J=7.2 Hz, 2H), 1.90-1.73 (m, 4H).

54. Synthesis of 7-(4-(4,5-dihydrothieno[2,3-c]pyridin-6(7H)-yl)butoxy)-1,8-naphthyridin-2(1H)-one (Compound 54)

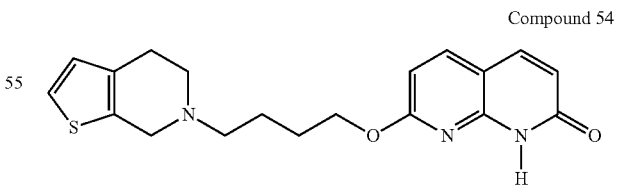

Compound 54

This compound was prepared in 14% yield using the procedures described for Compound 52 but using 4,5,6,7-tetrahydrothieno[2,3-c]pyridine as the amine starting material. MS (ESI): m/z 356 [M+H]$^+$. $^1$H NMR (400 MHz, CDCl$_3$): δ 9.41 (bs, 1H), 7.71 (d, J=8.4 Hz, 1H), 7.62 (d, J=9.6 Hz, 1H), 7.08 (d, J=5.2 Hz, 1H), 6.72 (d, J=4.8 Hz, 2H), 6.59 (d, J=8.8 Hz, 1H), 6.52 (d, J=9.2 Hz, 1H), 4.40 (t, J=6.4 Hz, 2H), 3.71(s, 2H), 2.80 (t, J=5.6 Hz, 2H), 2.75 (t, J=4.8 Hz, 2H), 2.63 (t, J=7.2 Hz, 2H), 1.90-1.73 (m, 4H).

55. Synthesis of 7-(4-(6-methoxy-3,4-dihydroisoquinolin-2(1H)-yl)butoxy)-1,8-naphthyridin-2(1H)-one (Compound 55)

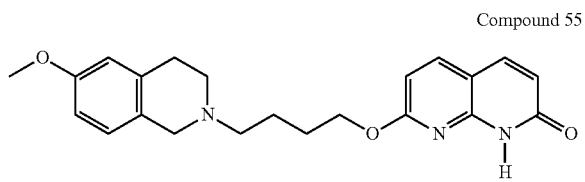 [SMILES: COc1ccc2c(c1)CCN(CCCCOc1ccc3ccc(=O)[nH]c3n1)C2]

Compound 55

This compound was prepared in 84% yield using the procedures described for Compound 52 but using 6-methoxy-1,2,3,4-tetrahydroisoquinoline as the amine starting material. MS (ESI): m/z 380 [M+H]$^+$. $^1$H NMR (400 MHz, CDCl$_3$): δ 9.69 (bs, 1H), 7.70 (d, J=8.8 Hz, 1H), 7.62 (d, J=9.6 Hz, 1H), 6.92 (d, J=8.4 Hz, 1H), 6.68 (dd, J$^1$=2.4 Hz, J$^2$=8.0 Hz, 2H), 6.62 (d, J=2.4 Hz, 1H), 6.58 (d, J=8.4 Hz, 1H), 6.52 (d, J=9.2 Hz, 1H), 4.40 (t, J=6.4 Hz, 2H), 3.76 (s, 3H), 3.59 (s, 2H), 2.89 (t, J=6.0 Hz, 2H), 2.74 (t, J=5.6 Hz, 2H), 2.59 (t, J=7.2 Hz, 2H), 1.89-1.75 (m, 4H).

56. Synthesis of 7-(4-(6-fluoro-3,4-dihydroisoquinolin-2(1H)-yl)butoxy)-1,8-naphthyridin-2(1H)-one (Compound 56)

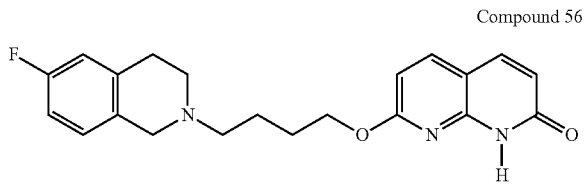 [SMILES: O=c1ccc2ccc(OCCCCN3CCc4cc(F)ccc4C3)nc2[nH]1]

Compound 56

This compound was prepared in 42% yield using the procedures described for Compound 52 but using 6-fluoro-1,2,3,4-tetrahydroisoquinoline as the amine starting material. MS (ESI): m/z 368 [M+H]$^+$. $^1$H NMR (400 MHz, CDCl$_3$): δ 9.59 (bs, 1H), 7.71 (d, J=8.4 Hz, 1H), 7.62 (d, J=9.2 Hz, 1H), 6.98-6.95 (m, 1H), 6.83-6.78 (m, 2H), 6.58 (d, J=8.8 Hz, 1H), 6.52 (d, J=9.2 Hz, 1H), 4.41 (t, J=6.0 Hz, 2H), 3.60 (s, 2H), 2.89 (t, J=6.0 Hz, 2H), 2.73 (t, J=6.0 Hz, 2H), 2.59 (t, J=7.6 Hz, 2H), 1.90-1.73 (m, 4H).

57. Synthesis of 2-(4-((7-oxo-7,8-dihydro-1,8-naphthyridin-2-yl)oxy)butyl)-1,2,3,4-tetrahydroisoquinoline-6-carbonitrile (Compound 57)

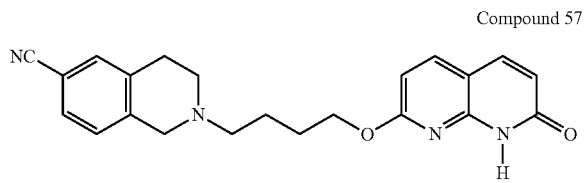 [SMILES: N#Cc1ccc2c(c1)CCN(CCCCOc1ccc3ccc(=O)[nH]c3n1)C2]

Compound 57

This compound was prepared in 41% yield using the procedures described for Compound 52 but using 1,2,3,4-tetrahydroisoquinoline-6-carbonitrile as the amine starting material. MS (ESI): m/z 375 [M+H]$^+$. $^1$H NMR (400 MHz, CDCl$_3$): δ 9.34 (s, 1H), 7.72 (d, J=8.4 Hz, 1H), 7.63 (d, J=9.2 Hz, 1H), 7.40 (s, 1H), 7.39 (d, J=7.6 Hz, 1H), 7.11 (d, J=8.4 Hz, 1H), 6.59 (d, J=8.0 Hz, 1H), 6.52 (d, J=9.6 Hz, 1H), 4.40 (t, J=6.0 Hz, 2H), 3.68 (s, 2H), 2.92 (t, J=6.0 Hz, 2H), 2.76 (t, J=6.0 Hz, 2H), 2.61 (t, J=7.6 Hz, 2H), 1.86 (m, 2H), 1.77 (m, 2H).

58. Synthesis of 7-(4-(6-(trifluoromethyl)-3,4-dihydroisoquinolin-2(1H)-yl)butoxy)-1,8-naphthyridin-2(1H)-one (Compound 58)

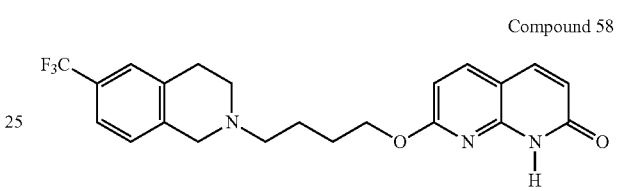

Compound 58

This compound was prepared in 43% yield using the procedures described for Compound 52 but using 6-(trifluoromethyl)-1,2,3,4-tetrahydroisoquinoline as the amine starting material. MS (ESI): m/z 418 [M+H]$^+$. $^1$H NMR (400 MHz, DMSO-d$_6$): δ 11.95 (s, 1H), 7.96 (d, J=8.4 Hz, 1H), 7.81 (d, J=9.2 Hz, 1H), 7.43 (d, J=9.2 Hz, 2H), 7.27 (d, J=8.0 Hz, 1H), 6.64 (d, J=8.4 Hz, 1H), 6.35 (d, J=9.6 Hz, 1H), 4.36 (t, J=6.4 Hz, 2H), 3.62 (s, 2H), 2.88 (t, J=6.0 Hz, 2H), 2.68 (t, J=5.2 Hz, 2H), 2.53 (t, J=7.2 Hz, 2H), 1.80 (m, 2H), 1.67 (m, 2H).

59. Synthesis of 7-(4-(6-chloro-3,4-dihydroisoquinolin-2(1H)-yl)butoxy)-1,8-naphthyridin-2(1H)-one (Compound 59)

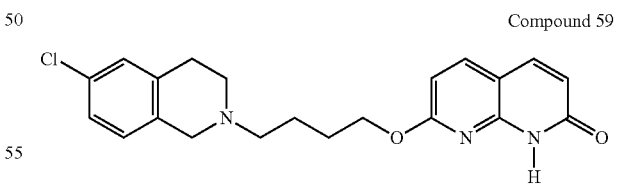

Compound 59

This compound was prepared in 37% yield using the procedures described for Compound 52 but using 6-chloro-1,2,3,4-tetrahydroisoquinoline as the amine starting material. MS (ESI): m/z 384 [M+H]$^+$. $^1$H NMR (400 MHz, CDCl$_3$): δ 9.41 (bs, 1H), 7.71 (d, J=8.4 Hz, 1H), 7.63 (d, J=9.6 Hz, 1H), 7.08 (d, J=6.0 Hz, 2H), 6.95 (d, J=8.8 Hz, 1H), 6.59 (d, J=8.8 Hz, 1H), 6.52 (d, J=9.2 Hz, 2H), 4.40 (t, J=6.0 Hz, 2H), 3.67 (s, 2H), 2.91 (t, J=6.4 Hz, 2H), 2.78 (t, J=5.6 Hz, 2H), 2.63 (t, J=7.2 Hz, 2H), 1.91-1.80 (m, 4H).

60. Synthesis of 7-(4-(5-chloro-3,4-dihydroisoquinolin-2(1H)-yl)butoxy)-1,8-naphthyridin-2(1H)-one (Compound 60)

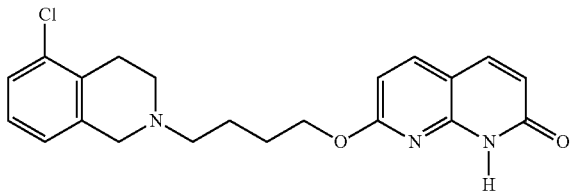

Compound 60

This compound was prepared in 42% yield using the procedures described for Compound 52 but using 5-chloro-1,2,3,4-tetrahydroisoquinoline as the amine starting material. MS (ESI): m/z 384 [M+H]$^+$. $^1$H NMR (400 MHz, CDCl$_3$): δ 9.59 (bs, 1H), 7.70 (d, J=8.4 Hz, 1H), 7.62 (d, J=9.2 Hz, 1H), 7.19 (d, J=7.6 Hz, 1H), 7.06 (t, J=7.6 Hz, 2H), 6.93 (d, J=7.2 Hz, 1H), 6.59 (d, J=8.4 Hz, 1H), 6.52 (d, J=10.0 Hz, 1H), 4.41 (t, J=6.4 Hz, 2H), 3.63 (s, 2H), 2.88 (t, J=6.0 Hz, 2H), 2.78 (t, J=5.6 Hz, 2H), 2.59 (t, J=7.6 Hz, 2H), 1.91-1.74 (m, 4H).

61. Synthesis of 7-(4-(5-(trifluoromethyl)-3,4-dihydroisoquinolin-2(1H)-yl)butoxy)-1,8-naphthyridin-2(1H)-one (Compound 61)

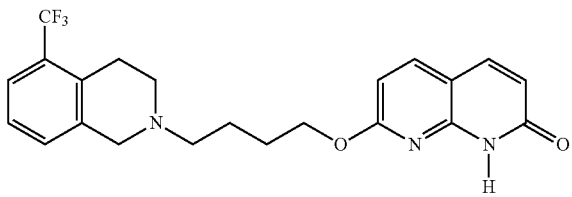

Compound 61

This compound was prepared in 33% yield using the procedures described for Compound 52 but using 5-(trifluoromethyl)-1,2,3,4-tetrahydroisoquinoline as the amine starting material. MS (ESI): m/z 418 [M+H]$^+$. $^1$H NMR (400 MHz, CDCl$_3$): δ 7.70 (d, J=8.8 Hz, 1H), 7.62 (d, J=9.6 Hz, 1H), 7.46 (m, 1H), 7.20 (m, 2H), 6.58 (d, J=8.4 Hz, 1H), 6.53 (d, J=9.2 Hz, 1H), 4.42 (t, J=6.0 Hz, 2H), 3.69 (s, 2H), 3.06 (t, J=5.6 Hz, 2H), 2.76 (t, J=6.0 Hz, 2H), 2.59 (t, J=7.2 Hz, 2H), 1.88 (m, 2H), 1.79 (m, 2H).

62. Synthesis of 2-(4-((7-oxo-7,8-dihydro-1,8-naphthyridin-2-yl)oxy)butyl)-1,2,3,4-tetrahydroisoquinoline-5-carbonitrile (Compound 62)

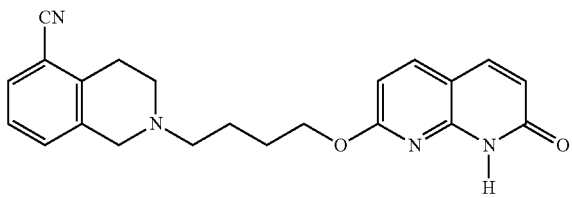

Compound 62

This compound was prepared in 41% yield using the procedures described for Compound 52 but using 1,2,3,4-tetrahydroisoquinoline-5-carbonitrile as the amine starting material. MS (ESI): m/z 375 [M+H]$^+$. $^1$H NMR (400 MHz, CDCl$_3$): δ 9.46 (s, 1H), 7.72 (d, J=8.4 Hz, 1H), 7.64 (d, J=10 Hz, 1H), 7.47 (d, J=7.6 Hz, 1H), 7.22 (m, 2H), 6.60 (d, J=8.4 Hz, 1H), 6.53 (d, J=9.6 Hz, 1H), 4.41 (t, J=6.4 Hz, 2H), 3.65 (s, 2H), 3.07 (t, J=5.6 Hz, 2H), 2.81 (t, J=6.0 Hz, 2H), 2.61 (t, J=7.2 Hz, 2H), 1.86 (m, 2H), 1.80 (m, 2H).

63. Synthesis of 7-(4-(8-(trifluoromethyl)-3,4-dihydroisoquinolin-2(1H)-yl)butoxy)-1,8-naphthyridin-2(1H)-one (Compound 63)

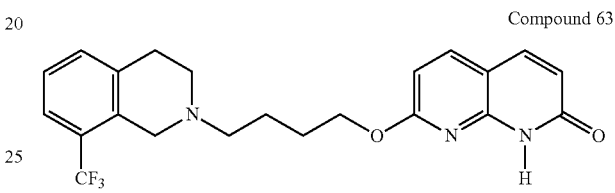

Compound 63

This compound was prepared in 29% yield using the procedures described for Compound 52 but using 8-(trifluoromethyl)-1,2,3,4-tetrahydroisoquinoline as the amine starting material. MS (ESI): m/z 418 [M+H]$^+$. $^1$H NMR (400 MHz, CDCl$_3$): δ 9.66 (bs, 1H), 7.70 (d, J=8.0 Hz, 1H), 7.62 (d, J=9.2 Hz, 1H), 7.44 (d, J=7.6 Hz, 1H), 7.28-7.19 (m, 2H), 6.59 (d, J=8.4 Hz, 1H), 6.52 (d, J=9.6 Hz, 1H), 4.41 (t, J=6.4 Hz, 2H), 3.79 (s, 2H), 2.97 (t, J=5.6 Hz, 2H), 2.77 (t, J=6.0 Hz, 2H), 2.62 (t, J=6.8 Hz, 2H), 1.81 (m, 4H).

64. Synthesis of 2-(4-((7-oxo-7,8-dihydro-1,8-naphthyridin-2-yl)oxy)butyl)-1,2,3,4-tetrahydroisoquinoline-8-carbonitrile (Compound 64)

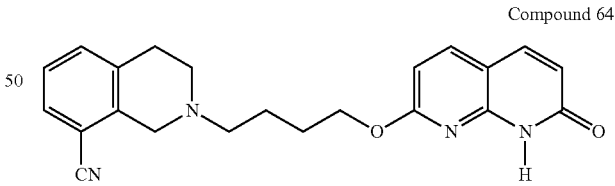

Compound 64

This compound was prepared in 49% yield using the procedures described for Compound 52 but using 1,2,3,4-tetrahydroisoquinoline-8-carbonitrile as the amine starting material. MS (ESI): m/z 375 [M+H]$^+$. $^1$H NMR (400 MHz, CDCl$_3$): δ 9.31 (s, 1H), 7.71 (d, J=8.4 Hz, 1H), 7.63 (d, J=9.2 Hz, 1H), 7.45 (d, J=7.6 Hz, 1H), 7.33 (d, J=7.6 Hz, 1H), 7.21 (t, J=7.2 Hz, 1H), 6.61 (d, J=8.4 Hz, 1H), 6.52 (d, J=9.2 Hz, 1H), 4.41 (t, J=6.0 Hz, 2H), 3.81 (s, 2H), 2.93 (t, J=6.0 Hz, 2H), 2.77 (t, J=6 Hz, 2H), 2.66 (t, J=7.2 Hz, 2H), 1.86 (m, 2H), 1.80 (m, 2H).

65. Synthesis of 7-(4-(7-methyl-3,4-dihydroisoquinolin-2(1H)-yl)butoxy)-1,8-naphthyridin-2(1H)-one (Compound 65)

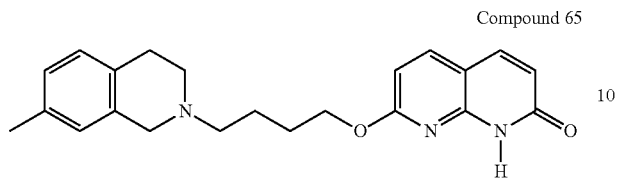

Compound 65

This compound was prepared in 36% yield using the procedures described for Compound 52 but using 7-methyl-1,2,3,4-tetrahydroisoquinoline as the amine starting material. MS (ESI): m/z 364 [M+H]$^+$. $^1$H NMR (400 MHz, CDCl$_3$): δ 9.52 (bs, 1H), 7.71(d, J=8.8 Hz, 1H), 7.63 (d, J=9.2 Hz, 1H), 6.97 (dd, J$^1$=8.0 Hz, J$^2$=16.8 Hz, 2H), 6.84 (s, 1H), 6.59 (d, J=8.4 Hz, 1H), 6.53 (d, J=9.6 Hz, 1H), 4.40 (t, J=6.0 Hz, 2H), 3.70 (s, 2H), 2.90 (t, J=5.2 Hz, 2H), 2.84 (t, J=5.6 Hz, 2H), 2.66 (t, J=7.2 Hz, 2H), 2.28 (s, 3H), 1.90-1.81 (m, 4H).

66. Synthesis of 7-(4-(2-phenyl-6,7-dihydro-2H-pyrazolo[4,3-c]pyridin-5(4H)-yl)butoxy)-1,8-naphthyridin-2(1H)-one (Compound 66)

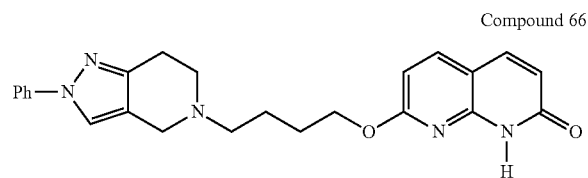 [SMILES: O=c1ccc2ccc(OCCCCN3CCc4nn(-c5ccccc5)cc4C3)nc2[nH]1]

Compound 66

This compound was prepared in 48% yield using the procedures described for Compound 52 but using 2-phenyl-4,5,6,7-tetrahydro-2H-pyrazolo[4,3-c]pyridine as the amine starting material. MS (ESI): m/z 416 [M+H]$^+$. $^1$H NMR (400 MHz, CDCl$_3$): δ 9.49 (bs, 1H), 7.71 (d, J=8.0 Hz, 1H), 7.64-7.61 (m, 4H), 7.41 (t, J=7.6 Hz, 2H), 7.26-7.21 (m, 1H), 6.59 (d, J=8.4 Hz, 1H), 6.52 (d, J=9.6 Hz, 1H), 4.41 (t, J=6.0 Hz, 2H), 3.61 (s, 2H), 2.91 (t, J=5.6 Hz, 2H), 2.85 (t, J=5.2 Hz, 2H), 2.64 (t, J=7.6 Hz, 2H), 1.91-1.74 (m, 4H).

67. Synthesis of 7-(4-(2-(pyridin-2-yl)-6,7-dihydro-2H-pyrazolo[4,3-c]pyridin-5(4H)-yl)butoxy)-1,8-naphthyridin-2(1H)-one (Compound 67)

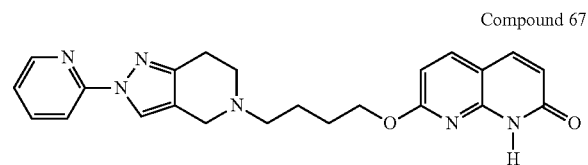 [SMILES: O=c1ccc2ccc(OCCCCN3CCc4nn(-c5ccccn5)cc4C3)nc2[nH]1]

Compound 67

This compound was prepared in 55% yield using the procedures described for Compound 52 but using 2-(pyridin-2-yl)-4,5,6,7-tetrahydro-2H-pyrazolo[4,3-c]pyridine as the amine starting material. MS (ESI): m/z 417 [M+H]$^+$. $^1$H NMR (400 MHz, CDCl$_3$): δ 9.15 (bs, 1H), 8.36 (dd, J$^1$=1.2 Hz, J$^2$=5.2 Hz, 1H), 8.25 (s, 1H), 7.88 (d, J=8.4 Hz, 1H), 7.78-7.70 (m, 2H), 7.62 (d, J=9.6 Hz, 1H), 7.14-7.10 (m, 1H), 6.59 (d, J=8.8 Hz, 1H), 6.51 (d, J=10.0 Hz, 1H), 4.40 (t, J=6.0 Hz, 2H), 3.63 (s, 2H), 2.91 (t, J=5.6 Hz, 2H), 2.86 (t, J=5.2 Hz, 2H), 2.65 (t, J=7.2 Hz, 2H), 1.91-1.64 (m, 4H).

68. Synthesis of 7-(4-(3,4-dihydroisoquinolin-2(1H)-yl)butoxy)-3,4-dihydro-1,8-naphthyridin-2(1H)-one (Compound 68)

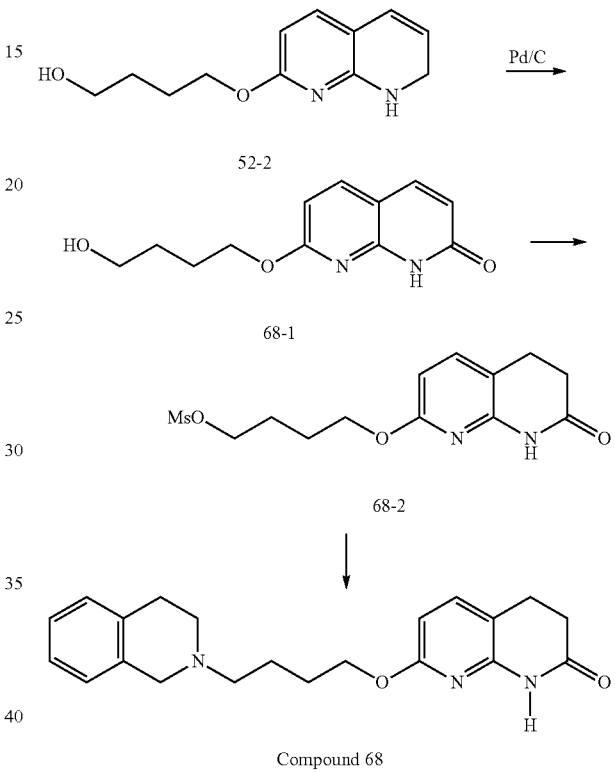

Compound 68

(a) Synthesis of 7-(4-hydroxybutoxy)-3,4-dihydro-1,8-naphthyridin-2(1H)-one (68-1)

To a mixture of 7-(4-hydroxybutoxy)-1,8-naphthyridin-2(1H)-one (52-2) (234 mg, 1 mmol) and 10% dry Pd/C (20 mg) in methanol (10 mL), was added concentrated hydrochloric acid (0.5 mL). The mixture was stirred at 50° C. overnight under hydrogen. The mixture was filtered, and the filtrate was concentrated to dryness to give compound 68-1 (200 mg, 85% yield) as a yellow solid. MS (ESI): m/z 237 [M+H]$^+$.

(b) Synthesis of 4-(7-oxo-5,6,7,8-tetrahydro-1,8-naphthyridin-2-yloxy)butyl methanesulfonate (68-2)

To a solution of 7-(4-hydroxybutoxy)-3,4-dihydro-1,8-naphthyridin-2(1H)-one (68-1) (200 mg, 0.84 mmol) and triethylamine (254 mg, 2.52 mmol) in dichloromethane (10 mL) stirred at 0° C., was added methanesulfonyl chloride (192 mg, 1.68 mmol), and the mixture was stirred at room temperature for 16 h. Water was added and the aqueous phase was extracted with dichloromethane (20 mL×3), and the combined organic phase was dried over sodium sulfate and concentrated to afford compound 68-2 (192 mg, 80% yield) as a yellow oil. MS (ESI): m/z 315 [M+H]+.

(c) Synthesis of 7-(4-(3,4-dihydroisoquinolin-2 (1H)-yl)butoxy)-3,4-dihydro-1,8-naphthyridin-2 (1H)-one (Compound 68)

To a mixture of 4-(7-oxo-5,6,7,8-tetrahydro-1,8-naphthyridin-2-yloxy)butyl methanesulfonate (68-2) (32 mg, 0.1 mmol), potassium carbonate (138 mg, 1 mmol) and 1,2,3,4-tetrahydroisoquinoline (14 mg, 0.1 mmol) in acetonitrile (4 mL), was added sodium iodide (15 mg, 0.1 mmol). After stirring at 80° C. for 5 h, the reaction mixture was filtered and the filtrate was concentrated. The residue was purified by prep-HPLC to give Compound 68 (18 mg, 51% yield) as a yellow solid. MS (ESI): m/z 352 [M+H]+. $^1$H NMR (400 MHz, CDCl$_3$): δ 7.55 (bs, 1H), 7.35 (d, J=8.4 Hz, 1H), 7.11 (m, 3H), 7.01 (m, 1H), 6.35 (d, J=8.4 Hz, 1H), 4.23 (t, J=6.0 Hz, 2H), 3.67 (s, 2H), 2.92 (t, J=6.0 Hz, 2H), 2.86 (t, J=7.6 Hz, 2H), 2.77 (t, J=6.0 Hz, 2H), 2.62 (m, 4H), 1.81 (m, 4H).

69. Synthesis of 7-(4-(6,7-dihydrothieno[3,2-c]pyridin-5(4H)-yl)butoxy)-3,4-dihydro-1,8-naphthyridin-2(1H)-one (Compound 69)

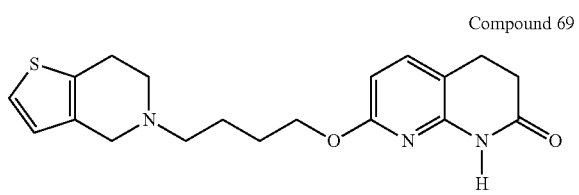 [SMILES: O=C1CCc2ccc(OCCCCN3CCc4sccc4C3)nc2N1]

Compound 69

This compound was prepared in 24% yield using the procedures described for Compound 68 but using 4,5,6,7-tetrahydrothieno[3,2-c]pyridine as the amine starting material. MS (ESI): m/z 358 [M+H]+. $^1$H NMR (400 MHz, CDCl$_3$): δ 7.72 (bs, 1H), 7.35 (d, J=8.4 Hz, 1H), 7.07 (d, J=4.8 Hz, 1H), 6.72 (d, J=5.2 Hz, 1H), 6.34 (d, J=8.0 Hz, 2H), 4.23 (t, J=6.0 Hz, 2H), 3.59 (s, 2H), 2.92-2.81 (m, 6H), 2.63 (dd, J$^1$=7.6 Hz, J$^2$=14.8 Hz, 2H), 1.83-1.73 (m, 4H).

70. Synthesis of 7-(4-(4,5-dihydrothieno[2,3-c]pyridin-6(7H)-yl)butoxy)-3,4-dihydro-1,8-naphthyridin-2(1H)-one (Compound 70)

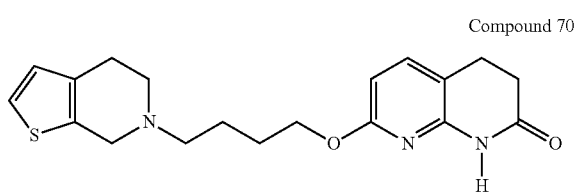 [SMILES: O=C1CCc2ccc(OCCCCN3CCc4ccsc4C3)nc2N1]

Compound 70

This compound was prepared in 25% yield using the procedures described for Compound 68 but using 4,5,6,7-tetrahydrothieno[2,3-c]pyridine as the amine starting material. MS (ESI): m/z 358 [M+H]+. $^1$H NMR (400 MHz, CDCl$_3$): δ 7.62 (bs, 1H), 7.35 (d, J=8.0 Hz, 1H), 7.08 (d, J=4.8 Hz, 1H), 6.77 (d, J=5.2 Hz, 1H), 6.34 (d, J=8.4 Hz, 2H), 4.23 (t, J=6.0 Hz, 2H), 3.71 (s, 2H), 2.88-2.75 (m, 6H), 2.63 (dd, J$^1$=8.4 Hz, J$^2$=16.0 Hz, 2H), 1.85-1.70 (m, 4H).

71. Synthesis of 7-(4-(6-methoxy-3,4-dihydroisoquinolin-2(1H)-yl)butoxy)-3,4-dihydro-1,8-naphthyridin-2(1H)-one (Compound 71)

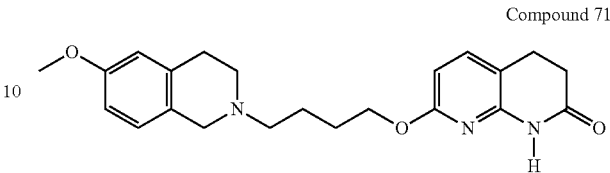

Compound 71

This compound was prepared in 37% yield using the procedures described for Compound 68 but using 6-methoxy-1,2,3,4-tetrahydroisoquinoline as the amine starting material. MS (ESI): m/z 382 [M+H]+. $^1$H NMR (400 MHz, CDCl$_3$): δ 7.67 (bs, 1H), 7.35 (d, J=8.0 Hz, 1H), 7.01 (d, J=8.4 Hz, 1H), 6.70 (dd, J$^1$=2.8 Hz, J$^2$=8.4 Hz, 1H), 6.55 (d, J=2.8 Hz, 1H), 6.35 (d, J=8.0 Hz, 1H), 4.23 (t, J=6.4 Hz, 2H), 3.76 (s, 3H), 3.60 (s, 2H), 2.84 (dd, J$^1$=7.2 Hz, J$^2$=15.6 Hz, 4H), 2.72 (t, J=5.6 Hz, 2H), 2.64 (t, J=7.2 Hz, 2H), 2.56 (t, J=7.2 Hz, 2H), 1.83-1.72 (m, 4H).

72. Synthesis of 7-(4-(6-fluoro-3,4-dihydroisoquinolin-2(1H)-yl)butoxy)-3,4-dihydro-1,8-naphthyridin-2(1H)-one (Compound 72)

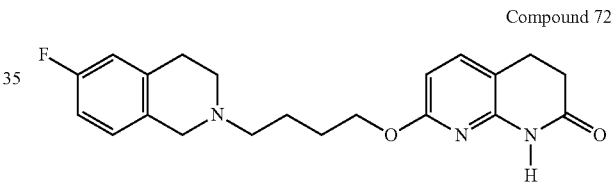

Compound 72

This compound was prepared in 41% yield using the procedures described for Compound 68 but using 6-fluoro-1,2,3,4-tetrahydroisoquinoline as the amine starting material. MS (ESI): m/z 370 [M+H]+. $^1$H NMR (400 MHz, CDCl$_3$): δ 7.68 (bs, 1H), 7.35 (d, J=8.4 Hz, 1H), 6.97 (dd, J$^1$=6.0 Hz, J$^2$=8.0 Hz, 1H), 6.83-6.78 (m, 2H), 6.35 (d, J=8.0 Hz, 1H), 4.23 (t, J=6.4 Hz, 2H), 3.58 (s, 2H), 2.90-2.84 (m, 4H), 2.72 (t, J=5.6 Hz, 2H), 2.63 (t, J=7.2 Hz, 2H), 2.56 (t, J=7.6 Hz, 2H), 1.83-1.72 (m, 4H).

73. Synthesis of 2-(4-((7-oxo-5,6,7,8-tetrahydro-1,8-naphthyridin-2-yl)oxy)butyl)-1,2,3,4-tetrahydroisoquinoline-6-carbonitrile (Compound 73)

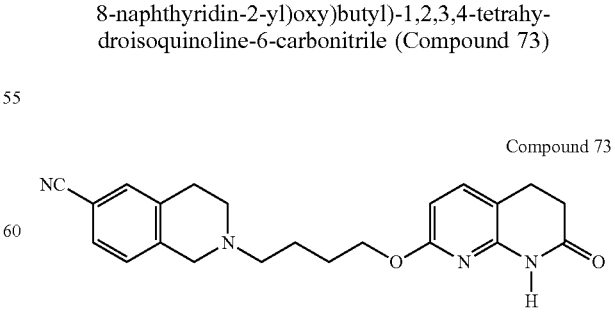

Compound 73

This compound was prepared in 42% yield using the procedures described for Compound 68 but using 1,2,3,4-tetrahydroisoquinoline-6-carbonitrile as the amine starting material. MS (ESI): m/z 377 [M+H]$^+$. $^1$H NMR (400 MHz, CDCl$_3$): δ 8.06 (brs, 1H), 7.56-7.52 (m, 2H), 7.40 (d, J=8.4 Hz, 1H), 7.25 (d, J=8.0 Hz, 1H), 6.34 (d, J=8.0 Hz, 1H), 4.26-3.77 (m, 6H), 3.29-3.25 (m, 4H), 2.88 (t, J=7.6 Hz, 2H), 2.66 (t, J=7.6 Hz, 2H), 2.07-2.01 (m, 2H), 1.90-1.85 (m, 2H).

74. Synthesis of 7-(4-(6-(trifluoromethyl)-3,4-dihydroisoquinolin-2(1H)-yl)butoxy)-3,4-dihydro-1,8-naphthyridin-2(1H)-one (Compound 74)

Compound 74

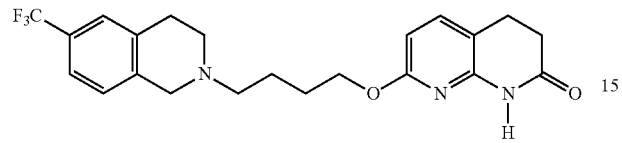

This compound was prepared in 43% yield using the procedures described for Compound 68 but using 6-(trifluoromethyl)-1,2,3,4-tetrahydroisoquinoline as the amine starting material. MS (ESI): m/z 420 [M+H]$^+$. $^1$H NMR (400 MHz, CDCl$_3$): δ 7.63 (bs, 1H), 7.35 (m, 3H), 7.11 (d, J=8.8 Hz, 1H), 6.34 (d, J=8.0 Hz, 1H), 4.23 (t, J=6.4 Hz, 2H), 3.67 (s, 2H), 2.94 (t, J=5.6 Hz, 2H), 2.86 (t, J=8.0 Hz, 2H), 2.76 (t, J=5.6 Hz, 2H), 2.60 (m, 4H), 1.77 (m, 4H).

75. Synthesis of 7-(4-(6-chloro-3,4-dihydroisoquinolin-2(1H)-yl)butoxy)-3,4-dihydro-1,8-naphthyridin-2(1H)-one (Compound 75)

Compound 75

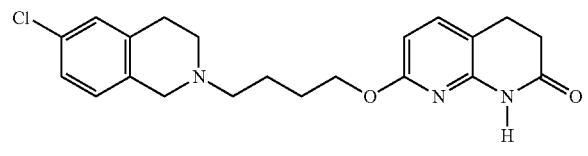

This compound was prepared in 50% yield using the procedures described for Compound 68 but using 6-chloro-1,2,3,4-tetrahydroisoquinoline as the amine starting material. MS (ESI): m/z 386 [M+H]$^+$. $^1$H NMR (400 MHz, CDCl$_3$): δ 7.58 (bs, 1H), 7.35 (d, J=8.4 Hz, 1H), 7.08 (d, J=7.2 Hz, 1H), 6.94 (d, J=8.8 Hz, 2H), 6.35 (d, J=8.0 Hz, 1H), 4.23 (t, J=6.0 Hz, 2H), 3.60 (s, 2H), 2.89-2.84 (m, 4H), 2.73 (t, J=5.6 Hz, 2H), 2.64 (t, J=7.6 Hz, 2H), 2.58 (t, J=7.2 Hz, 2H), 1.85-1.73 (m, 4H).

76. Synthesis of 7-(4-(5-chloro-3,4-dihydroisoquinolin-2(1H)-yl)butoxy)-3,4-dihydro-1,8-naphthyridin-2(1H)-one (Compound 76)

Compound 76

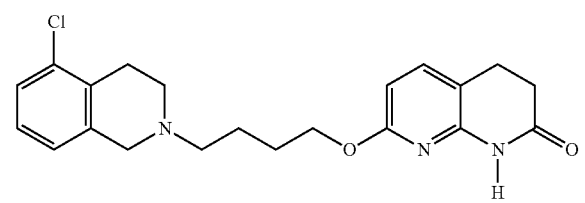

This compound was prepared in 34% yield using the procedures described for Compound 68 but using 5-chloro-1,2,3,4-tetrahydroisoquinoline as the amine starting material. MS (ESI): m/z 386 [M+H]$^+$. $^1$H NMR (400 MHz, CDCl$_3$): δ 7.73 (bs, 1H), 7.35 (d, J=8.4 Hz, 1H), 7.62 (d, J=8.0 Hz, 1H), 7.06 (t, J=8.0 Hz, 1H), 6.93 (d, J=7.2 Hz, 2H), 6.34 (d, J=8.0 Hz, 1H), 4.23 (t, J=6.4 Hz, 2H), 3.63 (s, 2H), 2.89-2.83 (m, 4H), 2.78 (t, J=6.4 Hz, 2H), 2.63 (t, J=6.8 Hz, 2H), 2.58 (t, J=7.2 Hz, 2H), 1.84-1.73 (m, 4H).

77. Synthesis of 7-(4-(5-(trifluoromethyl)-3,4-dihydroisoquinolin-2(1H)-yl)butoxy)-3,4-dihydro-1,8-naphthyridin-2(1H)-one (Compound 77)

Compound 77

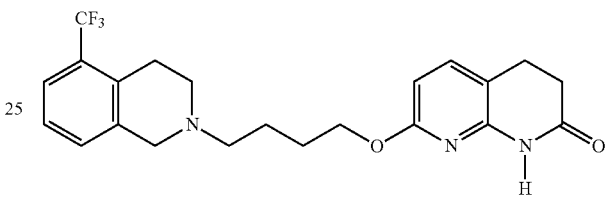

This compound was prepared in 36% yield using the procedures described for Compound 68 but using 5-(trifluoromethyl)-1,2,3,4-tetrahydroisoquinoline as the amine starting material. MS (ESI): m/z 420 [M+H]$^+$. $^1$H NMR (400 MHz, CDCl$_3$): δ 7.58 (bs, 1H), 7.48 (m, 1H), 7.35 (d, J=8.0 Hz, 1H), 7.20 (m, 2H), 6.35 (d, J=8.4 Hz, 1H), 4.24 (t, J=6.4 Hz, 2H), 3.69 (s, 2H), 3.07 (t, J=5.6 Hz, 2H), 2.86 (t, J=8.0 Hz, 2H), 2.76 (t, J=6.0 Hz, 2H), 2.64 (t, J=8.0 Hz, 2H), 2.58 (t, J=7.2 Hz, 2H), 1.80 (m, 4H).

78. Synthesis of 2-(4-((7-oxo-5,6,7,8-tetrahydro-1,8-naphthyridin-2-yl)oxy)butyl)-1,2,3,4-tetrahydroisoquinoline-5-carbonitrile (Compound 78)

Compound 78

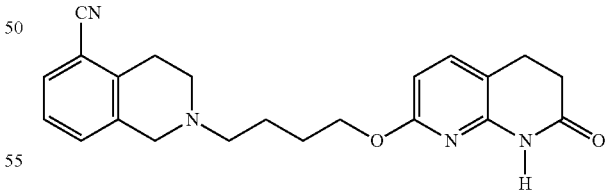

This compound was prepared in 32% yield using the procedures described for Compound 68 but using 1,2,3,4-tetrahydroisoquinoline-5-carbonitrile as the amine starting material. MS (ESI): m/z 377 [M+H]$^+$. $^1$H NMR (400 MHz, CDCl$_3$): δ 7.60 (brs, 1H), 7.48 (dd, J=1.6 Hz, 7.2 Hz, 1H), 7.37 (dd, J=0.8 Hz, 8.0 Hz, 1H), 7.27-7.20 (m, 2H), 6.36 (d, J=8.0 Hz, 1H), 4.24 (t, J=6.4 Hz, 2H), 3.65 (s, 2H), 3.08 (t, J=5.8 Hz, 2H), 2.87 (t, J=7.4 Hz, 2H), 2.80 (t, J=6.0 Hz, 2H), 2.67-2.58 (m, 4H), 1.85-1.73 (m, 4H).

79. Synthesis of 7-(4-(8-(trifluoromethyl)-3,4-dihydroisoquinolin-2(1H)-yl)butoxy)-3,4-dihydro-1,8-naphthyridin-2(1H)-one (Compound 79)

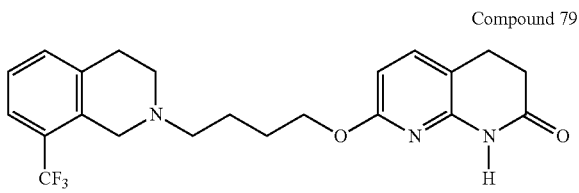 [SMILES: O=C1CCc2ccc(OCCCCN3CCc4cccc(C(F)(F)F)c4C3)nc2N1]

Compound 79

This compound was prepared in 38% yield using the procedures described for Compound 68 but using 8-(trifluoromethyl)-1,2,3,4-tetrahydroisoquinoline as the amine starting material. MS (ESI): m/z 420 [M+H]⁺. ¹H NMR (400 MHz, CDCl₃): δ 7.64 (bs, 1H), 7.44 (d, J=7.2 Hz, 1H), 7.34 (d, J=8.0 Hz, 1H), 7.28 (d, J=7.2 Hz, 1H), 7.21(m, 1H), 6.35 (d, J=8.0 Hz, 1H), 4.24 (t, J=6.4 Hz, 2H), 3.78 (s, 2H), 2.97 (t, J=6.0 Hz, 2H), 2.86 (t, J=8.0 Hz, 2H), 2.75 (t, J=6.0 Hz, 2H), 2.62 (m, 4H), 1.80 (m, 4H).

80. Synthesis of 2-(4-((7-oxo-5,6,7,8-tetrahydro-1,8-naphthyridin-2-yl)oxy)butyl)-1,2,3,4-tetrahydroisoquinoline-8-carbonitrile (Compound 80)

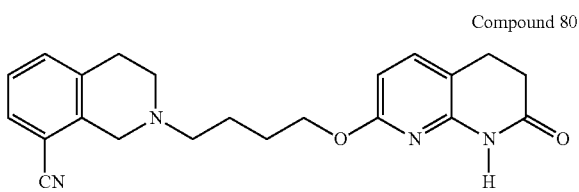 [SMILES: N#Cc1cccc2c1CN(CCCCOc1ccc3c(n1)NC(=O)CC3)CC2]

Compound 80

This compound was prepared in 51% yield using the procedures described for Compound 68 but using 1,2,3,4-tetrahydroisoquinoline-8-carbonitrile as the amine starting material. MS (ESI): m/z 377 [M+H]⁺. ¹H NMR (400 MHz, CDCl₃): δ 7.65 (brs, 1H), 7.46-7.45 (m, 1H), 7.35 (t, J=8.6 Hz, 2H), 7.22 (t, J=7.6 Hz, 1H), 6.37 (d, J=8.0 Hz, 1H), 4.24 (t, J=6.0 Hz, 2H), 3.81 (s, 2H), 2.93 (t, J=5.8 Hz, 2H), 2.86 (t, J=7.6 Hz, 2H), 2.76 (t, J=6.0 Hz, 2H), 2.66-2.62 (m, 4H), 1.84-1.73 (m, 4H).

81. Synthesis of 7-(4-(7-methyl-3,4-dihydroisoquinolin-2(1H)-yl)butoxy)-3,4-dihydro-1,8-naphthyridin-2(1H)-one (Compound 81)

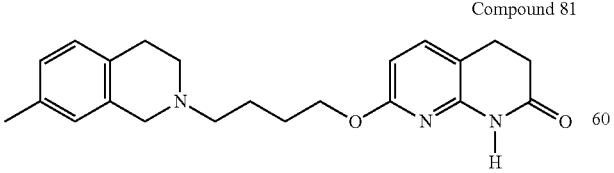

Compound 81

This compound was prepared in 41% yield using the procedures described for Compound 68 but using 7-methyl-1,2,3,4-tetrahydroisoquinoline as the amine starting material. MS (ESI): m/z 366 [M+H]⁺. ¹H NMR (400 MHz, CDCl₃): δ 7.69 (bs, 1H), 7.34 (d, J=8.0 Hz, 1H), 6.98 (d, J=7.6 Hz, 1H), 6.93 (d, J=8.0 Hz, 1H), 6.83 (s, 1H), 6.35 (d, J=8.0 Hz, 1H), 4.23 (t, J=6.4 Hz, 2H), 3.59 (s, 2H), 2.85 (t, J=7.2 Hz, 2H), 2.72 (t, J=6.0 Hz, 2H), 2.64 (t, J=7.6 Hz, 2H), 2.56 (t, J=7.2 Hz, 2H), 2.28 (s, 3H), 1.86-1.72 (m, 4H).

82. Synthesis of 7-(4-(2-phenyl-6,7-dihydro-2H-pyrazolo[4,3-c]pyridin-5(4H)-yl)butoxy)-3,4-dihydro-1,8-naphthyridin-2(1H)-one (Compound 82)

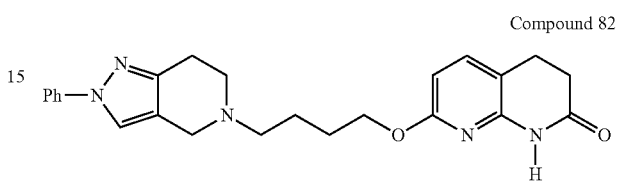

Compound 82

This compound was prepared in 28% yield using the procedures described for Compound 68 but using 2-phenyl-4,5,6,7-tetrahydro-2H-pyrazolo[4,3-c]pyridine as the amine starting material. MS (ESI): m/z 418 [M+H]⁺. ¹H NMR (400 MHz, CDCl₃): δ 7.67 (bs, 1H), 7.61 (d, J=6.8 Hz, 3H), 7.43 (m, 2H), 7.35 (d, J=8.0 Hz, 1H), 7.23 (t, J=7.6 Hz, 1H), 6.35 (d, J=8.4 Hz, 1H), 4.23 (t, J=6.4 Hz, 2H), 3.61 (s, 2H), 2.91 (t, J=5.6 Hz, 2H), 2.87-2.83 (m, 4H), 2.65-2.61 (m, 4H), 1.85-1.73 (m, 4H).

83. Synthesis of 8-(4-(3,4-dihydroisoquinolin-2(1H)-yl)butoxy)-4,5-dihydro-1H-pyrido[2,3-d][1,3]diazepin-2(3H)-one (Compound 83)

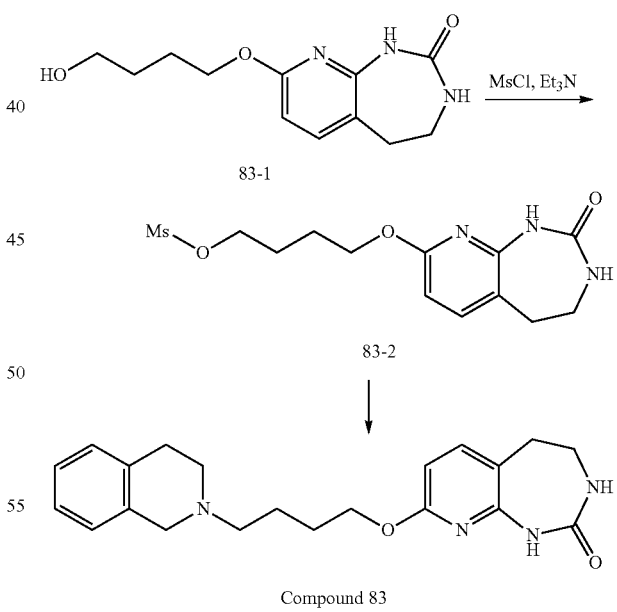

Compound 83

(a) Synthesis of 4-(2-oxo-2,3,4,5-tetrahydro-1H-pyrido[2,3-d][1,3]diazepin-8-yloxy)butyl methanesulfonate (83-2)

To a mixture of 8-(4-hydroxybutoxy)-4,5-dihydro-1H-pyrido[2,3-d][1,3]diazepin-2(3H)-one (580 mg, 2.31 mmol)

and triethylamine (700 mg, 6.93 mmol) in dichloromethane (20 mL) stirred at 0° C., was added methanesulfonyl chloride (531 mg, 4.62 mmol). The mixture was stirred at room temperature for 2 h. Water was added and the aqueous phase was extracted with dichloromethane (50 mL×3). The combined organic phase was dried with sodium sulfate and evaporated to give 700 mg (92% yield) of compound 83-2 as a pale white solid. MS (ESI): m/z 330.0 [M+H]+. 1H NMR (400 MHz, CDCl3): δ 8.43 (s, 1H), 7.37 (d, J=8.0 Hz, 1H), 6.25 (d, J=8.0 Hz, 1H), 5.15 (s, 1H), 4.32 (t, J=6.0 Hz, 2H), 4.24 (d, J=6.0 Hz, 2H), 4.14-4.10 (m, 2H), 3.0 (s, 3H), 2.99 (s, 2H), 2.0-1.88 (m, 4H).

(b) Synthesis of 8-(4-(3,4-dihydroisoquinolin-2 (1H)-yl)butoxy)-4,5-dihydro-1H-pyrido[2,3-d][1,3] diazepin-2(3H)-one (Compound 83)

A mixture of 4-(2-oxo-2,3,4,5-tetrahydro-1H-pyrido[2,3-d][1,3]diazepin-8-yloxy) butyl-methanesulfonate (83-2) (20 mg, 0.06 mmol), 1,2,3,4-tetrahydroisoquinoline (16 mg, 0.12 mmol) and potassium carbonate (25 mg, 0.18 mmol) in acetonitrile (1 mL) was stirred at 80° C. for 3 h. The reaction mixture was filtered. The filtrate was concentrated and the residue was purified by prep-TLC (dichloromethane:methanol=40:1) to give 10 mg (45% yield) of Compound 83 as a yellow oil. MS (ESI): m/z 367.1 [M+H]+. 1H NMR (400 MHz, CDCl3): δ 8.48 (s, 1H), 7.35 (d, J=8.0 Hz, 1H), 7.15-7.09 (m, 3H), 7.2 (t, J=5.2 Hz, 1H), 6.25 (t, J=4.0 Hz, 1H), 4.23 (t, J=6.0 Hz, 2H), 4.13-4.09 (m, 2H), 3.64 (s, 2H), 2.99 (t, J=8.8 Hz, 2H), 2.91 (t, J=6.0 Hz, 2H), 2.75 (t, J=6.0 Hz, 2H), 2.58 (t, J=6.4 Hz, 2H), 1.91-1.74 (m, 4H).

84. Synthesis of 8-(4-(6-fluoro-3,4-dihydroisoquinolin-2(1H)-yl)butoxy)-4,5-dihydro-1H-pyrido[2,3-d][1,3]diazepin-2(3H)-one (Compound 84)

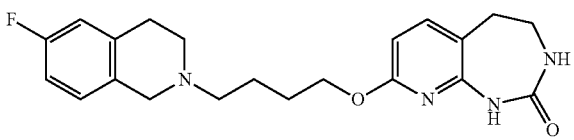

Compound 84

This compound was prepared in 53% yield using the procedures described for Compound 83 but using 6-fluoro-1,2,3,4-tetrahydroisoquinoline as the amine starting material. MS (ESI): m/z 385.1 [M+H]+. 1H NMR (400 MHz, CDCl3): δ 8.47 (s, 1H), 7.34 (d, J=8.0 Hz, 1H), 6.96 (t, J=7.2 Hz, 1H), 6.83-6.78 (m, 2H), 6.24 (d, J=8.0 Hz, 1H), 4.22 (t, J=6.0 Hz, 2H), 4.12-4.08 (m, 2H), 3.58 (s, 2H), 3.98 (t, J=8.4 Hz, 2H), 2.88 (t, J=6.0 Hz, 2H), 2.71 (t, J=6.0 Hz, 2H), 2.56 (t, J=7.2 Hz, 2H), 1.88-1.81 (m, 2H), 1.79-1.72 (m, 2H).

85. Synthesis of 8-(4-(6-chloro-3,4-dihydroisoquinolin-2(1H)-yl)butoxy)-4,5-dihydro-1H-pyrido[2,3-d][1,3]diazepin-2(3H)-one (Compound 85)

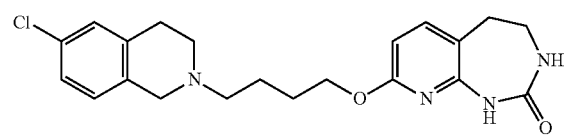

Compound 85

This compound was prepared in 38% yield using the procedures described for Compound 83 but using 6-chloro-1,2,3,4-tetrahydroisoquinoline as the amine starting material. MS (ESI): m/z 401.1 [M+H]+. 1H NMR (400 MHz, CDCl3): δ 8.47 (s, 1H), 7.35 (d, J=8.0 Hz, 1H), 7.16-7.02 (m, 2H), 6.94 (d, J=8.0 Hz, 1H), 6.24 (q, J=4.4 Hz, 8.4 Hz, 1H), 4.22 (t, J=6.4 Hz, 2H), 4.11 (t, J=6.4 Hz, 2H), 3.64 (s, 2H), 2.99 (t, J=8.4 Hz, 2H), 2.87 (t, J=5.6 Hz, 2H), 2.71 (t, J=5.6 Hz, 2H), 2.57 (t, J=7.6 Hz, 2H), 1.88-1.79 (m, 2H), 1.78-1.64 (m, 2H).

86. Synthesis of 8-(4-(6,7-dihydrothieno[3,2-c]pyridin-5(4H)-yl)butoxy)-4,5-dihydro-1H-pyrido[2,3-d][1,3]diazepin-2(3H)-one (Compound 86)

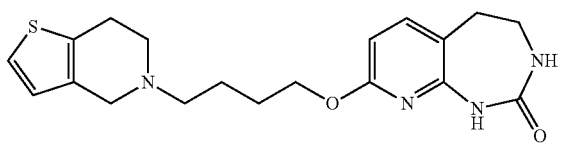

Compound 86

This compound was prepared in 61% yield using the procedures described for Compound 83 but using 4,5,6,7-tetrahydrothieno[3,2-c]pyridine as the amine starting material. MS (ESI): m/z 373.1 [M+H]+. 1H NMR (400 MHz, CDCl3): δ 8.47 (s, 1H), 7.35 (d, J=8.0 Hz, 1H), 7.07 (d, J=5.2 Hz, 1H), 6.72 (d, J=5.2 Hz, 1H), 6.24 (d, J=8.0 Hz, 1H), 4.22 (t, J=6.0 Hz, 2H), 4.09 (t, J=6.0 Hz, 2H), 3.56 (s, 2H), 2.99 (t, J=8.8 Hz, 2H), 2.90 (t, J=5.6 Hz, 2H), 2.80 (t, J=5.6 Hz, 2H), 2.60 (t, J=7.2 Hz, 2H), 1.88-1.81 (m, 2H), 1.79-1.72 (m, 2H).

87. Synthesis of 8-(4-(4,5-dihydrothieno[2,3-e]pyridin-6(7H)-yl)butoxy)-4,5-dihydro-1H-pyrido[2,3-d][1,3]diazepin-2(3H)-one (Compound 87)

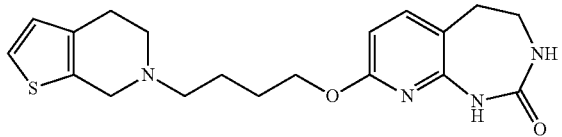

Compound 87

This compound was prepared in 51% yield using the procedures described for Compound 83 but using 4,5,6,7-tetrahydrothieno[2,3-c]pyridine as the amine starting material. MS (ESI): m/z 373.2 [M+H]+. 1H NMR (400 MHz, CDCl3): δ 8.47 (s, 1H), 7.36 (d, J=8.0 Hz, 1H), 7.09 (d, J=4.8 Hz, 1H), 6.78 (d, J=4.8 Hz, 1H), 6.25 (d, J=8.0 Hz, 1H), 4.22 (t, J=6.0 Hz, 2H), 4.10 (t, J=6.4 Hz, 2H), 3.70 (s, 2H), 3.00 (t, J=8.4 Hz, 2H), 2.81-2.75 (m, 4H), 2.62 (d, J=7.6 Hz, 2H), 1.89-1.72 (m, 4H).

88. Synthesis of 8-(4-(5-chloro-3,4-dihydroisoquinolin-2(1H)-yl)butoxy)-4,5-dihydro-1H-pyrido[2,3-d][1,3]diazepin-2(3H)-one (Compound 88)

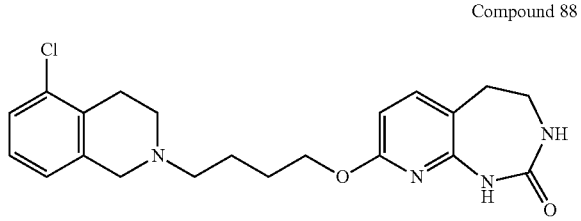 [SMILES: O=C1NCCc2ccc(OCCCCN3CCc4c(Cl)cccc4C3)nc2N1]

Compound 88

This compound was prepared in 33% yield using the procedures described for Compound 83 but using 5-chloro-1,2,3,4-tetrahydroisoquinoline as the amine starting material. MS (ESI): m/z 401.1 [M+H]⁺. ¹H NMR (400 MHz, CDCl₃): δ 8.48 (s, 1H), 7.35 (d, J=8.0 Hz, 1H), 7.20 (d, J=8.0 Hz, 1H), 7.07 (t, J=7.6 Hz, 1H), 6.94 (d, J=7.6 Hz, 1H), 6.25 (d, J=8.0 Hz, 1H), 4.23 (t, J=6.0 Hz, 2H), 4.11 (t, J=8.8 Hz, 2H), 3.62 (s, 2H), 2.99 (t, J=8.8 Hz, 2H), 2.88 (t, J=6.0 Hz, 2H), 2.76 (t, J=5.6 Hz, 2H), 2.57 (t, J=7.2 Hz, 2H), 1.89-1.64 (m, 4H).

89. Synthesis of 8-(4-(2-phenyl-6,7-dihydro-2H-pyrazolo[4,3-c]pyridin-5(4H)-yl)butoxy)-4,5-dihydro-1H-pyrido[2,3-d][1,3]diazepin-2(3H)-one (Compound 89)

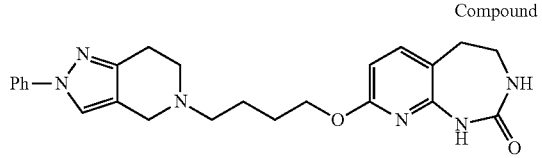

Compound 89

This compound was prepared in 47% yield using the procedures described for Compound 83 but using 2-phenyl-4,5,6,7-tetrahydro-2H-pyrazolo[4,3-c]pyridine as the amine starting material. MS (ESI): m/z 433.1 [M+H]⁺. ¹H NMR (400 MHz, CDCl₃): δ 8.48 (bs, 1H), 7.63-7.61 (m, 3H), 7.35 (d, J=8.0 Hz, 2H), 7.35 (d, J=8.0 Hz, 1H), 7.23 (t, J=7.4 Hz, 1H), 6.24 (d, J=8.0 Hz, 1H), 5.17 (brs, 1H), 4.22 (t, J=6.2 Hz, 2H), 4.10 (t, J=8.6 Hz, 2H), 3.59 (s, 2H), 2.98 (t, J=8.6 Hz, 2H), 2.92-2.89 (m, 2H), 2.84-2.82 (m, 2H), 2.62 (t, J=7.4 Hz, 2H), 1.87-1.74 (m, 4H).

90. Synthesis of 8-(4-(2-(pyridin-2-yl)-6,7-dihydro-2H-pyrazolo[4,3-c]pyridin-5(4H)-yl)butoxy)-4,5-dihydro-1H-pyrido[2,3-d][1,3]diazepin-2(3H)-one (Compound 90)

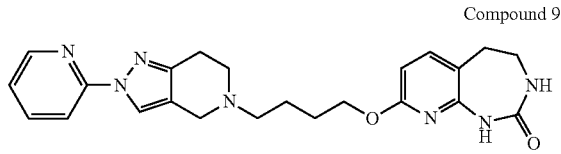

Compound 90

This compound was prepared in 51% yield using the procedures described for Compound 83 but using 2-(pyridin-2-yl)-4,5,6,7-tetrahydro-2H-pyrazolo[4,3-c]pyridine as the amine starting material. MS (ESI): m/z 434.2 [M+H]⁺. ¹H NMR (400 MHz, CDCl₃): δ 8.47 (bs, 1H), 3.35 (d, J=4.0 Hz, 1H), 8.24 (s, 1H), 7.87 (d, J=8.0 Hz, 1H), 7.78-7.73 (m, 1H), 7.33 (d, J=8.0 Hz, 1H), 7.13-7.09 (m, 1H), 6.23 (d, J=8.0 Hz, 1H), 5.35 (bs, 1H), 4.21 (t, J=6.0 Hz, 2H), 4.09 (t, J=8.4 Hz, 2H), 3.59 (s, 2H), 2.97 (t, J=8.8 Hz, 2H), 2.89 (d, J=5.6 Hz, 2H), 2.84-2.77 (m, 2H), 2.61 (t, J=7.2 Hz, 2H), 1.88-1.72 (m, 4H).

91. Synthesis of 7-(4-(3,4-dihydroisoquinolin-2(1H)-yl)butoxy)-3,4-dihydroquinolin-2(1H)-one (Compound 91)

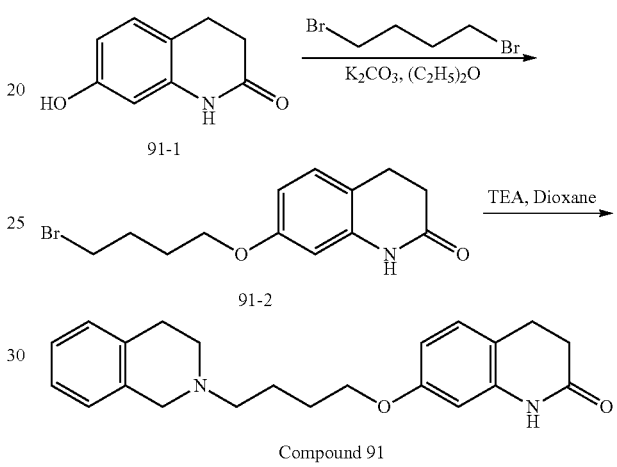

Compound 91

A mixture of 7-hydroxy-3,4-dihydroquinolin-2(1H)-one (9H) (40 mg, 0.25 mmol) and potassium carbonate (52 mg, 0.38 mmol) in ethyl ether (5 mL) was refluxed for 4 h. The reaction mixture was concentrated in vacuo, and then water (10 mL) was added to the residue. The resulting suspension was extracted with ethyl acetate (30 mL×3). The combined organic layers were washed with water (20 mL), brine (20 mL), and dried over sodium sulfate. After filtration, the filtrate was concentrated in vacuo to give compound 91-2 as a brown oil, which was dissolved in dioxane (3 mL).

To the dioxane solution was added triethylamine (39 mg, 0.75 mmol) and 1,2,3,4-tetrahydroisoquinoline (40 mg, 0.3 mmol). The mixture was heated to 110° C. and stirred for 2 h. The solvent was concentrated and the residue was purified by flash column chromatography on silica gel to give Compound 91 as a yellow solid (8 mg, 9% yield). MS (ESI): m/z 351 [M+H]⁺. ¹H NMR (400 MHz, CDCl₃): δ 8.26 (s, 114), 7.11 (m, 3H), 7.02 (m, 2H), 6.52 (dd, J=8.0 Hz, 1H), 6.33 (d, J=2.0 Hz, 1H), 4.97 (t, J=6.0 Hz, 2H), 3.65 (s, 2H), 2.90 (m, 4H), 2.75 (t, J=6.0 Hz, 2H), 2.58 (m, 4H), 1.83 (m, 2H), 1.78 (m, 2H).

92. Synthesis of 6-(4-(4-(naphthalen-1-yl)piperazin-1-yl)butoxy)-1H-indazole (Compound 92)

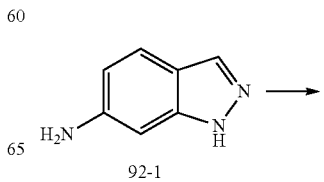

92-1

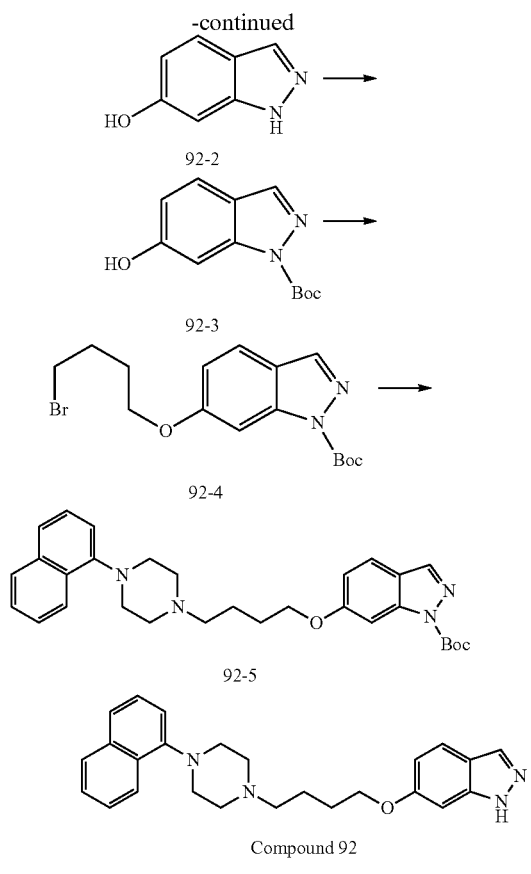

(a) Synthesis of 1H-indazol-6-ol (92-2)

To a suspension of compound 92-1 (4.5 g, 33.8 mmol) in 20 mL of ice water was added 6 mL of conc. sulfuric acid dropwise at 0° C. The mixture was stirred at room temperature for 1 h and then heated to 110° C. for another hour. The mixture was cooled and adjusted to pH 6 with 2 M sodium hydride to give a suspension. The suspension was filtered. The solid was collected and dried in vacuo to afford the crude product as a brown solid (2.5 g, yield: 55.6%). MS (ESI): m/z 135 [M+H]$^+$.

(b) Synthesis of tert-butyl 6-hydroxy-1H-indazole-1-carboxylate (92-3)

A mixture of compound 92-2 (5.3 g, 25.1 mmol), di-tert-butyl dicarbonate (5.5 g, 25.1 mmol), triethylamine (2.79 g, 27.6 mmol), and N,N-dimethyl-pyridin-4-amine (153 mg, 1.26 mmol) in tetrahydrofuran (20 mL) was heated to 75° C. for 4 h. Solvent was then evaporated in vacuo, and the crude product was purified with column chromatography (silica gel, ethyl acetate/dichloromethane=1/8) to afford compound 92-3 as a yellow oil (2.3 g, yield: 22.4%). MS (ESI): m/z 235 [M+H]$^+$.

(c) Synthesis of tert-butyl 6-(4-bromobutoxy)-1H-indazole-1-carboxylate (92-4)

A suspension of compound 92-3 (2.3 g, 5.62 mmol), 1,4-dibromobutane (2.4 g, 11.2 mmol), and potassium carbonate (1.55 g, 11.2 mmol, 2.0 eq.) in acetonitrile (10 mL) was heated to 75° C. for 5 h. The solvent was then evaporated in vacuo, and the crude product was purified by column chromatography (silica gel, ethyl acetate/petroleum ether=1/10) to afford compound 92-4 as a colorless oil (1.75 g, yield: 54.2%). MS (ESI): m/z 392, 390 [M+H]$^+$.

(d) Synthesis of tert-butyl 6-(4-(4-(naphthalen-1-yl)piperazin-1-yl)butoxy)-1H-indazole-1-carboxylate (92-5)

A mixture of compound 92-4 (100 mg, 0.174 mmol), 1-(naphthalen-1-yl)piperazine (41 mg, 0.190 mmol), and potassium carbonate (27 mg, 0.190 mmol) in acetonitrile (2 mL) was heated to 75° C. for 4 h. The solvent was evaporated in vacuo, and the crude mixture was purified with prep-TLC (silica gel, ethyl acetate/dichloromethane=1/40) to afford compound 92-5 as a colorless oil (76 mg, yield: 87.4%). MS (ESI): m/z 501 [M+H]$^+$.

(e) Synthesis of 6-(4-(4-(naphthalen-1-yl)piperazin-1-yl)butoxy)-1H-indazole (hydrogen chloride salt) (Compound 92)

A mixture of compound 92-5 (76 mg, 0.152 mmol) and conc. hydrogen chloride (0.5 mL) in tetrahydrofuran (2 mL) was heated to 75° C. for 1 h. The mixture was cooled to room temperature to give a suspension. The solid was collected by filtration, washed with cold 0.5 mL of methanol, and dried in vacuum to afford compound 92 (60 mg, yield: 83.5%) as a white solid. MS (ESI): m/z 401 [M+H]$^+$. $^1$H NMR (400 MHz, CDCl$_3$): δ 9.96 (bs, 1H), 8.21-8.18 (m, 1H), 7.96 (d, J=0.8 Hz, 1H), 7.83-7.81 (m, 1H), 7.60 (dd, J=8.8 Hz, 0.8 Hz, 1H), 7.55 (d, J=8.0 Hz, 1H), 7.49-7.46 (m, 2H), 7.40 (t, J=8.0 Hz, 1H), 7.09 (d, J=7.2 Hz, 1H), 6.86-6.83 (m, 2H), 4.06 (t, J=6.4 Hz, 2H), 3.17 (s, 4H), 2.79 (s, 4H), 2.59 (t, J=7.6 Hz, 2H), 1.95-1.88 (m, 2H), 1.84-1.77 (m, 2H).

93. Synthesis of 6-(4-(4-(2-ethoxyphenyl)piperazin-1-yl)butoxy)-1H-indazole (Compound 93)

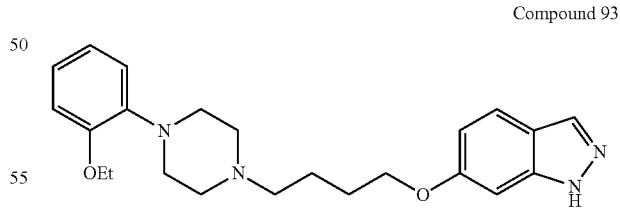

Compound 93

This compound was prepared in 74% yield as a hydrochloride salt using the same procedures described for Compound 92 but using 1-(2-ethoxyphenyl)-piperazine as the amine starting material. MS (ESI): m/z 395 [M+H]$^+$. $^1$H NMR (400 MHz, CDCl$_3$): δ 10.3 (bs, 1H), 7.96 (s, 1H), 7.59 (d, J=9.2 Hz, 1H), 6.99-6.80 (m, 6H), 4.06 (q, J=7.2 Hz, 2H), 4.01 (d, J=6.4 Hz, 2H), 3.14 (s, 4H), 2.69 (s, 4H), 2.50 (t, J=7.2 Hz, 2H), 1.90-1.83 (m, 2H), 1.79-1.71 (m, 2H), 1.45 (t, J=7.2 Hz, 3H).

94. Synthesis of 6-(4-(4-(pyridin-2-yl)piperazin-1-yl)butoxy)-1H-indazole (Compound 94)

Compound 94

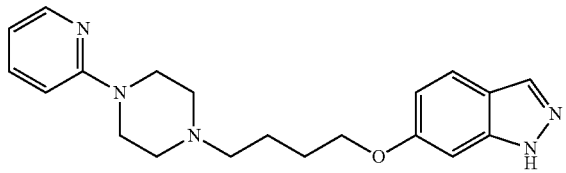

This compound was prepared in 75% yield as a hydrochloride salt using the same procedures described for Compound 92 but using 1-(pyridin-2-yl)piperazine as the amine starting material. MS (ESI): m/z 352 [M+H]$^+$. $^1$H NMR (400 MHz, CDCl$_3$): δ 8.19 (dd, J=5.2 Hz, 0.8 Hz, 1H), 7.96 (s, 1H), 7.60 (d, J=8.8 Hz, 1H), 7.49-7.46 (m, 1H), 6.85-6.81 (m, 2H), 6.66-6.61 (m, 2H), 4.04 (t, J=6.0 Hz, 2H), 3.56 (t, J=4.8 Hz, 4H), 2.60 (t, J=4.8 Hz, 4H), 2.49 (t, J=7.2 Hz, 2H), 1.92-1.85 (m, 2H), 1.79-1.73 (m, 2H).

95. Synthesis of 6-(4-(4-(2,3-dimethylphenyl)piperazin-1-yl)butoxy)-1H-indazole (Compound 95)

Compound 95

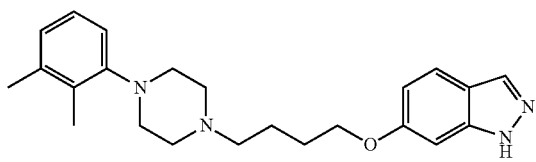

This compound was prepared in 55% yield as a hydrochloride salt using the same procedures described for Compound 92 but using 1-(2,3-dimethylphenyl)piperazine as the amine starting material. MS (ESI): m/z 379 [M+H]$^+$. $^1$H NMR (400 MHz, CDCl$_3$): δ 10.0 (bs, 1H), 7.97 (s, 1H), 7.60 (d, J=8.8 Hz, 1H), 7.07 (t, J=8.0 Hz, 1H), 6.93-6.89 (m, 2H), 6.84-6.81 (m, 2H), 4.04 (t, J=6.4 Hz, 2H), 2.93 (t, J=4.8 Hz, 2H), 2.66 (s, 4H), 2.52 (t, J=7.6 Hz, 2H), 2.27 (s, 3H), 2.22 (s, 3H), 1.90-1.85 (m, 2H), 1.80-1.75 (m, 2H).

96. Synthesis of 6-(4-(4-(o-tolyl)piperazin-1-yl)butoxy)-1H-indazole (Compound 96)

Compound 96

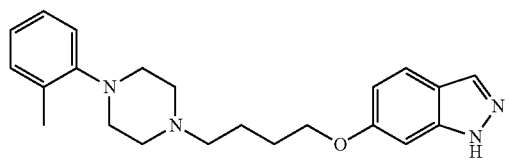

This compound was prepared in 90% yield as a hydrochloride salt using the same procedures described for Compound 92 but using 1-(2-methylphenyl)piperazine as the amine starting material. MS (ESI): m/z 365 [M+H]$^+$. $^1$H NMR (400 MHz, CDCl$_3$): δ 9.95 (bs, 1H), 7.97 (s, 1H), 7.60 (d, J=8.8 Hz, 1H), 7.17 (t, J=7.6 Hz, 2H), 7.04-6.96 (m, 2H), 6.85-6.81 (m, 2H), 4.05 (t, J=6.4 Hz, 2H), 2.97 (t, J=4.4 Hz, 4H), 2.65 (s, 4H), 2.52 (t, J=7.2 Hz, 2H), 2.30 (s, 3H), 1.91-1.85 (m, 2H), 1.81-1.75 (m, 2H).

97. Synthesis of 6-(4-(4-(2-chlorophenyl)piperazin-1-yl)butoxy)-1H-indazole (Compound 97)

Compound 97

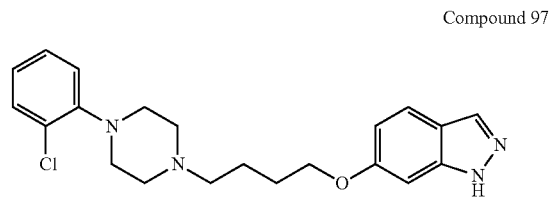 [SMILES: Clc1ccccc1N1CCN(CCCCOc2ccc3cn[nH]c3c2)CC1]

This compound was prepared in 74% yield as a hydrochloride salt using the same procedures described for Compound 92 but using 1-(2-chlorophenyl)piperazine as the amine starting material. MS (ESI): m/z 387, 385 [M+H]$^+$. $^1$H NMR (400 MHz, CDCl$_3$): δ 9.94 (bs, 1H), 7.96 (s, 1H), 7.60 (d, J=8.0 Hz, 1H), 7.35 (d, J=8.0 Hz, 1H), 7.24-7.20 (m, 1H), 7.04 (d, J=6.4 Hz, 1H), 6.98-6.95 (m, 1H), 6.85-6.82 (m, 2H), 4.05 (t, J=6.4 Hz, 2H), 3.10 (s, 4H), 2.68 (s, 4H), 2.52 (t, J=7.6 Hz, 2H), 1.92-1.85 (m, 2H), 1.80-1.74 (m, 2H).

98. Synthesis of 6-(4-(4-(3-chlorophenyl)piperazin-1-yl)butoxy)-1H-indazole (Compound 98)

Compound 98

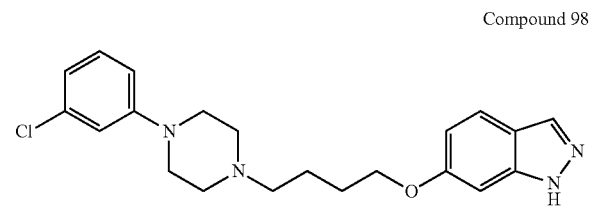 [SMILES: Clc1cccc(N2CCN(CCCCOc3ccc4cn[nH]c4c3)CC2)c1]

This compound was prepared in 26% yield as a hydrochloride salt using the same procedures described for Compound 92 but using 1-(3-chlorophenyl)piperazine as the amine starting material. MS (ESI): m/z 387, 385 [M+H]$^+$. $^1$H NMR (400 MHz, CDCl$_3$): δ 9.97 (bs, 1H), 7.96 (d, J=0.8 Hz, 1H), 7.60 (dd, J=8.4 Hz, 0.8 Hz, 1H), 7.18-7.14 (m, 1H), 6.88-6.77 (m, 6H), 4.04 (t, J=6.4 Hz, 2H), 3.22 (t, J=5.2 Hz, 4H), 2.62 (t, J=5.2 Hz, 4H), 2.51-2.47 (m, 2H), 1.90-1.85 (m, 2H), 1.79-1.73 (m, 2H).

99. Synthesis of 6-(4-(4-(3-methoxypyridin-2-yl)piperazin-1-yl)butoxy)-1H-indazole (Compound 99)

Compound 99

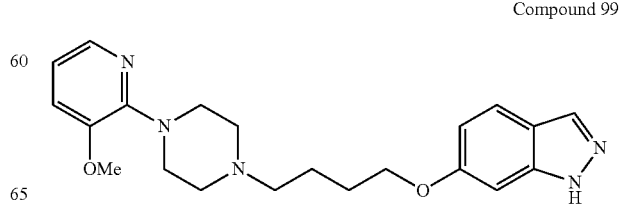

This compound was prepared in 42% yield as a hydrochloride salt using the same procedures described for Compound 92 but using 1-(3-methoxypyridin-2-yl)piperazine as the amine starting material. MS (ESI): m/z 382 [M+H]$^+$. $^1$H NMR (400 MHz, CDCl$_3$): δ 10.7 (bs, 1H), 7.96 (s, 1H), 7.90 (d, J=5.6 Hz, 1H), 7.59 (d, J=8.8 Hz, 1H), 7.04 (d, J=8.8 Hz, 1H), 6.88-6.80 (m, 3H), 4.03 (t, J=6.4 Hz, 2H), 3.85 (s, 3H), 3.45 (s, 4H), 2.66 (s, 4H), 2.51-2.47 (m, 2H), 1.89-1.85 (m, 2H), 1.77-1.73 (m, 2H).

B. In Vitro Pharmacology

Compound Handling: Compound stock concentration was 10 mM in DMSO. Compounds were diluted to 100× top testing concentration in DMSO. Serial dilutions were made in 100% DMSO, test concentrations were 0.5 nM up to 10 µM. Dopamine (0.1 nM up to 3 µM) and aripiprazole (i.e., 7-{4-[4-(2,3-dichlorophenyl)piperazin-1-yl]butoxy}-3,4-dihydroquinolin-2(1H)-one) (0.05 nM up to 10 µM) were included as controls on all assays plates.

Cell Lines: Activities of the compounds were assessed using a Chinese Hamster Ovary (CHO—K1) cell line that recombinantly expressed the long isoform of human D2 receptor (DRD2L PathHunter cells). The D2 receptor DNA sequence was modified to contain a "ProLink" at its C-terminus which allowed complementation with an "enzyme acceptor" (EA)-tagged β-arrestin protein. The recruitment of the O-arrestin by the D2 receptor led to complementation of the ProLink and EA and formation of active β-galactosidase which generated a D2-specific signal that was measured. The cAMP assay was measured in the same D2-expressing cell line. The D2 receptor inhibited cAMP formation so that the basal levels of cAMP were increased by the addition of an adenylate cyclase stimulator, forskolin.

cAMP HTRF Agonist Assay: Two days prior to testing, a vial of high density stock of DRD2L PathHunter cells was thawed, and cells were diluted into 10 mL of growth media (Ham's F12/10% HI FBS/1% PSG) and used to seed a T225 flask containing 50 mL of growth media. Cells were cultured for 2 days.

On the day of the assay, cells were dissociated in 5 mL cell dissociation buffer (enzyme free—Invitrogen) for 10-15 minutes at 37° C. Dissociated cells were diluted with 10 mL of growth media and counted. Cell counts were routinely ~2×10$^7$ per T225. Cells were then pelleted at 1500 rpm for 5 min. Supernatant was aspirated, and cells were re-suspended in HBSS/20 mM Hepes, pH 7.4 to a cell density of 1×10$^6$/mL.

Five minutes before testing, 0.5 mM IBMX was added to the cell suspension. An intermediate dilution of compound (2 µl 100× compound into 98 µL HBSS/20 mM Hepes with 20 µM forskolin) was performed. Cells were mixed, and 5 µL of diluted compound was dispensed into each well of an assay plate. The plate was incubated for 30 min at room temperature (RT).

cAMP levels were determined using the Cisbio HTRF method. HRTF reagents (cAMP-HTRF acceptor fluorophore (d2) conjugate and cryptate-labeled anti-cAMP antibody) were prepared according to maunfacturers instructions. 5 µL of each were added to each well of an assay plate and incubated for 1 h at RT. The plate was then read on an Envision reader using the HTRF protocol, and data were exported for analysis.

The agonist E$_{max}$ results were expressed as a percent of the dopamine control response ((measured specific response/control specific agonist response)×100) obtained in the presence of test article. The EC$_{50}$ values (concentration producing a half-maximal specific response) were determined by non-linear regression analysis of the concentration-response curves. According to the cAMP agonist assay, the most active D2 agonists will have the most amount of activity as measured by E$_{max}$ (i.e., as represented by the grading system in the Table, from most active to least active D2 agonist is **>*>**>*). Conversely, according to the cAMP agonist assay, the most active D2 antagonists will have the least amount of activity as measured by E$_{max}$ (i.e., *>>*>****).

Arrestin Agonist Assay: One day prior to testing, a vial of high density stock of DRD2L PathHunter cells was thawed, and 1×10$^7$ cells diluted into 40 mL of growth media (Ham's F12/10% HI FBS/1% PSG). 20 µL cells per well were seeded directly into assay plates, and the plates were allowed to rest for 1 h at RT before incubating in a plate incubator overnight.

On the day of the assay, an intermediate dilution of compounds was performed (5 µL 100× compound into 95 µL growth media, 5× final concentration). 5 µL diluted compound was added to cells in each well, and the assay plate was incubated for 90 min at 37° C. 12.5 µL PathHunter detection reagent was added to each well of the assay plate, which was then covered and incubated for 1 h at RT. The plate was read on an Envision reader using the Luminescence protocol, and the data were exported for analysis.

The agonist E$_{max}$ results were expressed as a percent of the dopamine control response ((measured specific response/control specific agonist response)×100) obtained in the presence of test article. The EC$_{50}$ values (concentration producing a half-maximal specific response) were determined by non-linear regression analysis of the concentration-response curves. According to the arrestin agonist assay, the most active D2 agonists will have the most amount of activity as measured by E$_{max}$ (i.e., as represented by the grading system in the Table, from most active to least active D2 agonist is **>*>**>*). Conversely, according to the arrestin agonist assay, the most active D2 antagonists will have the least amount of activity as measured by E$_{max}$ (i.e., *>>*>****).

Arrestin Antagonist Assay: One day prior to testing, a vial of high density stock of DRD2L PathHunter cells was thawed, and 1×10$^7$ cells diluted into 40 mL of growth media (Ham's F12/10% HI FBS/1% PSG). 20 µL cells per well were seeded directly into assay plates, and the plates were allowed to rest for 1 h at RT before incubating in a plate incubator overnight.

On the day of the assay, an intermediate dilution of compounds was performed (5 µL 100× compound into 95 µL growth media, 5× final concentration). 5 µL diluted compound was added to each well of the assay plate, which was then covered and incubated for 30 min at 37° C. A 6×EC$_{80}$ stock of dopamine was prepared in growth media (EC$_{80}$=500 nM), and 5 µL added to the wells of the assay plate. The plate was incubated for 30 min at 37° C. 15 µL PathHunter detection reagent was added to each well of the assay plate, which was then covered and incubated for 1 h at RT. The plate was read on an Envision reader using the Luminescence protocol, and the data were exported for analysis.

The antagonist I$_{max}$ results were expressed as percent inhibition of an EC$_{80}$ concentration of dopamine (concentration that produces 80% of the maximum response to dopamine). The IC$_{50}$ values (concentration producing a half-maximal inhibitory response) were determined by non-linear regression analysis of the concentration-response curves. According to the arrestin antagonist assay, the most active D2 antagonists will have the most amount of inhibition as measured by I$_{max}$ (i.e., as represented by the grading system in the Table, from most active to least active D2 antagonist is **>*>**>*). Conversely, according to the arrestin antagonist assay, the most active D2 agonists will have the least amount of inhibition as measured by $I_{max}$ (i.e., *>>*>****).

The potency and activity of the compounds provided herein in receptor assays is summarized in the table below.

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 1 | 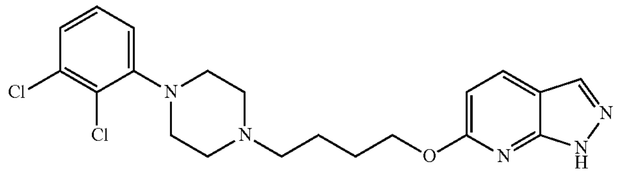 [SMILES: Clc1cccc(N2CCN(CCCCOc3ccc4cn[nH]c4n3)CC2)c1Cl] | 6-(4-(4-(2,3-dichlorophenyl)piperazin-1-yl)butoxy)-1H-pyrazolo[3,4-b]pyridine | ** |  | NA | NA | ** | ** |
| 2 | 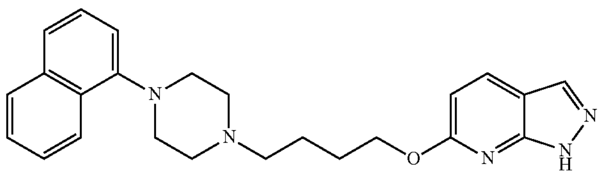 [SMILES: c1ccc2c(N3CCN(CCCCOc4ccc5cn[nH]c5n4)CC3)cccc2c1] | 6-(4-(4-(naphthalen-1-yl)piperazin-1-yl)butoxy)-1H-pyrazolo[3,4-b]pyridine | *** | * | *** | * | * | * |
| 3 | 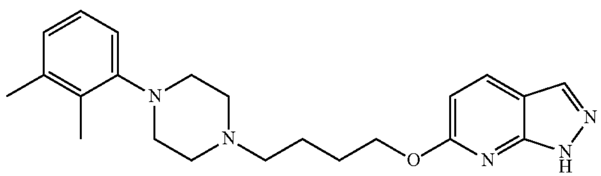 [SMILES: Cc1cccc(N2CCN(CCCCOc3ccc4cn[nH]c4n3)CC2)c1C] | 6-(4-(4-(2,3-dimethylphenyl)piperazin-1-yl)butoxy)-1H-pyrazolo[3,4-b]pyridine | *** | * | NA | NA |  | ** |
| 4 | 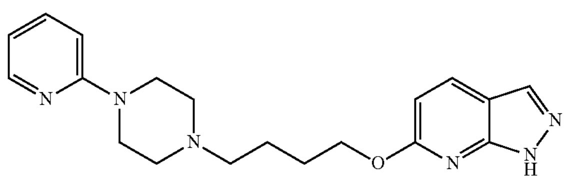 [SMILES: c1ccc(N2CCN(CCCCOc3ccc4cn[nH]c4n3)CC2)nc1] | 6-(4-(4-(pyridin-2-yl)piperazin-1-yl)butoxy)-1H-pyrazolo[3,4-b]pyridine | ** |  | * | **** | NA | NA |
| 5 | 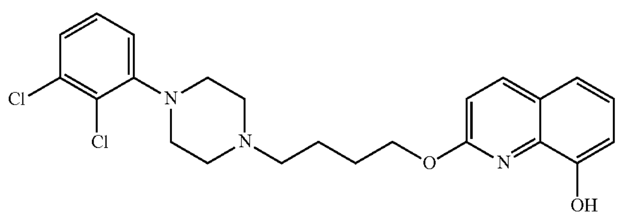 [SMILES: Oc1cccc2ccc(OCCCCN3CCN(c4cccc(Cl)c4Cl)CC3)nc12] | 2-(4-(4-(2,3-dichlorophenyl)piperazin-1-yl)butoxy)quinolin-8-ol | * |  | *** | * |  | ** |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 6 | 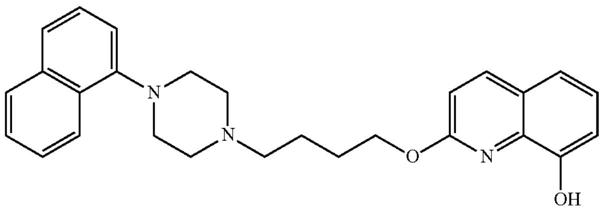 [SMILES: Oc1cccc2ccc(OCCCCN3CCN(c4cccc5ccccc45)CC3)nc12] | 2-(4-(4-(naphthalen-1-yl)piperazin-1-yl)butoxy)quinolin-9-ol | * |  |  |  |  | * |
| 7 | 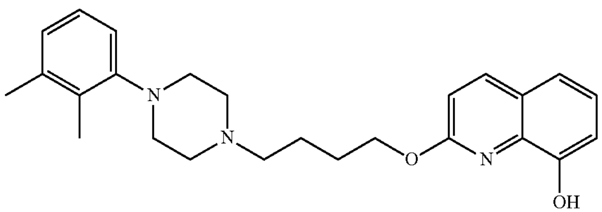 [SMILES: Cc1cccc(N2CCN(CCCCOc3ccc4cccc(O)c4n3)CC2)c1C] | 2-(4-(4-(2,3-dimethylphenyl)piperazin-1-yl)butoxy)quinolin-8-ol | * |  | NA | NA |  | ** |
| 8 | 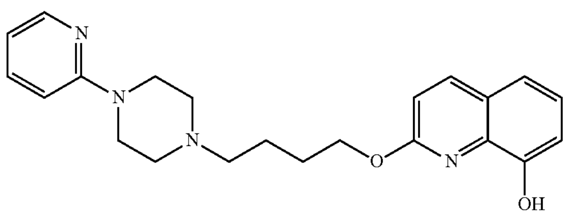 [SMILES: Oc1cccc2ccc(OCCCCN3CCN(c4ccccn4)CC3)nc12] | 2-(4-(4-(pyridin-2-yl)piperazin-1-yl)butoxy)quinolin-8-ol | *** | * | * | **** | NA | NA |
| 23 | 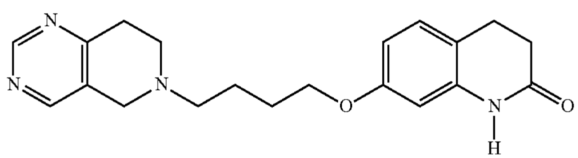 [SMILES: O=C1CCc2ccc(OCCCCN3CCc4ncncc4C3)cc2N1] | 7-(4-(7,8-dihydropyrido[4,3-d]pyrimidin-6(5H)-yl)butoxy)-3,4-dihydroquinolin-2(1H)-one |  | * | ** | * | * | ** |
| 24 | 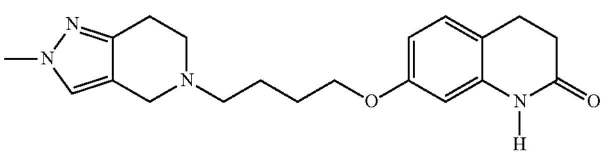 [SMILES: Cn1cc2c(n1)CCN(CCCCOc1ccc3c(c1)NC(=O)CC3)C2] | 7-(4-(2-methyl-6,7-dihydro-2H-pyrazolo[4,3-c]pyridin-5(4H)-yl)butoxy)-3,4-dihydroquinolin-2(1H)-one | * |  |  | ** | * | ** |

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 25 | 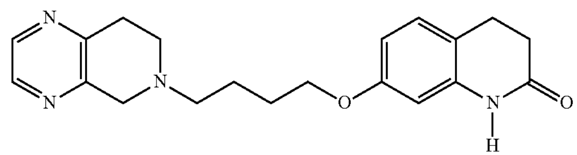 [SMILES: O=C1CCc2ccc(OCCCCN3CCc4nccnc4C3)cc2N1] | 7-(4-(7,8-dihydropyrido[3,4-b]pyrazin-6(5H)-yl)butoxy)-3,4-dihydroquinolin-2(1H)-one | * | * |  | ** | * | ** |
| 26 | 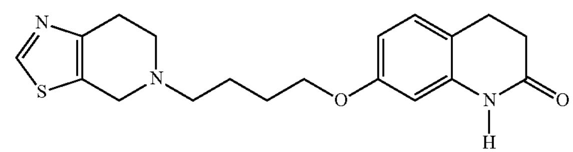 [SMILES: O=C1CCc2ccc(OCCCCN3CCc4ncsc4C3)cc2N1] | 7-(4-(6,7-dihydrothiazolo[5,4-c]pyridin-5(4H)-yl)butoxy)-3,4-dihydroquinolin-2(1H)-one | * |  | **** | * | * | **** |
| 40 | 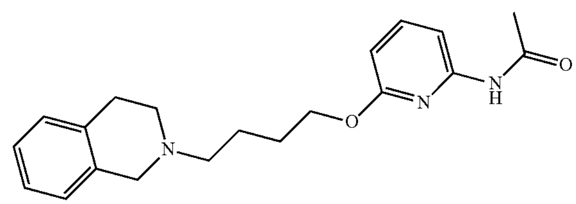 [SMILES: CC(=O)Nc1cccc(OCCCCN2CCc3ccccc3C2)n1] | N-(6-(4-(3,4-dihydroisoquinolin-2(1H)-yl)butoxy)pyridin-2-yl)acetamide | NA | NA | NA | NA |  | ** |
| 41 | 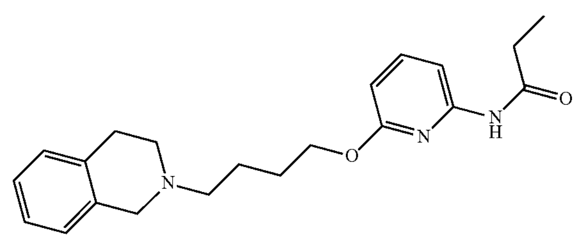 [SMILES: CCC(=O)Nc1cccc(OCCCCN2CCc3ccccc3C2)n1] | N-(6-(4-(3,4-dihydroisoquinolin-2(1H)-yl)butoxy)pyridin-2-yl)propionamide | NA | NA | NA | NA |  | ** |
| 42 | 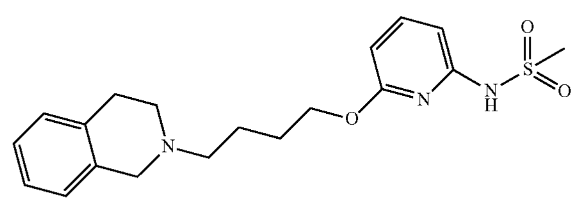 [SMILES: CS(=O)(=O)Nc1cccc(OCCCCN2CCc3ccccc3C2)n1] | N-(6-(4-(3,4-dihydroisoquinolin-2(1H)-yl)butoxy)pyridin-2-yl)methanesulfonamide | NA | NA | NA | NA | * | **** |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 43 | 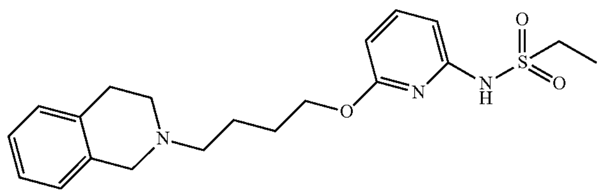 [SMILES: CCS(=O)(=O)Nc1cccc(OCCCCN2CCc3ccccc3C2)n1] | N-(6-(4-(3,4-dihydroisoquinolin-2(1H)-yl)butoxy)pyridin-2-yl)ethanesulfonamide | NA | NA | NA | NA |  | ** |
| 52 | 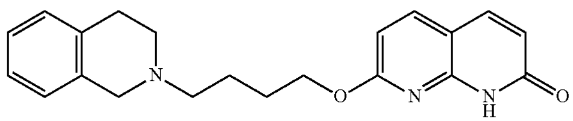 [SMILES: O=c1ccc2ccc(OCCCCN3CCc4ccccc4C3)nc2[nH]1] | 7-(4-(3,4-dihydroisoquinolin-2(1H)-yl)butoxy)-1,8-naphthyridin-2(1H)-one | ** | * | **** | * | * | ** |
| 68 | 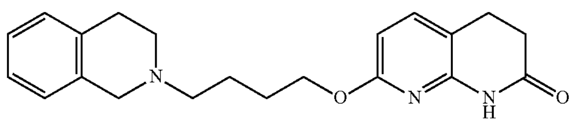 [SMILES: O=C1CCc2ccc(OCCCCN3CCc4ccccc4C3)nc2N1] | 7-(4-(3,4-dihydroisoquinolin-2(1H)-yl)butoxy)-3,4-dihydro-1,8-naphthyridin-2(1H)-one | ** |  | NA | NA | * | ** |
| 53 | 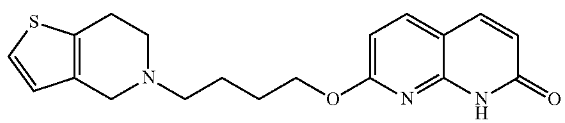 [SMILES: O=c1ccc2ccc(OCCCCN3CCc4sccc4C3)nc2[nH]1] | 7-(4-(6,7-dihydrothieno[3,2-c]pyridin-5(4H)-yl)butoxy)-1,8-naphthyridin-2(1H)-one | **** | * | NA | NA | * | ** |
| 69 | 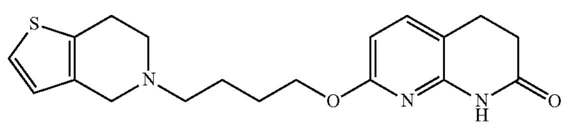 [SMILES: O=C1CCc2ccc(OCCCCN3CCc4sccc4C3)nc2N1] | 7-(4-(6,7-dihydrothieno[3,2-c]pyridin-5(4H)-yl)butoxy)-3,4-dihydro-1,8-naphthyridin-2(1H)-one | NA | NA | NA | NA | * | ** |
| 54 | 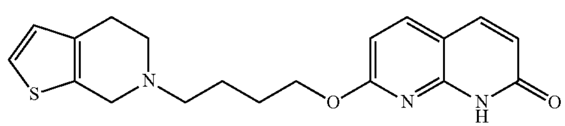 [SMILES: O=c1ccc2ccc(OCCCCN3CCc4ccsc4C3)nc2[nH]1] | 7-(4-(4,5-dihydrothieno[2,3-c]pyridin-6(7H)-yl)butoxy)-1,8-naphthyridin-2(1H)-one | NA | NA | NA | NA | ** | ** |
| 70 | 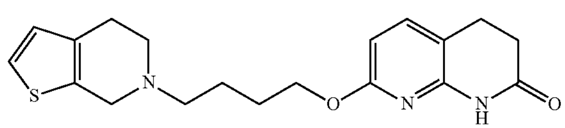 [SMILES: O=C1CCc2ccc(OCCCCN3CCc4ccsc4C3)nc2N1] | 7-(4-(4,5-dihydrothieno[2,3-c]pyridin-6(7H)-yl)butoxy)-3,4-dihydro-1,8-naphthyridin-2(1H)-one | NA | NA | NA | NA |  | ** |

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 44 | 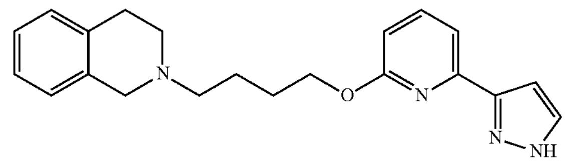 [SMILES: c1cc(OCCCCN2CCc3ccccc3C2)nc(-c2cc[nH]n2)c1] | 2-(4-((6-(1H-pyrazol-3-yl)pyridin-2-yl)oxy)butyl)-1,2,3,4-tetrahydroisoquinoline | **** | * | **** | * | * | ** |
| 51 | 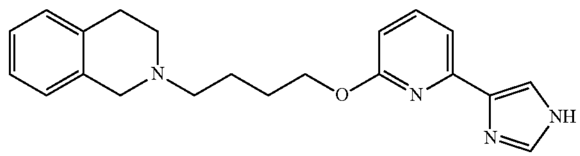 [SMILES: c1cc(OCCCCN2CCc3ccccc3C2)nc(-c2c[nH]cn2)c1] | 2-(4-((6-(1H-imidazol-4-yl)pyridin-2-yl)oxy)butyl)-1,2,3,4-tetrahydroisoquinoline | NA | NA | NA | NA |  | ** |
| 27 | 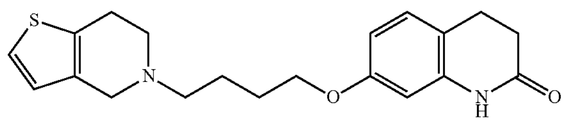 [SMILES: O=C1CCc2ccc(OCCCCN3CCc4sccc4C3)cc2N1] | 7-(4-(6,7-dihydrothieno[3,2-c]pyridin-5(4H)-yl)butoxy)-3,4-dihydroquinolin-2(1H)-one | **** | * | NA | NA | * | ** |
| 28 | 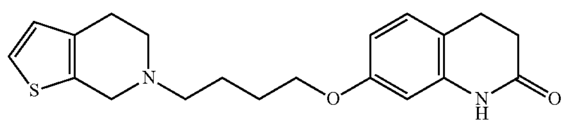 [SMILES: O=C1CCc2ccc(OCCCCN3CCc4ccsc4C3)cc2N1] | 7-(4-(4,5-dihydrothieno[2,3-c]pyridin-6(7H)-yl)butoxy)-3,4-dihydroquinolin-2(1H)-one | **** | * | NA | NA |  | ** |
| 9 | 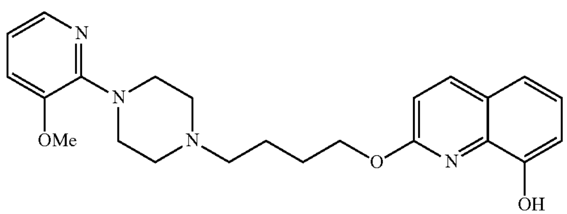 [SMILES: COc1cccnc1N1CCN(CCCCOc2ccc3cccc(O)c3n2)CC1] | 2-(4-(4-(3-methoxypyridin-2-yl)piperazin-1-yl)butoxy)quinolin-8-ol | ** |  | NA | NA | * | ** |

-continued

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 10 | 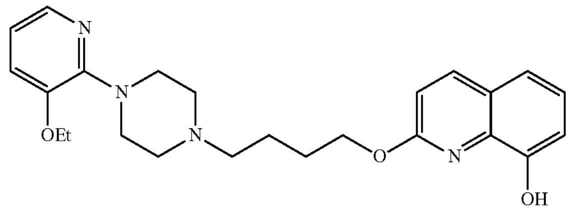 | 2-(4-(4-(3-ethoxypyridin-2-yl)piperazin-1-yl)butoxy)quinolin-8-ol | ** |  | **** | * | * | ** |
| 11 | 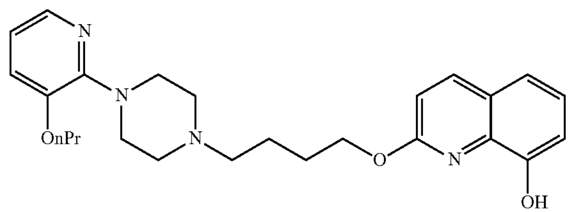 | 2-(4-(4-(3-propoxypyridin-2-yl)piperazin-1-yl)butoxy)quinolin-8-ol | NA | NA | NA | NA |  | ** |
| 12 | 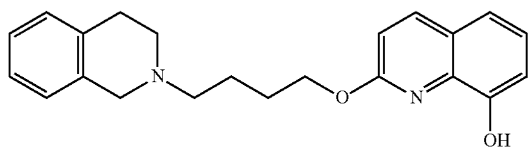 [SMILES: Oc1cccc2ccc(OCCCCN3CCc4ccccc4C3)nc12] | 2-(4-(3,4-dihydroisoquinolin-2(1H)-yl)butoxy)quinolin-8-ol | NA | NA | *** | * | * | **** |
| 13 | 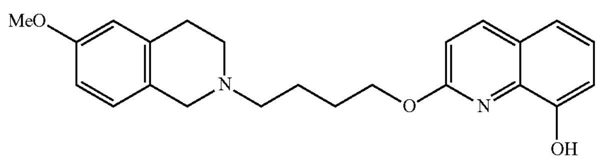 [SMILES: COc1ccc2c(c1)CCN(CCCCOc1ccc3cccc(O)c3n1)C2] | 2-(4-(6-methoxy-3,4-dihydroisoquinolin-2(1H)-yl)butoxy)quinolin-8-ol | NA | NA | **** | * | * | **** |
| 14 | 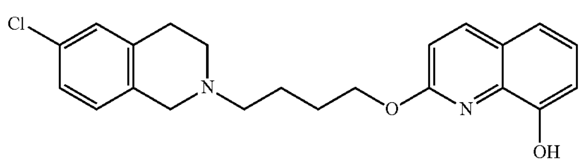 [SMILES: Oc1cccc2ccc(OCCCCN3CCc4cc(Cl)ccc4C3)nc12] | 2-(4-(6-chloro-3,4-dihydroisoquinolin-2(1H)-yl)butoxy)quinolin-8-ol | NA | NA | NA | NA | * | **** |

-continued

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 15 | 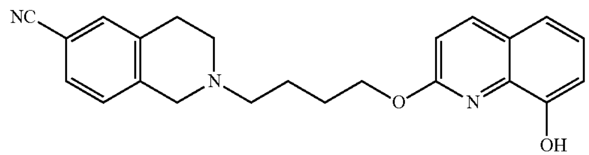 [SMILES: N#Cc1ccc2c(c1)CCN(CCCCOc1ccc3cccc(O)c3n1)C2] | 2-(4-((8-hydroxyquinolin-2-yl)oxy)butyl)-1,2,3,4-tetrahydroisoquinolin-6-carbonitrile | NA | NA | NA | NA | * | **** |
| 16 | 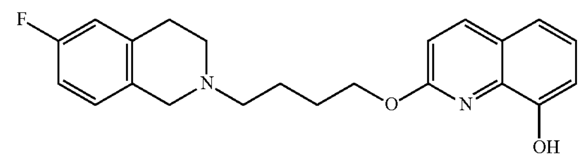 [SMILES: Oc1cccc2ccc(OCCCCN3CCc4cc(F)ccc4C3)nc12] | 2-(4-(6-fluoro-3,4-dihydroisoquinolin-2(1H)-yl)butoxy)quinolin-8-ol | NA | NA | NA | NA |  | ** |
| 17 | 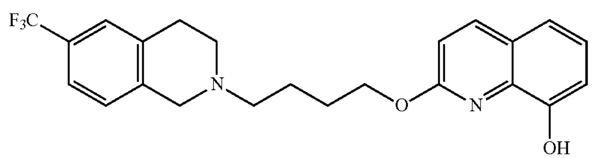 [SMILES: Oc1cccc2ccc(OCCCCN3CCc4cc(C(F)(F)F)ccc4C3)nc12] | 2-(4-(6-(trifluoromethyl)-3,4-dihydroisoquinolin-2(1H)-yl)butoxy)quinolin-8-ol | NA | NA | NA | NA | * | **** |
| 18 | 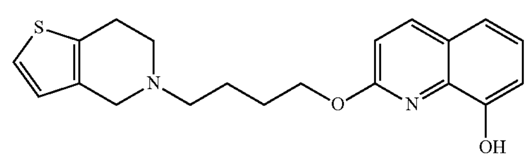 [SMILES: Oc1cccc2ccc(OCCCCN3CCc4sccc4C3)nc12] | 2-(4-(6,7-dihydrothieno[3,2-c]pyridin-5(4H)-yl)butoxy)quinolin-8-ol | NA | NA | NA | NA | * | **** |
| 19 | 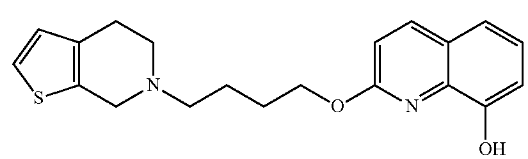 [SMILES: Oc1cccc2ccc(OCCCCN3CCc4ccsc4C3)nc12] | 2-(4-(4,5-dihydrothieno[2,3-c]pyridin-6(7H)-yl)butoxy)quinolin-8-ol | NA | NA | NA | NA | * | **** |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 20 | 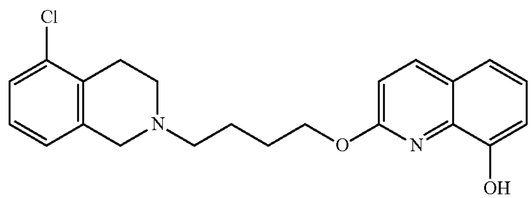 [SMILES: Oc1cccc2ccc(OCCCCN3CCc4c(Cl)cccc4C3)nc12] | 2-(4-(5-chloro-3,4-dihydroisoquinolin-2(1H)-yl)butoxy)quinolin-8-ol | * | * |  | ** | NA | NA |
| 21 | 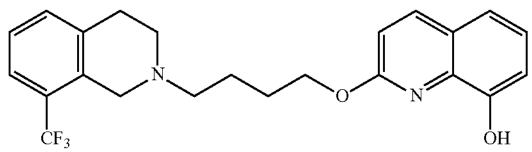 [SMILES: Oc1cccc2ccc(OCCCCN3CCc4cccc(C(F)(F)F)c4C3)nc12] | 2-(4-(8-(trifluoromethyl)-3,4-dihydroisoquinolin-2(1H)-yl)butoxy)quinolin-8-ol | ** |  | NA | NA |  | ** |
| 29 | 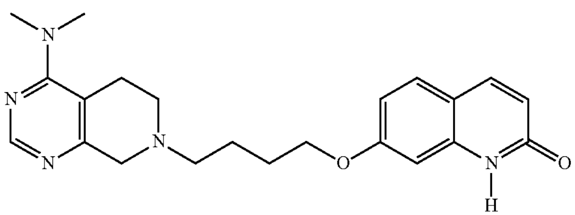 | 7-(4-(4-(dimethylamino)-5,6-dihydropyrido[3,4-d]pyrimidin-7(8H)-yl)butoxy)-3,4-dihydroquinolin-2(1H)-one | * |  |  |  |  | ** |
| 30 | 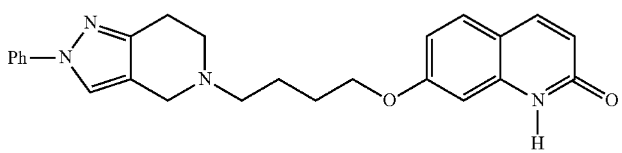 | 7-(4-(2-phenyl-6,7-dihydro-2H-pyrazolo[4,3-c]pyridin-5(4H)-yl)butoxy)-3,4-dihydroquinolin-2(1H)-one | * |  | **** | * | * | ** |
| 31 | 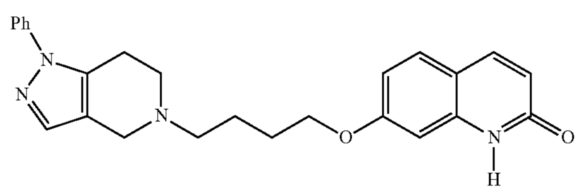 | 7-(4-(1-phenyl-6,7-dihydro-1H-pyrazolo[4,3-c]pyridin-5(4H)-yl)butoxy)-3,4-dihydroquinolin-2(1H)-one | ** |  |  | *** | NA | NA |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 32 | 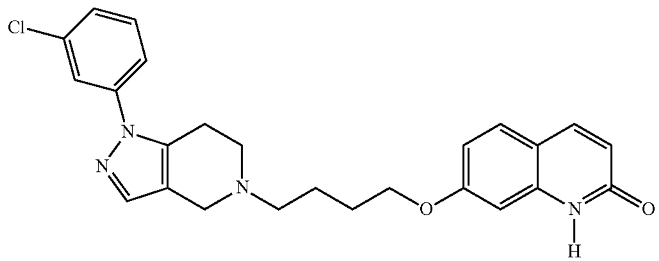 | 7-(4-(1-(3-chlorophenyl)-6,7-dihydro-1H-pyrazolo[4,3-c]pyridin-5(4H)-yl)butoxy)-3,4-dihydroquinolin-2(1H)-one | NA | NA | NA | NA | ** | ** |
| 33 | 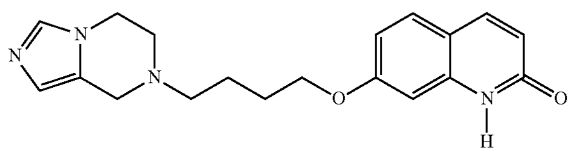 | 7-(4-(5,6-dihydroimidazo[1,5-a]pyrazin-7(8H)-yl)butoxy)-3,4-dihydroquinolin-2(1H)-one | NA | NA | NA | NA | * | *** |
| 83 | 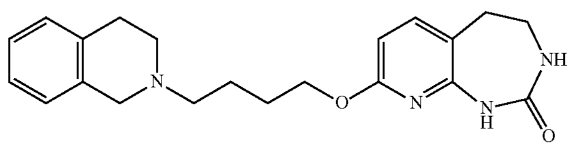 [SMILES: O=C1NCCc2ccc(OCCCCN3CCc4ccccc4C3)nc2N1] | 8-(4-(3,4-dihydroisoquinolin-2(1H)-yl)butoxy)-4,5-dihydro-1H-pyrido[2,3-d][1,3]diazepin-2(3H)-one | NA | NA | NA | NA | * | ** |
| 84 | 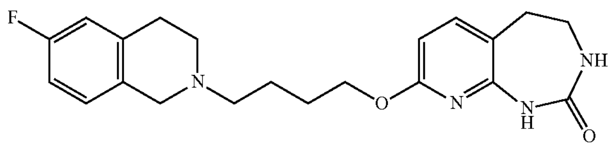 [SMILES: O=C1NCCc2ccc(OCCCCN3CCc4cc(F)ccc4C3)nc2N1] | 8-(4-(6-fluoro-3,4-dihydroisoquinolin-2(1H)-yl)butoxy)-4,5-dihydro-1H-pyrido[2,3-d][1,3]diazepin-2(3H)-one | NA | NA | NA | NA | * | ** |
| 85 | 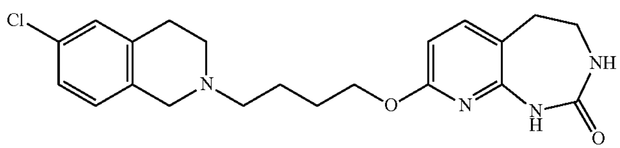 [SMILES: O=C1NCCc2ccc(OCCCCN3CCc4cc(Cl)ccc4C3)nc2N1] | 8-(4-(6-chloro-3,4-dihydroisoquinolin-2(1H)-yl)butoxy)-4,5-dihydro-1H-pyrido[2,3-d][1,3]diazepin-2(3H)-one | NA | NA | NA | NA | * | ** |

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 86 | 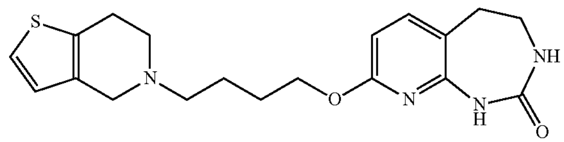 [SMILES: O=C1NCCc2ccc(OCCCCN3CCc4sccc4C3)nc2N1] | 8-(4-(6,7-dihydrothieno[3,2-c]pyridin-5(4H)-yl)butoxy)-4,5-dihydro-1H-pyrido[2,3-d][1,3]diazepin-2(3H)-one | NA | NA | NA | NA | * | ** |
| 87 | 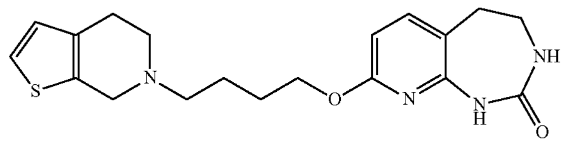 [SMILES: O=C1NCCc2ccc(OCCCCN3CCc4ccsc4C3)nc2N1] | 8-(4-(4,5-dihydrothieno[2,3-c]pyridin-6(7H)-yl)butoxy)-4,5-dihydro-1H-pyrido[2,3-d][1,3]diazepin-2(3H)-one | NA | NA | NA | NA | * | ** |
| 88 | 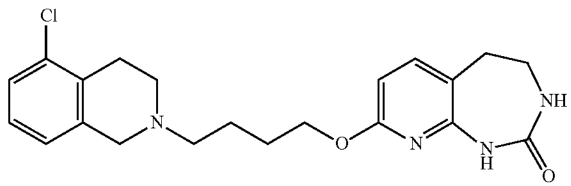 [SMILES: O=C1NCCc2ccc(OCCCCN3CCc4c(Cl)cccc4C3)nc2N1] | 8-(4-(5-chloro-3,4-dihydroisoquinolin-2(1H)-yl)butoxy)-4,5-dihydro-1H-pyrido[2,3-d][1,3]diazepin-2(3H)-one | ** | * | * |  |  |  |
| 55 | 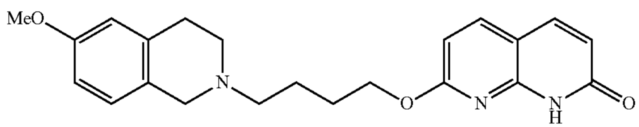 [SMILES: COc1ccc2c(c1)CCN(CCCCOc1ccc3ccc(=O)[nH]c3n1)C2] | 7-(4-(6-methoxy-3,4-dihydroisoquinolin-2(1H)-yl)butoxy)-1,8-naphthyridin-2(1H)-one | ** |  | **** | * | ** | ** |
| 71 | 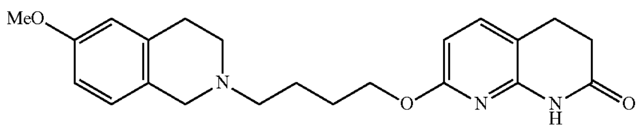 [SMILES: COc1ccc2c(c1)CCN(CCCCOc1ccc3c(n1)NC(=O)CC3)C2] | 7-(4-(6-methoxy-3,4-dihydroisoquinolin-2(1H)-yl)butoxy)-3,4-dihydro-1,8-naphthyridin-1(1H)-one | NA | NA | NA | NA | * | ** |
| 56 | 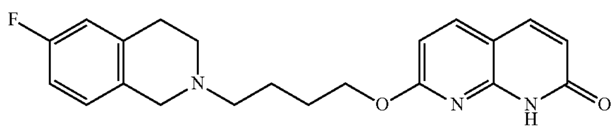 [SMILES: O=c1ccc2ccc(OCCCCN3CCc4cc(F)ccc4C3)nc2[nH]1] | 7-(4-(6-fluoro-3,4-dihydroisoquinolin-2(1H)-yl)butoxy)-1,8-naphthyridin-2(1H)-one | NA | NA | NA | NA | ** | ** |

-continued

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 72 | 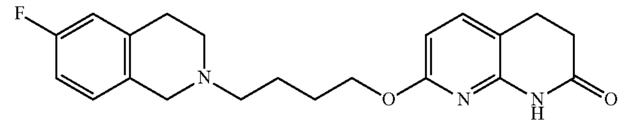 [SMILES: O=C1CCc2ccc(OCCCCN3CCc4cc(F)ccc4C3)nc2N1] | 7-(4-(6-fluoro-3,4-dihydroisoquinolin-2(1H)-yl)butoxy)-3,4-dihydro-1,8-naphthyridin-2(1H)-one | NA | NA | NA | NA | * | ** |
| 57 | 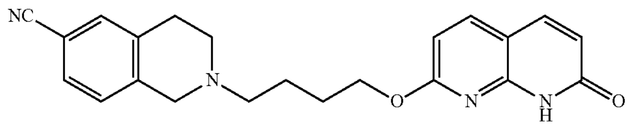 [SMILES: N#Cc1ccc2c(c1)CCN(CCCCOc1ccc3ccc(=O)[nH]c3n1)C2] | 2-(4-((7-oxo-7,8-dihydro-1,8-naphthyridin-2-yl)oxy)butyl)-1,2,3,4-tetrahydroisoquinoline-6-carbonitrile | NA | NA | NA | NA | * | ** |
| 73 | 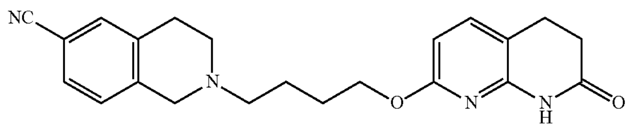 [SMILES: N#Cc1ccc2c(c1)CCN(CCCCOc1ccc3c(n1)NC(=O)CC3)C2] | 2-(4-((7-oxo-5,6,7,8-tetrahydro-1,8-naphthyridin-2-yl)oxy)butyl)-1,2,3,4-tetrahydroisoquinoline-6-carbonitrile | NA | NA | NA | NA |  | ** |
| 58 | 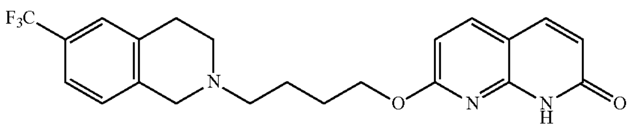 [SMILES: O=c1ccc2ccc(OCCCCN3CCc4cc(C(F)(F)F)ccc4C3)nc2[nH]1] | 7-(4-(6-(trifluoromethyl)-3,4-dihydroisoquinolin-2(1H)-yl)butoxy)-1,8-naphthyridin-2(1H)-one | ** |  | **** | * | * | ** |
| 74 | 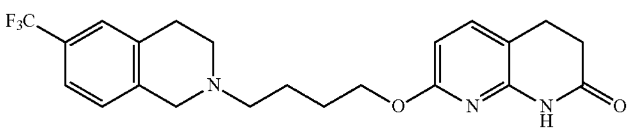 [SMILES: O=C1CCc2ccc(OCCCCN3CCc4cc(C(F)(F)F)ccc4C3)nc2N1] | 7-(4-(6-(trifluoromethyl)-3,4-dihydroisoquinolin-2(1H)-yl)butoxy)-3,4-dihydro-1,8-naphthyridin-2(1H)-one | *** | * | NA | NA |  | ** |
| 59 | 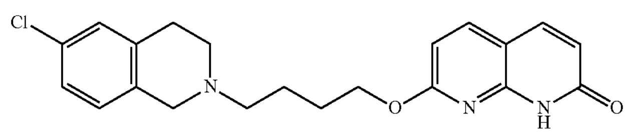 [SMILES: O=c1ccc2ccc(OCCCCN3CCc4cc(Cl)ccc4C3)nc2[nH]1] | 7-(4-(6-chloro-3,4-dihydroisoquinolin-2(1H)-yl)butoxy)-1,8-naphthyridin-2(1H)-one | **** | * | NA | NA | ** | ** |
| 75 | 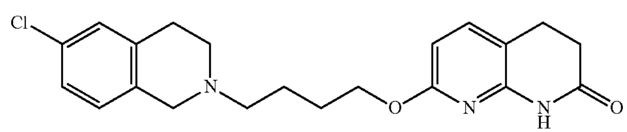 [SMILES: O=C1CCc2ccc(OCCCCN3CCc4cc(Cl)ccc4C3)nc2N1] | 7-(4-(6-chloro-3,4-dihydroisoquinolin-2(1H)-yl)butoxy)-3,4-dihydro-1,8-naphthyridin-2(1H)-one | **** | * | NA | NA | * | ** |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 60 | 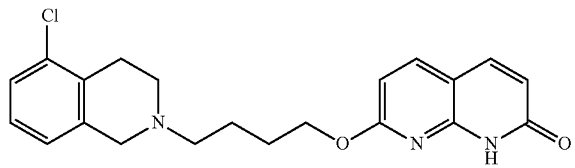 [SMILES: O=c1ccc2ccc(OCCCCN3CCc4c(Cl)cccc4C3)nc2[nH]1] | 7-(4-(5-chloro-3,4-dihydroisoquinolin-2(1H)-yl)butoxy)-1,8-naphthyridin-2(1H)-one | ** |  |  | ** | NA | NA |
| 76 | 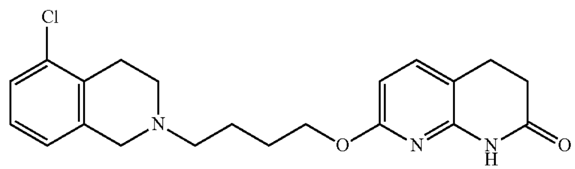 | 7-(4-(5-chloro-3,4-dihydroisoquinolin-2(1H)-yl)butoxy)-3,4-dihydro-1,8-naphthyridin-2(1H)-one | ** |  |  | ** | NA | NA |
| 61 | 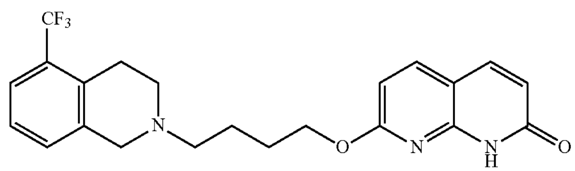 | 7-(4-(5-(trifluoromethyl)-3,4-dihydroisoquinolin-2(1H)-yl)butoxy)-1,8-naphthyridin-2(1H)-one | ** |  | * | **** | NA | NA |
| 77 | 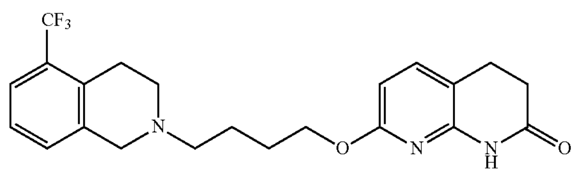 | 7-(4-(5-(trifluoromethyl)-3,4-dihydroisoquinolin-2(1H)-yl)butoxy)-3,4-dihydro-1,8-naphthyridin-2(1H)-one | * | * |  | * | NA | NA |
| 62 | 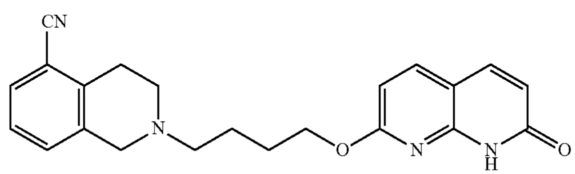 | 2-(4-((7-oxo-7,8-dihydro-1,8-naphthyridin-2-yl)oxy)butyl)-1,2,3,4-tetrahydroisoquinoline-5-carbonitrile | ** |  |  | * | NA | NA |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 78 | 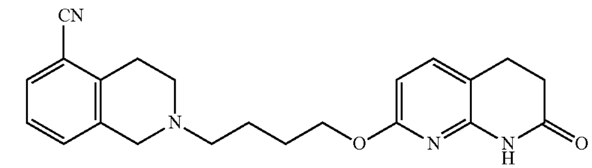 [SMILES: O=C1CCc2ccc(OCCCCN3CCc4c(Cl)cccc4C3)nc2N1] | 2-(4-((7-oxo-5,6,7,8-tetrahydro-1,8-naphthyridin-2-yl)oxy)butyl)-1,2,3,4-tetrahydroisoquinoline-5-carbonitrile | * | * | * | * | NA | NA |
| 63 | 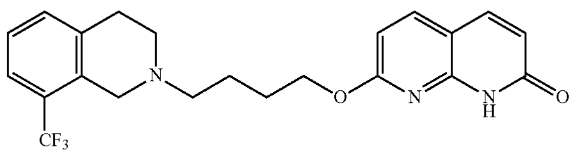 [SMILES: O=c1ccc2ccc(OCCCCN3CCc4cccc(C(F)(F)F)c4C3)nc2[nH]1] | 7-(4-(8-(trifluoromethyl)-3,4-dihydroisoquinolin-2(1H)-yl)butoxy)-1,8-naphthyridin-2(1H)-one | NA | NA | NA | NA | * | ** |
| 79 | 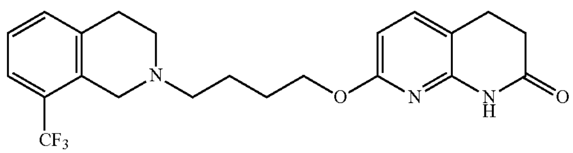 [SMILES: O=C1CCc2ccc(OCCCCN3CCc4cccc(C(F)(F)F)c4C3)nc2N1] | 7-(4-(8-(trifluoromethyl)-3,4-dihydroisoquinolin-2(1H)-yl)butoxy)-3,4-dihydro-1,8-naphthyridin-2(1H)-one | NA | NA | NA | NA |  | ** |
| 64 | 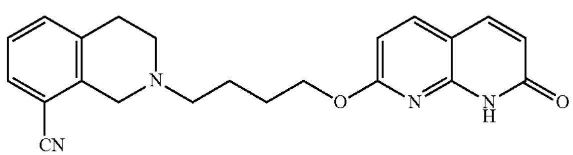 [SMILES: N#Cc1cccc2c1CN(CCCCOc1ccc3ccc(=O)[nH]c3n1)CC2] | 2-(4-((7-oxo-7,8-dihydro-1,8-naphthyridin-2-yl)oxy)butyl)-1,2,3,4-tetrahydroisoquinoline-8-carbonitrile | ** |  | **** | * | * | ** |
| 80 | 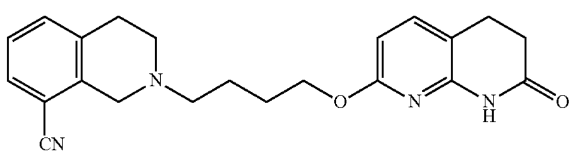 [SMILES: N#Cc1cccc2c1CN(CCCCOc1ccc3c(n1)NC(=O)CC3)CC2] | 2-(4-((7-oxo-5,6,7,8-tetrahydro-1,8-naphthyridin-2-yl)oxy)butyl)-1,2,3,4-tetrahydroisoquinoline-8-carbonitrile | NA | NA | NA | NA |  | ** |
| 65 | 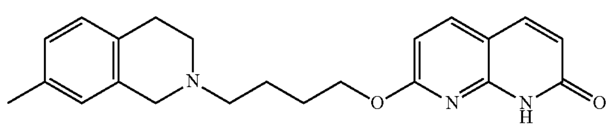 [SMILES: Cc1ccc2c(c1)CN(CCCCOc1ccc3ccc(=O)[nH]c3n1)CC2] | 7-(4-(7-methyl-3,4-dihydroisoquinolin-2(1H)-yl)butoxy)-1,8-naphthyridin-2(1H)-one | **** | * | NA | NA | * | ** |

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 81 | 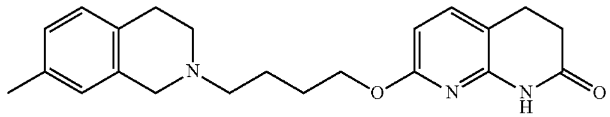 [SMILES: Cc1ccc2c(c1)CN(CCCCOc1ccc3c(n1)NC(=O)CC3)CC2] | 7-(4-(7-methyl-3,4-dihydroisoquinolin-2(1H)-yl)butoxy)-3,4-dihydro-1,8-naphthyridin-2(1H)-one | NA | NA | NA | NA | * | ** |
| 34 | 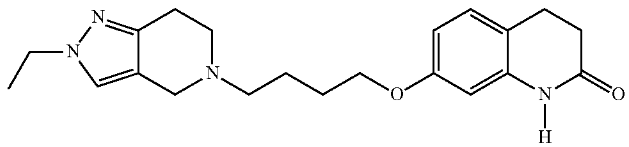 [SMILES: CCn1cc2c(n1)CCN(CCCCOc1ccc3c(c1)NC(=O)CC3)C2] | 7-(4-(2-ethyl-6,7-dihydro-2H-pyrazolo[4,3-c]pyridin-5(4H)-yl)butoxy)-3,4-dihydroquinolin-2(1H)-one |  | * |  | * | NA | NA |
| 35 | 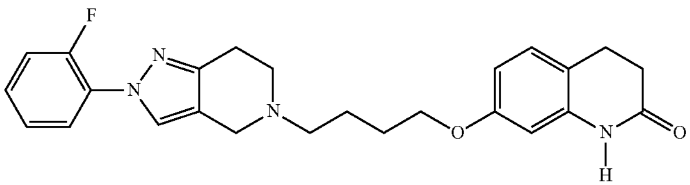 [SMILES: O=C1CCc2ccc(OCCCCN3CCc4nn(-c5ccccc5F)cc4C3)cc2N1] | 7-(4-(2-(2-fluorophenyl)-6,7-dihydro-2H-pyrazolo[4,3-c]pyridin-5(4H)-yl)butoxy)-3,4-dihydroquinolin-2(1H)-one | NA | NA | NA | NA | * | ** |
| 36 | 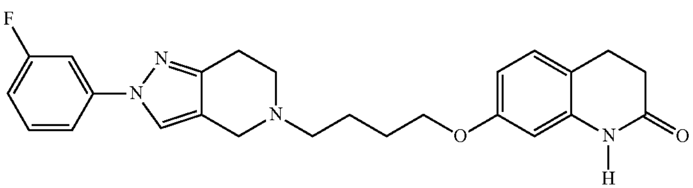 [SMILES: O=C1CCc2ccc(OCCCCN3CCc4nn(-c5cccc(F)c5)cc4C3)cc2N1] | 7-(4-(2-(3-fluorophenyl)-6,7-dihydro-2H-pyrazolo[4,3-c]pyridin-5(4H)-yl)butoxy)-3,4-dihydroquinolin-2(1H)-one | ** |  |  | ** | NA | NA |
| 37 | 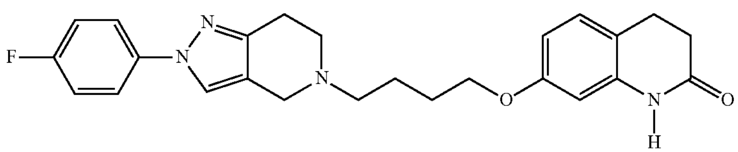 [SMILES: O=C1CCc2ccc(OCCCCN3CCc4nn(-c5ccc(F)cc5)cc4C3)cc2N1] | 7-(4-(2-(4-fluorophenyl)-6,7-dihydro-2H-pyrazolo[4,3-c]pyridin-5(4H)-yl)butoxy)-3,4-dihydroquinolin-2(1H)-one | NA | * |  | NA | * | **** |
| 38 | 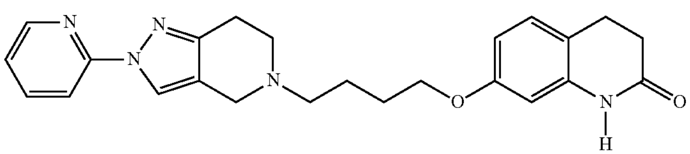 | 7-(4-(2-(pyridin-2-yl)-6,7-dihydro-2H-pyrazolo[4,3-c]pyridin-5(4H)-yl)butoxy)-3,4-dihydroquinolin-2(1H)-one | *** | | |  | * |  |

-continued

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 22 | 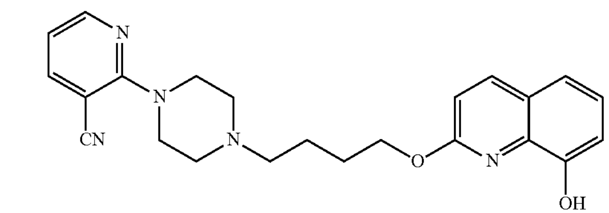 [SMILES: N#Cc1cccnc1N1CCN(CCCCOc2ccc3cccc(O)c3n2)CC1] | 2-(4-(4-(8-hydroxyquinolin-2-yl)oxy)butyl)piperazin-1-yl)nicotinonitrile | ** |  | * |  |  |  |
| 45 | 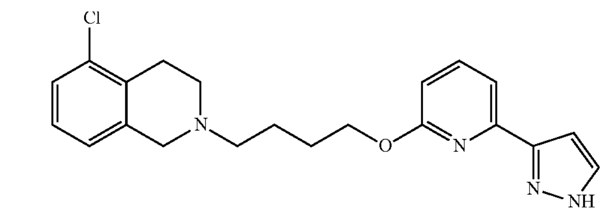 [SMILES: Clc1cccc2c1CCN(CCCCOc1cccc(-c3cc[nH]n3)n1)C2] | 2-(4-((6-(1H-pyrazol-3-yl)pyridin-2-yl)oxy)butyl)-5-chloro-1,2,3,4-tetrahydroisoquinoline | ** |  | * | **** | NA | NA |
| 46 | 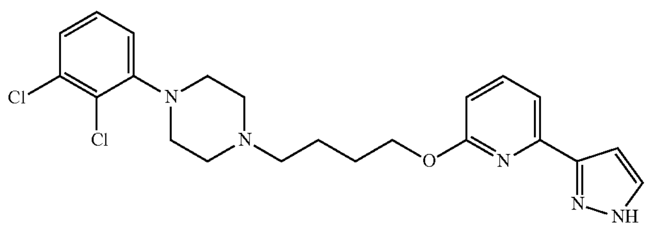 [SMILES: Clc1cccc(N2CCN(CCCCOc3cccc(-c4cc[nH]n4)n3)CC2)c1Cl] | 1-(4-((6-(1H-pyrazol-3-yl)pyridin-2-yl)oxy)butyl)-4-(2,3-dichlorophenyl)piperazine | ** | * | **** | * | ** | * |
| 47 | 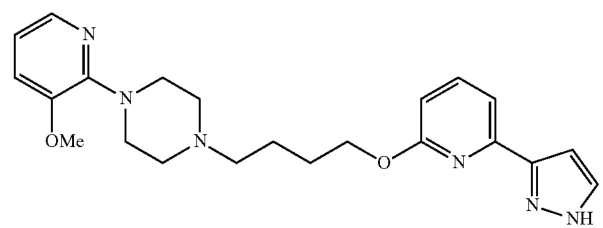 [SMILES: COc1cccnc1N1CCN(CCCCOc2cccc(-c3cc[nH]n3)n2)CC1] | 1-(4-((6-(1H-pyrazol-3-yl)pyridin-2-yl)oxy)butyl)-4-(3-methoxypyridin-2-yl)piperazine | ** | * | **** | * | ** | * |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 66 | 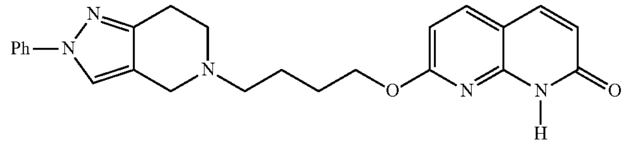 [SMILES: O=c1ccc2ccc(OCCCCN3CCc4nn(-c5ccccc5)cc4C3)nc2[nH]1] | 7-(4-(2-phenyl-6,7-dihydro-2H-pyrazolo[4,3-c]pyridin-5(4H)-yl)butoxy)-1,8-naphthyridin-2(1H)-one | *** | * | NA | NA | * | ** |
| 82 | 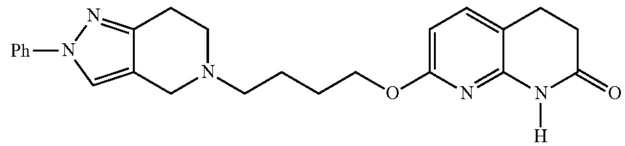 [SMILES: O=C1CCc2ccc(OCCCCN3CCc4nn(-c5ccccc5)cc4C3)nc2N1] | 7-(4-(2-phenyl-6,7-dihydro-2H-pyrazolo[4,3-c]pyridin-5(4H)-yl)butoxy)-3,4-dihydro-1,8-naphthyridin-2(1H)-one | NA | NA | NA | NA |  | ** |
| 89 | 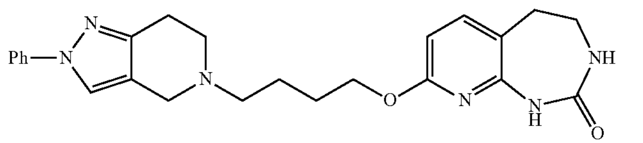 [SMILES: O=C1NCCc2ccc(OCCCCN3CCc4nn(-c5ccccc5)cc4C3)nc2N1] | 8-(4-(2-phenyl-6,7-dihydro-2H-pyrazolo[4,3-c]pyridin-5(4H)-yl)butoxy)-4,5-dihydro-1H-pyrido[2,3-d][1,3]diazepin-2(3H)-one | * |  | * |  | * | * |
| 67 | 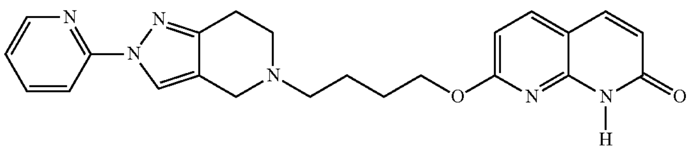 [SMILES: O=c1ccc2ccc(OCCCCN3CCc4nn(-c5ccccn5)cc4C3)nc2[nH]1] | 7-(4-(2-(pyridin-2-yl)-6,7-dihydro-2H-pyrazolo[4,3-c]pyridin-5(4H)-yl)butoxy)-1,8-naphthyridin-2(1H)-one | *** | * | NA | NA |  | ** |
| 90 | 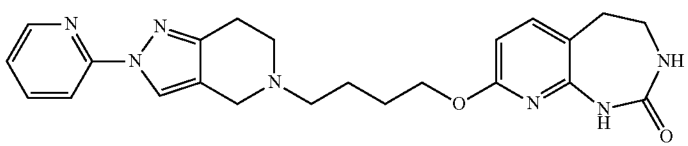 [SMILES: O=C1NCCc2ccc(OCCCCN3CCc4nn(-c5ccccn5)cc4C3)nc2N1] | 8-(4-(2-(pyridin-2-yl)-6,7-dihydro-2H-pyrazolo[4,3-c]pyridin-5(4H)-yl)butoxy)-4,5-dihydro-1H-pyrido[2,3-d][1,3]diazepin-2(3H)-one | ** |  | * | **** | NA | NA |
| 39 | 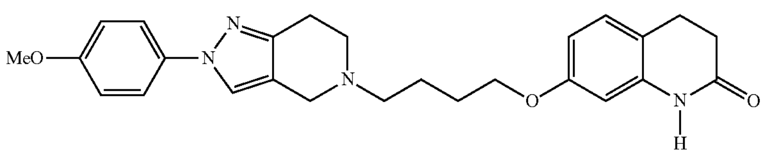 [SMILES: COc1ccc(-n2cc3c(n2)CCN(CCCCOc2ccc4c(c2)NC(=O)CC4)C3)cc1] | 7-(4-(2-(4-methoxyphenyl)-6,7-dihydro-2H-pyrazolo[4,3-c]pyridin-5(4H)-yl)butoxy)-3,4-dihydroquinolin-2(1H)-one | NA | NA | NA | NA | * | **** |

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 48 | 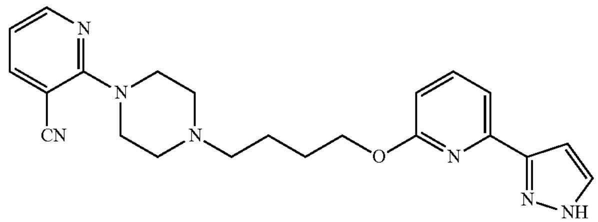 [SMILES: N#Cc1cccnc1N1CCN(CCCCOc2cccc(-c3cc[nH]n3)n2)CC1] | 2-(4-(4-((6-(1H-pyrazol-3-yl)pyridin-2-yl)oxy)butyl)piperazin-1-yl)nicotinonitrile | *** |  |  |  | * |  |
| 49 | 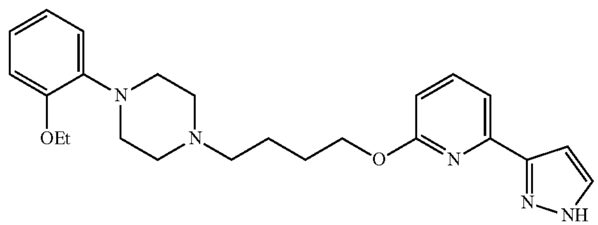 [SMILES: CCOc1ccccc1N1CCN(CCCCOc2cccc(-c3cc[nH]n3)n2)CC1] | 1-(4-((6-(1H-pyrazol-3-yl)pyridin-2-yl)oxy)butyl)-4-(2-ethoxyphenyl)piperazine | ** | * | **** | * | ** | * |
| 50 | 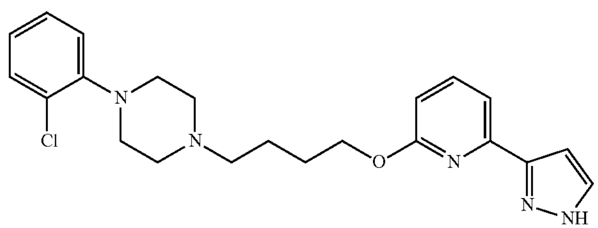 [SMILES: Clc1ccccc1N1CCN(CCCCOc2cccc(-c3cc[nH]n3)n2)CC1] | 1-(4-((6-(1H-pyrazol-3-yl)pyridin-2-yl)oxy)butyl)-4-(2-chlorophenyl)piperazine | ** | * | ** |  | ** | * |
| 91 | 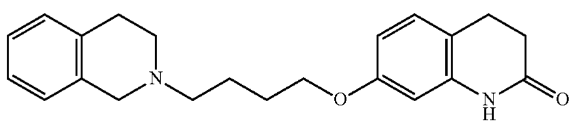 [SMILES: O=C1CCc2ccc(OCCCCN3CCc4ccccc4C3)cc2N1] | 7-(4-(3,4-dihydroisoquinolin-2(1H)-yl)butoxy)-3,4-dihydroquinolin-2(1H)-one | *** |  | **** | * | * | ** |

| Compound Number | Compound Structure | IUPAC Name | cAMP (agonist mode) IC$_{50}$$^a$ | cAMP (agonist mode) E$_{max}$$^b$ | β-arrestin (agonist mode) EC$_{50}$$^a$ | β-arrestin (agonist mode) E$_{max}$$^b$ | β-arrestin (antagonist mode) IC$_{50}$$^a$ | β-arrestin (antagonist mode) I$_{max}$$^b$ |
|---|---|---|---|---|---|---|---|---|
| 92 | 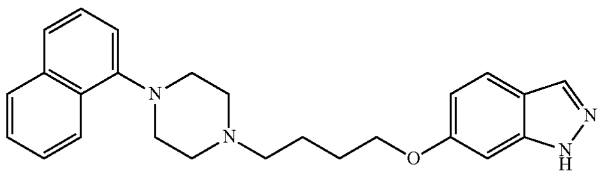 [SMILES: c1ccc2c(N3CCN(CCCCOc4ccc5cn[nH]c5c4)CC3)cccc2c1] | 6-(4-(4-(naphthalen-1-yl)piperazin-1-yl)butoxy)-1H-indazole | * |  | ** |  | * | * |
| 93 | 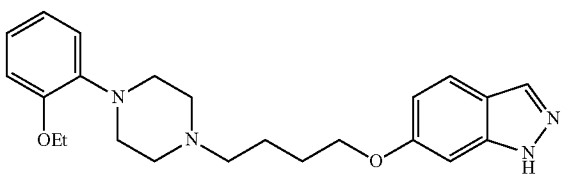 [SMILES: CCOc1ccccc1N1CCN(CCCCOc2ccc3cn[nH]c3c2)CC1] | 6-(4-(4-(2-ethoxyphenyl)piperazin-1-yl)butoxy)-1H-indazole | ** |  | **** | * | * | ** |
| 94 | 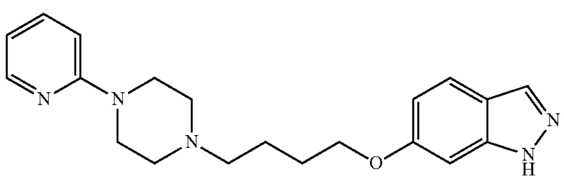 [SMILES: c1ccc(N2CCN(CCCCOc3ccc4cn[nH]c4c3)CC2)nc1] | 6-(4-(4-(pyridin-2-yl)piperazin-1-yl)butoxy)-1H-indazole | ** |  |  | ** | NA | NA |
| 95 | 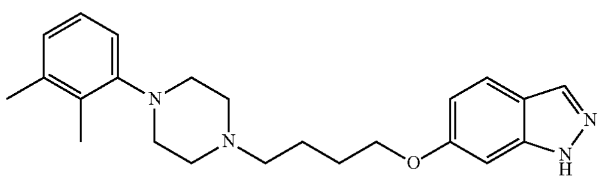 [SMILES: Cc1cccc(N2CCN(CCCCOc3ccc4cn[nH]c4c3)CC2)c1C] | 6-(4-(4-(2,3-dimethylphenyl)piperazin-1-yl)butoxy)-1H-indazole | *** | * | NA | NA | ** | ** |

-continued

| Compound Number | Compound Structure | IUPAC Name | cAMP (agonist mode) IC$_{50}$[a] | cAMP (agonist mode) E$_{max}$[b] | β-arrestin (agonist mode) EC$_{50}$[a] | β-arrestin (agonist mode) E$_{max}$[b] | β-arrestin (antagonist mode) IC$_{50}$[a] | β-arrestin (antagonist mode) I$_{max}$[b] |
|---|---|---|---|---|---|---|---|---|
| 96 | 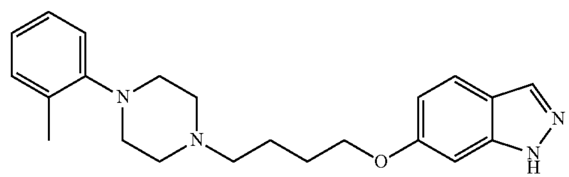 [SMILES: Cc1ccccc1N1CCN(CCCCOc2ccc3cn[nH]c3c2)CC1] | 6-(4-(4-(o-tolyl)piperazin-1-yl)butoxy)-1H-indazole | * |  | *** | * |  | ** |
| 97 | 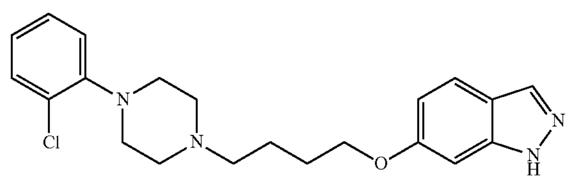 [SMILES: Clc1ccccc1N1CCN(CCCCOc2ccc3cn[nH]c3c2)CC1] | 6-(4-(4-(2-chlorophenyl)piperazin-1-yl)butoxy)-1H-indazole | ** | * | **** | * | ** | * |
| 98 | 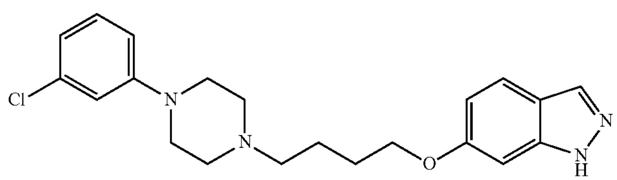 [SMILES: Clc1cccc(N2CCN(CCCCOc3ccc4cn[nH]c4c3)CC2)c1] | 6-(4-(4-(3-chlorophenyl)piperazin-1-yl)butoxy)-1H-indazole | * | * | * |  |  |  |
| 99 | 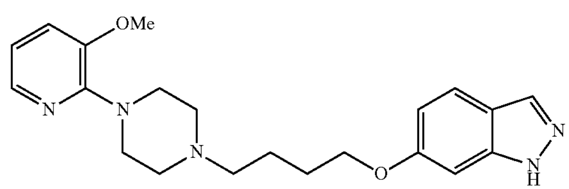 [SMILES: COc1cccnc1N1CCN(CCCCOc2ccc3cn[nH]c3c2)CC1] | 6-(4-(4-(3-methoxypyridin-2-yl)piperazin-1-yl)butoxy)-1H-indazole | *** |  | **** | * | * | ** |

[a] <10 mM***; 10 nM to 100 nM; 100 nM to 1 μM*; 1 μM to 10 μM**; >10 μM NA
[b] >75%***; 50-75%; 25-50%*; 10-25%**; <10%*; <10% NA

What is claimed:
1. A compound of formula (I):

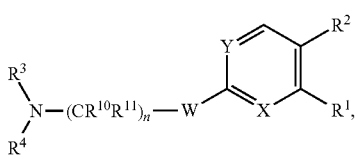

or a pharmaceutically acceptable salt or stereoisomer thereof, wherein
n is 2, 3, or 4;
W is O, $NR^5$, or CH2;
X is N
Y is N or CH;
each $R^{10}$ and each $R^{11}$ are independently H, F, OH, or $(C_1-C_4)$alkyl;
(i) $R^1$ is amido, sulfonamido, optionally substituted imidazolyl, or optionally substituted pyrazolyl; and $R^2$ is H, halogen, CN, $(C_1-C_4)$alkyl, or $(C_1-C_3)$alkoxyl; or
(ii) $R^1$ and $R^2$ together with the carbon atoms to which they are attached form a 5-, 6-, or 7-membered aryl, heteroaryl, cycloalkyl, or heterocyclyl ring, each of which is optionally substituted with one to three $R^6$, wherein the only ring heteroatoms in said heteroaryl or heterocyclyl ring is one or more nitrogen atoms;
$R^3$ and $R^4$ together with the nitrogen atom to which they are attached form an optionally substituted heterocyclyl Q;
Q is

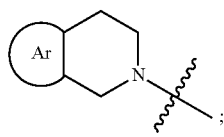

$R^5$ is H or $(C_1-C_3)$alkyl;
each $R^6$ is independently OH, keto, halogen, CN or $(C_3-C_3)$alkoxyl;
$R^7$ is 5- to 10-membered aryl or heteroaryl, each optionally substituted with one to three substituents selected from the group consisting of halogen, alkoxy, —$CF_3$ and —CN; and
Ring Ar is a benzo, pyrazolo, pyrido, thieno, pyrimido, pyrazino, furarano, pyridazino, thiazolo, or imidazolo ring, each optionally substituted with one to three substituents.

2. The compound of claim 1, wherein n is 4.
3. The compound of claim 1, wherein W is O.
4. The compound of claim 1, wherein each of $R^{10}$ and $R^{11}$ is H.
5. The compound of claim 1, wherein $R^1$ is

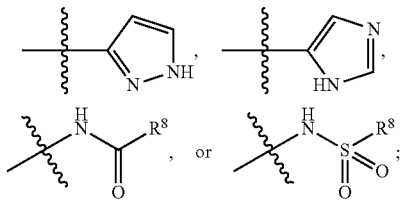

wherein $R^8$ is $(C_1-C_5)$alkyl or optionally substituted phenyl.
6. The compound of claim 1, wherein

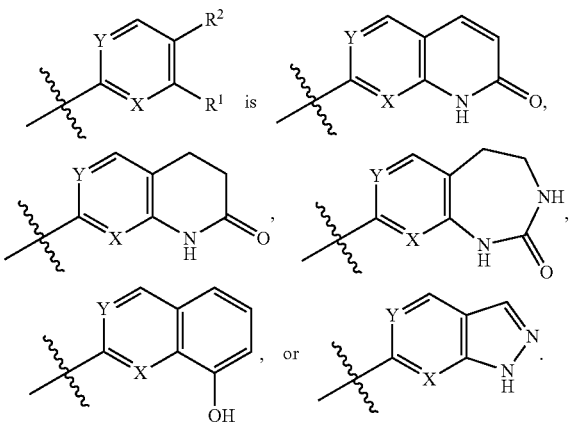

7. The compound of claim 5, wherein $R^1$ is

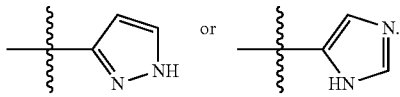 [SMILES: *c1cc[nH]n1 ; "or" ; *c1cnc[nH]1]

8. The compound of claim 1, wherein Ring Ar is a benzo, pyrazolo, thieno, pyrimido, pyrazino, thiazolo, imidazolo, furans, gar pyridazino ring, each of which is optionally substituted with one to three substituents, independently selected from halo, cyano, alkylamino, dialkylamino. $(C_1-C_3)$alkyl optionally substituted with one or more fluoro, $(C_1-C_3)$alkoxyl optionally substituted with one or more fluoro, optionally substituted phenyl, and optionally substituted pyridyl.

9. A pharmaceutical composition comprising a compound of claim 1, or a pharmaceutically acceptable salt or stereoisomer thereof, and a pharmaceutically acceptable excipient, diluent, or carrier.

10. The compound of claim 1, wherein:
W is O;
n is 4; and
each of $R^{10}$ and $R^{11}$ is H.

11. The compound of claim 10, wherein Q is

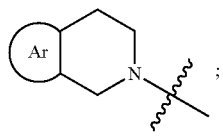

and

Ring Ar is a benzo, mazolo, pyrido, thieno, pyrimido, pyrazino, furano, pyridazino, thiazolo, or imidazolo ring, each of which is optionally substituted with one to three substituents, independently selected from halo, cyano, alkylanxino, dialkylamino, ($C_{1-3}$)alkyl optionally substituted with one or more fluoro, ($C_1$-$C_3$) alkoxyl optionally substituted with one or more fluoro, optionally substituted phenyl, and optionally substituted pyridyl.

12. A compound, selected from:

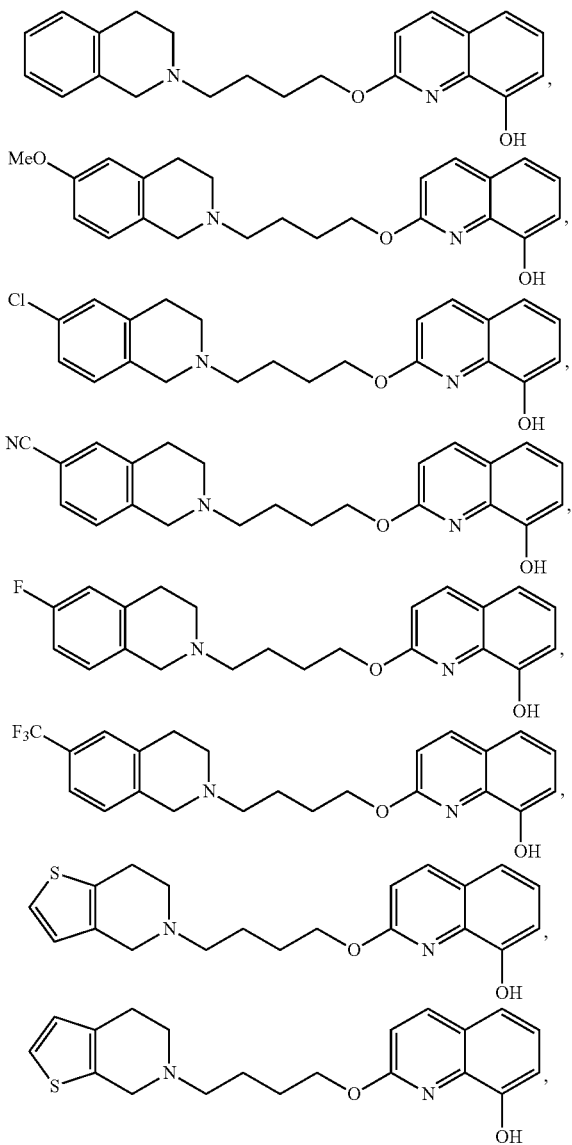

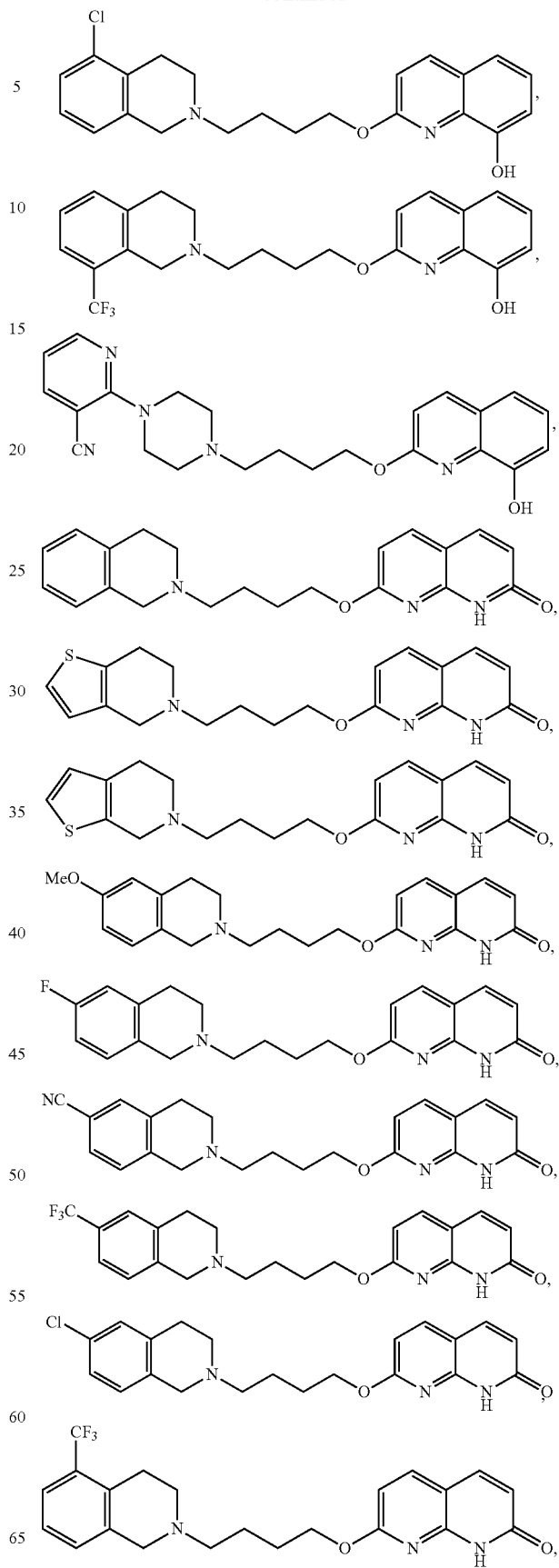

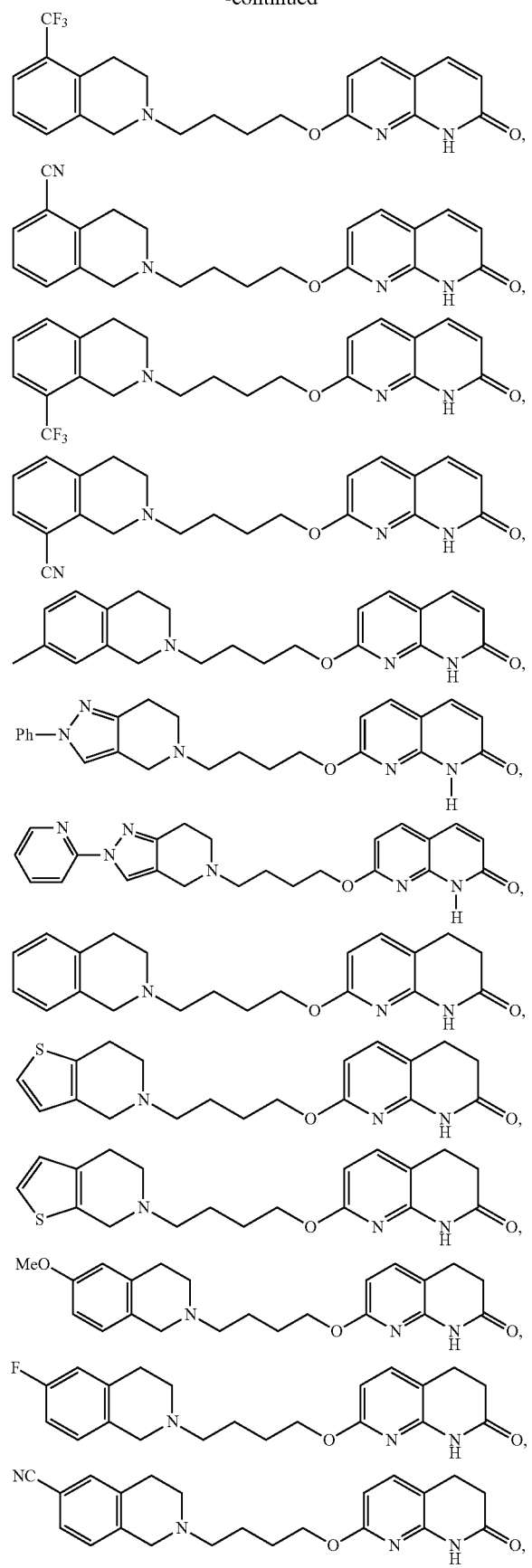
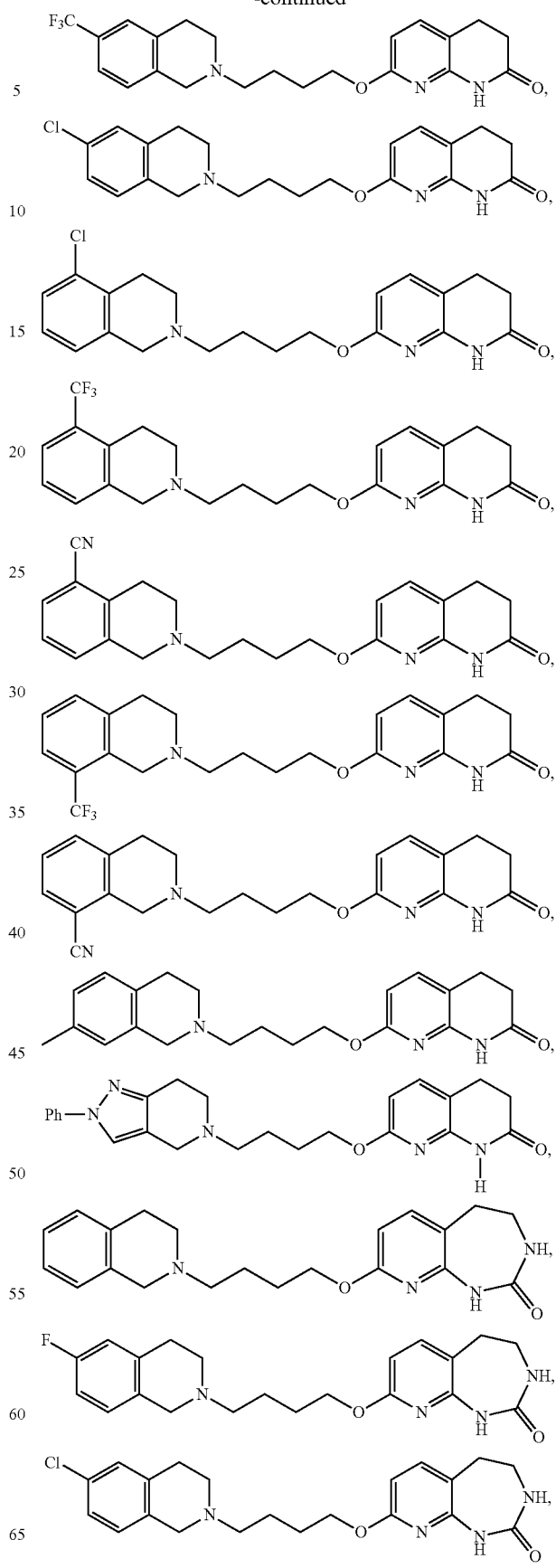

-continued

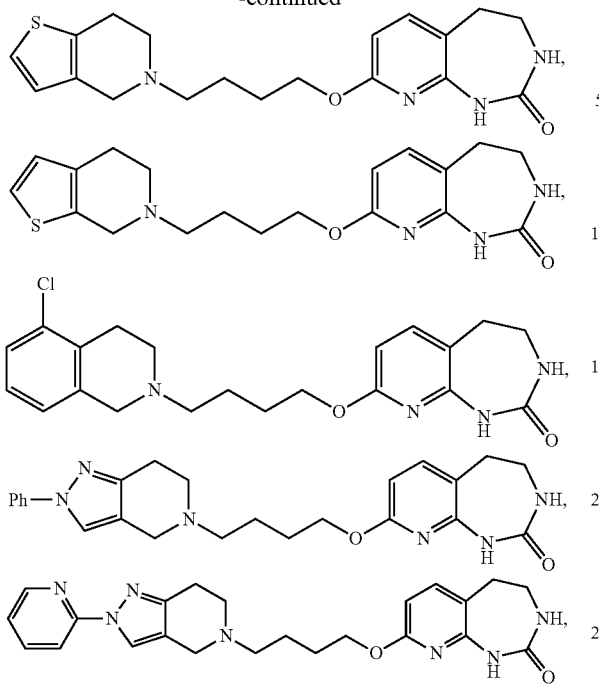

and pharmaceutically acceptable salts thereof.

13. A compound of formula (II-b):

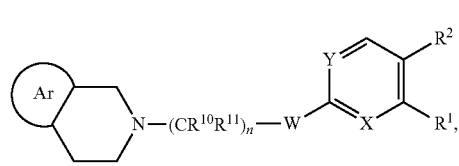
(II-b)

or a pharmaceutically acceptable salt or stereoisomer thereof, wherein n is 2, 3, or 4;
W is O, NR$^5$, or CH$_2$;

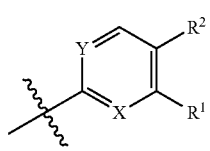

is

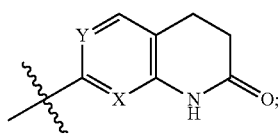

X is N or CH;
Y is N or CH;
each R$^{10}$ and each R$^{11}$ are independently H, F, OH, or (C$_1$-C$_4$)alkyl;

R$^5$ is H (C$_1$-C$_3$)alkyl; and

Ring Ar is a benzo, pyrazolo, pyrido, thieno, pyrimido, pyrazino, furano, pyridazmo, thiazolo, or imidazolo ring, each optionally substituted with one to three substituents;

provided that:

when Ar is an optionally substituted benzo ring, then

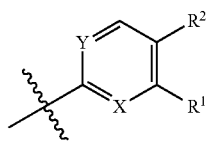

is not

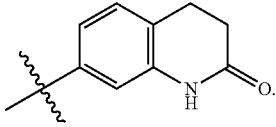 [SMILES: *c1ccc2c(c1)NC(=O)CC2]

14. The compound of claim 13, wherein X is CH.
15. The compound of claim 14 which is selected from;

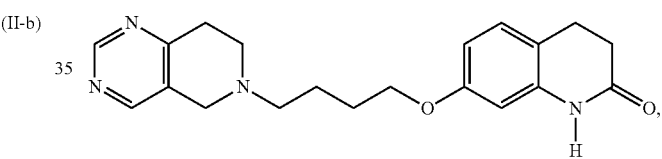

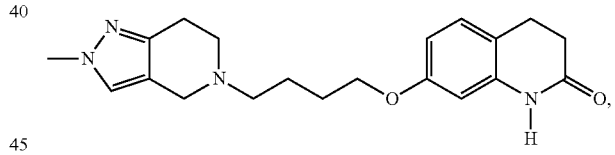

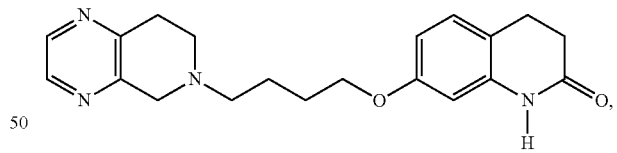

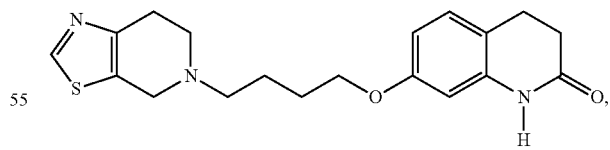

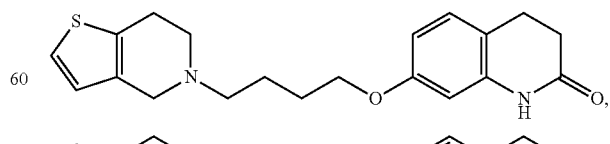

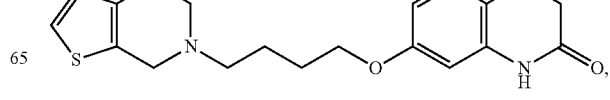

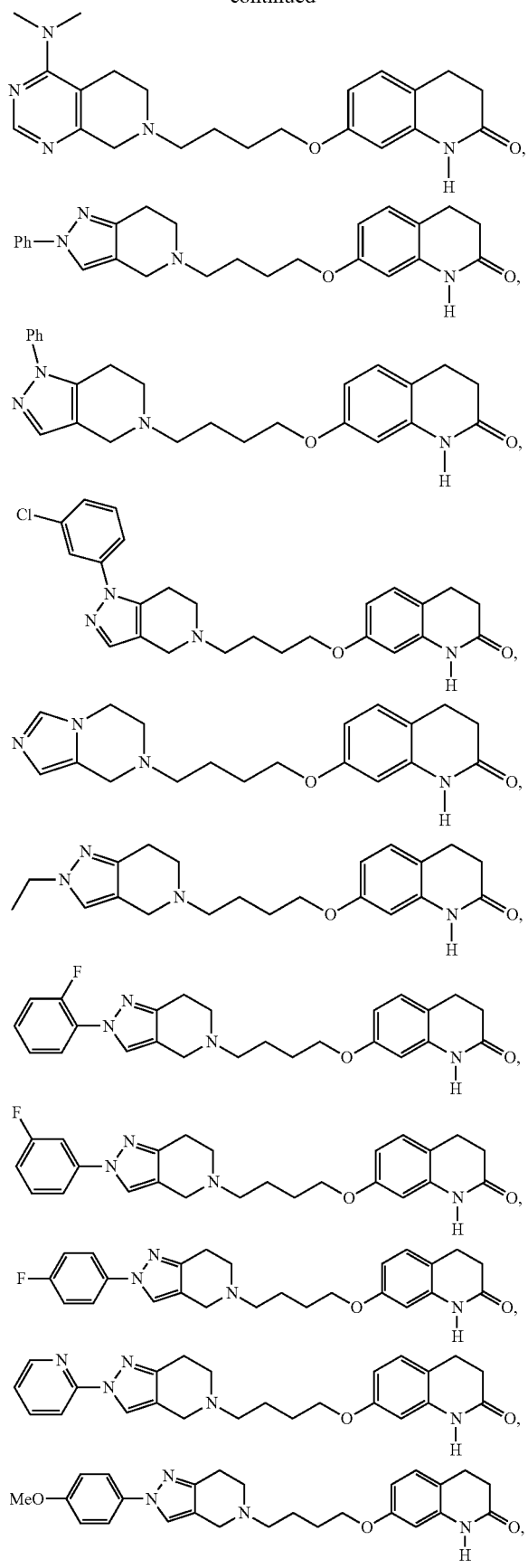

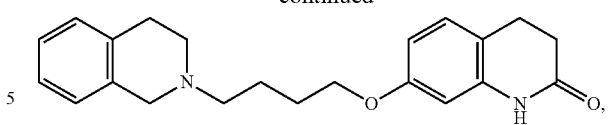

and pharmaceutically acceptable salts thereof.

16. A compound of formula (I):

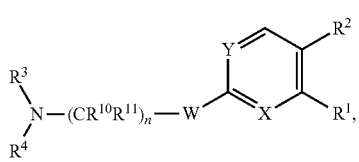

or a pharmaceutically acceptable salt or stereoisomer thereof, wherein n is 2, 3, or 4;

W is O, $NR^5$, or $CH_2$;

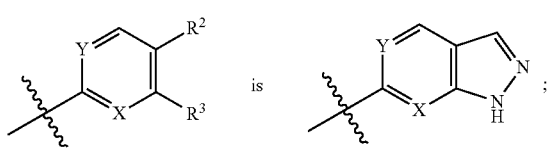

is

X is N or CH;

Y is N or CH;

each $R^{10}$ and each $R^{11}$ are independently H, F, OH, or $(C_1-C_4)$alkyl;

$R^3$ and $R^4$ together with the nitrogen atom to which they are attached form an optionally substituted heterocyclyl Q;

Q is

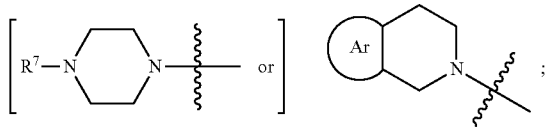

$R^5$ is H or $(C_1-C_3)$alkyl;

each $R^6$ is independently OH, keto, halogen, CN, $(C_1-C_3)$alkyl, or $(C_1-C_3)$alkoxyl;

$R^7$ is phenyl, pyridyl, pyridazinyl, pyrazinyl, pyrimidinyl, or naphthyl, each of which is optionally substituted with one substituent selected from halo, cyano, alkylamino, dialkylamino, $(C_1-C_3)$alkyl optionally substituted with one or more fluoro, and $(C_1-C_3)$alkoxyl substituted with one or more fluoro; and Ring Ar is a benzo, pyrazole, pyrido, thieno, pyrimido, pyrazino, furano, pyridazino, thiazolo, or imidazolo ring, each optionally substituted with one to three substituents;

provided that:
when Ar is an optionally substituted benzo ring then,
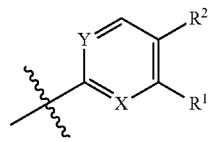
is not
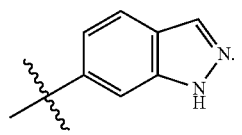 [SMILES: *c1ccc2cn[nH]c2c1]
* * * * *

UNITED STATES PATENT AND TRADEMARK OFFICE
CERTIFICATE OF CORRECTION

PATENT NO. : 9,951,088 B2  
APPLICATION NO. : 14/399334  
DATED : April 24, 2018  
INVENTOR(S) : Philip G. Jones et al.

Page 1 of 1

It is certified that error appears in the above-identified patent and that said Letters Patent is hereby corrected as shown below:

In the Claims

At Column 157, Line 65, "furarano" should be replaced with "furano"

At Column 158, Line 51, "furans, gar" should be replaced with "furano, or"

At Column 159, Line 11, "Ring Ar is a benzo, mazolo" should be replaced with "Ring Ar is a benzo, pyrazolo"

At Column 159, Line 16, "cyano, alkylanxino, dialkylamino, (C1-3)alkyl" should be replaced with "cyano, alkylamino, dialkylamino, (C1-C3)alkyl"

At Column 164, Line 3, "pyridazmo" should be replaced with "pyridazino"

At Column 166, Line 30, the chemical structure " 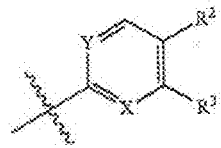 " should be replaced with " 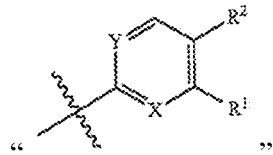 "

At Column 166, Line 64, "Ring Ar is a benzo, pyrazole, pyrido, thieno, pyrirnido" should be replaced with "Ring Ar is a benzo, pyrazolo, pyrido, thieno, pyrimido"

Signed and Sealed this  
Twenty-ninth Day of May, 2018

Andrei Iancu  
*Director of the United States Patent and Trademark Office*